(12) United States Patent
Altschul et al.

(10) Patent No.: US 11,224,599 B2
(45) Date of Patent: *Jan. 18, 2022

(54) THERAPEUTIC AGENTS AND METHODS

(71) Applicant: Pop Test Oncology LLC, Cliffside Park, NJ (US)

(72) Inventors: Randice Lisa Altschul, Cliffside Park, NJ (US); Neil David Theise, New York City, NY (US); Andreas J. Kesel, Munich (DE); Myron Rapkin, Indianapolis, IN (US); Rebecca O'Brien, Shell Knob, MO (US); Anthony R. Arment, Fairborn, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/242,495

(22) Filed: Apr. 28, 2021

(65) Prior Publication Data

US 2021/0353623 A1 Nov. 18, 2021

Related U.S. Application Data

(63) Continuation-in-part of application No. 16/338,547, filed as application No. PCT/US2017/054874 on Oct. 3, 2017, now Pat. No. 11,040,037.

(60) Provisional application No. 62/517,289, filed on Jun. 9, 2017, provisional application No. 62/501,811, filed on May 5, 2017, provisional application No. 62/474,738, filed on Mar. 22, 2017, provisional application No. 62/449,195, filed on Jan. 23, 2017, provisional application No. 62/442,478, filed on Jan. 5, 2017, provisional application No. 62/440,636, filed on Dec. 30, 2016, provisional application No. 62/441,076, filed on Dec. 30, 2016, provisional application No. 62/433,988, filed on Dec. 14, 2016, provisional application No. 62/420,578, filed on Nov. 11, 2016, provisional application No. 62/412,414, filed on Oct. 25, 2016, provisional application No. 62/404,036, filed on Oct. 4, 2016.

(51) Int. Cl.
| | | |
|---|---|---|
| *A61K 31/506* | (2006.01) | |
| *A61K 9/00* | (2006.01) | |
| *A61K 31/14* | (2006.01) | |
| *A61K 31/175* | (2006.01) | |
| *A61K 31/195* | (2006.01) | |
| *A61K 31/58* | (2006.01) | |
| *A61K 45/06* | (2006.01) | |

(52) U.S. Cl.
CPC .......... *A61K 31/506* (2013.01); *A61K 9/0014* (2013.01); *A61K 31/14* (2013.01); *A61K 31/175* (2013.01); *A61K 31/195* (2013.01); *A61K 31/58* (2013.01); *A61K 45/06* (2013.01)

(58) Field of Classification Search
CPC .... A61K 31/506; A61K 31/14; A61K 31/175; A61K 31/195; A61K 31/395; A61K 31/58; A61K 45/06; A61P 31/12; C07C 211/41; C07C 2603/74; C07C 309/51; C07C 335/40; C07D 317/54; C07D 498/08; C07H 19/067; C07H 99/00; C07J 17/00; C07J 41/005; C07J 41/0083
See application file for complete search history.

(56) References Cited

U.S. PATENT DOCUMENTS

| | | | | |
|---|---|---|---|---|
| 3,342,810 | A * | 9/1967 | Sensi | A61K 31/395 540/458 |
| 8,193,172 | B2 * | 6/2012 | Sennef | A61K 31/56 514/174 |
| 8,658,128 | B2 * | 2/2014 | Altschul | A61P 25/22 424/1.11 |
| 9,598,459 | B2 * | 3/2017 | Altschul | A61K 31/58 |
| 9,636,351 | B2 * | 5/2017 | Altschul | A61K 9/10 |
| 9,713,622 | B2 * | 7/2017 | Leibowitch | A61K 31/513 |
| 9,855,284 | B2 * | 1/2018 | Altschul | C07J 41/0005 |
| 10,238,666 | B2 * | 3/2019 | Altschul | A61K 31/57 |
| 10,517,881 | B2 * | 12/2019 | Altschul | A61K 31/7068 |
| 11,040,037 | B2 * | 6/2021 | Altschul | A61K 31/58 |
| 2020/0101087 | A1 * | 4/2020 | Altschul | A61K 31/513 |

OTHER PUBLICATIONS

Andersen et al., "The proximal origin of SARS-CoV-2", 2020, Nat. Med., vol. 26, pp. 450-452. https://doi.org/10.1038/s41591-020-0820-9 (Year: 2020).*

* cited by examiner

*Primary Examiner* — My-Chau T. Tran
(74) *Attorney, Agent, or Firm* — Abelman, Frayne & Schwab; Stefan Knirr

(57) ABSTRACT

The invention provides glucocorticoid receptor antagonists for treatment of infection, neoplasia, and fatty liver disease.

6 Claims, 15 Drawing Sheets

TPR-1

MR-1

Proton nuclear magnetic resonance (1H NMR) spectrum of MR-1 dissolved in deuterated chloroform (CDCl$_3$)

PT155-3

700.35 MHz proton(1H) nuclear magnetic resonance (NMR) spectrum of PT155-3 dissolved in deuterated DMSO-d6

PT160

PT161-1

PT161

PT162

PT165

700.35 MHz proton (1H) nuclear magnetic resonance (NMR) spectrum of crude PT165 dissolved in DMSO-d6

PT166

400.132 MHz proton (1H) nuclear magnetic resonance (NMR) spectrum (300.0 K) of PT166 dissolved in DMSO-d6

*M. tuberculosis sulfolipid-1*

+ TPR-1 →

*M. tuberculosis sulfolipid-1/TPR-1 complex*

The complexation of the anionic Mycobacterium tuberculosis virulence factor sulfolipid-1 (SL-1) by the cationic rifamycin antibiotic TPR-1

700.35 MHz proton (1H) nuclear magnetic resonance (NMR) spectrum of PENT dissolved in DMSO-d6

THERAPEUTIC AGENTS AND METHODS

CROSS-REFERENCE TO RELATED APPLICATIONS

This application is a divisional of prior filed U.S. application Ser. No. 16/338,547, filed Apr. 1, 2019, which claims benefit under 35 USC § 119(e) of U.S. Provisional Patent Application No. 62/404,036, filed Oct. 4, 2016; U.S. Provisional Patent Application No. 62/412,414, filed Oct. 25, 2016; U.S. Provisional Patent Application No. 62/433,988, filed Dec. 14, 2016; U.S. Provisional Patent Application No. 62/440,636, filed Dec. 30, 2016; U.S. Provisional Patent Application No. 62/441,076, filed Dec. 30, 2016; U.S. Provisional Patent Application No. 62/420,578, filed Nov. 11, 2016; U.S. Provisional Patent Application No. 62/442,478, filed Jan. 5, 2017; U.S. Provisional Patent Application No. 62/449,195, filed Jan. 23, 2017; U.S. Provisional Patent Application No. 62/474,738, filed Mar. 22, 2017; U.S. Provisional Patent Application No. 62/501,811, filed May 5, 2017; U.S. Provisional Patent Application No. 62/517,289, filed Jun. 9, 2017; the disclosures of which are incorporated herein by reference in their entireties.

BACKGROUND OF THE INVENTION

Two categories of diseases affect plants and animals and have significant costs in terms of societal function, economics, and health and well-being: neoplasia and infection. Neoplasia is the abnormal growth of tissues from epigenetic or genetic changes in once normal cells which then produce benign or malignant proliferations, mass forming, or more generally spreading patterns, or both. Infections involve the invasion of a plant or animal by microorganisms such as bacteria, viruses, fungi, yeasts and parasites which then, with multiplication, lead to disease/injury. Together, these easily comprise the majority of human diseases requiring clinical care and attention, diseases involving animals (inclusive of pets and livestock), and diseases of plants, both decorative and agricultural.

The most common treatments of infections involve antimicrobial compounds given locally, topically, or systemically. Neoplasia may be treated surgically, chemotherapeutically, radiotherapeutically or, more recently, through manipulation of the immune system. This application covers a set of compounds that function as anti-microbial therapeutic agents or as anti-neoplastic agents or as both. They may function as single agents, paired together in combinations of two or three or more, or in combination with unrelated compounds, also in combinations of two or three or more.

The invention provides glucocorticoid receptor antagonists for treatment of infection, neoplasia, and fatty liver disease. For example, the molecules PT150, PT155, PT156 and PT157 are potent glucocorticoid receptor (GR) antagonists. PT150 is a steroidal hormone with high binding affinity for the human GR and comparatively low affinities for other hormonal receptors (e.g. progesterone, estrogen, mineralocorticoid, androgen). Its binding yields significant biological antagonism. PT155, PT156 and PT157 are varying organization of the PT150 molecule with a phenylsemithiocarbazone modification—this modification can lead to binding to other PT150 molecules or co-crystallization with them. All these compounds, PT150 and its derivatives, have some degree of anti-bacterial, anti-viral, anti-fungal and anti-neoplastic affects, relating to the ubiquity of cortisol or cortisol-like receptor binding in mammals (human and non-human) and in pathogens which have evolved to exploit the cortisol "stress hormone" response to infection and resultant inflammation. (Reynolds AR Acute oral administration of the novel, competitive and selective glucocorticoid receptor antagonist ORG 34517 reduces the severity of ethanol withdrawal and related hypothalamic-pituitary-adrenal axis activation. Drug Alcohol Depend. 2015 Sep. 1; 154:100-4).

In particular, binding of these compounds to form GR-compound complexes which then bind to glucocorticoid response elements in viral genomes leads to inactivation or suppression of viral gene function and, thereby, to inhibition of viral physiology, including inactivation of viral replication, viral encoating, viral shedding and elimination of pro-virus of chronic latent viral infections. Other mechanisms for viral suspicion are suspected to include binding to cytoplasmic molecules important for processing and shepherding of viral particles.

In addition, the GR antagonists (PT150, PT155, PT156 and PT157) also affect non-alcoholic fatty liver disease (NAFLD), a progressive chronic disease in the setting of metabolic syndrome (indicated by obesity, diabetes mellitus, hyperlipidemia, and hypertension). Hepatic metabolic dysfunction in this setting has been shown to be related to GR modulation of Hes1 gene expression. The GR directly interferes with Hes1 promoter activity, triggering the recruitment of histone deacetylase (HDAC) activities to the Hes1 gene. Genetic restoration of hepatic Hes1 levels in steatotic animals normalizes hepatic triglyceride (TG) levels. Increased glucocorticoid action leads to inhibition of Hes1 and may be a central mediator in the fatty liver phenotype in individuals with NAFLD. GR-antagonism may thus alleviate the core manifestations of NAFLD.

The invention further provides rifampin-like compound and combination therapies for infection. For example, TPR-1 is an unrelated compound related to the anti-microbial agent rifampicin (Rifampin). Rifampin has long been in use as an anti-microbial agent, but its use is limited by development of resistant strains as well as by its chemical instability. The latter issue is particularly important for its agricultural utility. Rifampicin is easily oxidized by atmospheric oxygen to its naphthoquinone form[1]. Furthermore, rifampicin is easily hydrolysed, in reversal of its synthesis reaction, to 3-formylrifamycin SV and 1-amino-4-methylpiperazine[1]. Both these chemical instabilities prevent use of rifampicin for free field agricultural applications, since rifampicin is not stable enough against atmospheric oxygen, humidity, and other environmental influences like UV irradiation by sun light. TPR-1, on the other hand, is not oxidized by atmospheric oxygen, since it is zwitterionic like rifampicin (Kesel A J. Retinazone inhibits certain blood-borne human viruses including Ebola virus Zaire. Antivir Chem Chemother. 2014 Apr. 11; 23(5):197-215. doi: 10.3851/IMP2568), but its zwitterionic state is locked by the quaternary ammonium moiety at the piperazine. It shows enhanced stability towards hydrolysis and UV light. In combination with PT150 and PT155, creating compounds PT159 and PT160 respectively, synergy is expected for treatment of susceptible micro-organisms.

TPR-1 also is able to circumvent multidrug-resistant tuberculosis (MDR-TB) and extensively drug-resistant tuberculosis (XDR-TB) resistance mechanisms of circulating *M. tuberculosis* strains (Ulrike Lemke, et al. The glucocorticoid receptor controls hepatic dyslipidemia through Hes1. Cell Metab 2008, 8, 212-223), by scavenging the *M. tuberculosis* virulence factor sulfolipid-1 (SL-1), a tetraacyl-sulfotrehalose glycolipid (Floss H G, Yu T W. Rifamycin-mode of action, resistance, and biosynthesis. Chem Rev.

2005 February; 105(2):621-32; Maggi M, Pasqualucci C R, Ballotta R, Sensi P. 1966. Rifampicin: a new orally active rifamycin. Chemotherapia 11:285-292), and its congeners like diacyl sulfoglycolipid (Ac$_2$SGL) (Przybylski P et al. 2014. 13C and 15N CP/MAS, 1H-15N SCT CP/MAS and FTIR spectroscopy as tools for qualitative detection of the presence of zwitterionic and nonionic forms of ansa-macrolide 3-formylrifamycin SV and its derivatives in solid state. Magn. Res. Chem. 52:10-21; Middlebrook G, Coleman C M, Schaefer W B. 1959. Sulfolipid from virulent tubercle bacilli. Proc. Natl. Acad. Sci. U.S.A. 45:1801-1804). SL-1 is contained in pathogenic mycobacteria (H$_{37}$Rv, Vallée), but not in apathogenic (H$_{37}$Ra); its amounts have been positively correlated with strain virulence.

The invention further provides p53 reactivating cell cycle checkpoint inhibitor for treating neoplasia. For example, PT162 acts as a protein p53-reactivating cell cycle checkpoint inhibitor[1], inducing cell cycle arrest and/or apoptosis in cancer cells by restoring DNA-binding activity of mutant p53 protein. Tumor protein p53 (TP53) has been described as "the guardian of the genome" because of its role in conserving stability by preventing genome mutation. Hence its gene TP53 is classified as a tumor suppressor gene.

TP53 protein is mutated in ca. 50% of human cancers (See Kesel et al. 2014), in fact TP53 is the most commonly mutated gene in human cancer (See Lemke et al. 2008). TP53 is the 'guardian of the genome' with DNA-binding activity. Upon DNA damage p53 is activated by tetramerization to bind like a transcription factor to p53 response elements in human genomic DNA[2-4]. The transcriptional activity leads to induction of apoptosis in cancer cells. However, in cancer cells p53 can be mutated in such a way that p53 tetramerization and DNA binding (Kesel et al. 2014; Lemke et al. 2014; Floss et al., 2005) is prevented. Therefore, these cancer cells survive instead of DNA damage induced by antineoplastic chemotherapy (alkylating agents, platinum complexes, and other currently applied cytostatics/cytotoxics).

TP53 reactivators are already known[3,5], acting by several mechanisms. Many of them inhibit MDM2 (also called HDM2 in humans), an ubiquitin ligase rendering p53 protein being destroyed in the human proteasome. Other investigational drugs reactivate mutant p53 tetramerization and DNA binding capacity, and restore transcriptional activity of p53 protein in malignant cells. PT162 binds to the p53 tetramerization domain (p53 TD), since p53 TD contains a large proportion of acidic and hydrophobic amino acid residues and PT162 itself is pentacationic and hydrophobic. This enables binding by both electrostatic interaction and hydrophobic interaction.

The invention also provides for mitotic inhibitor as single agent and in combination for neoplasia. For example, PT166 represents a derivative of colchicine, a mitotic inhibitor like demecolcine (colcemid), paclitaxel, docetaxel, cabazitaxel, podophyllotoxin, vincristine, vinblastine, vindesine, vinorelbine and other *Vinca* alkaloid derivatives. It acts as a cancerostatic, stopping cancer cell growth by depolymerizing microtubules and inhibiting spindle formation during metaphase of mitosis through binding to the subunit of tubulin (-tubulin).

The combination of PT162 and PT166 is labeled PT167 and shows synergism between the two distinct anti-neoplastic properties.

All references cited herein are incorporated herein by reference in their entireties.

BRIEF SUMMARY OF THE INVENTION

The invention provides a compound selected from the group consisting of: TPR-1, or pharmaceutically acceptable salts thereof; OR-1, or pharmaceutically acceptable salts thereof; MR-1, or pharmaceutically acceptable salts thereof; TCY1, or pharmaceutically acceptable salts thereof; KM-1, or pharmaceutically acceptable salts thereof; TCY-1, or pharmaceutically acceptable salts thereof; PT157, or pharmaceutically acceptable salts thereof; PT158, or pharmaceutically acceptable salts thereof; PT159, or pharmaceutically acceptable salts thereof; PT160, or pharmaceutically acceptable salts thereof; PT162, or pharmaceutically acceptable salts thereof; PT163, or pharmaceutically acceptable salts thereof; PT164, or pharmaceutically acceptable salts thereof; PT165, or pharmaceutically acceptable salts thereof; PT166, or pharmaceutically acceptable salts thereof; PT167, or pharmaceutically acceptable salts thereof, and combinations thereof. The invention provides a pharmaceutical composition comprising a therapeutically effective amount of at least one active agent, wherein the active agent is selected from the group consisting of: TPR-1, OR-1, MR-1, TCY1, PT150, PT157, PT158, PT159, PT160, PT162, PT163, PT164, PT165, PT166, PT167, combinations thereof, and pharmaceutically acceptable salts thereof; and at least one pharmaceutically acceptable excipient.

The invention provides a pharmaceutical composition in a dosage form selected from the group consisting of a minicapsule, a capsule, a tablet, an implant, a troche, a lozenge, a minitablet, a temporary or permanent suspension, an injectable, an ovule, a suppository, a wafer, a chewable tablet, a quick or fast dissolving tablet, an effervescent tablet, a buccal or sublingual solid, a granule, a film, a sprinkle, a pellet, a topical formulation, a patch, a bead, a pill, a powder, a triturate, a smart pill, a smart capsule, a platelet, a strip, and a sachet. The invention provides a pharmaceutical composition in a dosage form for topical application, and at least one pharmaceutically acceptable excipient. The invention provides a pharmaceutical composition in a dosage form for topical application wherein said formulation is in a form selected from the group consisting of: cream, lotion, gel, oil, ointment, suppository, spray, foam, liniment, aerosol, buccal and sublingual tablet or a transdermal device or patch for absorption through the skin or mucous membranes. The invention provides a kit for treating or preventing a condition in a patient, the kit comprising: (a) the pharmaceutical composition of the invention in a therapeutically effective amount; and (b) at least one blister package; a lidded blister; a blister card or packet; a clamshell; an intravenous (IV) package, IV packette or IV container; a tray or a shrink wrap comprising the pharmaceutical composition of (a) and instructions for using the pharmaceutical composition.

The invention provides a method of preventing and/or treating a pathogenic infection in patient, the method comprising the steps of: selecting a patient in need of preventing and/or treating a pathogenic infection; administering to the patient at least one agent selected from the group consisting of TPR-1, OR-1, MR-1, TCY1, PT150, PT157, PT158, PT159, PT160, PT162, PT163, PT164, PT165, PT166, PT167, combinations thereof, and pharmaceutically acceptable salts thereof; wherein the pathogenic infection is prevented and/or treated in the patient. The invention provides a method of the invention wherein the pathogenic infection is selected from the group consisting of viral infection, bacterial infection, fungal infection, parasitic infection, and combinations thereof. The invention provides a method of any one of the invention, wherein the pathogenic infection is a viral infection. The invention provides a method of any one of the invention wherein the viral infection is selected from the group consisting of Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, Vaccinia virus, Cowpox virus, Monkeypox virus.

The invention provides method of preventing and/or treating a pathogenic infection in a patient, the method comprising the steps of: selecting a patient in need of preventing and/or treating a pathogenic infection; administering to the patient at least one first agent which is selected from the group consisting of molecules with potential to bind viral PS, annexin-5, anti-PS monoclonal or polyclonal antibodies, bavituximab, and/or bind to viral glucocorticoid response elements (GREs), retinazone and RU486 or derivatives, cell entry inhibitors, uncoating inhibitors, reverse transcriptase inhibiotrs, integrase inhibitors, transcription inhibitors, antisense translation inhibitors, ribozyme translation inhibitors, prein processing and targeting inhibitors, protease inhibitors, assembly inhibitors, release phase inhibitos, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof; and administering to the patient at least one second agent selected from the group consisting of TPR-1, OR-1, MR-1, TCY1, PT150, PT157, PT158, PT159, PT160, PT162, PT163, PT164, PT165, PT166, PT167, combinations thereof, and pharmaceutically acceptable salts thereof; wherein the pathogenic infection is prevented and/or treated in the patient. The invention provides a method of the invention, wherein the at least one first agent is administered prior to, concurrently with, or subsequently to the at least one second agent. The invention provides a method of the invention, wherein the at least one first agent and at least one second agent are in a pharmaceutical composition. The invention provides a method of the invention, wherein the at least one first agent and at least one second agent are in the same dosage form. The invention provides a method of the invention, wherein the at least one first agent and at least one second agent are in separate dosage forms. The invention provides a method of the invention, wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The invention provides a method of the invention, wherein the pathogenic infection is selected from the group consisting of viral infection, bacterial infection, fungal infection, parasitic infection, and combinations thereof. The invention provides a method of the invention, wherein the pathogenic infection is a viral infection. The invention provides a method of the invention, wherein the viral infection is selected from the group consisting of Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, Vaccinia virus, Cowpox virus, Monkeypox virus.

The invention provides a pharmaceutical composition comprising: at least one agent selected from the group consisting of TPR-1, OR-1, MR-1, TCY1, PT150, PT157, PT158, PT159, PT160, PT162, PT163, PT164, PT165, PT166, PT167, combinations thereof, and pharmaceutically acceptable salts thereof; optionally at least one second active agent selected from the group consisting of molecules with potential to bind viral PS, annexin-5, anti-PS monoclonal or polyclonal antibodies, bavituximab, and/or bind to viral glucocorticoid response elements (GREs), retinazone and RU486 or derivatives, cell entry inhibitors, uncoating inhibitors, reverse transcriptase inhibiotrs, integrase inhibitors, transcription inhibitors, antisense translation inhibitors, ribozyme translation inhibitors, prein processing and targeting inhibitors, protease inhibitors, assembly inhibitors, release phase inhibitos, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof; wherein the pharmaceutical composition further comprises at least one pharmaceutically acceptable excipient.

The invention provides a pharmaceutical composition of the invention, wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The invention provides a pharmaceutical composition of the invention, wherein the at least one first agent and at least one second agent are in the same dosage form. The invention provides a pharmaceutical composition of the invention, wherein the at least one first agent and at least one second agent are in separate dosage forms. The invention provides a pharmaceutical composition of the invention, wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The invention provides a pharmaceutical composition of the invention, wherein the pharmaceutical composition is in a form for topical administration.

The invention provides a method of treating and/or preventing a viral condition in a patient comprising: selecting the patient in need of treating and/or preventing a viral condition; administering at least one active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the viral condition is to prevent acute viral infection from becoming chronic active or latent infection with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, Vaccinia virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the viral condition is to prevent chronic latent viral infection from becoming active (reactivation), to diminish intensity of viral reactivation, to diminish length of viral reactivation, to speed time to resolution and healing of viral reactivation, to speed time to suppression of viral reactivation, to increase likelihood of viral eradication, and/or to diminish infectivity of viral reactivation with: Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, Vaccinia virus, Cowpox virus, Monkeypox virus.

The invention provides a method of treating and/or preventing a viral condition in a patient comprising: selecting a patient in need of treating and/or preventing a viral condition; administering at least one active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the viral condition is to inactivate latent pro-viral genome eliminating ("curing") chronic viral infections with Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (or Human Herpes Virus-8; HHV-8), Variola (Small Pox) virus, Vaccinia virus, Cowpox virus, Monkeypox virus.

The invention provides a method of treating and/or preventing a viral condition in a patient comprising: selecting a patient in need of treating and/or preventing a viral condition; administering an active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the viral condition is to prevent or eliminate acute viral infection, to diminish intensity of viral infection, to diminish length of viral infection, to speed time to resolution and healing of viral infection, to speed time to suppression of viral infection, to increase likelihood of viral eradication, and/or to diminish infectivity of viral infection.

The invention provides a method of the invention, wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amapari virus, Pichindé virus, Tacaribe virus, Junin virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amapari virus, Pichindé virus, Tacaribe virus, Junin virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); *Variola major* (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus). The invention provides a method of treating and/or preventing a viral condition in a patient comprising: selecting a patient in need of treating and/or preventing a viral condition; administering to the patient at least one active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the viral condition is to prevent acute viral infection from becoming chronic active or latent infection.

The invention provides a method of the invention, wherein the viral condition is selected from the group consisting of Ebola and Marburg virus (Filoviridae); Ross River virus, chikungunya virus, Sindbis virus, eastern equine encephalitis virus (Togaviridae, Alphavirus), vesicular stomatitis virus (Rhabdoviridae, Vesiculovirus), Amapari virus, Pichindé virus, Tacaribe virus, Junin virus, Machupo virus (Arenaviridae, Mammarenavirus), West Nile virus, dengue virus, yellow fever virus (Flaviviridae, Flavivirus); human immunodeficiency virus type 1 (Retroviridae, Lentivirus); Moloney murine leukemia virus (Retroviridae, Gammaretrovirus); influenza A virus (Orthomyxoviridae); respiratory syncytial virus (Paramyxoviridae, Pneumovirinae, Pneumovirus); vaccinia virus (Poxviridae, Chordopoxvirinae, Orthopoxvirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus); *Autographa californica* nucleopolyhedrovirus (Baculoviridae, Alphabaculoviridae) (an insect virus); Ebola and Marburg virus (Filoviridae); Semliki Forest virus, Ross River virus, chikungunya virus, O'nyong-nyong virus, Sindbis virus, eastern/western/Venezuelan equine encephalitis virus (Togaviridae, Alphavirus); rubella (German measles) virus (Togaviridae, Rubivirus); rabies virus, Lagos bat virus, Mokola virus (Rhabdoviridae, Lyssavirus); Amapari virus, Pichindé virus, Tacaribe virus, Junin virus, Machupo virus, Guanarito virus, Sabia virus, Lassa virus (Arenaviridae, Mammarenavirus); West Nile virus, dengue virus, yellow fever virus, Zika virus, Japanese encephalitis virus, St. Louis encephalitis virus, tick-borne encephalitis virus, Omsk hemorrhagic fever virus, Kyasanur Forest virus (Flaviviridae, Flavivirus); human hepatitis C virus (Flaviviridae, Hepacivirus); human immunodeficiency virus type 1 (Retroviridae, Lentivirus); influenza A/B virus (Orthomyxoviridae, the common 'flu' virus); respiratory syncytial virus (Paramyxoviridae, Pneumovirinae, Pneumovirus); Hendra virus, Nipah virus (Paramyxoviridae, Paramyxovirinae, Henipavirus); measles virus (Paramyxoviridae, Paramyxovirinae, Morbillivirus); variola major (smallpox) virus (Poxviridae, Chordopoxvirinae, Orthopoxvirus); human hepatitis B virus (Hepadnaviridae, Orthohepadnavirus); hepatitis delta virus (hepatitis D virus) (unassigned Family, Deltavirus); herpes simplex virus type 1, herpes simplex virus type 2 (Herpesviridae, Alphaherpesvirinae, Simplexvirus); human cytomegalovirus (Herpesviridae, Betaherpesvirinae, Cytomegalovirus).

The invention provides a method of treating and/or preventing neoplasia in a patient comprising: selecting a patient in need of treating and/or preventing neoplasia;—administering an active agent selected from the group consisting of PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, wherein the neoplasia prevented or treated is selected for the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention provides a method of the invention, wherein the neoplasia is chemoresistant ER/GR+ breast cancer. The invention provides a method of the invention, wherein the administration of active agent, reduces toxicities and side effects when given systemically. The invention provides a method of the invention, wherein the active agent given systemically through oral or intravenous routes. The invention provides a method of the invention, wherein the active agent is targeted to tumor by intra-arterial infusion to reduce systemic side effects of GR blockade. The invention provides a method of the invention, wherein the active agent is given to accomplish cure or remission of tumor. The invention provides a method of the invention, wherein the active agent is given to accomplish reduction of tumor burden to enhance effectiveness of subsequent surgical resection. The invention provides a method of the invention, wherein the active agent is given to accomplish reduction of tumor burden to make an unresectable tumor resectable. The invention provides a method of the invention, wherein the neoplasia is hepatocellular carcinoma (HCC).

BRIEF DESCRIPTION OF SEVERAL VIEWS OF THE DRAWINGS

The invention will be described in conjunction with the following drawings in which like reference numerals designate like elements and wherein:

FIG. 13 is the complexation of the anionic *Mycobacterium tuberculosis* virulence factor sulfolipid-1 (SL-1) by the cationic rifamycin antibiotic TPR-1.

DETAILED DESCRIPTION OF THE INVENTION

Figure 1:
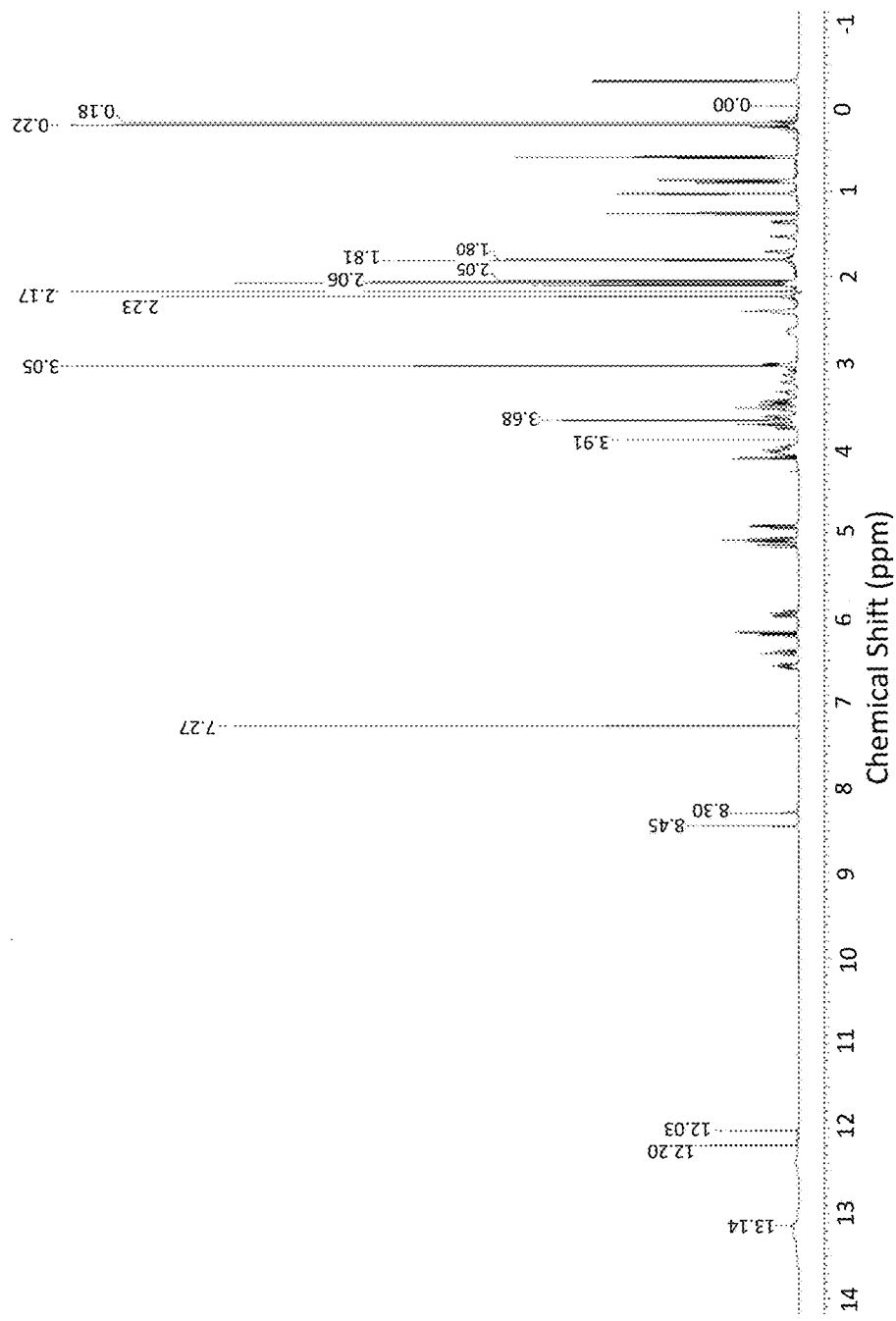
FIG. 1 is the Proton nuclear magnetic resonance (1H NMR) spectrum of TPR-1 dissolved in deuterated chloroform (CDCl3).
Figure 2:
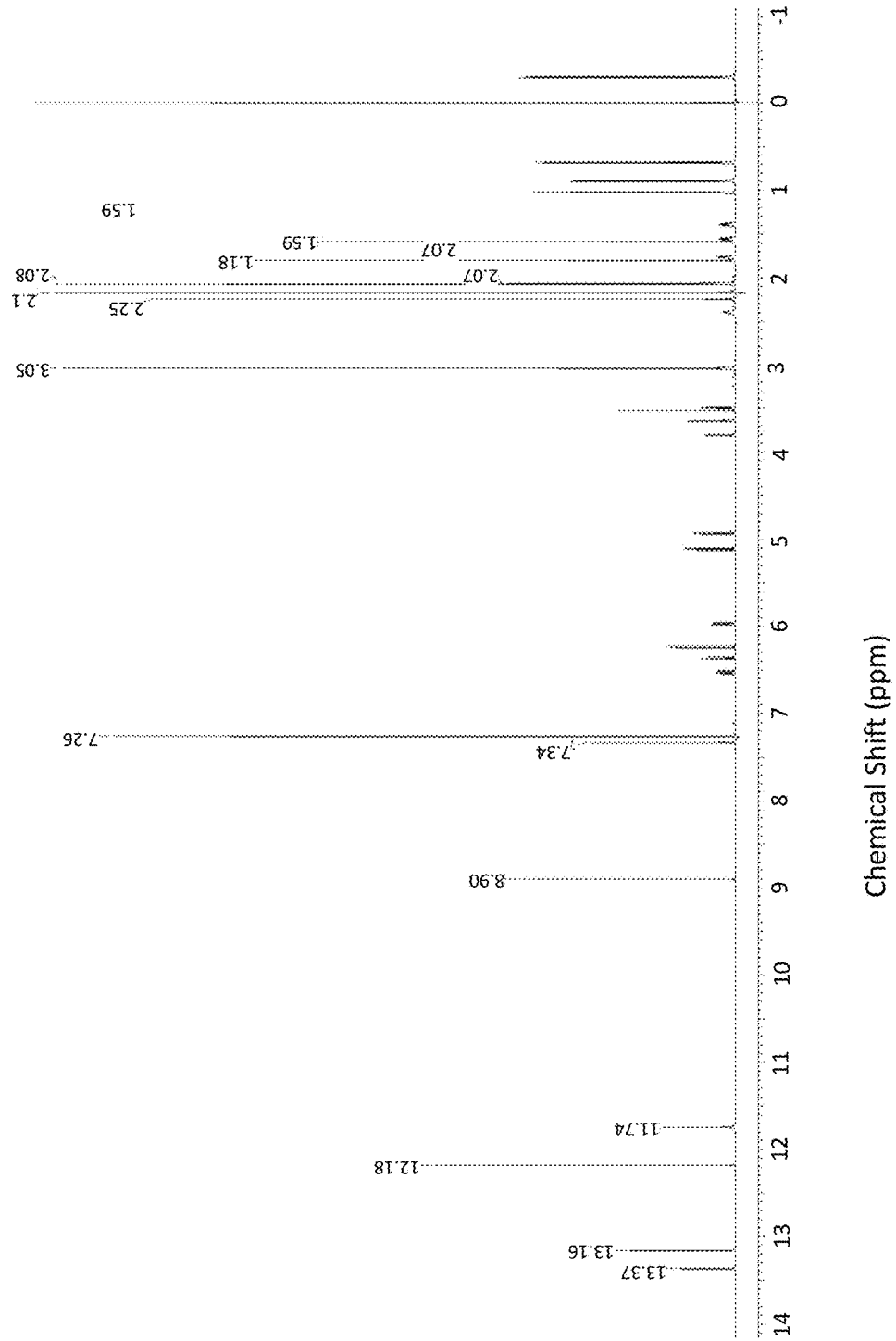
FIG. 2 is the Proton nuclear magnetic resonance (1H NMR) spectrum of OR-1 dissolved in deuterated chloroform (CDCl3).
Figure 3:
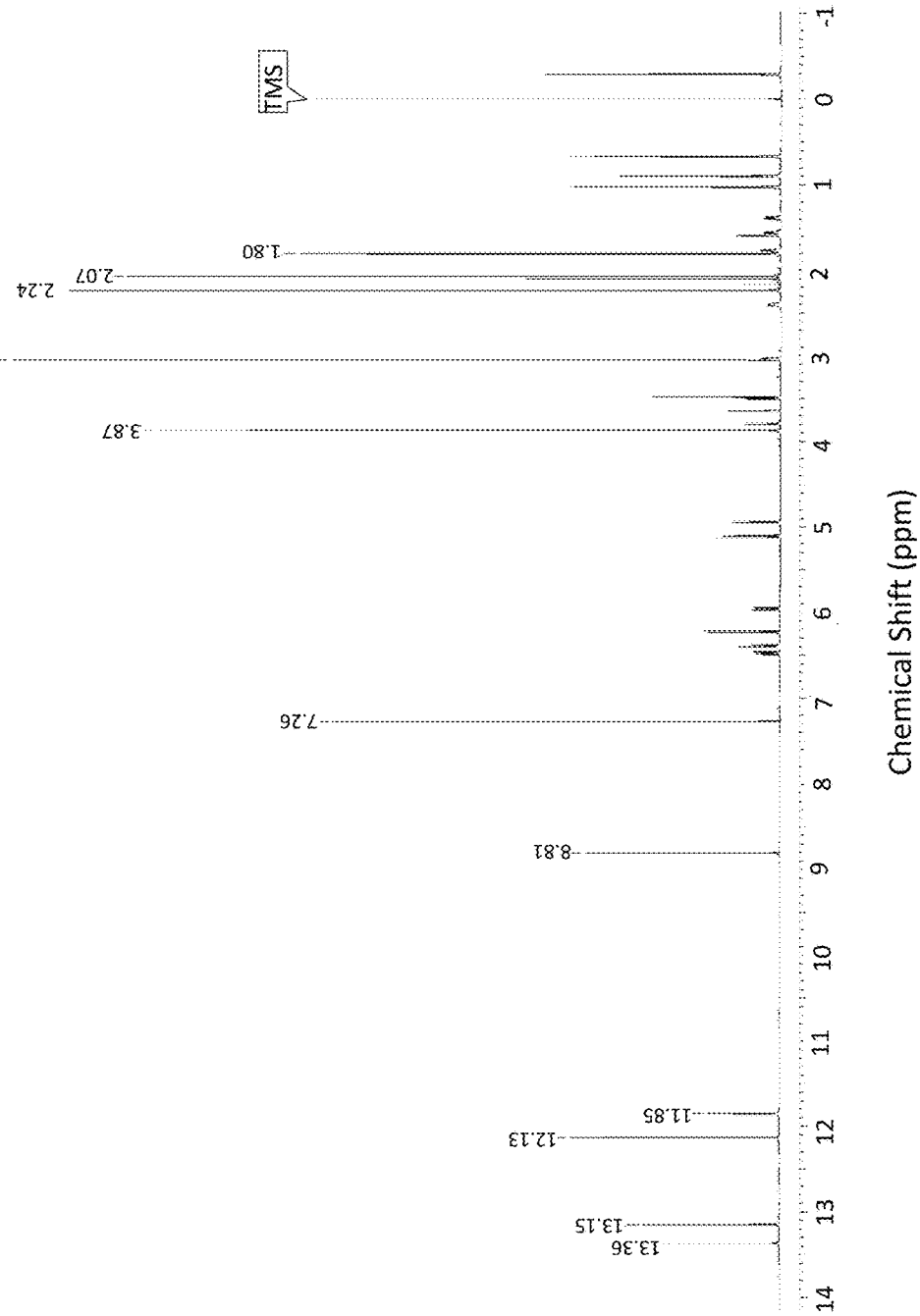
FIG. 3 is the Proton nuclear magnetic resonance (1H NMR) spectrum of MR-1 dissolved in deuterated chloroform (CDCl3).
Figure 4:
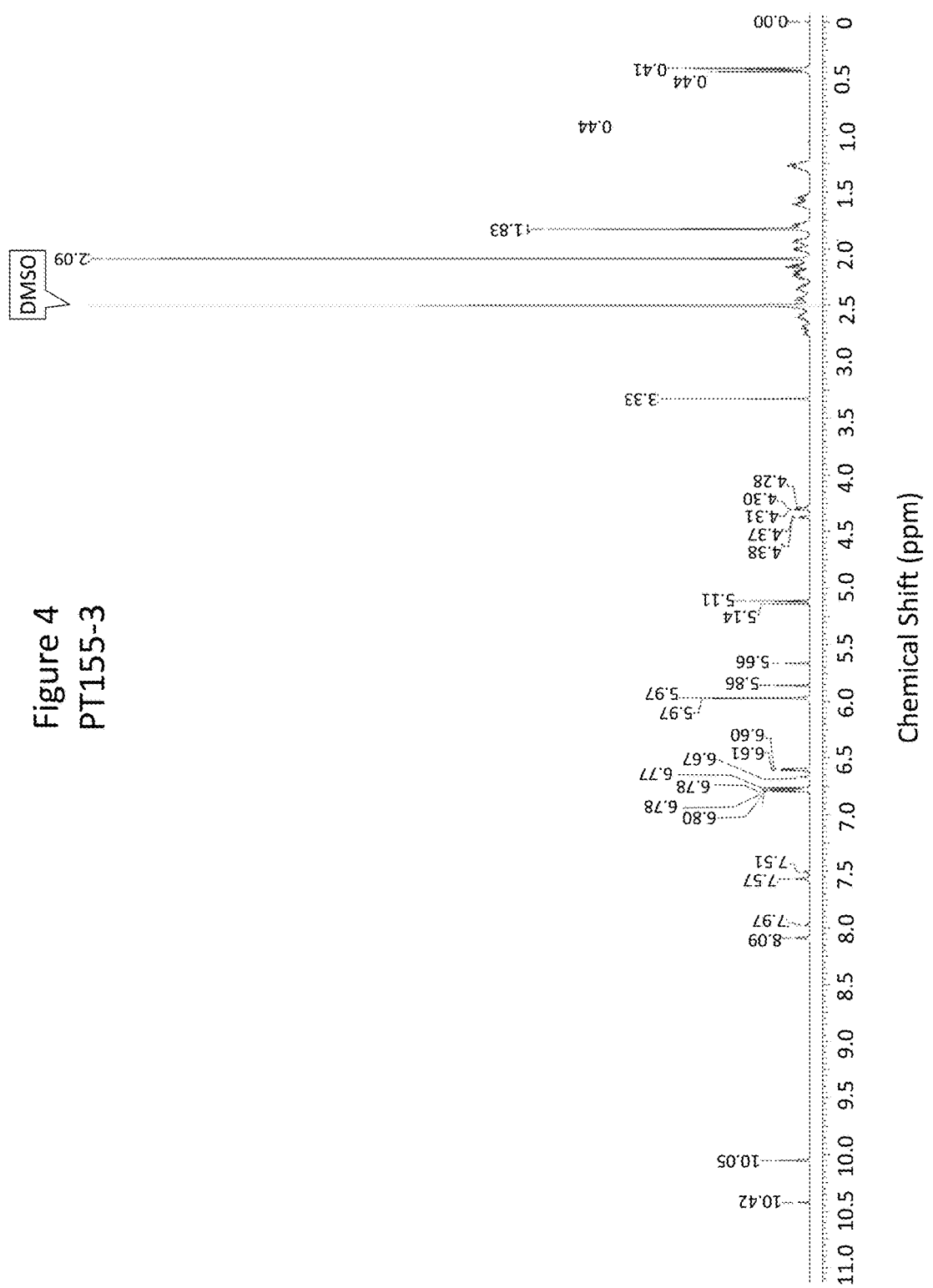
FIG. 4 is the 700.35 MHz proton (1H) nuclear magnetic resonance (NMR) spectrum of PT155-3 dissolved in DMSO-d6.
Figure 5:
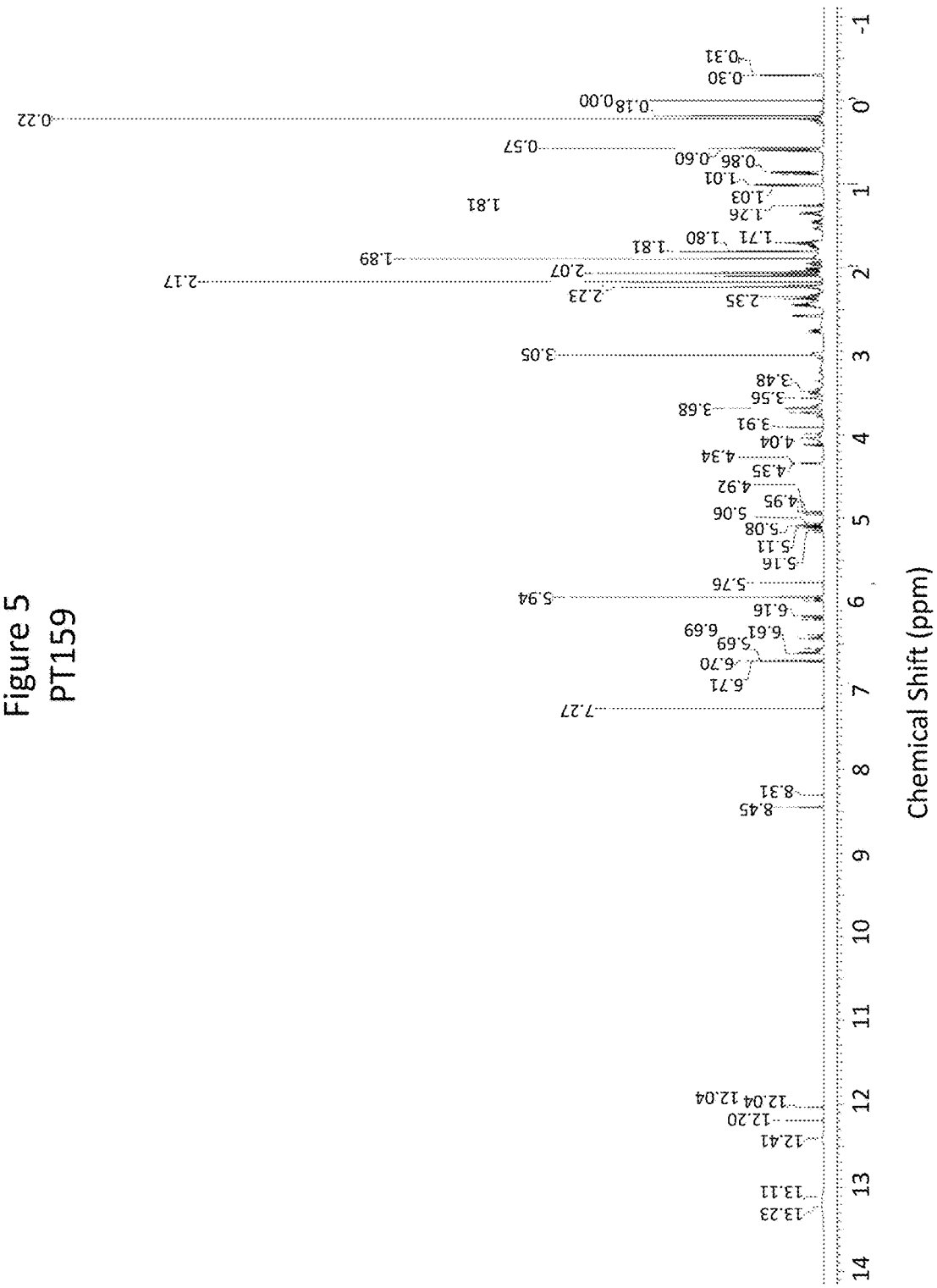
FIG. 5 is the 700.35 MHz proton (1H) nuclear magnetic resonance (NMR) spectrum of PT159 dissolved in CDCl3.
Figure 6:
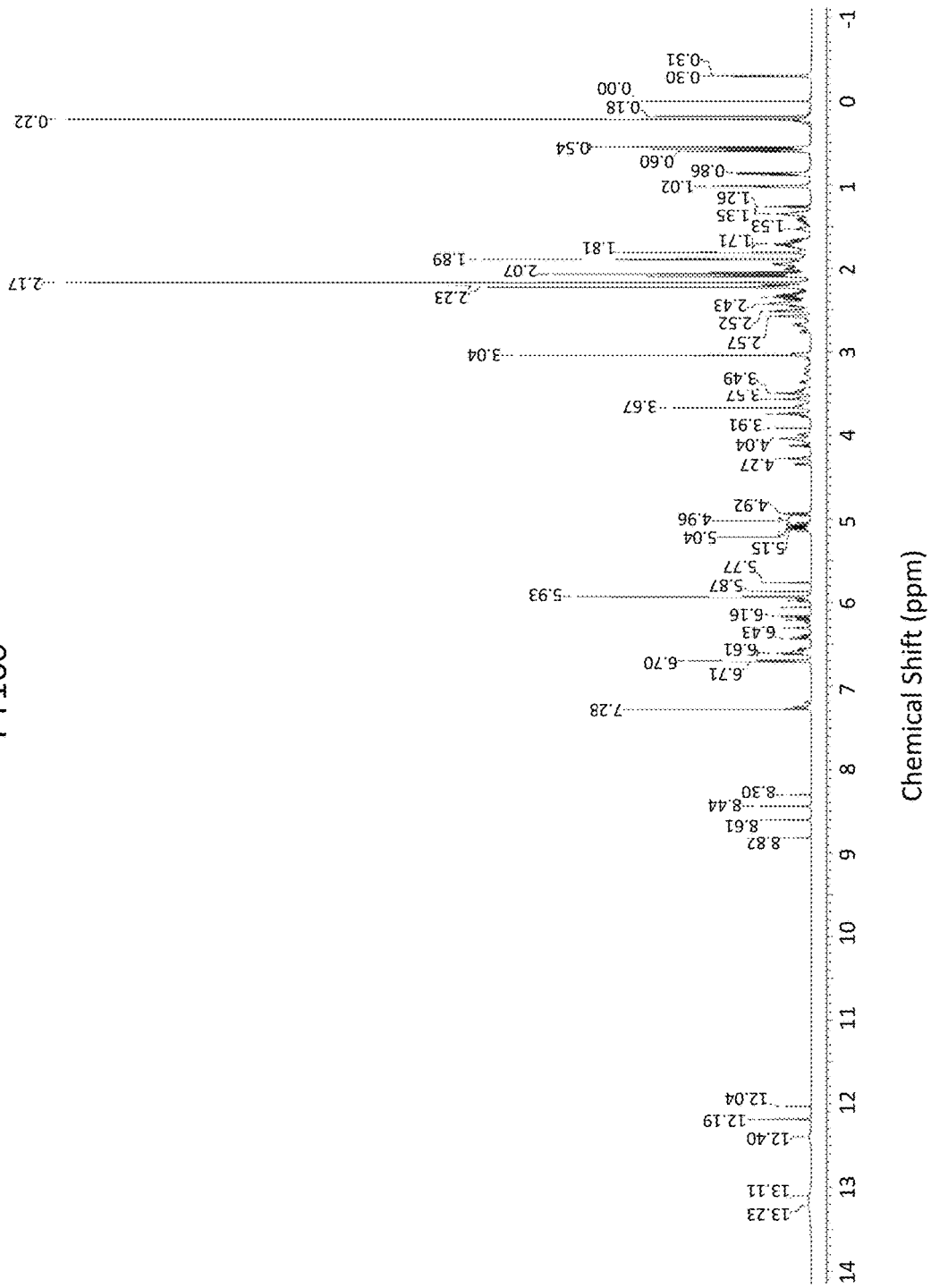
FIG. 6 is the 700.35 MHz proton (1H) nuclear magnetic resonance (NMR) spectrum of PT160 dissolved in CDCl3.
Figure 7:
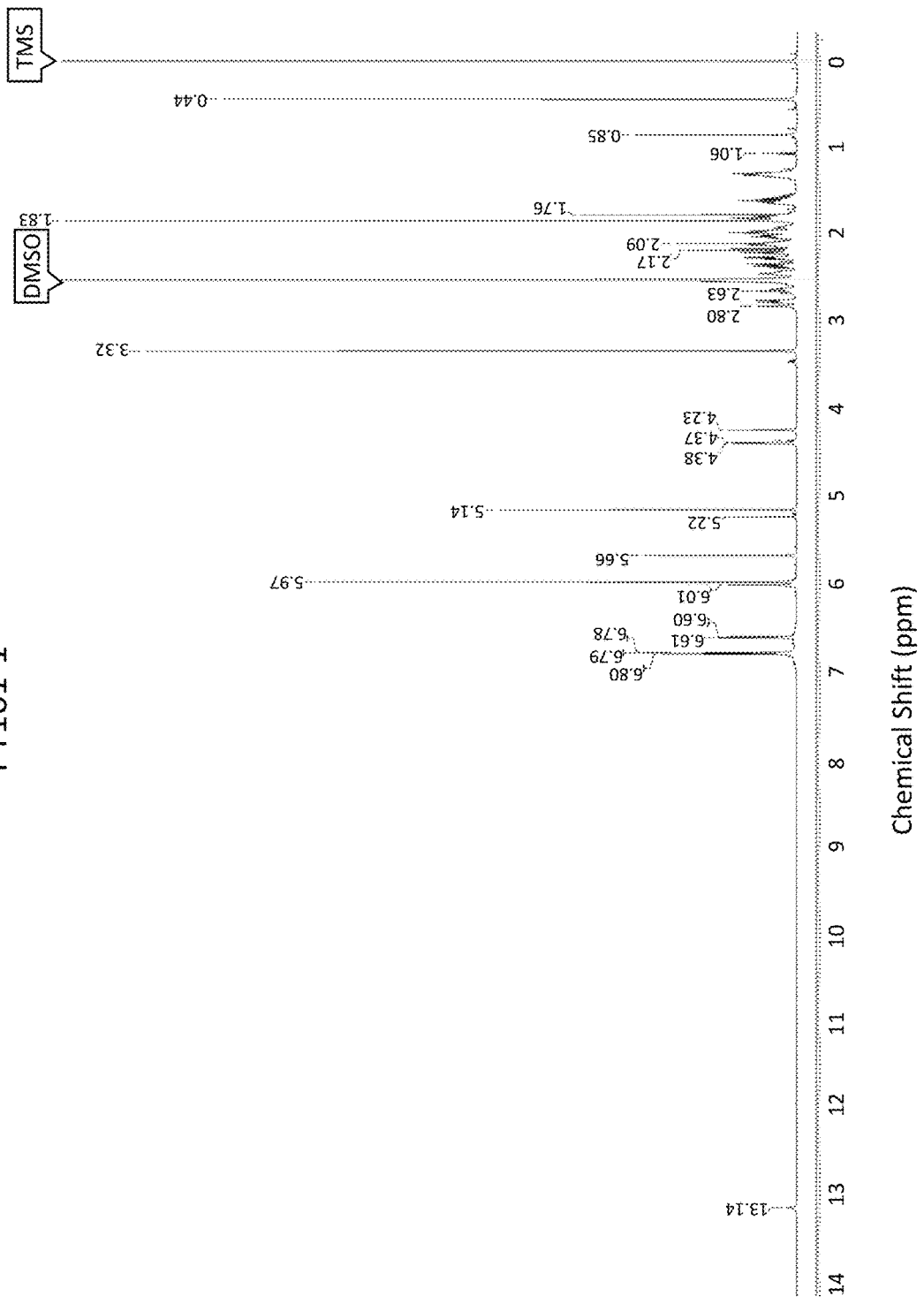
FIG. 7 is the 700.35 MHz proton (1H) nuclear magnetic resonance (NMR) spectrum of crude PT161-1 dissolved in DMSO-d6.
Figure 8:
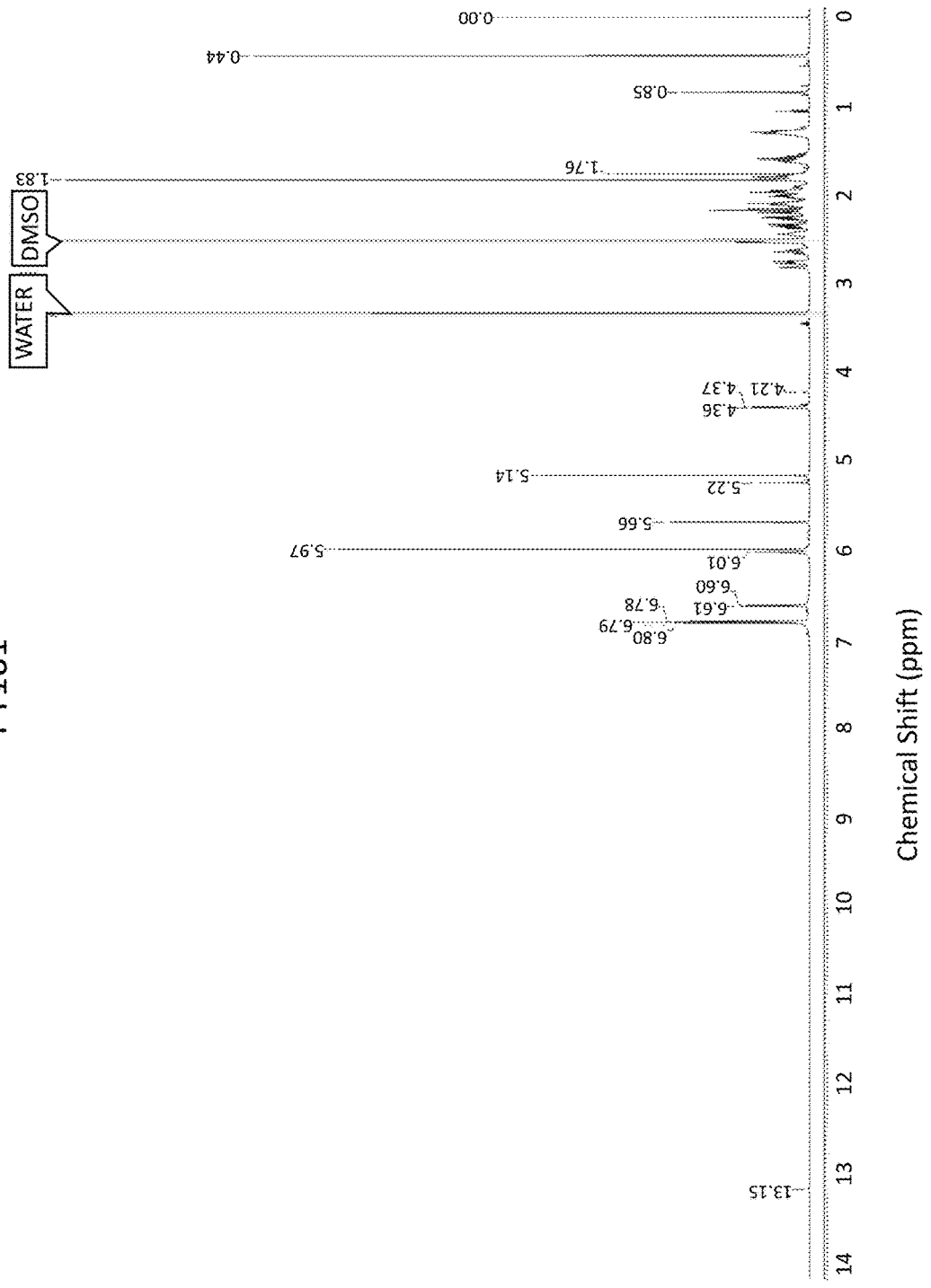
FIG. 8 is the 700.35 MHz proton (1H) nuclear magnetic resonance (NMR) spectrum of PT161 dissolved in DMSO-d6.
Figure 9:
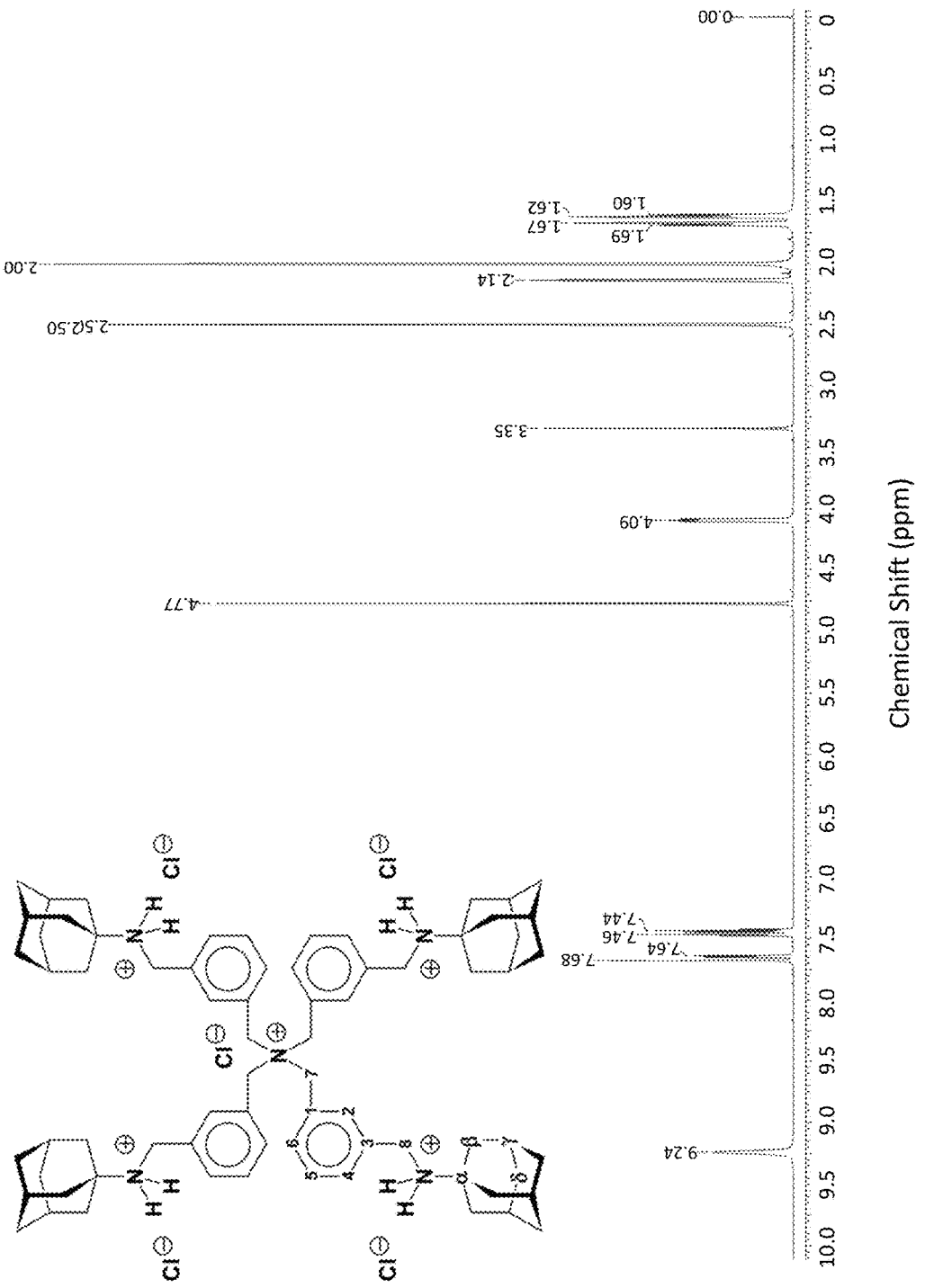
FIG. 9 is the 700.35 MHz proton (1H) nuclear magnetic resonance (NMR) spectrum of PT162 dissolved in DMSO-d6.
Figure 10:
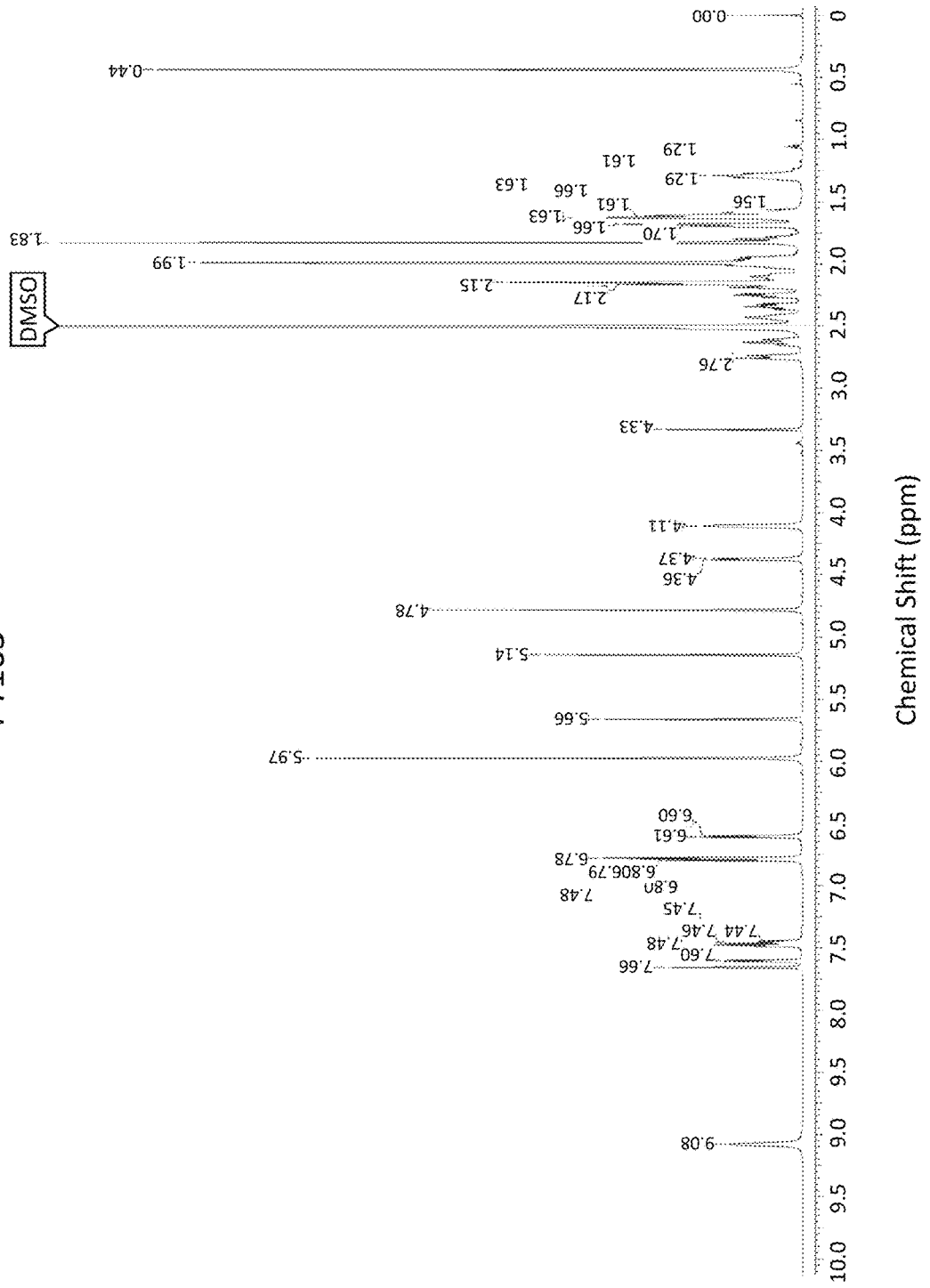
FIG. 10 is the 700.35 MHz proton (1H) nuclear magnetic resonance (NMR) spectrum of PT165 dissolved in DMSO-d6.
Figure 11:
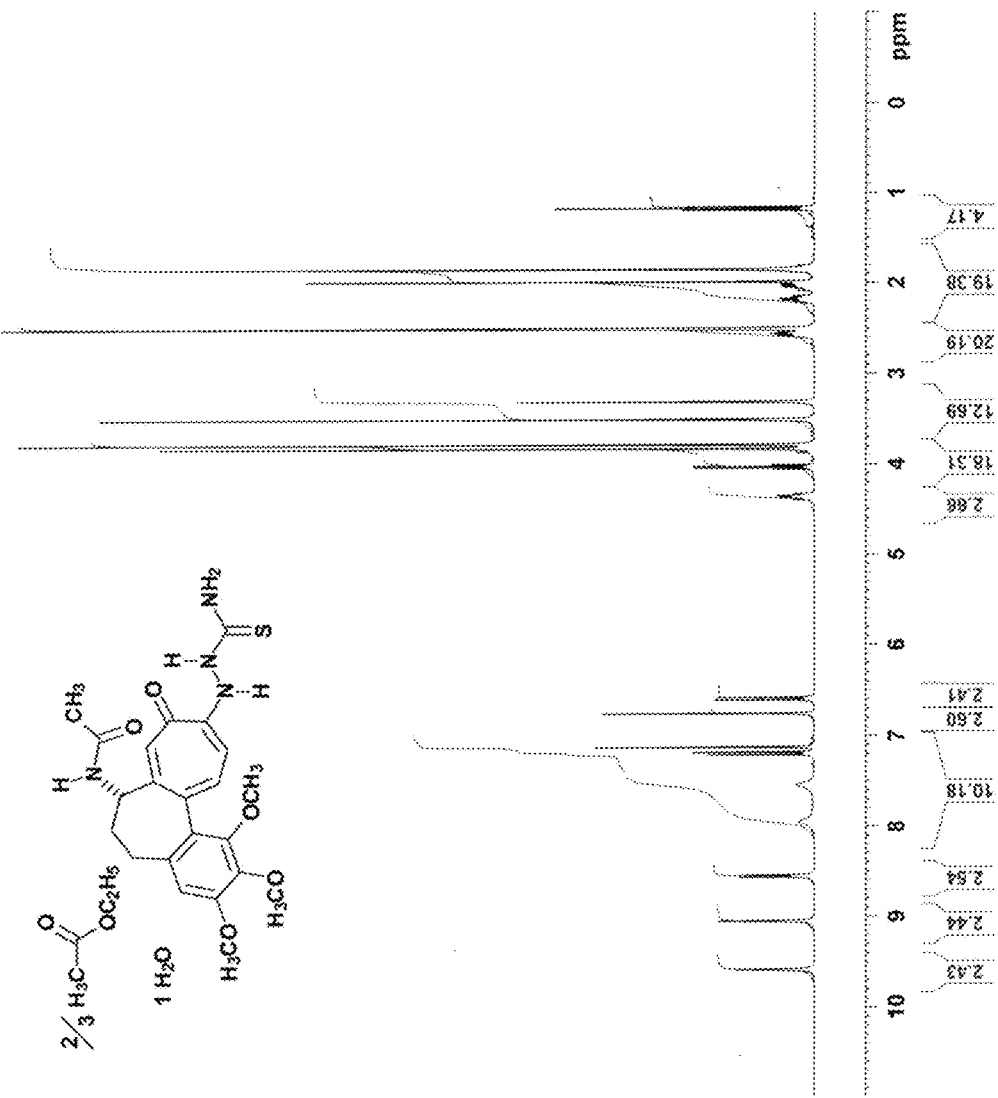
FIG. 11 is the 400.132 MHz proton ($^1$H) nuclear magnetic resonance (NMR) spectrum (300.0 K) of PT166 dissolved in DMSO-$d_6$.
Figure 12:
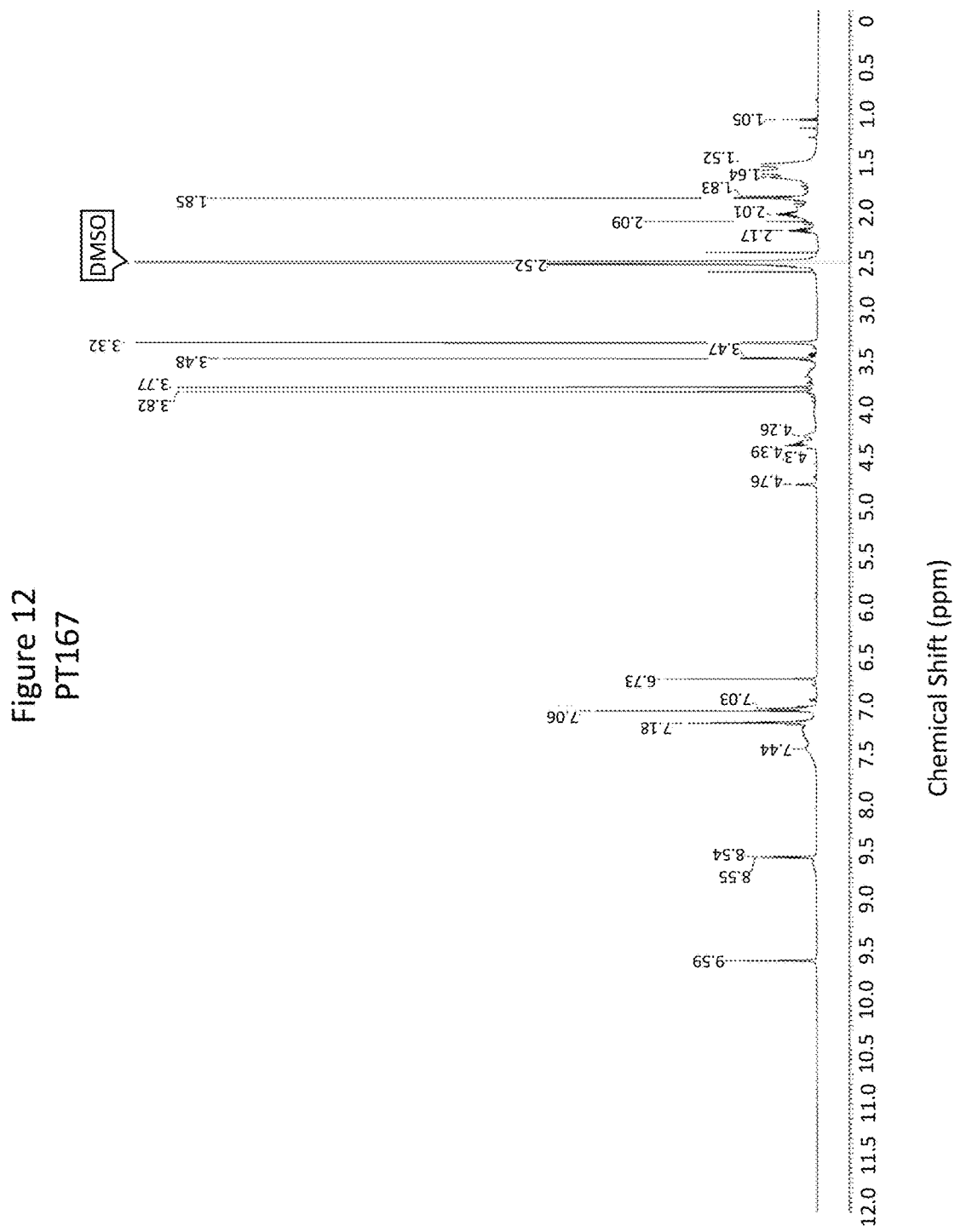
FIG. 12 is the 700.35 MHz proton ($^1$H) nuclear magnetic resonance (NMR) spectrum of PT167 dissolved in DMSO-d6.
Figure 14:
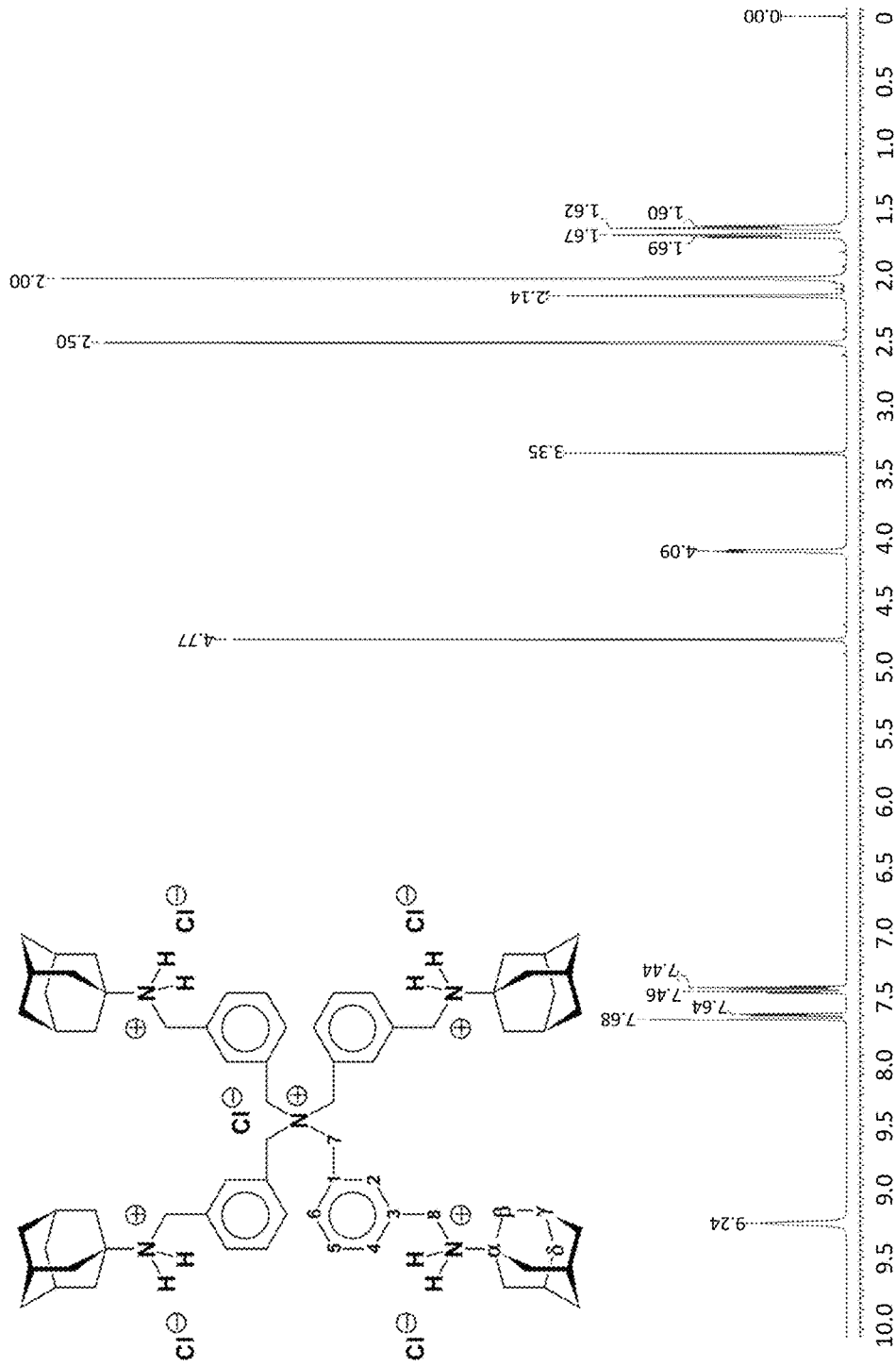
FIG. 14 is the 700.35 MHz proton (1H) nuclear magnetic resonance (NMR) spectrum of PENT dissolved in DMSO-d6.

As used herein, the term "effective amount" refers to the amount of a therapy that is sufficient to result in the prevention of the development, recurrence, or onset of a disease or condition, such as neoplasia or infection, and one or more symptoms thereof, to enhance or improve the prophylactic effect(s) of another therapy, reduce the severity, the duration of a disease or condition, ameliorate one or more symptoms of a disease or condition prevent the advancement of a disease or condition, cause regression of a disease or condition, and/or enhance or improve the therapeutic effect(s) of another therapy. An amount is "effective" as used herein, when the amount provides an effect in the subject. As used herein, the term "effective amount" means an amount of a compound or composition sufficient to significantly induce a positive benefit, including independently or in combinations the benefits disclosed herein, but low enough to avoid serious side effects, i.e., to provide a reasonable benefit to risk ratio, within the scope of sound judgment of the skilled artisan. For those skilled in the art, the effective amount, as well as dosage and frequency of administration, may easily be determined according to their knowledge and standard methodology of merely routine experimentation based on the present disclosure.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing" and "prevention" in the context of the administration of a therapy to a subject refer to the prevention or inhibition of the recurrence, onset, and/or development of a disease or condition, or a symptom thereof in a subject resulting from the administration of a therapy (e.g., a prophylactic or therapeutic agent), or a combination of therapies (e.g., a combination of prophylactic or therapeutic agents).

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the terms "therapies" and "therapy" can refer to any method(s), composition(s), and/or agent(s) that can be used in the prevention, treatment and/or management of a disease or condition.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, and/or the amelioration of one or more symptoms thereof resulting from the administration of one or more therapies.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

"Active compound" as used herein refers to the various embodiments of compounds described as ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof as set forth herein, either as single active agents, in combination with another active agent or agents as set forth herein, or in combination with other agents, for example as set forth herein.

"Plant" as used herein includes all members of the plant kingdom, including higher (or "vascular") plants and lower ("non-vascular") plants, and particularly including all plants in the divisions Filicinae, Gymnospermae (or "gymnosperm"), and Angiospermae (or "Angiosperm") Nonvascular plants of the present disclosure include, but are not limited to, bryophytes. "Plant" as used herein, means live plants and live plant parts, including fresh fruit, vegetables and seeds. Also, the term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

A plant of the present disclosure includes, but is not limited to, a crop plant, a turfgrass, an ornamental species, a species grown for timber or pulp, a species grown for biofuels or species grown for pharmaceuticals. Additionally, plants of the present disclosure include, but are not limited to, tobacco, tomato, potato, sugar beet, pea, carrot, cauliflower, broccoli, soybean, canola, sunflower, alfalfa, cotton, rapeseed, *Arabidopsis*, peach, pepper, apple, chili, peanut, orange, grape, coffee, cassava, spinach, lettuce, cucumber, wheat, maize, rye, rice, turfgrass, oat, barley, sorghum, millet, sugarcane, or banana.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. Nullizygotes are individuals missing the transgene by segregation. A "control plant" as used herein refers not only to whole plants, but also to plant parts, including seeds and seed parts.

"Angiosperm" as used herein includes, but is not limited to, plants of the sub-classes Monocotyledoneae (or monocots) and Dicotyledoneae (or dicots).

Monocotyledoneae (or monocots) as used herein includes but is not limited to Amaryllidaceae—the Amaryllis Family, Gramineae (Poaceae)—the Grass Family, Liliaceae—the Lily Family, Orchidaceae—the Orchid Family, Palmae (Aracaceae)—the Palm Family; and Lemnacea—the duckweed family.

Dicotyledoneae (or dicots) as used herein includes but is not limited to Cactacae—the Cactus Family, Compositae (Asteraceae)—the Sunflower Family, Cruciferae (Brassicaceae)—the Mustard Family, Cucurbitaceae—the Gourd Family, Ericaceae—the Heath Family, Euphorbiaceae—the Spurge Family, Lauraceae—the Laurel Family, Leguminosae (Fabaceae)—the Pea Family, Rosaceae—the Rose Family, Rutaceae—the Rue Family, Solanaceae—the Nightshade Family, and Umbelliferae (Apiaceae)—the Carrot family.

Gymnospermae (or "Gymnosperms") as used herein includes but is not limited to conifers. "Conifer," as used herein, refers to a member of the order Coniferae in the sub-phylum Gymnospermae in the phylum Spermaphyta. Exemplary conifers which may be used in practicing the present disclosure are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*); and Western larch (*Laryx occidentalis*). "Duckweed" as used herein includes plants of the genus Lemna (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus Spirodela (*S. intermedia, S. polyrrhiza, S. punctata*); genus Wolffia (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus Wolfiella (*Wl. caudata, Wl. denticulata, Wl. gladiata, Wl. hyalina, Wl. lingulata, Wl. repunda, Wl. rotunda*, and *Wl. neotropica*). Particular examples of plants include but are not limited to all cereal and grain crops, herbs and spices, oil seed crops, sugarcane, vegetable crops, brassica vegetables, bulb vegetables, cucurbit vegetables and fruit, leafy vegetables, fruiting vegetables, legume vegetables, root and tuber vegetables, tree, vine and shrub crops, berry crops, citrus (e.g., orange, grapefruit, Mandarin (including Tangerine and Satsuma), lemon, lime, and kumquat), pome fruit (e.g., apple, pear, quince, Asian pear, loquat, etc.), stone fruit (e.g., peach, apricot, prune, plum, cherries, almond, etc.), miscellaneous tree food crops, non-food tree crops, tree nuts, tropical and subtropical trees and fruit, vine crops, pasture grasses, forage legumes, and rangeland, grass seed or sod production, pastures, cotton, corn, soybeans, rice, wheat, greenhouse/shadehouse grown plants, ornamental, plant nurseries, Christmas trees, golf courses and other commercial or residential turf areas such as athletic fields, lawns, municipal areas and cemeteries, or other ornamental turf areas, forestry, tobacco, orchids, flowers and roses, foliage crops, algae such as green algae, bryophytes (mosses, liverworts, hornworts), etc. Note that "foliage crops" refers to the types of plants (ferns, etc.) that are typically used in home or commercial settings for decorative purposes; this alone constitutes a very large commercial industry.

"Plant part" as used herein refers to seeds, roots, leaves, shoots, fruits (e.g., apples, pineapples, citrus fruit, etc.), vegetables, tubers, flowers (e.g., cut flowers such as roses, as well as the reproductive parts of plants), petals, stem, trunk, etc., harvested or collected from a plant as described herein. The plant part of a vascular plant may be a non-vascular part, such as a seed or meristem (growing tip of a shoot).

"Applying" as described herein can be carried out directly or indirectly by any suitable technique, including topically or systemically applying to the plant or plant part, applying to the media in which the plant or plant part is grown, stored, displayed or maintained (e.g., adding to water in which the stems of cut flowers are placed), injected into the plant or plant part, etc. Note that the plant may be grown in any suitable media, including but not limited to soil, potting soil, soilless media such as sand, hydroponic media (including solution culture, medium culture, deep water culture, aeroponic culture), etc.

"Agricultural composition" as described herein may be in any suitable form, including but not limited to: wettable powders, dry flowables, soluble powders, water dispersibles, liquids, dusts, emulsifiable concentrates, flowables, fumigants, water dispersible granules, liquid concentrates, granules, water soluble packages, wettable powders in water soluble films, emulsions, etc.

"Crop" as used herein means a plant species or variety that is grown to be harvested as food, livestock fodder, fuel raw material, or for any other economic purpose. As a non-limiting example, said crops can be maize, cereals, such as wheat, rye, barley and oats, sorghum, rice, sugar beet and fodder beet, fruit, such as pome fruit (e.g. apples and pears), citrus fruit (e.g. oranges, lemons, limes, grapefruit, or mandarins), stone fruit (e.g. peaches, nectarines or plums), nuts (e.g. almonds or walnuts), soft fruit (e.g. cherries, strawberries, blackberries or raspberries), the plantain family or grapevines, leguminous crops, such as beans, lentils, peas and soya, oil crops, such as sunflower, safflower, rapeseed, canola, castor or olives, cucurbits, such as cucumbers, melons or pumpkins, fibre plants, such as cotton, flax or hemp, fuel crops, such as sugarcane, miscanthus or switchgrass, vegetables, such as potatoes, tomatoes, peppers, lettuce, spinach, onions, carrots, egg-plants, asparagus or cabbage, ornamentals, such as flowers (e.g. petunias, pelargoniums, roses, tulips, lilies, or chrysanthemums), shrubs, broad-leaved trees (e.g. poplars or willows) and evergreens (e.g. conifers), grasses, such as lawn, turf or forage grass or other useful plants, such as coffee, tea, tobacco, hops, pepper, rubber or latex plants.

A "pest", as used here, is an organism that is harmful to plants, animals, humans or human concerns, and includes, but is not limited to crop pests (as later defined), household pests, such as cockroaches, ants, etc., and disease vectors, such as malaria mosquitoes.

A "plant pest", "plant pathogen" or "crop pest", as used in the application interchangeably, refers to organisms that specifically cause damage to plants, plant parts or plant products, particularly plants, plant parts or plant products, used in agriculture. Note that the term "plant pest" or "crop pest" is used in the meaning that the pest targets and harms plants. Pests particularly belong to invertebrate animals (e.g. insects (including agricultural pest insects, insect pests of ornamental plants, insect pests of forests). Relevant crop pest examples include, but are not limited to, aphids, caterpillars, flies, wasps, and the like, nematodes (living freely in soil or particularly species that parasitize plant roots, such as root-knot nematode and cyst nematodes such as soybean cyst nematode and potato cyst nematode), mites (such as spider mites, thread-footed mites and gall mites) and gastropods (including slugs such as *Deroceras* spp., *Milax* spp., *Tandonia* sp., *Limax* spp., *Arion* spp. and *Veronicella* spp. and snails such as *Helix* spp., *Cernuella* spp., *Theba* spp., *Cochlicella* spp., *Achatina* spp., *Succinea* spp., *Ovachlamys* spp., *Amphibulima* spp., *Zachrysia* spp., *Bradybaena* spp., and *Pomacea* spp.), pathogenic fungi (including Ascomycetes (such as *Fusarium* spp., *Thielaviopsis* spp., *Verticillium* spp., *Magnaporthe* spp.), Basidiomycetes (such as *Rhizoctonia* spp., *Phakospora* spp., *Puccinia* spp.), and fungal-like Oomycetes (such as *Pythium* spp. and *Phytophthora* spp.), bacteria (such as *Burkholderia* spp. and Proteobacteria such as *Xanthomonas* spp. and *Pseudomonas* spp.), Phytoplasma, Spiroplasma, viruses (such as tobacco mosaic virus and cauliflower mosaic virus), and protozoa.

"Microbe", as used herein, means bacterium, virus, fungus, yeast and the like and "microbial" means derived from a microbe.

"Fungus", as used herein, means a eukaryotic organism, belonging to the group of Eumycota. The term fungus in the present invention also includes fungal-like organisms such as the Oomycota. Oomycota (or oomycetes) form a distinct phylogenetic lineage of fungus-like eukaryotic microorganisms. This group was originally classified among the fungi but modern insights support a relatively close relationship with the photosynthetic organisms such as brown algae and diatoms, within the group of heterokonts.

"Pest infection" or "pest disease" as used herein refers to any inflammatory condition, disease or disorder in a living organism, such as a plant, animal or human, which is caused by a pest.

"Fungal infection" or "fungal disease" as used herein refers to any inflammatory condition, disease or disorder in a living organism, such as a plant, animal or human, which is caused by a fungus.

"Active substance", "active ingredient" or "active principle", as used interchangeably herein, means any biological, biochemical or chemical element and its derivatives, fragments or compounds based thereon, including microorganisms, having general or specific action against harmful organisms on a subject, and in particular on plants, parts of plants or on plant products, as they occur naturally or by manufacture, including any impurity inevitably resulting from the manufacturing process.

"Agrochemical", as used herein, means suitable for use in the agrochemical industry (including agriculture, horticulture, floriculture and home and garden uses, but also products intended for non-crop related uses such as public health/pest control operator uses to control undesirable insects and rodents, household uses, such as household fungicides and insecticides and agents, for protecting plants or parts of plants, crops, bulbs, tubers, fruits (e.g. from harmful organisms, diseases or pests); for controlling, preferably promoting or increasing, the growth of plants; and/or for promoting the yield of plants, crops or the parts of plants that are harvested (e.g. its fruits, flowers, seeds etc.). Examples of such substances will be clear to the skilled person and may for example include compounds that are active as insecticides (e.g. contact insecticides or systemic insecticides, including insecticides for household use), herbicides (e.g. contact herbicides or systemic herbicides, including herbicides for household use), fungicides (e.g. contact fungicides or systemic fungicides, including fungicides for household use), nematicides (e.g. contact nematicides or systemic nematicides, including nematicides for household use) and other pesticides or biocides (for example agents for killing insects or snails); as well as fertilizers; growth regulators such as plant hormones; micro-nutrients, safeners, pheromones; repellants; insect baits; and/or active principles that are used to modulate (i.e. increase, decrease, inhibit, enhance and/or trigger) gene expression (and/or other biological or biochemical processes) in or by the targeted plant (e.g. the plant to be protected or the plant to be controlled), such as nucleic acids (e.g., single stranded or double stranded RNA, as for example used in the context of RNAi technology) and other factors, proteins, chemicals, etc. known per se for this purpose, etc. Examples of such agrochemicals will be clear to the skilled person; and for example include, without limitation: glyphosate, paraquat, metolachlor, acetochlor, mesotrione, 2,4-D, atrazine, glufosinate, sulfosate, fenoxaprop, pendimethalin, picloram, trifluralin, bromoxynil, clodinafop, fluroxypyr, nicosulfuron, bensulfuron, imazetapyr, dicamba, imidacloprid, thiamethoxam, fipronil, chlorpyrifos, deltamethrin, lambda-cyhalotrin, endosulfan, methamidophos, carbofuran, clothianidin, cypermethrin, abamectin, diflufenican, spinosad, indoxacarb, bifenthrin, tefluthrin, azoxystrobin, thiamethoxam, tebuconazole, mancozeb, cyazofamid, fluazinam, pyraclostrobin, epoxiconazole, chlorothalonil, copper fungicides, trifloxystrobin, prothioconazole, difenoconazole, carbendazim, propiconazole, thiophanate, sulphur, boscalid and other known agrochemicals or any suitable combination (s) thereof.

An "agrochemical composition" as used herein means a composition for agrochemical use, as further defined, comprising at least one active substance, optionally with one or more additives favoring optimal dispersion, atomization, deposition, leaf wetting, distribution, retention and/or uptake of agrochemicals. It will become clear from the further description herein that an agrochemical composition as used herein includes biological control agents or biological pesticides (including but not limited to biological biocidal, biostatic, fungistatic and fungicidal agents) and these terms will be interchangeably used in the present application. Accordingly, an agrochemical composition as used herein includes compositions comprising at least one biological molecule as an active ingredient, substance or principle for controlling pests in plants or in other agro-related settings (such for example in soil). Non-limiting examples of biological molecules being used as active principles in the agrochemical compositions disclosed herein are proteins (including antibodies and fragments thereof, such as but not limited to heavy chain variable domain fragments of antibodies, including VHH's), nucleic acid sequences, (poly-) saccharides, lipids, vitamins, hormones glycolipids, sterols, and glycerolipids.

As a non-limiting example, the additives in the agrochemical compositions disclosed herein may include but are not limited to diluents, solvents, adjuvants, surfactants, wetting agents, spreading agents, oils, stickers, thickeners, penetrants, buffering agents, acidifiers, anti-settling agents, anti-freeze agents, photo-protectors, defoaming agents, biocides and/or drift control agents.

A "biostatic composition" or a "biostatic agent" as used herein means any active ingredient, substance or principle or a composition comprising any active ingredient, substance or principle for biostatic use (as further defined herein) comprising at least one active biostatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "biocidal composition" or a "biocidal agent" as used herein means any active ingredient, substance or principle or a composition comprising any active ingredient, substance or principle for biocidal use (as further defined herein) comprising at least one active biocidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungistatic composition" or a "fungistatic agent" as used herein means any active ingredient, substance or principle or a composition comprising any active ingredient, substance or principle for fungistatic use (as further defined herein) comprising at least one active fungistatic substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

A "fungicidal composition" or a "fungicidal agent" as used herein means any active ingredient, substance or principle or a composition comprising any active ingredient, substance or principle for fungicidal use (as further defined herein) comprising at least one active fungicidal substance or ingredient, optionally combined with one or more additives favoring optimal dispersion, atomization, deposition, leaf wetting, distribution, retention and/or uptake of the active substance or ingredient. As a non-limiting examples such additives are diluents, solvents, adjuvants, (ionic) surfactants, wetting agents, spreading agents, oils, stickers, thickeners, penetrants, buffering agents, acidifiers, anti-settling agents, anti-freeze agents, photo-protectors, defoaming agents, biocides, protease inhibitors and/or drift control agents.

"Agrochemical use", as used herein, not only includes the use of agrochemicals as defined above (for example, pesticides, growth regulators, nutrients/fertilizers, repellants, defoliants etc.) that are suitable and/or intended for use in field grown crops (e.g., agriculture), but also includes the use of agrochemicals as defined above (for example, pesticides, growth regulators, nutrients/fertilizers, repellants, defoliants etc.) that are meant for use in greenhouse grown crops (e.g. horticulture/floriculture) or hydroponic culture systems and even the use of agrochemicals as defined above that are suitable and/or intended for non-crop uses such as uses in private gardens, household uses (for example, herbicides or insecticides for household use), or uses by pest control operators (for example, weed control etc.).

"Biostatic (effect)" or "biostatic use", as used herein, includes any effect or use of an active substance (optionally comprised in a biostatic, biocidal, fungicidal or fungistatic composition as defined herein) for controlling, modulating or interfering with the harmful activity of a pest, such as a plant pest or a plant pathogen, including but not limited to inhibiting the growth or activity of the pest, altering the behavior of the pest, and repelling or attracting the pest in plants, plant parts or in other agro-related settings, such as for example for household uses or in soil.

"Fungicidal (effect)" or "Fungicidal use", as used herein, includes any effect or use of an active substance (optionally comprised in a fungicidal composition as defined herein) for controlling, modulating or interfering with the harmful activity of a fungus, including but not limited to killing the fungus, inhibiting the growth or activity of the fungus, altering the behavior of the fungus, and repelling or attracting the fungus in plants, plant parts or in other agro-related settings, such as for example for household uses or in soil.

"Biostatic activity", as used herein, means to interfere with the harmful activity of a pest, including but not limited to inhibiting the growth or activity of the pest, altering the behavior of the pest, repelling or attracting the pest.

Pesticidal, biocidal, or biostatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

"Fungicidal activity", as used herein, means to interfere with the harmful activity of a fungus, including but not limited to killing the fungus, inhibiting the growth or activity of the fungus, altering the behavior of the fungus, and repelling or attracting the fungus.

"Fungistatic activity", as used herein, means to interfere with the harmful activity of a fungus, including but not limited to inhibiting the growth or activity of the fungus, altering the behavior of the fungus, and repelling or attracting the fungus.

Fungicidal or fungistatic activity of an active ingredient, substance or principle or a composition or agent comprising a pesticidal, biocidal, or biostatic active ingredient, substance or principle, can be expressed as the minimum inhibitory activity (MIC) of an agent (expressed in units of concentration such as e.g. mg/mL), without however being restricted thereto.

A "carrier", as used herein, means any solid, semi-solid or liquid carrier in or on(to) which an active substance can be suitably incorporated, included, immobilized, adsorbed, absorbed, bound, encapsulated, embedded, attached, or comprised. Non-limiting examples of such carriers include nanocapsules, microcapsules, nanospheres, microspheres, nanoparticles, microparticles, liposomes, vesicles, beads, a gel, weak ionic resin particles, liposomes, cochleate delivery vehicles, small granules, granulates, nano-tubes, buckyballs, water droplets that are part of an water-in-oil emulsion, oil droplets that are part of an oil-in-water emulsion, organic materials such as cork, wood or other plant-derived materials (e.g. in the form of seed shells, wood chips, pulp, spheres, beads, sheets or any other suitable form), paper or cardboard, inorganic materials such as talc, clay, microcrystalline cellulose, silica, alumina, silicates and zeolites, or even microbial cells (such as yeast cells) or suitable fractions or fragments thereof.

Microbicides and Plant Defense Activators

In some embodiments, an active compound and/or composition of active compounds as described herein may be applied in combination with a microbicide. "Microbicide" as used herein refers to a substance with the ability to kill or to inhibit the growth of microorganisms (e.g., bacteria (including cyanobacteria), fungal cells, protozoa, algae, etc.), which microbicide is not an active compound in the group herein disclosed of triazole derivatives. Common microbicides used for microbial control in plants include copper compounds. Examples of copper compounds include, but are not limited to, Bordeaux mixture, copper hydroxide, copper oxychloride, copper sulfate, cuprous oxide, mancopper or oxine-copper. However, microorganisms (e.g., bacteria such as Xanthomonas and Pseudomonas) may become resistant to treatment with copper.

In some embodiments, resistant microorganisms (e.g., copper-resistant bacteria) are rendered more susceptible to a microbicides and/or the effectiveness of treatment with a microbicides is enhanced upon application in combination with an active compound or composition of active agents as described herein (e.g., fruit or vegetable yield is increased as compared to diseased plant producing the fruit or vegetable that is untreated or treated only with the microbicide).

Other microbicides include, but are not limited to, azoles such as azaconazole, bitertanol, bixafen, carpropamid, propiconazole, difenoconazole, diniconazole, cyproconazole, epoxiconazole, fluquinconazole, flusilazole, flutriafol, hexaconazole, imazalil, imibenconazole, ipconazole, iprodione, tebuconazole, tetraconazole, fenbuconazole, metconazole, myclobutanil, perfurazoate, penconazole, paclobutrazol, prothioconazole, pyrimenthanil, bromuconazole, pyrifenox, prochloraz, spiroxamine, triadimefon, triadimenol, triflumizole or triticonazole; pyrimidinyl carbinoles such as ancymidol, fenarimol, fluopicolide, flurprimidol, or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl (mefanoxam), ofurace or oxadixyl; benzimidazoles such as benomyl, carbendazim, debacarb, fuberidazole or thiabendazole; dicarboximides such as chlozolinate, dichlozoline, iprodione, myclozoline, procymidone or vinclozolin; carboxamides such as carboxin, boscalid, fenfuram, flutolanil, mepronil, oxycarboxin or thifluzamide; guanidines such as guazatine, dodine or iminoctadine; strobilurines such as azoxystrobin, fluoxastrobin, pyraclostrobin, picoxystrobin, oryzastrobin, dimoxystrobin, kresoximmethyl, metominostrobin, SSF-129, methyl 2[(2-trifluoromethyl)-pyrid-6-yloxymethyl]-3-methoxy-acrylate or 2-[{.alpha.[(.alpha.-methyl-3-trifluoromethyl-benzyl)imino]-oxyl}-o-tolyl-]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, harpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, thiophanate-methyl, triazoxide, tricyclazole, triforine, validamycin, (S)-5-methyl-2-methylthio-5-phenyl-3-phenylamino-3,5-dihydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfonamide (IKF-916), N-(1-cyano-1,2-dimethylpropyl)-2-(2,4-dichlorophenoxy)-propionamide (AC 382042) or iprovalicarb (SZX 722).

An "antibiotic" as used herein is a type of "microbicide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin. Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

Other microbicides that may be used in combination with the active compounds of the present disclosure include bacteriophages (bacterial viruses) such as *Bacillus*. Examples of bacteriophage microbicides include, but are not limited to, AGRIPHAGE (OmniLytics, Inc., Salt Lake City, Utah) and SERENADE (AgraQuest, Davis, Calif.).

In some embodiments, an active compound or composition of active agents as described herein is applied in combination with a plant defense activator. A "plant defense activator" as used herein is a compound that improves disease resistance by activating a plant's natural defense mechanisms, e.g., induces the plant to produce disease-fighting compounds. Examples of plant defense activators include, but are not limited to, prohexadione-calcium (Apogee), Cropset (plant booster element complex), probenazole, potassium phosphate (e.g., PROPHYT, Helena Chemical Company), harpin protein (e.g., MESSENGER, Eden Biosciences Ltd, Bothell, Wash.), acibenzolar or acibenzolar-S-methyl (e.g., ACTIGARD, Syngenta Crop Production, Inc, Greensboro, N.C.), streptomycin sulfate, *Reynoutria sachalinensis* extract (reysa), etc.

Agrochemical Compositions

Active compounds or composition of active agents of the present disclosure can be used to prepare agrochemical compositions in like manner as other antimicrobial compounds. Active compounds described herein can be used for protecting plants against diseases that are caused by microorganisms, including biofilm-forming microorganisms. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic microorganisms.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds or composition of active agents as described herein can be used in the form of compositions and can be applied to the crop area or plant to be treated, simultaneously or in succession with further compounds and/or compositions. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Suitable carriers and adjuvants can be solid or liquid and are substances useful in formulation technology, e.g. natural or regenerated mineral substances, solvents, dispersants, wetting agents, tackifiers, thickeners, binders or fertilizers.

The active compounds or composition of active agents as described herein are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

The formulation, i.e. the compositions containing the active compound or composition of active agents as described herein and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers.

Further surfactants customarily employed in the art of formulation are known to the expert or can be found in the relevant literature.

The agrochemical formulations will usually contain from 0.1 to 99% by weight, preferably from 0.1 to 95% by weight, of a compound described herein, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

Methods of Use

Target crops or plants to be treated with active compounds and compositions of the disclosure typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, pineapple, turf (including grass species grown and maintained as turfgrass) and natural rubber plants, as well as ornamentals (flowers, shrubs, broad-leafed trees and evergreens, such as conifers). This list does not represent any limitation.

Bacterial infections. The methods, active compounds and compositions can be used to treat bacterial infections in a variety of plants, with specific examples including but not limited to those set forth below.

Citrus. In citrus trees (including orange, lemon, lime, and grapefruit) active compounds and compositions as described herein can be used to treat or control a variety of microbial diseases, including but not limited to canker (caused by *Xanthomonas campestris* or *Xanthomonas axonopodis* infection), bacterial spot (caused by *Xanthomonas campestris* pv. Citrumelo infection); Black Pit (fruit) (caused by *Pseudomonas syringae* infection); Blast (caused by *Pseudomonas syringae* infection) citrus variegated chlorosis (caused by *Xylella fastidiosa* infection), and Citrus Huanglongbing (HLB) caused by Candidatus *Liberibacter asiaticus*.

Pome Fruit. In pome fruits (including apple, pear, quince, Asian pear, and loquat), active compounds and compositions as described herein can be used to treat or control a variety of microbial infections, including but not limited to Fire Blight (caused by *Erwinia amylovora* infection), Crown Gall (caused by *Agrobacterium tumefaciens* infection); Blister spot (caused by *Pseudomonas syringae* infection) and Hairy root (caused by *Agrobacterium rhizogenes* infection).

Peppers. In pepper plants, active compounds and compositions as described herein can be used to treat or control a variety of microbial infections, including but not limited to: Bacterial Spot (caused by *Xanthomonas campestris* pv. vesicatoria infection); Bacterial wilt (caused by *Ralstonia solanacearum* infection), and Syringae seedling blight and leaf spot (caused by *Pseudomonas sryingae* infection).

Tomatoes. In tomato plants, active compounds and compositions as described herein can be used to treat or control a variety of microbial infections, including but not limited to: Bacterial canker (caused by *Clavibacter michiganesis*), Bacterial speck (caused by *Pseudomonas syringae*), Bacterial spot (caused by *Xanthomonas campestris vesicatoria*), Bacterial stem rot and fruit rot (caused by *Erwinia carotovora*), Bacterial wilt (caused by *Ralstonia solanacearum*), Pith necrosis (caused by *Pseudomonas* corrugate), and Syringae leaf spot (caused by *Pseudomonas syringae*).

Soybeans. In soybeans, active compounds and compositions as described herein can be used to treat or control a variety of microbial infections, including but not limited to: Bacterial blight (caused by *Pseudomonas* amygdale), Bacterial pustules (caused by *Xanthomonas axonopodis* pv. Glycines), and Bacterial wilt (caused by *Ralstonia solanacearum* or *Curtobacterium flaccumfaciens*).

Corn, Cotton, Wheat and Rice. In corn, cotton, wheat and rice, active compounds and compositions as described herein can be used to treat or control a variety of microbial infections, including but not limited to: bacterial blights, leaf spots and leaf streak caused by *Xanthomonas* species; bacterial sheath rot, stripe and spot caused by *Pseudomonas* species; and to bacterial stalk and top rot, wilt, foot rot, pink seed and lint degradation caused by *Erwinia* species.

Pineapple. In pineapple, active compounds and compositions as described herein can be used to treat or control a variety of microbial infections, including but not limited to: Bacterial heart rot and Fruit collapse (caused by *Erwinia chrysanthemi*), Bacterial fruitlet brown rot (caused by *Erwinia ananas*), Marbled fruit and Pink fruit (caused by *Erwinia herbicola*), Soft rot (caused by *Erwinia carotovora*), and Acetic souring (caused by Acetic acid bacteria).

The above listing is but a sampling, and active compounds and compositions as described herein may also be used to treat or control bacteria (some of which are named above) in a variety of plants. For example, the bacteria *Xylella fastidiosa* infects citrus trees as noted above (citrus variegated chlorosis), and also infects grapevines (Pierce's disease). Other plant hosts of *Xylella fastidiosa* include, but are not limited to, ornamentals (bacterial leaf spot, fire blight, bacterial leaf scorch, etc.), oleander (leaf scorch), almond, coffee, maple, mulberry, elm, sycamore, alfalfa, etc. Similarly, *Ralstonia solanacearum* infects soybeans (bacterial wilt) as well as banana (Moko disease), tobacco (Granville wilt), geranium (southern bacterial wilt), potato (brown rot) and a wide variety of other plants, including ginger and mulberry and turfgrass (bacterial wilt).

Fungal infections. In addition to treating or controlling bacterial infections, active compounds and compositions as described herein can be used to treat or control fungal infections such as rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice. Genera of plant-pathogenic fungi that can be treated or controlled by the active compounds, compositions, and methods described herein include but are not limited to: *Pythium* spp., *Fusarium* spp., *Rhizoctonia* spp., *Cercospora* spp., *Alternaria* spp., *Colletotrichum* spp., *Ustilago* spp., *Phoma* spp., *Gibberella* spp. *Penicillium* spp., *Glomerella* spp. *Diplodia* spp., *Curvularia* spp., *Sclerospora* spp., *Peronosclerospora* spp., *Puccinia* spp., *Aspergillus* spp., *Phomopsis* spp., *Diaporthe* spp., *Botrytis* spp., *Verticillium* spp., and *Phytophthors* spp. Fungal genera also include: *Sclerophthora* spp., *Erysipthe* spp., *Sclerotinia* spp., *Pyricularia* spp., Typhula spp., *Microdochium* spp., *Helminthosporium* spp., *Gaeumannomyces* spp., *Ophiospaerella* spp., *Magnaporthe* spp., and *Thielaviopsis* spp.

Particular fungal infections that can be treated or controlled by the methods, compounds and compositions described herein, in vegetables and greenhouse crops, include *Phytophthora* blight (caused by *Phytophthora capsici*) and *Pythium* damping-off (caused by *Pythium* spp). Note that *Phytophthora* also has adverse effects on crops ranging from pineapples to cotton. It can kill woody citrus seedlings and young citrus trees (oranges, grapefruits, lemons, limes). In the greenhouse, germinating seed and seedlings are very susceptible to damping-off caused by *Phytophthora, Pythium, Sclerotina* and *Rhizoctonia* species. The cost to the grower to lose his crop to any of these fungi is substantial. The loss can happen at transplant time or when the crop is ready to be harvested.

The problems of fungi are not restricted to traditional crops but also extend to forestry products and have worldwide scope. *Phytophthora cinnamomi* is a soil-borne water mould that leads to a condition in plants called "root rot" or "dieback." *P. cinnamomi* causes root rot affecting woody ornamentals including azalea, dogwood, forsythia, Fraser fir, hemlock, Japanese holly, juniper, *rhododendron*, white pine, and American chestnut. *P. cinnamomi* is responsible for the destruction of the elegant American chestnut tree. In Australia, *P. cinnamomi* has spread through the forests of western Australia, and into coastal forests of Victoria, where entire plant ecosystems are being obliterated. Given that *P. cinnamomi* is a soil-borne water mould that infects the roots, almost the entire action takes place below ground. This problem highlights the importance of developing new compounds to counter fungal infections, even those that directly affect only the roots of the plant rather than the more visible effects on fruits or vegetables.

Active compounds can be applied to plants or plant loci in accordance with known techniques. The compound(s) can be tank mixed with other agricultural, turf, ornamental nursery, forestry and all other plant-labeled compatible pesticides. The compound(s) can be applied to seed. The compound(s) can be applied to edible and non-edible crops. The compound(s) can be applied to roots and all other parts of all plants. The compound(s) can be applied in greenhouses. The compound(s) can be applied and used in food-processing facilities. The compound(s) can be applied to plastic food bags and containers. The compound(s) can be applied as a solid, as its free base, or as a salt. The salts can include, but are not limited to, HI, HCl, HBr, H2SO4, acetic acid, and trifluoroacetic acid. The compound(s) can be applied as a solution from 0.0001% to 99.9%. The compound(s) can be applied as a solid or solution with copper-based cidal compounds. The compound(s) can be applied with specific additional active agents, including but not limited to bactericides, fungicides, pesticides, biological insecticides and microbial insecticides.

Application can be carried out with any suitable equipment or technique, such as: Aerial—Fixed wing and Helicopter; Ground Broadcast Spray—Boom or boomless system, pull-type sprayer, floaters, pick-up sprayers, spray coupes, speed sprayers, and other broadcast equipment, water wagons and water bags; Low pressure boom sprayers, High pressure sprayers; Air blast sprayers; Low volume air sprayers (mist blowers); Ultra-low volume sprayers (ULV); Aerosol Generators (foggers); Dusters; Soil Injector; Hand-Held or High-Volume Spray Equipment—knapsack and backpack sprayers, pump-up pressure sprayers, hand guns, motorized spray equipment; Selective Equipment—Recirculating sprayers, shielded and hooded sprayers; Controlled droplet applicator (CDA) hand-held or boom-mounted applicators that produce a spray consisting of a narrow range of droplet size; Any and all greenhouse sprayers; Microsprinkler or drip irrigation systems; Chemigation.

One method of applying an active compound, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application), or by injection of the active compounds and combinations of the invention systemically to, for example, a palnt or tree. In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

Advantageous rates of application are normally from 5 g to 2, 3, 4, 5, 8 or 10 kg of active ingredient (a.i.) per hectare (ha). In some embodiments, rates of application are from 10 g to 1 kg a.i./ha, or from 20 g to 600 g a.i./ha. When used as seed drenching agent, convenient dosages are from 10 mg to 1 g of active substance per kg of seeds. In some embodiments, rates of application are from 0.1 kg/ha to 10 kg/ha, or from 0.5 kg/ha to 5 kg/ha, or from 1 kg/ha to 3 kg/ha.

Combination Treatments

In some embodiments, methods of enhancing the effects of a microbicide (such as a microbicide comprising copper, e.g., KOCIDE 2000 or KOCIDE 3000 (DuPont, with active ingredient copper hydroxide) are disclosed, comprising the step of applying an active compound in combination with a microbicide, the active compound being applied in an amount effective to enhance the effects of the microbicide.

In some embodiments, methods of enhancing the effects of a plant defense activator are disclosed, comprising the step of applying an active compound in combination with a plant defense activator, the active compound being applied in an amount effective to enhance the effects of the plant defense activator.

"Enhancing" the effects of a microbicide by applying an active compound in combination with the microbicide refers to increasing the effectiveness of the microbicide, such that the microorganism killing and/or growth inhibition is higher at a certain concentration of the microbicide applied in combination with the active compound than without. In some embodiments, a bacteria or other microorganism is "sensitized" to the effects of a microbicide, such that the bacteria or other microorganism that was resistant to the microbicide prior to applying the active compound (e.g., little to none, or less than 20, 10, 5 or 1% are killed upon application) is rendered vulnerable to that microbicide upon or after applying the active compound (e.g., greater than 20, 30, 40, 50, 60, 70, 80, 90, or 95% or more are killed).

Similarly, "enhancing" the effects of a plant defense activator by applying an active compound in combination with the plant defense activator refers to increasing the effectiveness of the plant defense activator, such that the microorganism killing and/or growth inhibition is higher at a certain concentration of the plant defense activator applied in combination with the active compound than without. In some embodiments, a bacteria or other microorganism is "sensitized" to the effects of a plant defense activator, such that the bacteria or other microorganism that was resistant to the effects of the plant defense activator prior to applying the active compound (e.g., little to none, or less than 20, 10, 5 or 1% are killed upon application) is rendered vulnerable to the effects of that plant defense activator upon or after applying the active compound (e.g., greater than 20, 30, 40, 50, 60, 70, 80, 90, or 95% or more are killed).

As used herein, the application of two or more compounds (inclusive of active compounds and microbicides) "in combination" means that the two compounds are applied closely enough in time that the application of or presence of one alters the biological effects of the other. The two compounds may be applied simultaneously (concurrently or contemporaneous) or sequentially. Applications according to some embodiments may be within a period of time that ranges from minutes (e.g., 1, 5, 10, 30, 60, or 90 minutes or more) to days (e.g., 1, 2, 5, 8 or 10 or more days), as appropriate for efficacious treatment.

Simultaneous, concurrent or contemporaneous application of the compounds may be carried out by mixing the compounds prior to application, or by applying the compounds at the same point in time but at different sites of the plant or using different types of applications, or applied at times sufficiently close that the results observed are indistinguishable from those achieved when the compounds are applied at the same point in time.

Sequential application of the compounds may be carried out by applying, e.g., an active compound, at some point in time prior to application of a microbicide, such that the prior application of active compound enhances the effects of the microbicide (e.g., percentage of microorganisms killed and/or slowing the growth of microorganisms). In some embodiments, an active compound is applied at some point in time prior to the initial application of a microbicide. Alternatively, the microbicide may be applied at some point in time prior to the application of an active compound, and optionally, applied again at some point in time after the application of an active compound.

The compounds, compositions and methods of the present disclosure may in particular implementations be constituted as comprising, consisting, or consisting essentially of, some or all of such features, aspects and embodiments, and various elements, ingredients, components, steps, and conditions may be further aggregated in whole or part to constitute various further implementations of the disclosure. For example, the compositions include those comprising, consisting of, or consisting essentially of (e.g., 50%, 60%, 70%, 80%, 90%, 95%, or 99% or more of the total weight or volume of the composition), a component such as an active compound and/or a biocide as provided herein.

Formulations

The compounds and compositions of the invention, such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, may be administered at a dose of less than 400 mg/day. In some embodiments, the compounds and compositions of the invention are administered at a dose of about 1 mg/day, about 2 mg/day, about 5 mg/day, about 10 mg/day, about 15 mg/day, about 20 mg/day, about 25 mg/day, about 30 mg/day, about 35 mg/day, about 40 mg/day, about 45 mg/day, about 50 mg/day, about 60 mg/day, about 70 mg/day, about 80 mg/day, about 90 mg/day, about 100 mg/day, about 120 mg/day, about 125 mg/day, about 140 mg/day, about 150 mg/day, about 160 mg/day, about 175 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, or about 500 mg/day. In certain embodiments, the compounds of the invention are administered at a dose of less than 1 mg/day, less than 2 mg/day, less than 5 mg/day, less than 10 mg/day, less than 15 mg/day, less than 20 mg/day, less than 25 mg/day, less than 30 mg/day, less than 35 mg/day, less than 40 mg/day, less than 45 mg/day, less than 50 mg/day, less than 60 mg/day, less than 70 mg/day, less than 80 mg/day, less than 90 mg/day, less than 100 mg/day, less than 120 mg/day, less than 125 mg/day, less than 140 mg/day, less than 150 mg/day, less than 160 mg/day, less than 175 mg/day, less than 180 mg/day, less than 190 mg/day, less than 200 mg/day, less than 225 mg/day, less than 250 mg/day, less than 275 mg/day, less than 300 mg/day, less than 325 mg/day, less than 350 mg/day, less than 375 mg/day, less than 400 mg/day, less than 425 mg/day, less than 450 mg/day, less than 475 mg/day, or less than 500 mg/day. In some embodiments, the compounds of the invention are administered at a dose of more than 1 mg/day, more than 2 mg/day, more than 5 mg/day, more than 10 mg/day, more than 15 mg/day, more than 20 mg/day, more than 25 mg/day, more than 30 mg/day, more than 35 mg/day, more than 40 mg/day, more than 45 mg/day, more than 50 mg/day, more than 60 mg/day, more than 70 mg/day, more than 80 mg/day, more than 90 mg/day, more than 100 mg/day, more than 120 mg/day, more than 125 mg/day, more than 140 mg/day, more than 150 mg/day, more than 160 mg/day, more than 175 mg/day, more than 180 mg/day, more than 190 mg/day, more than 200 mg/day, more than 225 mg/day, more than 250 mg/day, more than 275 mg/day, more than 300 mg/day, more than 325 mg/day, more than 350 mg/day, more than 375 mg/day, more than 400 mg/day, more than 425 mg/day, more than 450 mg/day, more than 475 mg/day, or more than 500 mg/day.

The compounds and compositions of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated, hi general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a smart capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage.

These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), antioxidants (ascorbic acid of sodium bisulfite) or the like.

The invention provides a smart pill or smart capsule, which is, in an exemplary embodiment, an ingestible drug delivery device configured for wireless communication with other ingestible drug delivery devices, said drug delivery device comprising: a capsule body comprising: a sensor for sensing at least one biologic condition within a patient and providing a first signal representative thereof; a bioactive substance module comprising a container for holding a volume and/or quantity of bioactive substance therein and a microactuator for dispensing said bioactive substance from said container to a location outside of said capsule body; an electronics module, coupled to said sensor and said bioactive substance module, said electronics module comprising a processor, a transponder and a memory (e.g., flash, OTP, etc.), said memory comprising data selected from the group consisting of: (a) data related to the patient who is permitted to ingest said ingestible drug medical device; (b) data related to said bioactive substance; (c) data related to a healthcare provider that enabled said electronics module; (d) data related to said sensor; (e) data related to the provenance of said ingested drug medical device; (f) combinations thereof, a power source coupled to said sensor, said bioactive substance module and said electronics module; and wherein said processor controls said transponder to transmit at least one wireless signal and to receive at least one wireless signal from at least one other ingestible medical device, and wherein said processor receives said first signal and analyzes said first signal with all of said data along with said received at least one wireless signal for controlling said microactuator for dispensing said bioactive substance.

In exemplary embodiments, ORG 34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, is variable in capsule/tablets/smart pills, resulting in intermittent, rather than constant dosing, the pills could be coded (e.g. by color or shape) to indicate which pills would be taken in which order (per part of a day, or per day or week or month of pill taking protocol) to achieve the correct balance or GCR blockade (e.g. like daily birth control pills with variable hormonal contents over the course of a month). In other words, some capsule/tablets/smart pills would have just the opiate, some would have opiate plus one or several different doses of PT150 in the same capsule/tablet/smart pill, etc. In exemplary embodiments, the patient would not be aware of the contents of any given capsule/tablet/smart pill, but would know when in the course of their dosing regimen they should take a particular coded version.

In exemplary embodiments, the smart capsules could identify both quantity of pills taken as well as the kind of pill taken (with or without the ORG 34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof) so as to provide a record for treating personnel as to what has been taken, but also to prevent opening of the smart pill if the wrong pill has been taken out of its intended sequence.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm). "Stabilized" nanoparticles are nanoparticles coated with a stabilizing material and having a reduced tendency for aggregation and loss of dispersion with respect to nanoparticles of the compound of the invention without a stabilizing coating. A nano-spray is a spray containing nanoparticles or a spray that produces nanoparticles. A nanodispersion is a dispersion containing nanoparticles. A nanosuspension is a suspension containing nanoparticles. The liquid formulations useful herein may comprise a solvent, solution, suspension, microsuspension, nanosuspension, emulsion, microemulsion, gel or even a melt containing the active component or components.

In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present invention can include nanoparticles, composite nanoparticles, nanosuspension, or nanocapsules of the present invention. In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, 111.) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a childproof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

Topical Formulations

The term "topical" as employed herein relates to the use of a compound, derivative or analogue as described herein, incorporated in a suitable pharmaceutical carrier, and applied at the site for exertion of local action. Accordingly, such topical compositions including those forms in which the compound is applied externally by direct contact with the skin surface to be treated. Conventional forms for this purpose include ointments, liniments, creams, shampoos, lotions, pastes, jellies, sprays, aerosols, soaps, and the like, and may be applied in patches or impregnated dressings depending on the part of the body to be treated. The term "ointment" embraces formulations (including creams) having oleaginous, absorption, water-soluble and emulsion-type bases, e.g., petrolatum, lanolin, polyethylene glycols, as well as mixtures of these. For topical use, the agent of the invention can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betain, chlorhexidine, benzalkonium chloride, and the like. Various matrices for slow release delivery may also be used. Typically, the dose to be applied is in the range of about 0.1 ng to about 100 mg per day, or about 1 ng to about 10 mg per day, or about 10 ng to about 1 mg per day depending on the formulation. Non-limiting examples of topical products can include, without limitation, application stick, mascara, eyebrow coloring products, eye shadow or other eye lid coloring products, eyeliner, make-up removal products, antiaging products, facial or body powder, nail polish, mousse, sprays, styling gels, nail conditioner, bath and shower gels, shampoos, conditioners, cream rinses, hair dyes and coloring products, hair conditioners, sun tanning lotions and creams and sprays, sunscreens and sunblocks, skin conditioners, cold creams, moisturizers, hair sprays, soaps, body scrubs, exfoliants, astringents, depilatories and permanent waving solutions, antidandruff formulations, antisweat and antiperspirant compositions, shaving, preshaving and after shaving products, moisturizers, deodorants, cold creams, cleansers, skin gels, and rinses.

Furthermore, the topical product can be applied topically through the use of a patch or other delivery device. Delivery devices can include, but are not limited to, those that can be heated or cooled, as well as those that utilize iontophoresis or ultrasound.

For instance, the topical product can be applied, for example, by applying a composition in the form of a skin lotion, clear lotion, milky lotion, cream, gel, foam, ointment, paste, emulsion, spray, conditioner, tonic, cosmetic, application stick, pencil, foundation, nail polish, after-shave, or the like which is intended to be left on the skin or other keratinous tissue (i.e., a "leave-on" composition). After applying the composition to the keratinous tissue (e.g., skin), it in one embodiment, is left on for a period of at least about 15 minutes, or at least about 30 minutes, or at least about 1 hour, or for at least several hours, e.g., up to about 12 hours. In one embodiment, the topical product is left on overnight. In another embodiment, the topical product is left on all day. Any part of the external portion of the face, hair, and/or nails can be treated, (e.g., face, lips, under-eye area, eyelids, scalp, neck, torso, arms, legs, chest, hands, legs, feet, fingernails, toenails, scalp hair, eyelashes, eyebrows, etc.)

Any suitable method can be used to apply the topical product, including but not limited to for example using the palms of the hands and/or fingers or a device or implement (e.g., a cotton ball, swab, pad, applicator pen, spray applicator, eyebrow brush, eyebrow brush pencil, pencil, mascara brush, etc.) Another approach to ensure a continuous exposure of the keratinous tissue to at least a minimum level of the topical product is to apply the compound by use of a patch applied, e.g., to the face. The patch can be occlusive, semi-occlusive or nonocclusive, and can be adhesive or non-adhesive. The topical product can be contained within the patch or be applied to the skin prior to application of the patch. The patch can also include additional actives such as chemical initiators for exothermic reactions such as those described in PCT application WO 9701313, and in U.S. Pat. Nos. 5,821,250, 5,981,547, and 5,972,957 to Wu, et al. The patch can be left on the for any suitable period of time. For example, a period of at least about 5 minutes, or at least about 15 minutes, or at least about 30 minutes, or at least about 1 hour, or at night as a form of night therapy, or in another embodiment all day.

Administration

The pharmaceutical compositions may be optimized for particular types of delivery. For example, pharmaceutical compositions for oral delivery are formulated using pharmaceutically acceptable carriers that are well known in the art. The carriers enable the agents in the composition to be formulated, for example, as a tablet, pill, capsule, solution, suspension, sustained release formulation; powder, liquid or gel for oral ingestion by the subject.

The pharmaceutical compositions may also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol. Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral, intranasal or respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices that deliver the formulation in an appropriate manner.

Typically, the composition may be applied repeatedly for a sustained period of time topically on the part of the body to be treated, for example, the eyelids, eyebrows, skin or scalp. The dosage regimen will generally involve regular, such as daily, administration for a period of treatment of at least one month, or at least three months, or at least six months.

Alternatively, the composition may be applied intermittently, or in a pulsed manner. Accordingly, an alternative embodiment of the invention is to apply the composition on an intermittent or pulsed dosage schedule. For example, the composition of the invention may be used for two or more days, stopped, then restarted again at a time from between 2 weeks to 3 months later, and at even more long-spaced intervals in the case of the scalp.

The routes of administration of a compound of the present invention will vary, naturally, with the location and nature of the condition to be treated, and include, e.g., inhalation, intradermal, transdermal, parenteral, intravenous, intramuscular, intranasal, subcutaneous, percutaneous, intratracheal, intraperitoneal, intratumoral, perfusion, lavage, direct injection, and oral administration and formulation. As detailed below, compounds of the invention may be administered as medical gases by inhalation or intubation, as injectable liquids by intravascular, intravenous, intra-arterial, intracerobroventicular, intraperitoneal, subcutaneous administration, as topical liquids or gels, or in solid oral dosage forms.

Moreover, the amounts may vary depending on the type of biological matter (cell type, tissue type, organism genus and species, etc.) and/or its size (weight, surface area, etc.). It will generally be the case that the larger the organism, the larger the dose. Therefore, an effective amount for a mouse will generally be lower than an effective amount for a rat, which will generally be lower than an effective amount for a dog, which will generally be lower than an effective amount for a human. The effective concentration of a compound of the present invention to achieve stasis, for example, in a human depends on the dosage form and route of administration. For inhalation, in some embodiments effective concentrations are in the range of 50 ppm to 500 ppm, delivered continuously. For intravenous administration, in some embodiments effective concentrations are in the range of 0.5 to 50 milligrams per kilogram of body weight delivered continuously.

Similarly, the length of time of administration may vary depending on the type of biological matter (cell type, tissue type, organism genus and species, etc.) and/or its size (weight, surface area, etc.) and will depend in part upon dosage form and route of administration. In particular embodiments, a compound of the present invention may be provided for about or at least 30 seconds, 1 minute, 2 minutes, 3 minutes, 5 minutes, 10 minutes, 15 minutes, 30 minutes, 1 hour, 2 hours, 3 hours, four hours five hours, six hours, eight hours, twelve hours, twenty-four hours, or greater than twenty-four hours. A compound of the present invention may be administered in a single dos or multiple doses, with varying amounts of time between administered doses.

The treatments may include various "unit doses." Unit dose is defined as containing a predetermined-quantity of the therapeutic composition. The quantity to be administered, and the particular route and formulation, are within the skill of those in the clinical arts. A unit dose need not be administered as a single injection but may comprise continuous infusion over a set period of time. Alternatively, the amount specified may be the amount administered as the average daily, average weekly, or average monthly dose.

In the case of transplant, the present invention may be used pre- and or post-operatively to render host or graft materials quiescent. In a specific embodiment, a 30 surgical site may be injected or perfused with a formulation comprising an GR antagonist. The perfusion may be continued post-surgery, for example, by leaving a catheter implanted at the site of the surgery.

Further Delivery Devices or Apparatuses

In some embodiments it is contemplated that methods or compositions will involve a specific delivery device or apparatus. Any method discussed herein can be implemented with any device for delivery or administration including, but not limited, to those discussed herein. For topical administration of compounds of the invention may be formulated as solutions, gels, ointments, creams, suspensions, etc. as are well-known in the art. Systemic formulations may include those designed for administration by injection or infusion, e.g., subcutaneous, intravenous, intramuscular, intrathecal or intraperitoneal injection, as well as those designed for transdermal, transmucosal, oral or pulmonary administration.

The invention provides a topical pharmaceutical formulation for use in treatment of a subject, comprising the composition of the invention, and at least one pharmaceutically acceptable excipient.

The invention provides a method for treating a patient in need of such treatment comprising administration of the topical pharmaceutical composition of the invention.

The invention provides a topical pharmaceutical formulation for use in treatment of a subject, comprising a composition of the invention, and at least one pharmaceutically acceptable excipient. The invention further provides a topical formulation of the invention wherein said formulation is in a form selected from the group consisting of: cream, lotion, gel, oil, ointment, suppository, spray, foam, liniment, aerosol, buccal and sublingual tablet or a transdermal device or patch for absorption through the skin or mucous membranes. The invention further provides a topical formulation of the invention wherein said pharmaceutical formulation is a transdermal patch. The invention further provides a topical formulation of the invention wherein said pharmaceutical formulation is a buccal formulation.

For oral administration, the Compounds of the invention to be formulated as tablets, pills, dragees, capsules, liquids, gels, syrups, slurries, suspensions and the like, for oral ingestion by a patient to be treated or oral liquid preparations such as, for example, suspensions, elixirs and solutions.

For buccal administration, the compositions may take the form of tablets, lozenges, etc. formulated in conventional manner. Other intramucosal delivery might be by suppository or intranasally.

For administration directly to the lung by inhalation the compound of invention may be conveniently delivered to the lung by a number of different devices.

Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers.

PUMPS and Infusion Devices: An infusion pump or perfusor infuses fluids, medication or nutrients into a patient's circulatory system. Infusion pumps can administer fluids in very reliable and inexpensive ways. For example, they can administer as little as 0.1 mL per hour injections (too small for a drip), injections every minute, injections with repeated boluses requested by the patient, up to maximum number per hour (e.g. in patient-controlled analgesia), or fluids whose volumes vary by the time of day.

Implantable Drug Delivery System: Another drug delivery system comprises one or more ball semiconductor aggregations and facilitating release of a drug stored in a reservoir. The first aggregate is used for sensing and memory, and a second aggregation for control aspects, such as for pumping and dispensing of the drug. The system may communicate with a remote control system, or operate independently on local power over a long period for delivery of the drug based upon a request of the patient, timed-release under control by the system, or delivery in accordance with measured markers.

Formulations

The pharmaceutical compositions may be for human or animal usage in human and veterinary medicine and will typically comprise any one or more of a pharmaceutically acceptable diluent, carrier, or excipient.

The compounds of the invention may be administered enterally or parenterally, and for humans preferably in a daily dosage of 0.001-100 mg per kg body weight, preferably 0.01-10 mg per kg body weight. Mixed with pharmaceutically suitable auxiliaries, e.g., as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids, including nanosuspensions, the compounds can also be applied in the form of a solution, suspension, emulsion, e.g., for use as an injection preparation, for rectal or IV administration or eye drops, or as a spray, e.g., for use as a nasal spray, or formulated in a patch, with or without the addition of penetration enhancers, for transdermal delivery.

For making dosage units, e.g., tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The compounds of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g., for use as an injection preparation or eye drops, or as a spray, e.g., for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Diagnostic Systems and Kits

A diagnostic kit may comprise some or all of the following components: 1) one or more standards comprised of one or more of the biomarker(s) of the invention, such as cortisol; 2) a ligand, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a ligand carrier, such as an antibody carrier, for example, a lateral flow device, or a microplate with bound antibody, or polystyrene beads. An example of such a kit is set forth in U.S. Patent Application Publication No. 20120201747 (Altschul et al.), incorporated herein in its entirety.

Neoplasia, Cancer, Tumors, Proliferative Diseases, Malignancies and their Metastases The invention provides a method for treating neoplasia in a patient in need of such treatment, comprising: administering to the patient therapeutically effective amounts of a GCR (glucocorticoid receptor) antagonist as exemplified herein, such as ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, optionally in combination with, for example, a neoplasia treating agent. The term "neoplasia" as used herein refers also to tumors, proliferative diseases, malignancies and their metastases. Examples for cancer diseases are Adenocarcinomas of the head and neck (including salivary glands and oral cavity), gastrointestinal tract (including pharynx, esophagus, stomach, small intestine, large intestine, anus), lung, liver (including hepatocellular carcinoma, cholangiocarcinoma, and mixed tumors), extrahepatic biliary tract and gallbladder, pancreas (including ductal and acinar types), genitourinary tracts (ovaries, fallopian tubes, endometrium, cervix, and vagina, ureters, urinary bladder, testicles, epididymis, prostate), and skin adnexa; squamous cell carcinomas of the head and neck (including salivary glands and oral cavity), gastrointestinal tract (including pharynx, esophagus, anus), lung, intrahepatic and extrahepatic biliary tree (including gallbladder), pancreas, genitourinary tracts (including endometrium, cervix, vagina, ureters, urinary bladder, testicles, epididymis, prostate), and skin adnexa; germ cell tumors (including malignant teratoma, embryonal carcinoma, struma ovarii, yolk sac tumor, seminoma, choriocarcinoma); sarcomas (including leiomyosarcomas, rhabdomyosarcomas, angiosarcomas, hemangioendotheliomas, liposarcomas, chondosarcomas, fibrosarcomas, Ewing sarcoma, malignant nerve sheathe tumors, alveolar soft part sarcomas, clear cell sarcomas, synovial sarcoma, osteosarcomas); malignancies of the central nervous system (including astrocytomas, oligodendroglioma, glioblastoma, medulloblastoma); salivary gland malignancies (including adenoid cystic carcinoma, adenosquamous carcinoma, clear cell carcinoma, cystadenocarcinoma, mucoepidermoid carcinoma); mixed type carcinomas (including hepatocellular-cholangiocarcinomas, carcinosarcomas, mixed adenoneurondocrine carcinomas, adenosquamous carcinomas); hepatocellular carcinoma; blastic malignancies (including hepatoblastoma, neuroblastoma, ganglioneuroblastoma, nephroblastoma); renal cell carcinomas; neuroendocrine carcinomas; thyroid carcinomas (including papillary, follicular, medullary, anaplastic carcinomas); parathyroid carcinomas, pituitary gland carcinomas, adrenal gland carcinomas (including adrenocortical carcinomas, pheochromocytoma), and combinations thereof.

Cancer Therapies

Any therapy (e.g., therapeutic or prophylactic agent) which is useful, has been used, is currently being used, or may be used for the prevention, treatment and/or management of cancer can be used to prevent, treat, and/or manage the patient whose neoplasia and/or cancer stem cells are monitored in accordance with the compounds and methods of the invention. Also, such neoplasia and/or cancer stem cell monitoring can be employed in conjunction with any therapy for cancer according to the instant invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, anti-angiogenesis therapies, targeted therapies, and/or biological therapies including immunotherapies and surgery. In certain embodiments, a prophylactically and/or therapeutically effective regimen comprises the administration of a combination of therapies. In certain embodiments, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof can be administered as an agent, alone or in combination with other active agents and/or other therapies, to treat and/or prevent neoplasia. In certain embodiments, RU486 (mifepristone) can be administered as an agent to treat or prevent neoplasia.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ORG 34517; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride;

forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3 TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin a. sub.vb.sub.3 antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodeiglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer and/or cancer stem cells includes: i) antibodies, antibody fragments, and proteins that are either naked or conjugated to a therapeutic moiety that target certain cell surface targets on cancer stem cells, or ii) small molecules known in the art including ones that can be further optimized (e.g., via chemistry) or identified via a cancer stem cell-based screen (e.g., such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mc1-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., leflunamide), T cell receptor modulators, cytokine receptor modulators, and modulators mast cell modulators. Particularly preferred auxiliary immunomodulatory substances are cytokines, such as monokines, lymphokines, interleukins or chemokines, that further promote the innate immune response, such as IL-1, IL-1 receptor antagonist, IL-2, EL-3, EL-4, IL-5, IL-6, EL-7, IL-8, EL-9, ELIO, IL-12, EL-13, EL-14, EL-15, EL-16, IL-17, EL-18, IL-19, EL-20, EL-21, EL-22, DL-23, EL-24, IL-25, EL-26, EL-27, EL-28, EL-29, EL-30, EL-31, EL-32, EL-33, INF-alpha, EFN-beta, INF-gamma, GM-CSF, G-CSF, M-CSF, LT-beta or TNF-alpha, growth factors, such as hGH. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent. In some embodiments, the therapy(ies) is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab).sub.2 fragments, and antigen-binding fragments thereof) such as antibodies that specifically bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) is not an anti-angiogenic agent.

In certain embodiments, the therapy(ies) is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine). In some embodiments of the invention, the therapy(ies) includes the administration cantharidin or an analog thereof. The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to alkylating agents, antimetabolites, plant alkaloids, cytotoxic agents, chemotherapeutic agents (e.g., a steroid, cytosine arabinoside, fluoruracil, methotrexate, aminopterin, mitomycin C, demcolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, *Pseudomonas* exotoxin, a bacterial endotoxin or the lipid A moiety of a bacterial endotoxin), growth modulators and RNase. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody or an antibody conjugated to a therapeutic moiety or an antibody fragment conjugated to a therapeutic moiety.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of IL-3R (i.e., the CD123 antigen). In other embodiments, the antibody, antibody-conjugate, antibody fragment, or antibody fragment-conjugate binds to the IL-3R, containing both the .alpha. and .beta. subunits. Methods for preparing antibodies to IL-3R and mimetics of antibodies to IL-3R are described in U.S. Pat. No. 6,733,743 B2, which is incorporated herein by reference in its entirety.

In other embodiments, the agent that binds to a marker on cancer stem cells is a ligand. In some embodiments, the ligand is a cytokine that binds to a cytokine receptor on cancer stem cells. In a particular embodiment, the ligand is interleukin-3 (IL-3) which can be conjugated to a therapeutic moiety that includes a chemotherapeutic agent, a plant-, fungus-, or bacteria-derived toxin, or a radionuclide. The IL-3-conjugate prophylactic and/or therapeutic therapy or regimen can be in the form of a recombinant fusion protein in embodiments where the conjugate is a toxin and the toxin is a protein, such as diphtheria toxin. Methods for preparing and isolating an IL-3-diphtheria toxin fusion protein (IL3DT) are described in Frankel et al., "Diphtheria toxin fused to human interleukin-3 is toxic to blasts from patients with myeloid leukemias," Leukemia 14:576 (2000) and Urieto et al., Protein Expression and Purification 33: 123-133 (2004), the disclosures of which are incorporated by reference in their entireties.

In certain embodiments, antibodies or fragments thereof that bind to a marker on cancer stem cells are substantially non-immunogenic in the treated subject. Methods for obtaining non-immunogenic antibodies include, but are not limited to, chimerizing the antibody, humanizing the antibody, and isolating antibodies from the same species as the subject receiving the therapy. Antibodies or fragments thereof that bind to markers in cancer stem cells can be produced using techniques known in the art. See, for example, paragraphs 539-573 of U.S. Publication No. 2005/0002934, which is incorporated by reference in its entirety.

In some embodiments, the therapy comprises the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation based therapy. Non-limiting examples of such therapies include a chemotherapy and radiation therapy as described supra.

Currently available therapies and their dosages, routes of administration and recommended usage are known in the art and have been described in such literature as the Physician's Desk Reference (60th ed., 2006).

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two prophylactically and/or therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first prophylactically and/or therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Pathogenic Infections

In a preferred embodiment the pathogen is an intracellular pathogen, i.e. a pathogen capable of growing and reproducing inside the cells of a host. Bacterial examples which may be prevented and/or treated by the compositons and methods of the invention include but are not limited to *Francisella tularensis, Listeria monocytogenes, Salmonella, Brucella, Legionella, Mycobacterium, Nocardia, Rhodococcus equi, Yersinia, Neisseria meningitidis, Chlamydia, Rickettsia, Coxiella, Mycobacterium*, such as *Mycobacterium leprae* and *Treponema pallidum*. Fungal examples include but are not limited to *Histoplasma capsulatum, Cryptococcus neoformans* and *Pneumocystis jirovecii*. Examples of protozoa include but are not limited to Apicomplexans (e.g. *Plasmodium* spp., *Toxoplasma gondii* and *Cryptosporidium parvum*) and Trypanosomatids (e.g. *Leishmania* spp. and *Trypanosoma cruzi*).

The following is an exemplary but non-limiting discussion of various disease agents that could be the subject of prevention and/or treatment in accordance with the present invention.

Bacterial Pathogens

There are hundreds of bacterial pathogens in both the Gram-positive and Gram-negative families that cause significant illness and mortality around the word, despite decades of effort developing antibiotic agents. Antibiotic resistance is a growing problem in bacterial disease. Bacterial pathogens may be prevented and/or treated by the compositons and methods of the invention.

One of the bacterial diseases with highest disease burden is tuberculosis, caused by the bacterium *Mycobacterium tuberculosis*, which kills about 2 million people a year, mostly in sub-Saharan Africa. Pathogenic bacteria contribute to other globally important diseases, such as pneumonia, which can be caused by bacteria such as *Streptococcus* and *Pseudomo-* nas, and food borne illnesses, which can be caused by bacteria such as *Shigella, Campylobacter*, and *Salmonella*. Pathogenic bacteria also cause infections such as tetanus, typhoid fever, diphtheria, syphilis, and leprosy.

Conditionally pathogenic bacteria are only pathogenic under certain conditions, such as a wound facilitates entry of bacteria into the blood, or a decrease in immune function. For example, *Staphylococcus* or *Streptococcus* are also part of the normal human flora and usually exist on the skin or in the nose without causing disease, but can potentially cause skin infections, pneumonia, meningitis, and even overwhelming sepsis, a systemic inflammatory response producing shock, massive vasodilation and death. Some species of bacteria, such as *Pseudomonas aeruginosa, Burkholderia cenocepacia*, and *Mycobacterium avium*, are opportunistic pathogens and cause disease mainly in people suffering from immunosuppression or cystic fibrosis.

Other bacteria invariably cause disease in humans, such as obligate intracellular parasites (e.g., *Chlamydophila, Ehrlichia, Rickettsia*) that are capable of growing and reproducing only within the cells of other organisms. Still, infections with intracellular bacteria may be asymptomatic, such as during the incubation period. An example of intracellular bacteria is *Rickettsia*. One species of *Rickettsia* causes typhus, while another causes Rocky Mountain spotted fever. *Chlamydia*, another phylum of obligate intracellular parasites, contains species that can cause pneumonia or urinary tract infection and may be involved in coronary heart disease. *Mycobacterium, Brucella, Francisella, Legionella*, and *Listeria* can exist intracellular, though they are facultative (not obligate) intracellular parasites.

Gram-positive bacteria include *Staphylococcus aureus; Staphylococcus epidermidis; Staphylococcus saprophyticus; Streptococcus pyogenes* (Lancefield group A, beta-hemolytic); *Streptococcus agalactiae* (Lancefield group B, beta-hemolytic); *Streptococcus Viridans* group (most are alpha-hemolytic) including, for example, the Mitus group (*S. mitus, S. sanguis, S. parasanguis, S. gordonii, S. crista, S. infantis, S. oralis, S. peroris*), the *Salivarius* group (*S. salivarius, S. vestibularis, S. thermophilus*), the *Mutans* group (*S. mutans, S. sobrinus, S. criceti, S. rattus, S. downei, S. macacae*), and the *Anginosus* group (*S. anginosus, S. constellatus, S. intermedius*); Streptococcus, e.g., *S. bovis, S. equinus* (Lancefield group D, alpha-hemolytic); Streptococcuspneumoniae (no Lancefield antigen; alpha-hemolytic); *Peptostreptococcus* and *Peptococcus; Entercoccus faecalis; Enterococcus faeccium; Cornybacterium diphtheria; Bacillus anthracis; Bacillus cereus; Clostridium C. botulinum* (more rarely, *C. baratii* and *C. butyricum*); *Clostridium tetani; Clostridium perfringens; Clostridium difficile; Clostridium sordellii; Listeria monocytogenes; Actinomyces israelii; Nocardia* asteroids; *Streptomyces*.

Gram-negative bacteria include *Neisseria meningitides; Neisseria gonorrhoeae;*

*Moraxella* (subgenera *Branhamella*) *catarrhalis; Kingella* (most commonly kingae); *Acinetobacter baumannii, Oligella ureolytica; Oligella urethralis; Escherichia coli; Shigella* (*S. dysenteriae, S. flexneri, S. boydii, S. sonnei*); *Salmonella* non typhoidal, including *S. enterica* serotype *enteritidis, S. enterica* serotype *typhimurium, S. enterica* serotype *Choleraesuis, S. bongori, Salmonella S. enterica* serotype *Typhi; Yersinia enterocolitica, Klebsiella pneumoniae; Proteus mirabilis; Enterobacter; Cronobacter* (formerly called *Enterobacter sakazakii*); *Serratia; Edwardsiella; Citrobacter; Hafnia; Providencia; Vibrio cholera; Vibrio parahemolyticus; Campylobacter; Helicobacter* (formerly called *Campylobacter*) *pylori, Pseudomonas aeruginosa; Burkholderia cepacia; Burkholderia mallei; Burkholderia pseudomallei; Stenotrophomonas maltophilia; Bacteroides fragilis, Bacteroides melaninogenicus; Fusobacterium; Haemophilus* influenza; *Haemophilus ducreyi; Gardnerella* (formerly called *Haemophilus*) *vaginalis; Bordetella pertussis; Legionella; Yersinia pestis; Francisella tularensis; Brucella B. melitensis* (infects sheep/goats); *B. abortus* (abortions in cows); *B. suis* (pigs); *B. canis* (dogs); *B. maris* (marine animals); *Pasteurella multocida; Streptobacillus moniliformis*; Spirillum minus; *Treponema pallidum; Treponema pallidum* subspecies *pertenue; Treponema pallidum* subspecies *endemicum; Treponema pallidum* subspecies *carateum; Borrelia burgdorferi; Borrelia; Leptospira; Chlamydia trachomatis; Chlamydia pneumonia; Chlamydia psittaci; Rickettsiae rickettsia; Rickettsiae akari; Rickettsiae prowazekii; Rickettsiae typhi; Rickettsiae tsutsugamushi; Rickettsiae parkeri; Rickettsiae africae; Rickettsia conorii; Rickettsia australis; Rickettsia siberica; Rickettsia japonica; Bartonella Quintana; Bartonella henselae; Bartonella bacilliformis; Coxiella burnetii; Ehrlichia; Anaplasma phagocytophilum; Neorickettsia; Orientia; Klebsiella granulomatis* (formerly called *Calymmatobacterium granulomatis*); *Capnocytophaga*.

Other bacteria include *Mycobacterium tuberculosis; Mycobacterium bovis; Mycobacterium leprae; Mycobacterium avium-intracellulare* or *avium* complex (MAI or MAC); *Mycobacterium ulcerans; Mycobacterium kansasii; Mycobacterium marinum; Mycobacterium scrofulaceum; Mycobacterium fortuitum; Mycobacterium chelonei; Mycobacterium abscessus; Mycoplasma pneumonia; Ureaplasma urealyticum*.

Viruses

A non-exhaustive list of viruses and their species which can be prevented and/or treated by the compostions and methods of the invention include, for example: Abadina virus (Reoviridae), Abelson murine leukemia virus (Retroviridae), Abras virus (Bunyaviridae), Absettarov virus (Flaviviridae), Abu Hammad virus (Bunyaviridae), Abu Mina virus (Bunyaviridae), Acado virus (Reoviridae), Acara virus (Bunyaviridae), Acciptrid herpesvirus (Herpesviridae), *Acheta domestica* densovirus (Parvoviridae), *Acrobasis zelleri* entomopoxvirus (Poxviridae), Adelaide River virus (Rhabdoviridae), Adeno-associated virus (Parvoviridae), *Aedes aegypti* densovirus (Parvoviridae), *Aedes aegypti* entomopoxvirus (Poxviridae), *Aedes albopictus* densovirus (Parvoviridae), *Aedes pseudoscutellaris* densovirus (Parvoviridae), African green monkey cytomegalovirus (Herpesviridae), African green monkey HHV-like virus (Herpesviridae), African green monkey polyomavirus (Papovaviridae), African horse sickness viruses (Reoviridae), African swine fever virus, African swine fever-like viruses, AG-virus (Bunyaviridae), AG-virus, (Bunyaviridae), *Agaricus bisporus* virus, Aguacate virus (Bunyaviridae), Ahlum water-borne virus (Tombusviridae), Aino virus (Bunyaviridae), Akabane virus (Bunyaviridae), AKR (endogenous) murine leukemia virus (Retroviridae), Alajuela virus (Bunyaviridae), Alcelaphine herpesvirus (Herpesviridae), Alenquer virus (Bunyaviridae), Aleutian disease virus (Parvoviridae), Aleutian mink disease virus (Parvoviridae), Alfuy virus (Flaviviridae), Allerton virus (Herpesviridae), Allitrich herpesvirus (Herpesviridae), *Allomyces arbuscula* virus, Almeirim virus (Reoviridae), Almpiwar virus (Rhabdoviridae), Altamira virus, (Reoviridae), Amapari virus (Arenaviridae), American ground squirrel herpesvirus, (Herpesviridae), *Amsacta moorei* entomopoxvirus (Poxviridae), Amyelosis chronic stunt virus (Caliciviridae), Ananindeua virus (Bunyaviridae), Anatid herpesvirus (Herpesviridae), Andasibe virus (Reoviridae), Anhanga virus (Bunyaviridae), Anhembi virus (Bunyaviridae), *Anomala cuprea* entomopoxvirus (Poxviridae), Anopheles A virus (Bunyaviridae), Anopheles virus (Bunyaviridae), Antequera virus (Bunyaviridae), Aotine herpesvirus (Herpesviridae), Apeu virus (Bunyaviridae), *Aphodius tasmaniae* entomopoxvirus (Poxviridae), Apoi virus (Flaviviridae), Aransas Bay virus (Bunyaviridae), Arbia virus (Bunyaviridae), Arboledas virus (Bunyaviridae), Arbroath virus (Reoviridae), Argentine turtle herpesvirus (Herpesviridae), Arkonam virus (Reoviridae), Aroa virus (Flaviviridae), *Arphia conspersa* entomopoxvirus (Poxviridae), Aruac virus (Rhabdoviridae), Arumowot virus (Bunyaviridae), Asinine herpesvirus (Herpesviridae), Atlantic cod ulcus syndrome virus (Rhabodoviridae), Atlantic salmon reovirus Australia (Reoviridae), Atlantic salmon reovirus Canada (Reoviridae), Atlantic salmon reovirus USA (Reoviridae), *Atropa belladorma* virus (Rhabdoviridae), Aucuba bacilliform virus, Badnavirus, Aujeszky's disease virus (Herpesviridae), Aura virus (Togaviridae), Auzduk disease virus (Poxviridae), Avalon virus (Bunyaviridae), Avian adeno-associated virus (Parvoviridae), Avian carcinoma, Mill Hill virus (Retroviridae), Avian encephalomyelitis virus (Picornaviridae), Avian infectious bronchitis virus (Coronaviridae), Avian leukosis virus—RSA (Retroviridae), Avian myeloblastosis virus (Retroviridae), Avian myelocytomatosis virus (Retroviridae), Avian nephrites virus (Picornaviridae), Avian paramyxovirus (Paramyxoviridae), Avian reovirus (Reoviridae), B virus (Parvoviridae), B-lymphotropic papovavirus (Papovaviridae), Babahoya virus (Bunyaviridae), Babanki virus (Togaviridae), Baboon herpesvirus (Herpesviridae), Baboon polyomavirus (Papovaviridae), Bagaza virus (Flaviviridae), *Bahia grande* virus (Rhabdoviridae), Bahig virus (Bunyaviridae), Bakau virus (Bunyaviridae), Baku virus (Reoviridae), Bald eagle herpesvirus (Herpesviridae), Bandia virus (Bunyaviridae), Bangoran virus (Rhabdoviridae), Bangui virus (Bunyaviridae), Banzi virus (Flaviviridae), Barmah Forest virus (Togaviridae), Barranqueras virus (Bunyaviridae), Barur virus (Rhabdoviridae), Batai virus (Bunyaviridae), Batarna virus (Bunyaviridae), Batken virus (Bunyaviridae), Bauline virus (Reoviridae), Beak and feather disease virus (Circoviridae), BeAn virus (Rhabdoviridae), BeAr virus (Bunyaviridae), Bebaru virus (Togaviridae), Belem virus (Bunyaviridae), Belmont virus ((Bunyaviridae)), Belterra virus (Bunyaviridae), Benevides virus (Bunyaviridae), Benfica virus (Bunyaviridae), Berne virus, (Coronaviridae), Berrimah virus (Rhabdoviridae), Bertioga virus (Bunyaviridae), Bhanja virus (Bunyaviridae), Bimbo virus (Rhabdoviridae), Bimiti virus (Bunyaviridae), Birao virus (Bunyaviridae), BivensArm virus (Rhabdoviridae), BK virus (Papovaviridae), Bluetongue viruses (Reoviridae), Bobaya virus (Bunyaviridae), Bobia virus (Bunyaviridae), Bobwhite quail herpesvirus (Herpesviridae), Boid herpesvirus (Herpesviridae), *Bombyx mori* densovirus (Parvoviridae), Boolarra virus (Nodaviridae), Boraceia virus (Bunyaviridae), Border disease virus (Flaviviridae), Boma disease virus, Botambi virus (Bunyaviridae), Boteke virus, (Rhabdoviridae), Bouboui virus (Flaviviridae), Bovine adeno-associated virus (Parvoviridae), Bovine adenoviruses (Adenoviridae), Bovine astrovirus (Astroviridae), Bovine coronavirus (Coronaviridae), Bovine diarrhea virus (Flaviviridae), Bovine encephalitis herpesvirus (Herpesviridae), Bovine enteric calicivirus (Caliciviridae), Bovine enterovirus (Picornaviridae), Bovine ephemeral fever virus (Rhabdoviridae), Bovine herpesvirus (Herpesviridae), Bovine immunodeficiency virus (Retroviridae), Bovine leukemia virus (Retroviridae), Bovine mamillitis virus (Herpesviridae), Bovine papillomavirus (Papovaviridae), Bovine papular stomatitis virus (Poxviridae), Bovine parainfluenza virus (Paramyxoviridae), Bovine parvovirus (Parvoviridae), Bovine polyomavirus (Papovaviridae), Bovine Respiratory Syncytial Virus (Paramyxoviridae), Bovine rhinovirus (Picornaviridae), Bovine syncytial virus (Retroviridae), Bozo virus (Bunyaviridae), Broadhaven virus (Reoviridae), Bruconha virus (Bunyaviridae), Brus Laguna virus (Bunyaviridae), Budgerigar fledgling disease virus (Papovaviridae), Buenaventura virus (Bunyaviridae), Buffalopox virus (Poxviridae), Buggy Creek virus (Togaviridae), Bujaru virus (Bunyaviridae), Bukalasa bat virus (Flaviviridae), Bunyamwera virus (Bunyaviridae), Bunyip creek virus (Reoviridae), Bushbush virus (Bunyaviridae), Bussuquara virus (Flaviviridae), Bwamba virus (Bunyaviridae), Cache Valley virus (Bunyaviridae), Cacipacore virus (Flaviviridae), Caddo Canyon virus (Bunyaviridae), Caimito virus (Bunyaviridae), Calchaqui virus (Rhabdoviridae), California encephalitis virus (Bunyaviridae), California harbor sealpox virus (Poxviridae), *Callistephus chinensis* chlorosis virus (Rhabdoviridae), Callitrichine herpesvirus (Herpesviridae), Camel contagious ecthyma virus (Poxviridae), Camelpox virus (Poxviridae), *Camptochironomus tentans* entomopoxvirus (Poxviridae), Cananeia virus (Bunyaviridae), Canarypox virus (Poxviridae), Candiru virus (Bunyaviridae), Canid herpesvirus (Herpesviridae), Caninde virus (Reoviridae), Canine adeno-associated virus (Parvoviridae), Canine adenovirus (Adenoviridae), Canine calicivirus (Caliciviridae), Canine coronavirus (Coronaviridae), Canine distemper virus (Paramyxoviridae), Canine herpesvirus (Herpesviridae), Canine minute virus (Parvoviridae), Canine oral papillomavirus (Papovaviridae), Canine parvovirus (Parvoviridae), Canna yellow mottle virus (Badnavirus), Cape Wrath virus (Reoviridae), Capim virus (Bunyaviridae), Caprine adenovirus (Adenoviridae), Caprine arthritis encephalitis virus (Retroviridae), Caprine herpesvirus (Herpesviridae), Capuchin herpesvirus AL-(Herpesviridae), Capuchin herpesvirus AP-(Herpesviridae), Carajas virus (Rhabdoviridae), Caraparu virus (Bunyaviridae), Carey Island virus (Flaviviridae), *Casphalia extranea* densovirus (Parvoviridae), Catu virus (Bunyaviridae), Caviid herpesvirus ((Herpesviridae)), CbaAr virus (Bunyaviridae), Cebine herpesvirus (Herpesviridae), Cercopithecine herpesvirus (Herpesviridae), Cervid herpesvirus (Herpesviridae), CG-virus (Bunyaviridae), Chaco virus (Rhabdoviridae), Chagres virus (Bunyaviridae), Chamois contagious ecthyma virus (Poxviridae), Chandipura virus (Rhabdoviridae), Changuinola virus (Reoviridae), Charleville virus (Rhabdoviridae), Chelonid herpesvirus (Herpesviridae), Chelonid herpesvirus (Herpesvirzdae), Chelonid herpesvirus (Herpesviridae), Chenuda virus (Reoviridae), Chick syncytial virus (Retroviridae), Chicken anemia virus (Circoviridae), Chicken parvovirus (Paruoviridae), Chikungunya virus (Togaviridae), Chilibre virus (Bunyaviridae), Chim virus (Bunyaviridae), Chimpanzee herpesvirus (Herpesviridae), *Chironomus attenuatus* entomopoxvirus (Poxviridae), *Chironomus luridus* entomopoxvirus (Poxviridae), *Chironomus plumosus* erltomopoxvirus (Poxviridae), Chobar Gorge virus (Reoviridae), *Choristoneura biennis* entomopoxvirus (Poxviridae), *Choristoneura conflicta* entomopoxvirus (Poxviridae), *Choristoneura diversuma* entomopoxvirus (Poxviridae), *Chorizagrotis auxiliars* entomopoxvirus (Poxviridae), Chub reovirus Germany (Reoviridae), Ciconiid herpesvirus (Herpesviridae), Clo Mor virus (Bunyaviridae), CoAr-virus (Bunyaviridae), Coastal Plains virus (Rhabdoviridae), Cocal virus (Rhabdoviridae), Coital exanthema virus (Herpesviridae), ColAn-virus (Bunyaviridae), Colocasia bobone disease virus, (Rhabdoviridae), Colorado tick fever virus, (Reoviridae), Columbia SK virus, (Picornaviridae), Columbid herpesvirus, (Herpesviridae), Connecticut virus, (Rhabdoviridae), Contagious ecthyma virus, (Poxviridae), Contagious pustular dermatitis virus, (Poxviridae), Corfu virus, (Bunyaviridae), Corriparta virus, (Reoviridae), Cotia virus, (Poxviridae), Cowpox virus, (Poxviridae), Crimean-Congo hemorrhagic fever virus, (Bunyaviridae), CSIRO village virus, (Reoviridae), *Cynara* virus, (Rhabdoviridae), Cyprinid herpesvirus, (Herpesviridae), Dabakala virus, (Bunyaviridae), D'Aguilar virus, (Reoviridae), Dakar bat virus, (Flaviviridae), DakArk virus, (Rhabdoviridae), Deer papillomavirus, (Papovaviridae), *Demodema boranensis* entomopoxvirus, (Poxviridae), Dengue virus, (Flaviviridae), Dengue virus group, (Flaviviridae), Dependovirus, (Parvoviridae), Dera Ghazi Khan virus, (Bunyaviridae), Dera Ghazi Khan virus Group, (Bunyaviridae), *Dermolepida albohirtum* entomopoxvirus, (Poxviridae), Dhori virus, (Orthomyxoviridae), *Diatraea saccharalis* densovirus, (Parvoviridae), Dobrava-Belgrade virus, (Bunyaviridae), Dolphin distemper virus, (Paramyxoviridae), Dolphinpox virus, (Poxviridae), Douglas virus, (Bunyaviridae), Drosophila C virus, (Picornaviridae), Dry Tortugas virus, (Flaviviridae), duck adenovirus, (Adenoviridae), Duck adenovirus, (Adenoviridae), Duck astrovirus, (Astroviridae), Duck hepatitis B virus, (Hepadnaviridae), Duck plague herpesvirus syn. anatid herpesvirus, (Herpesviridae), Dugbe virus, (Bunyaviridae), Duvenhage virus, (Rhabdoviridae), Eastern equine encephalitis virus, (Togaviridae), Ebola virus Filoviridae, *Echinochloa hoja blanca* virus; Genus Tenuivirus, Echinochloa ragged stunt virus, (Reoviridae), ectromelia virus, (Poxviridae), Edge Hill virus, (Flaviviridae), Egtved virus syn. viral hemorrhagic septicemia virus, (Rhabdoviridae), Elapid herpesvirus, (Herpesviridae), Elephant loxondontal herpesvirus, (Herpesviridae), Elephant papillomavirus, (Papovaviridae), Elephantid herpesvirus, (Herpesviridae), Ellidaey virus, (Reoviridae), Embu virus, (Poxviridae), Encephalomyocarditis virus, (Picornaviridae), Enseada virus, (Bunyaviridae), Entamoeba virus, (Rhabdoviridae), Entebbe bat virus, (Flaviviridae), Epizootic hemorrhagic disease viruses, (Reoviridae), Epstein-Barr virus, (Herpesviridae), Equid herpesvirus, (Herpesviridae), Equid herpesvirus, (Nerpesviridae), Equid herpesvirus, (Herpesviridae), Equine abortion herpesvirus, (Herpesviridae), Equine adeno-associated virus, (Parvoviridae), Equine adenovirus, (Adenoviridae), Equine arteritis virus, (Arterivirus), Equine cytomegalovirus, (Herpesviridae), Equine encephalosis viruses, (Reoviridae), Equine herpesvirus, (Herpesviridae), Equine infectious anemia virus, (Retroviridae), Equine papillomavirus, (Papovaviridae), Equine rhinopneumonitis virus, (Herpesviridae), Equine rhinovirus, (Picornaviridae), Eret-virus, (Bunyaviridae), Erinaceid herpesvirus, (Herpesviridae), Erve virus, (Bunyaviridae), Erysimum latent virus, Tymovirus, Esocid herpesvirus, (Herpesviridae), Essaouira virus, (Reoviridae), Estero Real virus, (Bunyaviridae), Eubenangee virus, (Reoviridae), Euonymus fasciation virus, (Rhabdoviridae), European bat virus, (Rhabdoviridae), European brown hare syndrome virus, (Caliciviridae), European elk papillomavirus, (Papovaviridae), European ground squirrel cytomegalovirus, (Herpesviridae), European hedgehog herpesvirus, (Herpesviridae), Everglades virus, (Togaviridae), Eyach virus, (Reoviridae), Facey's Paddock virus, (Bunyaviridae), Falcon inclusion body disease, (Herpesviridae), Falconid herpesvirus, (Herpesviridae), Farallon virus, (Bunyaviridae), Felid herpesvirus, (Herpesviridae), Feline calicivirus, (Caliciviridae), Feline herpesvirus, (Herpesviridae), Feline immunodeficiency virus, (Retroviridae), Feline infectious peritonitis virus, (Coronaviridae), Feline leukemia virus, (Retroviridae), Feline parlleukopenia virus, (Parvoviridae), Feline parvovirus, (Parvoviridae), Feline syncytial virus, (Retroviridae), Feline viral rhinotracheitis virus, (Herpesviridae), Fetal rhesus kidney virus, (Papovaviridae), Field mouse herpesvirus, (Herpesviridae), Figulus subleavis entomopoxvirus, (Poxviridae), Fiji disease virus, (Reoviridae), Fin V-virus, (Bunyaviridae), Finkel-Biskis-Jinkins murine sarcoma virus, (Retroviridae), Flanders virus, (Rhabdoviridae), Flexal virus, (Arenaviridae), Flock house virus, Nodaviridae, Foot-and-mouth disease virus A, (Picornaviridae), Foot-and-mouth disease virus ASIA, (Picornaviridae), Foot-and-mouth disease virus, (Picornaviridae), Forecariah virus, (Bunyaviridae), Fort Morgan virus, (Togaviridae), Fort Sherman virus, (Bunyaviridae), Foula virus, (Reoviridae), Fowl adenoviruses, (Adenoviridae), Fowl calicivirus, (Caliciviridae), Fowlpox virus, (Poxviridae), Fraser Point virus, (Bunyaviridae), Friend murine leukemia virus, (Retroviridae), Frijoles virus, (Bunyaviridae), Frog herpesvirus, (Herpesviridae), Fromede virus, (Reoviridae), Fujinami sarcoma virus, (Retroviridae), Fukuoka virus, (Rhabdoviridae), Gabek Forest virus, (Bunyaviridae), Gadget's Gully virus, (Flaviviridae), *Galleria mellonella* densovirus, (Parvoviridae), Gallid herpesvirus, (Herpesviridae), Gamboa virus, (Bunyaviridae), Gan Gan virus, (Bunyaviridae), Garba virus, (Rhabdoviridae), Gardner-Arnstein feline sarcoma virus, (Retroviridae), *Geochelone carbonaria* herpesvirus, (Herpesviridae), *Geochelone chilensis* herpesvirus, (Herpesviridae), *Geotrupes sylvaticus* entomopoxvirus, (Poxviridae), *Gerbera* symptomless virus, (Rhabdoviridae), Germiston virus, (Bunyaviridae), Getah virus, (Togaviridae), Gibbon ape leukemia virus, (Retroviridae), Ginger chlorotic fleckvirus, Sobemovirus, Glycine mottle virus, Tombusviridae, Goat herpesvirus, (Herpesviridae), Goatpox virus, (Poxviridae), Goeldichironomus holoprasimus entomopoxvirus, (Poxviridae), Golden shiner reovirus, (Reoviridae), Gomoka virus, (Reoviridae), Gomphrena virus, (Rhabdoviridae), Gonometa virus, (Picornaviridae), Goose adenoviruses, (Adenoviridae), Goose parvovirus, (Parvoviridae), Gordil virus, (Bunyaviridae), Gorilla herpesvirus, (Herpesviridae), Gossas virus, (Rhabdoviridae), Grand Arbaud virus, (Bunyaviridae), Gray Lodge virus, (Rhabdoviridae), Gray patch disease agent of green sea turtle, (Herpesviridae), Great Island virus, (Reoviridae), Great Saltee Island virus, (Reoviridae), Great Saltee virus, (Bunyaviridae), Green iguana herpesvirus, (Herpesviridae), Green lizard herpesvirus, (Herpesviridae), Grey kangaroopox virus, (Poxviridae), Grimsey virus, (Reoviridae), Ground squirrel hepatitis B virus, (Hepadnaviridae), Group A-K rotaviruses, (Reoviridae), Gruid herpesvirus, (Herpesviridae), GUU-virus, (Bunyaviridae), Guajara virus, (Bunyaviridae), Guama virus, (Bunyaviridae), Guanarito virus, (Arenaviridae), Guaratuba virus, (Bunyaviridae), Guaroa virus, (Bunyaviridae), Guinea pig cytomegalovirus, (Herpesviridae), Guinea pig herpesvirus, (Herpesviridae), Guinea pig type C oncovirus, (Retroviridae), Gumbo Limbo virus, (Bunyaviridae), Gurupi virus, (Reoviridae), H-virus, (Parvoviridae), H virus, (Bunyaviridae), Hamster herpesvirus, (Herpesviridae), Hamster polyomavirus, (Papovaviridae), Hantaan virus, (Bunyaviridae), Hanzalova virus, (Flaviviridae), Hardy-Zuckerman feline sarcoma virus, (Retroviridae), Hare fibroma virus, (Poxviridae), Hart Park virus, (Rhabdoviridae), Hartebeest herpesvirus, (Herpesviridae), Harvey murine sarcoma virus, (Retroviridae), Hazara virus, (Bunyaviridae), HB virus, (Parvoviridae), Hepatitis virus, (Picornaviridae), Hepatitis virus, (Hepadnaviridae), Hepatitis virus, (Flaviviridae), Herpesvirus M, (Herpesviridae), Herpesvirus papio, (Herpesviridae), Herpesvirus platyrrhinae type, (Herpesviridae), Herpesvirus pottos, (Herpesviridae), Herpesvirus saimiri, (Herpesviridae), Herpesvirus salmonis, (Herpesviridae), Herpesvirus sanguinus, (Herpesviridae), Herpesvirus scophthalmus, (Herpesviridae), Herpesvirus sylvilagus, (Herpesviridae), Herpesvirus T, (Herpesviridae), Herpesvirus tarnarinus, (Herpesviridae), Highlands J virus, (Togaviridae), Hirame rhabdovirus, (Rhabdoviridae), Hog cholera virus, (Flaviviridae), HoJo virus, (Bunyaviridae), Hepatitis delta virus, Satellites, Deltavirus, Hsiung Kaplow herpesvirus, (Herpesviridae), Hepatitis E virus, (Caliciviridae), Hepatopancreatic parvo-like virus of shrimps, (Parvoviridae), Heron hepatitis B virus, (Hepadnaviridae), *Herpes ateles*, (Herpesviridae), *Herpes simiae* virus, (Herpesviridae), *Herpes simplex* virus, (Herpesviridae), Herpes virus B, (Herpesviridae), Herpesvirus aotus, (Herpesviridae), Herpesvirus ateles strain, (Herpesviridae), Herpesvirus cuniculi, (Herpesviridae), Herpesvirus cyclopsis, (Herpesviridae), Huacho virus, (Reoviridae), Hughes virus, (Bunyaviridae), Human adenoviruses, (Adenoviridae), Human astrovirus, (Astroviridae), Human calicivirus, (Caliciviridae), Human caliciviruses, (Caliciviridae), Human coronavirus E, (Coronaviridae), Human coronavirus OC, (Coronaviridae), Severe Acute Respiratory Syndrome Coronavirus (SARS-CoV), including Severe Acute Respiratory Syndrome Coronavirus 2 (SARS-CoV-2), Middle East Respiratory Syndrome Coronavirus (MERS-CoV), Human coxsackievirus, (Picornaviridae), Human cytomegalovirus, (Herpesviridae), Human echovirus, (Picornaviridae), Human enterovirus, (Picornaviridae), Human foamy virus, (Retroviridae), Human herpesvirus, (Herpesviridae), Human herpesvirus, Nerpesviridae, Human herpesvirus, (Herpesviridae), Human immunodeficiency virus, (Retroviridae), Human papillomavirus, (Papovaviridae), Human parainfluenza virus, (Paramyxoviridae), Human poliovirus, (Picornaviridae), Human Respiratory Syncytial Virus, (Paramyxoviridae), Human rhinovirus, (Picornaviridae), Human spumavirus, (Retroviridae), Human T-lymphotropic virus, (Retroviridae), Humpty Doo virus, (Rhabdoviridae), HV-virus, (Bunyaviridae), Hypr virus, (Flaviviridae), Laco virus, (Bunyaviridae), Ibaraki virus, (Reoviridae), Icoaraci virus, (Bunyaviridae), Ictalurid herpesvirus, (Herpesviridae), Len virus, (Reoviridae), Ife virus, (Reoviridae), Iguanid herpesvirus, (Herpesviridae), Ilesha virus, (Bunyaviridae), Ilheus virus, (Flaviviridae), Inclusion body rhinitis virus, (Herpesviridae), Infectious bovine rhinotracheitis virus, (Herpesviridae), Infectious bursal disease virus, Birnaviridae, Infectious hematopoietic necrosis virus, (Rhabdoviridae), Infectious laryngotracheitis virus, (Herpesviridae), Infectious pancreatic necrosis virus, Birnavirzdae, InfluenzaA virus (A/PR// (HN), (Orthomyxoviridae), Influenza B virus (B/Lee/), (Orthomyxoviridae), Influenza C virus (C/California/), (Orthomyxoviridae), Ingwavuma virus, (Bunyaviridae), Inini virus, (Bunyaviridae), Inkoo virus, (Bunyaviridae), Inner Frame virus, (Reoviridae), Ippy virus, (Arenaviridae), Irituia virus, (Reoviridae), Isfahan virus, (Rhabdoviridae), Israel turkey meningoencephalitis virus, (Flaviviridae), Issyk-Kul virus, (Bunyaviridae), Itaituba virus, (Bunyaviridae), Itaporanga virus, (Bunyaviridae), Itaqui virus, (Bunyaviridae), Itimirrn virus, (Bunyaviridae), Itupiranga virus, (Reoviridae), Jaagsiekte virus, (Retroviridae), Jacareacanga virus, (Reoviridae), Jamanxi virus, (Reoviridae), Jamestown Canyon virus, (Bunyaviridae), Japanaut virus, (Reoviridae), Japanese encephalitis virus, (Flaviviridae), Jan virus, (Reoviridae), JC virus, (Papovaviridae), Joa virus, (Bunyaviridae), Joinjakaka virus, (Rhabdoviridae), Juan Diaz virus, (Bunyaviridae), Jugra virus, (Flaviviridae), Juncopox virus, (Poxviridae), Junin virus, (Arenaviridae), *Junonia coenia* densovirus, (Parvoviridae), Jurona virus, (Rhabdoviridae), Jutiapa virus, (Flaviviridae), K virus, (Papovaviridae), K virus, (Bunyaviridae), Kachemak Bay virus, (Bunyaviridae), Kadarn virus, (Flaviviridae), Kaeng Khoi virus, (Bunyaviridae), Kaikalur virus, (Bunyaviridae), Kairi virus, (Bunyaviridae), Kaisodi virus, (Bunyaviridae), Kala Iris virus, (Reoviridae), Kamese virus, (Rhabdoviridae), Karnmavanpettai virus, (Reoviridae), Kannamangalam virus, (Rhabdoviridae), Kao Shuan virus, (Bunyaviridae), Karimabad virus, (Bunyaviridae), Karshi virus, (Flaviviridae), Kasba virus, (Reoviridae), Kasokero virus, (Bunyaviridae), Kedougou virus, (Flaviviridae), Kemerovo virus, (Reoviridae), Kenai virus, (Reoviridae), Kennedya virus Y, Potyviridae, Kern Canyon virus, (Rhabdoviridae), Ketapang virus, (Bunyaviridae), Keterah virus, (Bunyaviridae), Keuraliba virus, (Rhabdoviridae), Keystone virus, (Bunyaviridae), Kharagysh virus, (Reoviridae), Khasan virus, (Bunyaviridae), Kilham rat virus, (Parvoviridae), Kimberley virus, (Rhabdoviridae), Kindia virus, (Reoviridae), Kinkajou herpesvirus, (Herpesviridae), Kirsten murine sarcoma virus, (Retroviridae), Kismayo virus, (Bunyaviridae), Klamath virus, (Rhabdoviridae), Kokob era virus, (Flaviviridae), Kolongo virus, (Rhabdoviridae), Koolpinyah virus, (Rhabdoviridae), Koongol virus, (Bunyaviridae), Kotonkan virus, (Rhabdoviridae), Koutango virus, (Flaviviridae), Kowanyama virus, (Bunyaviridae), Kumlinge virus, (Flaviviridae), Kunjin virus, (Flaviviridae), Kwatta virus, (Rhabdoviridae), Kyzylagach virus, (Togaviridae), La Crosse virus, (Bunyaviridae), La Joya virus, (Rhabdoviridae), La-Piedad-Michoacan-Mexico virus, (Paramyxoviridae), Lacertid herpesvirus, (Herpesviridae), Lactate dehydrogenase-elevating virus, (Arterivirus), Lagos bat virus, (Rhabdoviridae), Lake Clarendon virus, (Reoviridae), Lake Victoria cormorant herpesvirus, (Herpesviridae), Langat virus, Flaviviridae, Langur virus, (Retroviridae), Lanj an virus, (Bunyaviridae), Lapine parvovirus, (Parvoviridae), Las Maloyas virus, (Bunyaviridae), Lassa virus, (Arenaviridae), Lato river virus, (Tombusviridae), Le Dantec virus, (Rhabdoviridae), Leanyer virus, (Bunyaviridae), Lebombo virus, (Reoviridae), Lednice virus, (Bunyaviridae), Lee virus, (Bunyaviridae), Leporid herpesvirus, (Herpesviridae), *Leucorrhinia dubia* densovirus, (Parvoviridae), Lipovnik virus, (Reoviridae), Liverpool vervet monkey virus, (Herpesviridae), Llano Seco virus, (Reoviridae), *Locusta migratona* entomopoxvirus, (Poxviridae), Lokem virus, (Bunyaviridae), Lone Star virus, (Bunyaviridae), Lorisine herpesvirus, (Herpesviridae), Louping ill virus, Flaviviridae, Lucke frog herpesvirus, (Herpesviridae), Lum virus, (Parvoviridae), Lukuni virus, (Bunyaviridae), Lumpy skin disease virus, (Poxviridae), Lundy virus, (Reoviridae), *Lymantria dubia* densovirus, (Parvoviridae), Lymphocytic choriomeningitis virus, (Arenaviridae), Machupo virus, (Arenaviridae), Macropodid herpesvirus (Herpesviridae), Madrid virus, (Bunyaviridae), Maguari virus, (Bunyaviridae), Main Drain virus, (Bunyaviridae), Malakal virus, (Rhabdoviridae), Malignant catarrhal fever virus of European cattle, (Herpesviridae), Malpais Spring virus, (Rhabdoviridae), *Malva silvestris* virus, (Rhabdoviridae), Manawa virus, (Bunyaviridae), Manawatu virus, (Nodaviridae), Manitoba virus, (Rhabdoviridae), Manzanilla virus, (Bunyaviridae), Map turtle herpesvirus, (Herpesviridae), Mapputta virus, (Bunyaviridae), Maprik virus, (Bunyaviridae), Maraba virus, (Rhabdoviridae), Marburg virus, (Filoviridae), Marco virus, (Rhabdoviridae), Marek's disease herpesvirus, (Herpesviridae), Marituba virus, (Bunyaviridae), Marmodid herpesvirus, (Herpesviridae), Marmoset cytomegalovirus, (Herpesviridae), Marmoset herpesvirus, (Herpesviridae), Marmosetpox virus, (Poxviridae), Marrakai virus, (Reoviridae), Mason-Pfizer monkey virus, (Retroviridae), Masou salmon reovirus, (Reoviridae), Matruh virus, (Bunyaviridae), Matucare virus, (Reoviridae), Mayaro virus, (Togaviridae), Mboke virus, (Bunyaviridae), Meaban virus, (Flaviviridae), Measles (Edmonston) virus, (Paramyxoviridae), Medical Lake macaque herpesvirus, (Herpesviridae), *Melanoplus sanguinipes* entomopoxvirus, (Poxviridae), Melao virus, (Bunyaviridae), Meleagrid herpesvirus, (Herpesviridae), Melilotus latent virus, (Rhabdoviridae), *Melolontha melolontha* entomopoxvirus, (Poxviridae), Mengovirus, (Picornaviridae), Mermet virus, (Bunyaviridae), Mice minute virus, (Parvoviridae), Mice pneumotropic virus, (Papovaviridae), *Microtus pennsylvanicus* herpesvirus, (Herpesviridae), Middelburg virus, (Togaviridae), Miller's nodule virus, (Poxviridae), Mill Door virus, (Reoviridae), Minatitlan virus, (Bunyaviridae), Mink calicivirus, (Caliciviridae), Mink enteritis virus, (Parvoviridae), Minnal virus, (Reoviridae), *Mirabilis mosaic* virus, Caulimovirus, Mirim virus, (Bunyaviridae), Mitchell river virus, (Reoviridae), Mobala virus, (Arenaviridae), Modoc virus, (Flaviviridae), Moju virus, (Bunyaviridae), Mojui dos Campos virus, (Bunyaviridae), Mokola virus, (Rhabdoviridae), Molluscum contagiosum virus, (Poxviridae), Molluscum-likepox virus, (Poxviridae), Moloney murine sarcoma virus, (Retroviridae), Moloney virus, (Retroviridae), Monkey pox virus, (Poxviridae), Mono Lake virus, (Reoviridae), *Montana myotis* leukoencephalitis virus, (Flaviviridae), Monte Dourado virus, (Reoviridae), Mopeia virus, (Arenaviridae), Moriche virus, (Bunyaviridae), Mosqueiro virus, (Rhabdoviridae), Mossuril virus, (Rhabdoviridae), Mount Elgon bat virus, (Rhabdoviridae), Mouse cytomegalovirus, (Herpesviridae), Mouse Elberfield virus, (Picornaviridae), Mouse herpesvirus strain, (Herpesviridae), Mouse mammary tumor virus, (Retroviridae), Mouse thymic herpesvirus, (Herpesviridae), Movar herpesvirus, (Herpesviridae), Mucambo virus, (Togaviridae), Mudjinbarry virus, (Reoviridae), Muir Springs virus, (Rhabdoviridae), Mule deerpox virus, (Poxviridae), Multimammate mouse papillomavirus, (Papovaviridae), Mumps virus, (Paramyxoviridae), Murid herpesvirus, (Herpesviridae), Murine adenovirus, (Adenoviridae), Z murine adenovirus, (Adenoviridae), Murine hepatitis virus, (Coronaviridae), Murine herpesvirus, (Herpesviridae), Murine leukemia virus, (Retroviridae), Murine parainfluenza virus, (Paramyxoviridae), Murine poliovirus, (Picornaviridae), Murine polyomavirus, (Papovaviridae), Murray Valley encephalitis virus, (Flaviviridae), Murre virus, (Bunyaviridae), Murutucu virus, (Bunyaviridae), Mykines virus, (Reoviridae), Mynahpox virus, (Poxviridae), Myxoma virus, (Poxviridae), Nairobi sheep disease virus, (Bunyaviridae), Naranjal virus, (Flaviviridae), Nasoule virus, (Rhabdoviridae), Navarro virus, (Rhabdoviridae), Ndelle virus, (Reoviridae), Ndumu virus, (Togaviridae), Neckar river virus, (Tombusviridae), Negishi virus, (Flaviviridae), Nelson Bay virus, New Minto virus, (Rhabdoviridae), Newcastle disease virus, (Paramyxoviridae), Ngaingan virus, (Rhabdoviridae), Ngari virus, (Bunyaviridae), Ngoupe virus, (Reoviridae), Nile crocodilepox virus, (Poxviridae), Nique virus, (Bunyaviridae), Nkolbisson virus, (Rhabdoviridae), Nola virus, (Bunyaviridae), North Clett virus, (Reoviridae), North End virus, (Reoviridae), Northern cereal mosaic virus, (Rhabdoviridae), Northern pike herpesvirus, (Herpesviridae), Northway virus, (Bunyaviridae), NorwaLk virus, (Caliciviridae), Ntaya virus, (Flaviviridae), Nugget virus, (Reoviridae), Nyabira virus, (Reoviridae), Nyamanini virus, Unassigned, Nyando virus, (Bunyaviridae), Oak-Vale virus, (Rhabdoviridae), Obodhiang virus, (Rhabdoviridae), Oceanside virus, (Bunyaviridae), Ockelbo virus, (Togaviridae), Odrenisrou virus, (Bunyaviridae), *Oedaleus senegalensis* entomopoxvirus, (Poxviridae), Oita virus, (Rhabdoviridae), Okhotskiy virus, (Reoviridae), Okola virus, (Bunyaviridae), Olifantsvlei virus, (Bunyaviridae), Omo virus, (Bunyaviridae), Omsk hemorrhagic fever virus, (Flaviviridae), *Onchorhynchus masou* herpesvirus, (Herpesviridae), O'nyong-nyong virus, (Togaviridae), *Operophtera brurnata* entomopoxvirus, (Poxviridae), Orangutan herpesvirus, (Herpesviridae), Orf virus, (Poxviridae), Oriboca virus, (Bunyaviridae), Oriximina virus, (Bunyaviridae), Oropouche virus, (Bunyaviridae), Orungo virus, (Reoviridae), Oryctes rhinoceros virus, Unassigned, Ossa virus, (Bunyaviridae), Ouango virus, (Rhabdoviridae), Oubi virus, (Bunyaviridae), Ourem virus, (Reoviridae), Ovine adeno-associated virus, (Parvoviridae), Ovine adenoviruses, (Adenoviridae), (Astroviridae), Ovine herpesvirus, (Herpesviridae), Ovine pulmonary adenocarcinoma virus, (Retroviridae), Owl hepatosplenitis herpesvirus, (Herpesviridae), P virus, (Bunyaviridae), Pacheco's disease virus, (Herpesviridae), Pacora virus, (Bunyaviridae), Pacui virus, (Bunyaviridae), Pahayokee virus, (Bunyaviridae), Palestina virus, (Bunyaviridae), Palyam virus, (Reoviridae), Pan herpesvirus, (Herpesviridae), Papio Epstein-Barr herpesvirus, (Herpesviridae), Para virus, (Bunyaviridae), Pararnushir virus, (Bunyaviridae), Parana virus, (Arenaviridae), Parapoxvirus of red deer in New Zealand, (Poxviridae), Paravaccinia virus, (Poxviridae), Parma wallaby herpesvirus, (Herpesviridae), Paroo river virus, (Reoviridae), Parrot herpesvirus, (Herpesviridae), Parry Creek virus, (Rhabdoviridae), Pata virus, (Reoviridae), Pates monkey herpesvirus pH delta, (Herpesviridae), Pathum Thani virus, (Bunyaviridae), Patois virus, (Bunyaviridae), Peaton virus, (Bunyaviridae), Percid herpesvirus, (Herpesviridae), Perdicid herpesvirus, (Herpesviridae), Perinet virus, (Rhabdoviridae), Peripianata fuliginosa densovirus, (Parvoviridae), Peste-des-petits-ruminants virus, (Paramyxoviridae), Petevo virus, (Reoviridae), Phalacrocoracid herpesvirus, (Herpesviridae), Pheasant adenovirus, (Adenoviridae), Phnom-Penh bat virus, (Flaviviridae), Phocid herpesvirus, (Herpesviridae), Phocine (seal) distemper virus, (Paramyxoviridae), Pichinde virus, (Arenaviridae), Picola virus, (Reoviridae), *Pieris rapae* densovirus, (Parvoviridae), Pigeon herpesvirus, (Herpesviridae), Pigeonpox virus, (Poxviridae), Badnavirus Piry virus, (Rhabdoviridae), Pisum virus, (Rhabdoviridae), Pixuna virus, (Togaviridae), Playas virus, (Bunyaviridae), Pleuronectid herpesvirus, (Nerpesviridae), Pneumonia virus of mice, (Paramyxoviridae), Pongine herpesvirus, (Herpesviridae), Pongola virus, (Bunyaviridae), Ponteves virus, (Bunyaviridae), Poovoot virus, (Reoviridae), Porcine adenoviruses, (Adenoviridae), Porcine astrovirus, (Astroviridae), Porcine circovirus, Circoviridae, Porcine enteric calicivirus, (Caliciviridae), Porcine enterovirus, (Picornaviridae), Porcine epidemic diarrhea virus, (Coronaviridae), Porcine hemagglutinating encephalomyelitis virus, (Coronaviridae), Porcine parvovirus, (Parvoviridae), Porcine respiratory and reproductive syndrome, (Arterivirus), Porcine rubulavirus, (Paramyxoviridae), Porcine transmissible gastroenteritis virus, (Coronaviridae), Porcine type C oncovirus, (Retroviridae), Porton virus, (Rhabdoviridae), Potosi virus, (Bunyaviridae), Powassan virus, (Flaviviridae), Precarious Point virus, (Bunyaviridae), Pretoria virus, (Bunyaviridae), Primate calicivirus, (Caliciviridae), Prospect Hill virus, (Bunyaviridae), *Pseudaletia includens* densovirus, (Parvoviridae), Pseudocowpox virus, (Poxviridae), Pseudolumpy skin disease virus, (Herpesviridae), Pseudorabies virus, (Herpesviridae), Psittacid herpesvirus, (Herpesviridae), Psittacinepox virus, (Poxviridae), Puchong virus, (Rhabdoviridae), Pueblo Viejo virus, (Bunyaviridae), Puffin Island virus, (Bunyaviridae), Punta Salinas virus, (Bunyaviridae), Punta Toro virus, (Bunyaviridae), Purus virus, (Reoviridae), Puumala virus, (Bunyaviridae), Qalyub virus, (Bunyaviridae), Quailpox virus, (Poxviridae), Quokkapox virus, (Poxviridae), Rabbit coronavirus, (Coronaviridae), Rabbit fibroma virus, (Poxviridae), Rabbit hemorrhagic disease virus, (Caliciviridae), Rabbit kidney vacuolating virus, (Papovaviridae), Rabbit oral papillomavirus, (Papovaviridae), Rabbitpox virus, (Poxviridae), Rabies virus, (Rhabdoviridae), Raccoon parvovirus, (Parvoviridae), Raccoonpox virus, (Poxviridae), Radi virus, (Rhabdoviridae), Rangifer tarandus herpesvirus, (Herpesviridae), Ranid herpesvirus, (Herpesviridae), Raphanus virus, (Rhabdoviridae), Rat coronavirus, (Coronaviridae), Rat cytomegalovirus, (Herpesviridae), Rat virus, R, (Parvoviridae), Raza virus, (Bunyaviridae), Razdan virus, (Bunyaviridae), Red deer herpesvirus, (Herpesviridae), Red kangaroopox virus, (Poxviridae), Reed Ranch virus, (Rhabdoviridae), herpesvirus, (Herpesviridae), Reindeer papillomavirus, (Papovaviridae), Reptile calicivirus, (Caliciviridae), Resistencia virus, (Bunyaviridae), Restan virus, (Bunyaviridae), Reticuloendotheliosis virus, (Retroviridae), Rhesus HHV-like virus, (Herpesviridae), Rhesus leukocyte associated herpesvirus strain, (Herpesviridae), Rhesus monkey cytomegalovirus, (Herpesviridae), Rhesus monkey papillomavirus, (Papovaviridae), Rheumatoid arthritis virus, (Parvoviridae), Rift Valley fever virus, (Bunyaviridae), Rinderpest virus, (Paramyxoviridae), Rio Bravo virus, (Flaviviridae), Rio Grande virus, (Bunyaviridae), RML virus, (Bunyaviridae), Rochambeau virus, (Rhabdoviridae), Rocio virus, (Flaviviridae), Ross River virus, (Togaviridae), Rost Islands virus, (Reoviridae), Rous sarcoma virus, (Retroviridae), Royal farm virus, (Flaviuiridae), RT parvovirus, (Parvoviridae), Rubella virus, (Togaviridae), Russian spring summer encephalitis virus, (Flaviviridae), S-virus, (Reoviridae), SA virus, (Herpesviridae), Sabio virus, (Arenaviridae), Sabo virus, (Bunyaviridae), Saboya virus, (Flaviviridae), Sacbrood virus, (Picornaviridae), Sagiyama virus, (Togaviridae), Saimiriine herpesvirus, (Herpesviridae), SaintAbb's Head virus, (Reoviridae), Saint-Floris virus, (Bunyaviridae), Sakhalin virus, (Bunyaviridae), Sal Viej a virus, (Flaviviridae), Salanga virus, (Bunyaviridae), Salangapox virus, (Poxviridae), Salehabad virus, (Bunyaviridae), Salmonid herpesvirus, (Herpesviridae), Salmonis virus, (Rhabdoviridae), Sambucus vein clearing virus, (Rhabdoviridae), SanAngelo virus, (Bunyaviridae), San Juan virus, (Bunyaviridae), San Miguel sealion virus, (Caliciviridae), San Perlita virus, (Flaviviridae), Sand rat nuclear inclusion agents, (Herpesviridae), Sandfly fever Naples virus, (Bunyaviridae), Sandfly fever Sicilian virus, (Bunyaviridae), Sandjimba virus, (Rhabdoviridae), Sango virus, (Bunyaviridae), Santa Rosa virus, (Bunyaviridae), Santarem virus, (Bunyaviridae), Sapphire II virus, (Bunyaviridae), Saraca virus, (Reoviridae), *Sarracenia purpurea* virus, (Rhabdoviridae), Sathuperi virus, (Bunyaviridae), Saumarez Reef virus, (Flaviviridae), Sawgrass virus, (Rhabdoviridae), *Schistocerca gregaria* entomopoxvirus, (Poxviridae), Sciurid herpesvirus, (Herpesviridae), Sciurid herpesvirus, (Herpesviridae), Sealpox virus, (Poxviridae), Seletar virus, (Reoviridae) Semliki Forest virus, (Togaviridae), Sena Madureira virus, (Rhabdoviridae), Sendai virus, (Paramyxoviridae), Seoul Virus, (Bunyaviridae), Sepik virus, (Flaviviridae), Serra do Navio virus, (Bunyaviridae), Shamonda virus, (Bunyaviridae), Shark River virus, (Bunyaviridae), Sheep associated malignant catarrhal fever of, (Herpesviridae), Sheep papillomavirus, (Papovaviridae), Sheep pulmonary adenomatosis associated herpesvirus, (Herpesviridae), Sheeppox virus, (Poxviridae), Shiant Islands virus, (Reoviridae), Shokwe virus, (Bunyaviridae), Shope fibroma virus, (Poxviridae), Shuni virus, (Bunyaviridae), *Sibine fusca* densovirus, (Parvoviridae), Sigma virus, (Rhabdoviridae), Sikte water-borne virus, (Tombusviridae), Silverwater virus, (Bunyaviridae), virus, (Bunyaviridae), Simian adenoviruses, (Adenoviridae), Simian agent virus, (Papovaviridae), Simian enterovirus, (Picornaviridae), Simian foamy virus, (Retroviridae), Simian hemorrhagic fever virus, (Arterivirus), Simian hepatitis A virus, (Picornaviridae), Simian immunodeficiency virus, (Retroviridae), Simian parainfluenza virus, (Paramyxoviridae), Simian rotavirus SA, (Reoviridae), Simian sarcoma virus, (Retroviridae), Simian T-lymphotropic virus, (Retroviridae), Simian type D virus, (Retroviridae), Simian vancella herpesvirus, (Herpesviridae), Simian virus, (Papovaviridae), *Simulium vittatum* densovirus, (Parvoviridae), Sindbis virus, (Togaviridae), Sixgun city virus, (Reoviridae), Skunkpox virus, (Poxviridae), Smelt reovirus, (Reoviridae), Snakehead rhabdovirus, (Rhabdoviridae), Snowshoe hare virus, (Bunyaviridae), Snyder-Theilen feline sarcoma virus, (Retroviridae), Sofyn virus, (Flaviviridae), Sokoluk virus, (Flaviviridae), Soldado virus, (Bunyaviridae), Somerville virus, (Reoviridae), Sparrowpox virus, (Poxviridae), Spectacled caimanpox virus, (Poxviridae), SPH virus, (Arenaviridae), Sphenicid herpesvirus, (Herpesviridae), Spider monkey herpesvirus, (Herpesviridae), Spondweni virus, (Flaviviridae), Spring viremia of carp virus, (Rhabdoviridae), Squirrel fibroma virus, (Poxviridae), Squirrel monkey herpesvirus, (Herpesviridae), Squirrel monkey retrovirus, (Retroviridae), SR-virus, (Bunyaviridae), Sripur virus, (Rhabdoviridae), StAbbs Head virus, (Bunyaviridae), St. Louis encephalitis virus, (Flaviviridae), Starlingpox virus, (Poxviridae), Stratford virus, (Flaviviridae), Strigid herpesvirus, (Herpesviridae), Striped bass reovirus, (Reoviridae), Striped Jack nervous necrosis virus, (Nodaviridae), Stump-tailed macaque virus, (Papovaviridae), Suid herpesvirus, (Herpesviridae), Sunday Canyon virus, (Bunyaviridae), Sweetwater Branch virus, (Rhabdoviridae), Swine cytomegalovirus, (Herpesviridae), Swine infertility and respiratory syndrome virus, (Arterivirus), Swinepox virus, (Poxviridae), Tacaiuma virus, (Bunyaviridae), Tacaribe virus, (Arenaviridae), Taggart virus, (Bunyaviridae), Tahyna virus, (Bunyaviridae), Tai virus, (Bunyaviridae), Taiassui virus, (Bunyaviridae), Tamana bat virus, (Flaviviridae), Tamdy virus, (Bunyaviridae), Tamiami virus, (Arenaviridae), Tanapox virus, (Poxviridae), Tanga virus, (Bunyaviridae), Tanjong Rabok virus, (Bunyaviridae), Taro bacilliform virus, (Badnavirus), Tataguine virus, (Bunyaviridae), Taterapox virus, (Poxviridae), Tehran virus, (Bunyaviridae), Telok Forest virus, (Bunyaviridae), Tembe virus, (Reoviridae), Tembusu virus, (Flaviviridae), Tench reovirus, (Reoviridae), Tensaw virus, (Bunyaviridae), Tephrosia symptomless virus, (Tombusviridae), Termeil virus, (Bunyaviridae), Tete virus, (Bunyaviridae), Thailand virus, (Bunyaviridae), Theiler's murine encephalomyelitis virus, (Picornaviridae), Thermoproteus virus, Lipothrixviridae, Thiafora virus, (Bunyaviridae), Thimiri virus, (Bunyaviridae), Thogoto virus, (Orthomyxoviridae), Thormodseyjarklettur virus, (Reoviridae), Thottapalayam virus, (Bunyaviridae), Tibrogargan virus, (Rhabdoviridae), Tick-borne encephalitis virus, (Flaviviridae), Tillamook virus, (Bunyaviridae), Tilligerry virus, (Reoviridae), Timbo virus, (Rhabdoviridae), Tilmboteua virus, (Bunyaviridae), Tilmaroo virus, (Bunyaviridae), Tindholmur virus, (Reoviridae), Tlacotalpan virus, (Bunyaviridae), Toscana virus, (Bunyaviridae), Tradescantia/Zebrina virus, Potyviridae, Trager duck spleen necrosis virus, (Retroviridae), Tree shrew adenovirus, (Adenoviridae), Tree shrew herpesvims, (Herpesviridae), Triatoma virus, (Picornaviridae), Tribec virus, (Reoviridae), Trivittatus virus, (Bunyaviridae), Trombetas virus, (Bunyaviridae), Trubanarnan virus, (Bunyaviridae), Tsuruse virus, (Bunyaviridae), Tucunduba virus, (Bunyaviridae), Tumor virus X, (Parvoviridae), Tupaia virus, (Rhabdoviridae), Tupaiid herpesvirus, (Herpesviridae), Turbot herpesvirus, (Herpesviridae), Turbot reovirus, (Reoviridae), Turkey adenoviruses, (Adenoviridae), Turkey coronavirus, (Coronaviridae), Turkey herpesvirus, (Herpesviridae), Turkey rhinotracheitis virus, (Paramyxoviridae), Turkeypox virus, (Poxviridae), Turlock virus, (Bunyaviridae), Turuna virus, (Bunyaviridae), Tyuleniy virus, (Flaviviridae) Uasin Gishu disease virus, (Poxviridae), Uganda S virus, (Flaviviridae), Ulcerative disease rhabdovirus, (Rhabdoviridae), Umatilla virus, (Reoviridae), Umbre virus, (Bunyaviridae), Una virus, (Togaviridae), Upolu virus, (Bunyaviridae), UR sarcoma virus, (Retroviridae), Urucuri virus, (Bunyaviridae), Usutu virus, (Flaviviridae), Uting a virus, (Bunyaviridae), Utive virus, (Bunyaviridae), Uukuniemi virus, (Bunyaviridae) Vaccinia subspecies, (Poxviridae), Vaccinia virus, (Poxviridae), Vaeroy virus, (Reoviridae), Varicella-zoster virus, (Herpesviridae), Variola virus, (Poxviridae), Vellore virus, (Reoviridae), Venezuelan equine encephalitis virus, (Togaviridae), Vesicular exanthema of swine virus, (Caliciviridae), Vesicular stomatitis Alagoas virus, Rhabdoviridae, Vesicular stomatitis Indiana virus, (Rhabdoviridae), Vesicular stomatitis New Jersey virus, (Rhabdoviridae), Vilyuisk virus, (Picornaviridae), Vinces virus, (Bunyaviridae), Viper retrovirus, (Retroviridae), Viral hemorrhagic septicemia virus, (Rhabdoviridae), Virgin River virus, (Bunyaviridae), Virus III, (Herpesviridae), Visna/maedi virus, (Retroviridae), Volepoxvirus, (Poxviridae), Wad Medani virus, (Reoviridae), Wallal virus, (Reoviridae), Walleye epidermal hyperplasia, (Herpesviridae), Wanowrie virus, (Bunyaviridae), Warrego virus, (Reoviridae), Weddel water-borne virus, Tombusviridae, Weldona virus, (Bunyaviridae), Wesselsbron virus, (Flaviviridae), West Nile virus, (Flaviviridae), Western equine encephalitis virus, (Togaviridae), Wexford virus, (Reoviridae), Whataroa virus, (Togaviridae), Wildbeest herpesvirus, (Herpesviridae), Witwatersrand virus, (Bunyaviridae), Wongal virus, (Bunyaviridae), Wongorr virus, (Reoviridae), Woodchuck hepatitis B virus, (Hepadnaviridae), Woodchuck herpesvirus marmota, (Herpesviridae), Woolly monkey sarcoma virus, (Retroviridae), Wound tumor virus, (Reoviridae), WVU virus, (Reoviridae), WW virus, (Reoviridae), Wyeomyia virus, (Bunyaviridae), Xiburema virus, (Rhabdoviridae), Xingu virus, (Bunyaviridae), Y sarcoma virus, (Retroviridae), Yaba monkey tumor virus, (Poxviridae), Yaba-virus, (Bunyaviridae), Yaba-virus, (Bunyaviridae), Yacaaba virus, (Bunyaviridae), Yaounde virus, (Flaviviridae), Yaquina Head virus, (Reoviridae), Yata virus, (Rhabdoviridae), Yellow fever virus, (Flaviviridae), Yogue virus, (Bunyaviridae), Yokapox virus, (Poxviridae), Yokase virus, (Flaviviridae), Yucca baciliform virus, Badnavirus, Yug Bogdanovac virus, (Rhabdoviridae), Zaliv Terpeniya virus, (Bunyaviridae), *Zea mays* virus, (Rhabdoviridae), Zegla virus, (Bunyaviridae), Zika virus, (Flaviviridae), Zirqa virus, (Bunyaviridae).

Combination Therapy

Compositions and methods for treating and/or preventing conditions as set forth herein in a subject are provided by the present invention. Methods of treating and/or preventing a condition in a subject are provided according to embodiments of the present invention which includes administering, in combination, a compound of the invention and at least one additional therapeutic agent selected from the group consisting of at least one anti-anxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof, in therapeutically effective amounts. In certain embodiments the agents are administered in the same dosage form. In certain embodiments the therapeutic agents are administered separately. In particular embodiments, the invention provides a composition a therapeutically effective amount of a GR antagonist and at least one additional therapeutic agent selected from the group consisting of at least one antianxiety drug, at least one anti-depressant drug, and at least one neuroleptic medication and combinations thereof, wherein the at least one anti-anxiety drug is selected from the group consisting of alprazolam, bromazepam, diazepam, lorazepam, clonazepam, temazepam, oxazepam, flunitrazepam, triazolam, chlordiazepoxide, flurazepam, estazolam, nitrazepam, and pharmaceutically acceptable salts, isomers, and mixtures thereof; and/or at least one anti-depressant drug selected from the group consisting of citalopram, escitalopram oxalate, fluoxetine, fluvoxamine, paroxetine, sertraline, dapoxetine; venlafaxine and duloxetine; harmaline, iproniazid, isocarboxazid, nialamide, pargyline, phenelzine, selegiline, toloxatone, tranylcypromine, brofaromine, moclobemide; amitriptyline, amoxapine, butriptyline, clomipramine, desipramine, dibenzepin, dothiepin, doxepin, imipramine, iprindole, lofepramine, melitracen, nortriptyline, opipramol, protriptyline, trimipramine; maprotiline, mianserin, nefazodone, trazodone, and pharmaceutically acceptable salts, isomers, and combinations thereof, and/or at least one neuroleptic drug selected from the group consisting of Haloperidol, Droperidol, Benperidol, Triperidol, Melperone, Lenperone, azaperone, Domperidone, risperidone, Chlorpromazine, Fluphenazine, Perphenazine, Prochlorperazine, Thioridazine, Trifluoperazine, Mesoridazine, Periciazine, Promazine, Triflupromazine, Levomepromazine, Promethazine, Pimozide, Cyamemazine, Chlorprothixene, Clopenthixol, Flupenthixol, Thiothixene, Zuclopenthixol, Clozapine, Olanzapine, Risperidone, Quetiapine, Ziprasidone, Amisulpride, Asenapine, Paliperidone, Iloperidone, Zotepine, Sertindole, Lurasidone, Aripiprazole, and pharmaceutically acceptable salts, isomers, and combinations thereof.

Androgen Receptor Antagonists

The compositions and methods of the invention may also make use of one or more androgen receptor antagonists, such as in a combination with the glucocorticoid receptor antagonist of the invention. For example, the invention provides with at least one glucocorticoid receptor antagonist in combination with at least one androgen receptor antagonist, such as for example, ARN 509 (4-{7-[6-Cyano-5-(trifluoromethyl)-3-pyridinyl]-8-oxo-6-thioxo-5,7-diazaspiro[3.4]oct-5-yl}-2-fluoro-N-methylbenzamide). ARN-509 is a novel androgen receptor (AR) antagonist for the treatment of castration-resistant prostate cancer (CRPC). ARN-509 inhibits AR nuclear translocation and AR binding to androgen response elements and, unlike bicalutamide, does not exhibit agonist properties in the context of AR overexpression.

Another exemplary antiadrogen is bicalutamide, which has the chemical name (R,S)—N-(4-cyano-3-(4-fluorophenylsulfonyl)-2-hydroxy-2-methyl-3-(t-riflu-oromethyl)propanamide, Flutamide (brand name Eulexin), nilutamide (brand names Anandron and Nilandron) and bicalutamide (brand name Casodex) are nonsteroidal, "pure" antiandrogens; 5-alpha-reductase inhibitors such as finasteride (brand names Proscar and Propecia), dutasteride (brand name Avodart), bexlosteride, izonsteride, turosteride, and epristeride are antiandrogenic as they prevent the conversion of testosterone to dihydrotestosterone (DHT); Spironolactone (brand names Aldactone and Spirotone), a synthetic 17-spirolactone corticosteroid; Cyproterone acetate (brand names Androcur, Climen, Diane 35, and Ginette 35) is a synthetic steroid, a potent antiandrogen that also possesses progestational properties. Hydroxyflutamide.

In some embodiments, steroidal or nonsteroidal androgen receptor antagonists include but are not limited to flutamide, hydroxyflutamide, enzalutamide bicalutamide, nilutamide, or hydroxysteroid dehydrogenase inhibitor.

In one embodiment, the androgen receptor antagonist is enzalutamide (marketed as Xtandi® Astellas Pharma US, Inc.), also known as and referred to herein as MDV3100, having the chemical name 4-(3-(4-cyano-3-(trifluoromethyl)phenyl)-5,5-dimethyl-4-oxo-2-thioxoimida-zolidin-1-yl)-2-fluoro-N-methylbenzamide.

The compositions and methods of the invention may also make use of one or more androgen receptor antagonist, such as in a combination with the glucocorticoid receptor antagonist of the invention. The androgen receptor antagonist may be selected from the group consisting of, for example, flutamide, nilutamide, enzalutamide, bicalutamide, ketonazole, abiraterone, abiraterone acetate, orteronel, finasteride, dutasteride, bexlosteride, izonsteride, turosteride, episteride, dexamethasone, prednisone, leuprolide, goserelin, triptorelin, histrelin, estrogen, MDV3100, Cyproterone acetate, Spironolactone, flutamide, hydroxyflutamide, enzalutamide and combinations thereof.

The selective androgen receptor (AR) antagonists embodied herein have utility for numerous conditions and diseases such as but not limited to male contraception; treatment of a variety of male hormone-related conditions such as hypersexuality and sexual deviation; treatment of conditions including benign prostatic hyperplasia, acne vugaris, androgenetic alopecia, and hirsutism; purposefully preventing or counteracting masculinisation in the case of transsexual women undergoing sex reassignment therapy; an antineoplastic agent and palliative, adjuvant or neoadjuvant hormonal therapy in prostate cancer; and decreasing the incidence of, halting or causing a regression of prostate cancer.

PARP Inhibitors

Suitable PARP inhibitors for use in the compositions and methods of the invention include, but are not limited to, 4-[[3-[4-(cyclopropanecarbonyl)piperazine-1-carbonyl]-4-fluorophenyl]-met-hyl]-2H-phthalazin-1-one (Compound B, i.e., Olaparib), 4-iodo-3-nitrobenzamide (Iniparib), 2-[(2R)-2-methylpyrrolidin-2-yl]-1H-benzimidazole-4-carboxamide (ABT-888), 8-Fluoro-2-{4-[(methylamino)methyl]-phenyl}-1,3,4,5-tetrahydro-6H-azepino-[5,4,3-cd]indol-6-one (AGO 14699), 4-methoxy-carbazole (CEP 9722), 2-[4-[(3S)-piperidin-3-yl]phenyl]indazole-7-carboxamide hydrochloride (MK 4827), and 3-aminobenzamide, or a pharmaceutically acceptable salt thereof.

In some embodiments, the Glucocorticoid receptor antagonists, e.g., ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof composition described herein, is administered in combination with a poly ADP-ribose polymerase (PARP) inhibitor (e.g., BSI201, Olaparib (AZD-2281), ABT-888, AG014699, CEP 9722, MK 4827, KU-0059436 (AZD2281), LT-673,3-aminobenzamide). Other example PARP inhibitors include, i.e., pharmacological inhibitors of the enzyme poly ADP ribose polymerase (PARP). Suitable PARP inhibitors maybe iniparib, olaparib, rucaparib, veliparib, or CEP 9722. Current PARP inhibitors in clinical trials include: Iniparib (Sanofi), Olaparib (AstraZeneca), Rucaparib (Pfizer), Veliparib (Abbott), CEP-9722 (Cephalon), MK4827 (Merck), BMN-673 (Biomarin), among others.

Immunoinflammatory Disorder

Another aspect of the present invention is directed to the use of the inventive compound and/or combination as a therapeutic agent for the prophylaxis and/or treatment of immunoinflammatory disorder. The term "immunoinflammatory disorder" encompasses a variety of conditions, including autoimmune diseases, proliferative skin diseases, and inflammatory dermatoses. Immunoinflammatory disorders result in the destruction of healthy tissue by an inflammatory process, dysregulation of the immune system, and unwanted proliferation of cells. Examples of immunoinflammatory disorders are acne vulgaris; acute respiratory distress syndrome; Addison's disease; allergic rhinitis; allergic intraocular inflammatory diseases, antineutrophil cytoplasmic antibody (ANCA)-associated small-vessel vasculitis; ankylosing spondylitis; arthritis, asthma; atherosclerosis; atopic dermatitis; autoimmune hepatitis; autoimmune hemolytic anemia; autoimmune hepatitis; Behcet's disease; Bell's palsy; bullous pemphigoid; cerebral ischemia; chronic obstructive pulmonary disease; cirrhosis; Cogan's syndrome; contact dermatitis; COPD; Crohn's disease; Cushing's syndrome; dermatomyositis; diabetes mellitus; discoid lupus erythematosus; eosinophilic fasciitis; erythema nodosum; exfoliative dermatitis; fibromyalgia; focal glomerulosclerosis; focal segmental glomerulosclerosis; giant cell arteritis; gout; gouty arthritis; graft versus host disease; hand eczema; Henoch-Schonlein purpura; herpes gestationis; hirsutism; idiopathic cerato-scleritis; idiopathic pulmonary fibrosis; idiopathic thrombocytopenic purpura; immune thrombocytopenic purpura inflammatory bowel or gastrointestinal disorders, inflammatory dermatoses; *Lichen planus*;

lupus nephritis; lymphomatous tracheobronchitis; macular edema; multiple sclerosis; myasthenia gravis; myositis; non-specific fibrosing lung disease; osteoarthritis; pancreatitis; pemphigoid gestationis; pemphigus vulgaris; periodontitis; polyarteritis nodosa; polymyalgia rheumatica; pruritus scroti; pruritis/inflammation, psoriasis; psoriatic arthritis; pulmonary histoplasmosis; rheumatoid arthritis; relapsing polychondritis; rosacea caused by sarcoidosis; rosacea caused by scleroderma; rosacea caused by Sweet's syndrome; rosacea caused by systemic lupus erythematosus; rosacea caused by urticaria; rosacea caused by zoster-associated pain; sarcoidosis; scleroderma; segmental glomerulosclerosis; septic shock syndrome; shoulder tendinitis or bursitis; Sjogren's syndrome; Still's disease; stroke-induced brain cell death; Sweet's disease; systemic lupus erythematosus; systemic sclerosis; Takayasu's arteritis; temporal arteritis; toxic epidermal necrolysis; transplant-rejection and transplant-rejection-related syndromes; tuberculosis; type-1 diabetes; ulcerative colitis; uveitis; vasculitis; and Wegener's granulomatosis.

As used herein, "non-dermal inflammatory disorders" include, for example, rheumatoid arthritis, inflammatory bowel disease, asthma, and chronic obstructive pulmonary disease. By "dermal inflammatory disorders" or "inflammatory dermatoses" is meant an inflammatory disorder selected from psoriasis, guttate psoriasis, inverse psoriasis, pustular psoriasis, erythrodermic psoriasis, acute febrile neutrophilic dermatosis, eczema, asteatotic eczema, dyshidrotic eczema, vesicular palmoplantar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, pityriasis rosea, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifiigum, erythema dyschromicum perstans, erythema multiforme, granuloma annulare, hand dermatitis, *Lichen nitidus, Lichen planus, Lichen sclerosus* et atrophicus, *Lichen simplex* chronicus, *Lichen spinulosus*, nummular dermatitis, pyoderma gangrenosum, sarcoidosis, subcorneal pustular dermatosis, urticaria, and transient acantholytic dermatosis. By "proliferative skin disease" is meant a benign or malignant disease that is characterized by accelerated cell division in the epidermis or dermis. Examples of proliferative skin diseases are psoriasis, atopic dermatitis, nonspecific dermatitis, primary irritant contact dermatitis, allergic contact dermatitis, basal and squamous cell carcinomas of the skin, lamellar ichthyosis, epidermolytic hyperkeratosis, premalignant keratosis, acne, and seborrheic dermatitis. As will be appreciated by one skilled in the art, a particular disease, disorder, or condition may be characterized as being both a proliferative skin disease and an inflammatory dermatosis. An example of such a disease is psoriasis.

Symptoms and signs of inflammation associated with specific conditions include: rheumatoid arthritis:—pain, swelling, warmth and tenderness of the involved joints; generalized and morning stiffness; insulin-dependent diabetes mellitus-insulitis; this condition can lead to a variety of complications with an inflammatory component, including:—retinopathy, neuropathy, nephropathy; coronary artery disease, peripheral vascular disease, and cerebrovascular disease; autoimmune thyroiditis:—weakness, constipation, shortness of breath, puffiness of the face, hands and feet, peripheral edema, bradycardia; multiple sclerosis:—spasticity, blurry vision, vertigo, limb weakness, paresthesias; uveoretinitis:—decreased night vision, loss of peripheral vision; lupus erythematosus:—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis; scleroderma:—Raynaud's disease; swelling of the hands, arms, legs and face; skin thickening; pain, swelling and stiffness of the fingers and knees, gastrointestinal dysfunction, restrictive lung disease; pericarditis; renal failure; other arthritic conditions having an inflammatory component such as rheumatoid spondylitis, osteoarthritis, septic arthritis and polyarthritis:—fever, pain, swelling, tenderness; other inflammatory brain disorders, such as meningitis, Alzheimer's disease, AIDS dementia encephalitis:—photophobia, cognitive dysfunction, memory loss; other inflammatory eye inflammations, such as retinitis:—decreased visual acuity; inflammatory skin disorders, such as, eczema, other dermatites (e.g., atopic, contact), psoriasis, burns induced by UV radiation (sun rays and similar UV sources):—erythema, pain, scaling, swelling, tenderness; inflammatory bowel disease, such as Crohn's disease, ulcerative colitis:—pain, diarrhea, constipation, rectal bleeding, fever, arthritis; asthma:—shortness of breath, wheezing; other allergy disorders, such as allergic rhinitis:—sneezing, itching, runny nose conditions associated with acute trauma such as cerebral injury following stroke-sensory loss, motor loss, cognitive loss; heart tissue injury due to myocardial ischemia:—pain, shortness of breath; lung injury such as that which occurs in adult respiratory distress syndrome:—shortness of breath, hyperventilation, decreased oxygenation, pulmonary infiltrates; inflammation accompanying infection, such as sepsis, septic shock, toxic shock syndrome:—fever, respiratory failure, tachycardia, hypotension, leukocytosis; other inflammatory conditions associated with particular organs or tissues, such as: (i) nephritis (e.g., glomeralonephritis):—oliguria, abnormal urinalysis; (ii) inflamed appendix:—fever, pain, tenderness, leukocytosis; (iii) gout:—pain, tenderness, swelling and erythema of the involved joint, elevated serum and/or urinary uric acid; (iv) inflamed gall bladder:—abdominal pain and tenderness, fever, nausea, leukocytosis; (v) congestive heart failure:—shortness of breath, rales, peripheral edema; (vi) Type II diabetes:—end organ complications including cardiovascular, ocular, renal, and peripheral vascular disease; (vii) lung (pulmonary) fibrosis:—hyperventilation, shortness of breath, decreased oxygenation; (viii) vascular disease, such as atherosclerosis and restenosis:—pain, loss of sensation, diminished pulses, loss of function; and (ix) alloimmunity leading to transplant rejection:—pain, tenderness, fever.

Neurodegenerative Disease

Another aspect of the present invention is directed to the use of the inventive compound and/or combination as a therapeutic agent for the prophylaxis and/or treatment of Neurodegenerative Disease. Exemplary active agents include, for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof.

The present invention also relates generally to the fields of neurology and psychiatry and to methods of protecting the cells of a mammalian central nervous system from damage or injury. Injuries or trauma of various kinds to the central nervous system (CNS) or the peripheral nervous system (PNS) can produce profound and long-lasting neurological and/or psychiatric symptoms and disorders. One form that this can take is the progressive death of neurons or other cells of the central nervous system (CNS), i.e., neurodegeneration or neuronal degeneration. Neuronal degeneration as a result of, for example; Alzheimer's disease, multiple sclerosis, cerebral-vascular accidents (CVAs)/stroke, traumatic brain injury, spinal cord injuries, degeneration of the optic nerve, e.g., ischemic optic neuropathy or retinal degeneration and other central nervous system disorders is an enormous medical and public health problem by virtue of both its high incidence and the frequency of long-term sequelae. Animal studies and clinical trials have shown that amino acid transmitters (especially glutamate), oxidative stress and inflammatory reactions contribute strongly to cell death in these conditions. Upon injury or upon ischemic insult, damaged neurons release massive amounts of the neurotransmitter glutamate, which is excitotoxic to the surrounding neurons. Glutamate is a negatively charged amino acid that is an excitatory synaptic transmitter in the mammalian nervous system. Although the concentration of glutamate can reach the millimolar range in nerve terminals its extracellular concentration is maintained at a low level to prevent neurotoxicity. It has been noted that glutamate can be toxic to neurons if presented at a high concentration. The term "excitotoxicity" has been used to describe the cytotoxic effect that glutamate (and other such excitatory amino acids) can have on neurons when applied at high dosages.

Patients with injury or damage of any kind to the central (CNS) or peripheral (PNS) nervous system including the retina may benefit from neuroprotective methods. This nervous system injury may take the form of an abrupt insult or an acute injury to the nervous system as in, for example, acute neurodegenerative disorders including, but not limited to; acute injury, hypoxia-ischemia or the combination thereof resulting in neuronal cell death or compromise. Acute injury includes, but is not limited to, traumatic brain injury (TBI) including, closed, blunt or penetrating brain trauma, focal brain trauma, diffuse brain damage, spinal cord injury, intracranial or intravertebral lesions (including, but not limited to, contusion, penetration, shear, compression or laceration lesions of the spinal cord or whiplash shaken infant syndrome). In addition, deprivation of oxygen or blood supply in general can cause acute injury as in hypoxia and/or ischemia including, but not limited to, cerebrovascular insufficiency, cerebral ischemia or cerebral infarction (including cerebral ischemia or infarctions originating from embolic occlusion and thrombosis, retinal ischemia (diabetic or otherwise), glaucoma, retinal degeneration, multiple sclerosis, toxic and ischemic optic neuropathy, reperfusion following acute ischemia, perinatal hypoxic-ischemic injury, cardiac arrest or intracranial hemorrhage of any type (including, but not limited to, epidural, subdural, subarachnoid or intracerebral hemorrhage).

Trauma or injury to tissues of the nervous system may also take the form of more chronic and progressive neurodegenerative disorders, such as those associated with progressive neuronal cell death or compromise over a period of time including, but not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases (amyotrophic lateral sclerosis), multiple sclerosis, degenerative ataxias, cortical basal degeneration, ALS-Parkinson's-dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease or spinocerebellar ataxia type 3 and olivopontocerebellar degenerations, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome) or prion diseases (including, but not limited to Creutzfeld-Jakob disease, Gerstmann-Strussler-Scheinker disease, Kuru disease or fatal familial insomnia).

In addition, trauma and progressive injury to the nervous system can take place in various psychiatric disorders, including but not limited to, progressive, deteriorating forms of bipolar disorder or schizoaffective disorder or schizophrenia, impulse control disorders, obsessive compulsive disorder (OCD), behavioral changes in temporal lobe epilepsy and personality disorders.

In one preferred embodiment the compounds and/or compositions of the invention would be used to provide neuroprotection in disorders involving trauma and progressive injury to the nervous system in various psychiatric disorders. These disorders would be selected from the group consisting of; schizoaffective disorder, schizophrenia, impulse control disorders, obsessive compulsive disorder (OCD) and personality disorders.

In addition, trauma and injury make take the form of disorders associated with overt and extensive memory loss including, but not limited to, neurodegenerative disorders associated with age-related dementia, vascular dementia, diffuse white matter disease (Binswanger's disease), dementia of endocrine or metabolic origin, dementia of head trauma and diffuse brain damage, dementia pugilistica or frontal lobe dementia, including but not limited to Pick's Disease.

Other disorders associated with neuronal injury include, but are not limited to, disorders associated with chemical, toxic, infectious and radiation injury of the nervous system including the retina, injury during fetal development, prematurity at time of birth, anoxic-ischemia, injury from hepatic, glycemic, uremic, electrolyte and endocrine origin, injury of psychiatric origin (including, but not limited to, psychopathology, depression or anxiety), injury from peripheral diseases and plexopathies (including plexus palsies) or injury from neuropathy (including neuropathy selected from multifocal, sensory, motor, sensory-motor, autonomic, sensory-autonomic or demyelinating neuropathies (including, but not limited to Guillain-Barre syndrome or chronic inflammatory demyelinating polyradiculoneuropathy) or those neuropathies originating from infections, inflammation, immune disorders, drug abuse, pharmacological treatments, toxins, trauma (including, but not limited to compression, crush, laceration or segmentation traumas), metabolic disorders (including, but not limited to endocrine or paraneoplastic), Charcot-Marie-Tooth disease (including, but not limited to, type 1a, 1b, 2, 4a or 1-X linked), Friedreich's ataxia, metachromatic leukodystrophy, Refsum's disease, adrenomyeloneuropathy, ataxia-telangiectasia, Djerine-Sottas (including, but not limited to, types A or B), Lambert-Eaton syndrome or disorders of the cranial nerves).

Further indications are cognitive disorders. The term "cognitive disorder" shall refer to anxiety disorders, delirium, dementia, amnestic disorders, dissociative disorders, eating disorders, mood disorders, schizophrenia, psychotic disorders, sexual and gender identity disorders, sleep disorders, somatoform disorders, acute stress disorder, obsessive-compulsive disorder, panic disorder, posttraumatic stress disorder, specific phobia, social phobia, substance withdrawal delirium, Alzheimer's disease, Creutzfeldt-Jakob disease, head trauma, Huntington's disease, HTV disease, Parkinson's disease, Pick's disease, learning disorders, motor skills disorders, developmental coordination disorder, communication disorders, phonological disorder, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, pica, rumination disorder, tic disorders, chronic motor or vocal tic disorder, Tourette's disorder, elimination disorders, encopresis, enuresis, selective mutism, separation anxiety disorder, dissociative amnesia, depersonalization disorder, dissociative fugue, dissociative identity disorder, anorexia nervosa, bulimia nervosa, bipolar disorders, schizophreniform disorder, schizoaffective disorder, delusional disorder, psychotic disorder, shared psychotic disorder, delusions, hallucinations, substance-induced psychotic disorder, orgasmic disorders, sexual pain disorders, dyspareunia, vaginismus, sexual dysfunction, paraphilias, dyssomnias, breathing-related sleep disorder, circadian rhythm sleep disorder, hypersomnia, insomnia, narcolepsy, dyssomnia, parasomnias, nightmare disorder, sleep terror disorder, sleepwalking disorder, parasomnia, body dysmorphic disorder, conversion disorder, hypochondriasis, pain disorder, somatization disorder, alcohol related disorders, amphetamine related disorders, caffeine related disorders, cannabis related disorders, cocaine related disorders, hallucinogen related disorders, inhalant related disorders, nicotine related disorders, opioid related disorders, phencyclidine-related disorder, abuse, persisting amnestic disorder, intoxication, withdrawal.

The term "bipolar and clinical disorders" shall refer to adjustment disorders, anxiety disorders, delirium, dementia, amnestic and other cognitive disorders, disorders usually first diagnosed in infancy (e.g.), childhood, or adolescence, dissociative disorders (e.g. dissociative amnesia, depersonalization disorder, dissociative fugue and dissociative identity disorder), eating disorders, factitious disorders, impulse-control disorders, mental disorders due to a general medical condition, mood disorders, other conditions that may be a focus of clinical attention, personality disorders, schizophrenia and other psychotic disorders, sexual and gender identity disorders, sleep disorders, somatoform disorders, substance-related disorders, generalized anxiety disorder (e.g. acute stress disorder, posttraumatic stress disorder), panic disorder, phobia, agoraphobia, obsessive-compulsive disorder, stress, acute stress disorder, anxiety neurosis, nervousness, phobia, posttraumatic stress disorder, posttraumatic stress disorder (PTSD), abuse, obsessive-compulsive disorder (OCD), manic depressive psychosis, specific phobias, social phobia, adjustment disorder with anxious features.

Examples for disorders usually first diagnosed in infancy, childhood, or adolescence are: mental retardation, learning disorders, mathematics disorder, reading disorder, disorder of written expression, motor skills disorders, developmental coordination disorder, communication disorders, expressive language disorder, phonological disorder, mixed receptive-expressive language disorder, stuttering, pervasive developmental disorders, Asperger's disorder, autistic disorder, childhood disintegrative disorder, Rett's disorder, pervasive developmental disorder, attention-deficit/hyperactivity disorder (ADHD), conduct disorder, oppositional defiant disorder, feeding disorder of infancy or early childhood, pica, rumination disorder, tic disorders, chronic motor or vocal tic disorder, Tourette's syndrome, elimination disorders, encopresis, enuresis, selective mutism, separation anxiety disorder, reactive attachment disorder of infancy or early childhood, stereotypic movement disorder.

Examples for substance-related disorders are: alcohol related disorders, amphetamine related disorders, caffeine related disorders, cannabis related disorders, cocaine related disorders, hallucinogen related disorders, inhalant related disorders, nicotine related disorders, opioid related disorders, psychotic disorder, psychotic disorder, phencyclidine-related disorder, abuse, persisting amnestic disorder, anxiety disorder, persisting dementia, dependence, intoxication, intoxication delirium, mood disorder, psychotic disorder, withdrawal, withdrawal delirium, sexual dysfunction, sleep disorder.

The term "neuroprotection" as used herein shall mean; inhibiting, preventing, ameliorating or reducing the severity of the dysfunction, degeneration or death of nerve cells, axons or their supporting cells in the central or peripheral nervous system of a mammal, including a human. This includes the treatment or prophylaxis of a neurodegenerative disease; protection against excitotoxicity or ameliorating the cytotoxic effect of a compound (for example, a excitatory amino acid such as glutamate; a toxin; or a prophylactic or therapeutic compound that exerts an immediate or delayed cytotoxic side effect including but not limited to the immediate or delayed induction of apoptosis) in a patient in need thereof.

The term "a patient in need of treatment with a neuroprotective drug" as used herein will refer to any patient who currently has or may develop any of the above syndromes or disorders, or any disorder in which the patient's present clinical condition or prognosis could benefit from providing neuroprotection to prevent the development, extension, worsening or increased resistance to treatment of any neurological or psychiatric disorder.

The term "treating" or "treatment" as used herein, refers to any indicia of success in the prevention or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluations.

In some embodiments this invention provides methods of neuroprotection. In certain embodiments, these methods comprise administering a therapeutically effective amount of the composition and/or combination of the invention to a patient who has not yet developed overt, clinical signs or symptoms of injury or damage to the cells of the nervous system but who may be in a high risk group for the development of neuronal damage because of injury or trauma to the nervous system or because of some known predisposition either biochemical or genetic or the finding of a verified biomarker of one or more of these disorders.

Thus, in some embodiments, the methods and compositions of the present invention are directed toward neuroprotection in a subject who is at risk of developing neuronal damage but who has not yet developed clinical evidence. This patient may simply be at "greater risk" as determined by the recognition of any factor in a subject's, or their families, medical history, physical exam or testing that is indicative of a greater than average risk for developing neuronal damage. Therefore, this determination that a patient may be at a "greater risk" by any available means can be used to determine whether the patient should be treated with the methods of the present invention.

Accordingly, in an exemplary embodiment, subjects who may benefit from treatment by the methods and the composition and/or combination of this invention can be identified using accepted screening methods to determine risk factors for neuronal damage. These screening methods include, for example, conventional work-ups to determine risk factors including but not limited to: for example, head trauma, either closed or penetrating, CNS infections, bacterial or viral, cerebrovascular disease including but not limited to stroke, brain tumors, brain edema, cysticercosis, porphyria, metabolic encephalopathy, drug withdrawal including but not limited to sedative-hypnotic or alcohol withdrawal, abnormal perinatal history including anoxia at birth or birth injury of any kind, cerebral palsy, learning disabilities, hyperactivity, history of febrile convulsions as a child, history of status epilepticus, family history of epilepsy or any seizure related disorder, inflammatory disease of the brain including lupis, drug intoxication either direct or by placental transfer, including but not limited to cocaine poisoning, parental consanguinity, and treatment with medications that are toxic to the nervous system including psychotropic medications.

The determination of which patients may benefit from treatment with a neuroprotective drug in patients who have no clinical signs or symptoms may be based on a variety of "surrogate markers" or "biomarkers".

As used herein, the terms "surrogate marker" and "biomarker" are used interchangeably and refer to any anatomical, biochemical, structural, electrical, genetic or chemical indicator or marker that can be reliably correlated with the present existence or future development of neuronal damage. In some instances, brain-imaging techniques, such as computer tomography (CT), magnetic resonance imaging (MRI) or positron emission tomography (PET), can be used to determine whether a subject is at risk for neuronal damage. Suitable biomarkers for the methods of this invention include, but are not limited to: the determination by MRI, CT or other imaging techniques, of sclerosis, atrophy or volume loss in the hippocampus or overt mesial temporal sclerosis (MTS) or similar relevant anatomical pathology; the detection in the patient's blood, serum or tissues of a molecular species such as a protein or other biochemical biomarker, e.g., elevated levels of ciliary neurotrophic factor (CNTF) or elevated serum levels of a neuronal degradation product; or other evidence from surrogate markers or biomarkers that the patient is in need of treatment with a neuroprotective drug.

It is expected that many more such biomarkers utilizing a wide variety of detection techniques will be developed in the future. It is intended that any such marker or indicator of the existence or possible future development of neuronal damage, as the latter term is used herein, may be used in the methods of this invention for determining the need for treatment with the compounds and methods of this invention.

A determination that a subject has, or may be at risk for developing, neuronal damage would also include, for example, a medical evaluation that includes a thorough history, a physical examination, and a series of relevant bloods tests. It can also include an electroencephalogram (EEG), CT, MRI or PET scan. A determination of an increased risk of developing neuronal damage or injury may also be made by means of genetic testing, including gene expression profiling or proteomic techniques. For psychiatric disorders that may be stabilized or improved by a neuroprotective drug, e.g., bipolar disorder, schizoaffective disorder, schizophrenia, impulse control disorders, etc. the above tests may also include a present state exam and a detailed history of the course of the patients symptoms such as mood disorder symptoms and psychotic symptoms over time and in relation to other treatments the patient may have received over time, e.g., a life chart. These and other specialized and routine methods allow the clinician to select patients in need of therapy using the methods and formulations of this invention. In some embodiments of the present invention compounds and/or compositions suitable for use in the practice of this invention will be administered either singly or concomitantly with at least one or more other compounds or therapeutic agents, e.g., with other neuroprotective drugs or antiepileptic drugs, anticonvulsant drugs. In these embodiments, the present invention provides methods to treat or prevent neuronal injury in a patient. The method includes the step of; administering to a patient in need of treatment, an effective amount of the compounds and/or compositions disclosed herein in combination with an effective amount of one or more other compounds or therapeutic agents that have the ability to provide neuroprotection or to treat or prevent seizures or epileptogenesis or the ability to augment the neuroprotective effects of the compounds of the invention.

As used herein the term "combination administration" of a compound, therapeutic agent or known drug with the combination of the present invention means administration of the drug and the one or more compounds at such time that both the known drug and/or combination will have a therapeutic effect. In some cases this therapeutic effect will be synergistic. Such concomitant administration can involve concurrent (i.e. at the same time), prior, or subsequent administration of the drug with respect to the administration of the composition and/or combination of the present invention. A person of ordinary skill in the art would have no difficulty determining the appropriate timing, sequence and dosages of administration for particular drugs of the present invention.

The said one or more other compounds or therapeutic agents may be selected from compounds that have one or more of the following properties: antioxidant activity; NMDA receptor antagonist activity, augmentation of endogenous GABA inhibition; NO synthase inhibitor activity; iron binding ability, e.g., an iron chelator; calcium binding ability, e.g., a Ca (II) chelator; zinc binding ability, e.g., a Zn (II) chelator; the ability to effectively block sodium or calcium ion channels, or to open potassium or chloride ion channels in the CNS of a patient.

Heart and Vascular Disease

Another aspect of the present invention is directed to the use of the inventive compound and/or combination such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, as a therapeutic agent for the prophylaxis and/or treatment of heart disease. Heart disease is a general term used to describe many different heart conditions. For example, coronary artery disease, which is the most common heart disease, is characterized by constriction or narrowing of the arteries supplying the heart with oxygen-rich blood, and can lead to myocardial infarction, which is the death of a portion of the heart muscle. Heart failure is a condition resulting from the inability of the heart to pump an adequate amount of blood through the body. Heart failure is not a sudden, abrupt stop of heart activity but, rather, typically develops slowly over many years, as the heart gradually loses its ability to pump blood efficiently. Risk factors for heart failure include coronary artery disease, hypertension, valvular heart disease, cardiomyopathy, disease of the heart muscle, obesity, diabetes, and/or a family history of heart failure.

Examples of cardiovascular diseases and disorders are: aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive card iomyopathy, hypertrophic cardiomyopathy, restrictive cardiomyopathy, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, cardiac hypertrophy, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, Sneddon syndrome, superior vena cava syndrome, syndrome X, tachycardia, Takayasu's arteritis, hereditary hemorrhagic telangiectasia, telangiectasis, temporal arteritis, tetralogy of Fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Vascular diseases are often the result of decreased perfusion in the vascular system or physical or biochemical injury to the blood vessel.

Peripheral vascular disease (PVD) is defined as a disease of blood vessels often encountered as narrowing of the vessels of the limbs. There are two main types of these disorders, functional disease which doesn't involve defects in the blood vessels but rather arises from stimuli such as cold, stress, or smoking, and organic disease which arises from structural defects in the vasculature such as atherosclerotic lesions, local inflammation, or traumatic injury. This can lead to occlusion of the vessel, aberrant blood flow, and ultimately to tissue ischemia.

One of the more clinically significant forms of PVD is peripheral artery disease (PAD). PAD is often treated by angioplasty and implantation of a stent or by artery bypass surgery. Clinical presentation depends on the location of the occluded vessel. For example, narrowing of the artery that supplies blood to the intestine can result in severe postprandial pain in the lower abdomen resulting from the inability of the occluded vessel to meet the increased oxygen demand arising from digestive and absorptive processes. In severe forms the ischemia can lead to intestinal necrosis. Similarly, PAD in the leg can lead to intermittent pain, usually in the calf, that comes and goes with activity. This disorder is known as intermittent claudication (IC) and can progress to persistent pain while resting, ischemic ulceration, and even amputation. Peripheral vascular disease is also manifested in atherosclerotic stenosis of the renal artery, which can lead to renal ischemia and kidney dysfunction.

One disease in which vascular diseases and their complications are very common is diabetes mellitus. Diabetes mellitus causes a variety of physiological and anatomical irregularities, the most prominent of which is the inability of the body to utilize glucose normally, which results in hyperglycemia. Chronic diabetes can lead to complications of the vascular system which include atherosclerosis, abnormalities involving large and medium size blood vessels (macroangiopathy) and abnormalities involving small blood vessels (microangiopathy) such as arterioles and capillaries.

Patients with diabetes mellitus are at increased risk of developing one or more foot ulcers as a result of established long-term complications of the disease, which include impaired nerve function (neuropathy) and/or ischemia. Local tissue ischemia is a key contributing factor to diabetic foot ulceration.

In addition to large vessel disease, patients with diabetes suffer further threat to their skin perfusion in at least two additional ways. First, by involvement of the non-conduit arteries, which are detrimentally affected by the process of atherosclerosis, and secondly, and perhaps more importantly, by impairment of the microcirculatory control mechanisms (small vessel disease). Normally, when a body part suffers some form of trauma, the body part will, as part of the body's healing mechanism, experience an increased blood flow. When small vessel disease and ischemia are both present, as in the case of many diabetics, this natural increased blood flow response is significantly reduced. This fact, together with the tendency of diabetics to form blood clots (thrombosis) in the microcirculatory system during low levels of blood flow, is believed to be an important factor in ulcer pathogenesis.

Neuropathy is a general term which describes a disease process which leads to the dysfunction of the nervous system, and is one of the major complications of diabetes mellitus, with no well-established therapies for either its symptomatic treatment or for prevention of progressive decline in nerve function.

The thickening and leakage of capillaries caused by diabetes primarily affect the eyes (retinopathy) and kidneys (nephropathy). The thickening and leakage of capillaries caused by diabetes are also associated with skin disorders and disorders of the nervous system (neuropathy).

The eye diseases associated with diabetes are nonproliferative diabetic retinopathy, proliferative diabetic retinopathy, diabetic maculopathy, glaucoma, cataracts and the like.

Other diseases, although not known to be related to diabetes are similar in their physiological effects on the peripheral vascular system. Such diseases include Raynaud syndrome, CREST syndrome, autoimmune diseases such as erythematosis, rheumatoid disease, and the like.

As used herein, the term "peripheral vascular diseases" comprises any peripheral vascular disease including peripheral and autonomic neuropathies. Examples of "peripheral vascular disease" include peripheral arterial disease, such as chronic arterial occlusion including arteriosclerosis, arteriosclerosis obliterans and thromboangiitis obliterans (Buerger's disease), macroangiopathy, microangiopathy, diabetes mellitus, thrombophlebitis, phlebemphraxis, Raynaud's disease, Raynaud's syndrome, CREST syndrome, health hazard due to vibration, Sudeck's syndrome, intermittent claudication, cold sense in extremities, abnormal sensation in extremities, sensitivity to the cold, Meniere's disease, Meniere's syndrome, numbness, lack of sensation, anesthesia, resting pain, causalgia (burning pain), disturbance of peripheral circulation function, disturbance of nerve function, disturbance of motor function, motor paralysis, diabetic peripheral circulation disorder, lumbar spinal canal stenosis, diabetic neuropathy, shock, autoimmune disease such as erythematosis, rheumatoid disease and rheumatoid arthritis, autonomic neuropathy, diabetic autonomic neuropathy, autonomic imbalance, orthostatic hypotension, erectile dysfunction, female sexual dysfunction, retrograde ejaculation, cystopathy, neurogenic bladder, defective vaginal lubrication, exercise intolerance, cardiac denervation, heat intolerance, gustatory sweating, diabetic complication, hyperglycemia, hypoglycemia unawareness, hypoglycemia unresponsiveness; glaucoma, neovascular glaucoma, cataract, retinopathy, diabetic retinopathy, diabetic maculopathy, occlusion of retinal artery, obstruction of central artery of retina, occlusion of retinal vein, macular edema, aged macular degeneration, aged disciform macular degeneration, cystoid macular edema, palpebral edema, retinal edema, chorioretinopathy, neovascular maculopathy, uveitis, iritis, retinal vasculitis, endophthalmitis, panophthalmitis, metastatic ophthalmia, choroiditis, retinal pigment epithelitis, conjunctivitis, cyclitis, scleritis, episcleritis, optic neuritis, retrobulbar optic neuritis, keratitis, blepharitis, exudative retinal detachment, corneal ulcer, conjunctival ulcer, chronic nummular keratitis, Thygeson keratitis, progressive Mooren's ulcer, damage of skin, skin ulcer including foot ulcer, diabetic ulcer, burn ulcer, lower leg ulcer, postoperative ulcer, traumatic ulcer, ulcer after herpes zoster, radiation ulcer, drug induced ulcer, frostbite (cold injury), chilblain, gangrene and sudden gangrene, angina pectoris/variant angiitis, coronary arteriosclerosis (chronic ischemic heart disease, asymptomatic ischemic heart disease, arteriosclerotic cardiovascular disease), myocardial infarction, heart failure, congestive heart failure and painless ischemic heart disease, pulmonary edema, hypertension, pulmonary hypertension; portal hypertension, diabetic nephropathy, decubitus, renal failure.

Psychotic Depression

The present invention relates to the use of a GCR antagonist, such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, for the prevention or treatment of psychotic depression. Psychotic major depression has long been recognized as a distinct psychiatric illness, having both psychotic and depressive components in a differential diagnosis. Psychotic major depression is very common. It has been estimated that twenty five percent of depressed patients admitted to the hospital have psychotic major depression (Coryell (1984) J. Nerv. Ment. Dis. 172:521). Like major depression, psychotic depression is often also a result of high circulating cortisol levels. Various evidence supports this concept. Psychosis has been associated with Cushing's syndrome (Gerson (1985) Can. J. Psychiatry 30:223-224; Saad (1984) Am. J. Med. 76:759-766). A GR antagonist has been used to treat acute psychiatric disturbances secondary to Cushing's syndrome. One study showed that a relatively high dose of such a GR antagonist (400 to 800 mg per day) was useful in rapidly reversing acute psychosis in patients with severe Cushing's' Syndrome due to adrenal cancers and ectopic secretion of ACTH from lung cancer (Van der Lely (1991) Ann. Intern. Med. 114:143; Van der Lely (1993) Pharmacy World & Science 15:89-90; Sartor (1996) supra). Relatively high dose mifepristone, in the range of 8-12 mg/kg/day, over a relatively short period of time (4 days), was also shown to be effective in the treatment of psychosis associated with psychotic major depression (International Patent Application WO 99/17779; Schatzberg and Belanoff).

Surgery-Associated Immune Suppression in the Elderly.

In healthy, young to middle aged subjects suffering from stress, there is a physiological balance between pro-inflammatory and anti-inflammatory mediators. In the elderly, the immune response is blunted as a result of the decline in several components of the immune system (immune senescence) and a shifting to a chronic pro-inflammatory status (the so-called "inflammaging" effect (Butcher and Lord, (2004) Aging Cell, pp. 151-160).

As production of cortisol remains reasonably constant with age, whereas summed levels of DHEA and DHEAS decrease gradually from the third decade, reaching 10-20% of their maximum by the eighth decade, Butcher and Lord (2004, supra) propose a model for age and stress, in which the age-related increase in the ratio of cortisol to DHEAS, combined with an elevated cortisol release during stress, leads to a significant reduction of immunity in aging subjects. This is proposed to explain that aging subjects are far more prone to infections under conditions of stress. (Butcher and Lord (2004, supra); Butcher et al. (2005, Aging Cell 5, pp. 319-324).

The present invention relates to the use of a GCR antagonist, such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, for the prevention or treatment of infections or infectious conditions, in an aging patient, such as a human subject. The beneficial effects of said GCR antagonists may be explained on the basis of their correcting influence on the cortisol/DHEA(S) ratio. It is believed that the effect in selected subjects, found to have high circulating cortisol by a saliva test as provided for by this invention, can be explained by the unbalanced immunosuppressive role of the increased cortisol/DHEAS ratio in the aged group in comparison to the balanced influence of cortisol and DHEAS on the immune system in normal subjects.

The meaning of the term 'aging subject' or 'aged subject' will be well understood in the context of the use according to this invention. Although it is not linked to an exact lower age limit this general notion refers in the human situation usually to a person of at least 55 years old, but it is more clear with a lowest age limit set at 60, 65, 70 or 75 years.

In the context of the invention, the infection or infectious condition can be caused by any of several agents, e.g., by bacteria, by viruses or by fungi. Also in the context of the present invention, the expression "infectious conditions" means silent or subclinical infections as well as conditions not resulting in a manifest infectious disease, but in which at least one parameter associated with an infectious disease, such as the white blood (e.g., neutrophil, basophil or eosinophil) cell counts or the level of some antibodies or some cytokines is higher than normal. Normal values are known to the expert and may be found in standard medical manuals.

Particular uses according to the invention relate to aging subjects suffering from an infection or an infectious condition concomitant to stress resulting from a trauma. The invention particularly relates to uses wherein the subject suffers from the consequences of a bone fracture and/or bone surgery, either for such injury or for joint replacement for osteoarthritis or rheumatoid arthritis. The invention also relates to uses wherein the subject suffers from an infection or an infectious condition concomitant to psychological stress, particularly acute emotional stress.

Post Traumatic Stress Disorder (PTSD)

PTSD is a severe anxiety disorder that can develop after exposure to any event that results in psychological trauma. This event may involve the threat of death to oneself or to someone else, or to one's own or someone else's physical, sexual, or psychological integrity, overwhelming the individual's ability to cope. As an effect of psychological trauma, PTSD is less frequent and more enduring than the more commonly seen acute stress response. Diagnostic symptoms for PTSD include re-experiencing the original trauma(s) through flashbacks or nightmares, avoidance of stimuli associated with the trauma, and increased arousal, such as difficulty falling or staying asleep, anger, and hyper-vigilance. Formal diagnostic criteria (both DSM-IV-TR and ICD-9) require that the symptoms last more than one month and cause significant impairment in social, occupational, or other important areas of functioning. (Diagnostic and statistical manual of mental disorders: DSM-IV. American Psychiatric Association. 1994. Washington, D.C.: American Psychiatric Association.)

PTSD displays biochemical changes in the brain and body that differ from other psychiatric disorders such as major depression. Abundant evidence suggests derangement of HPA-axis physiology in individuals diagnosed with PTSD, though the nature of the derangements is variable: some have low cortisol, some have normal levels, others have high levels of cortisol and for some, levels may be normal, but circadian rhythm is lost. It is postulated that these reflect different baseline mechanisms, but that when cortisol is high, either in a sustained way through the day or by loss of circadian rhythm with elevated night time levels, it is likely to be an important component of the clinical symptomatology (Lindley S E, et al. Basal and dexamethasone suppressed salivary cortisol concentrations in a community sample of patients with posttraumatic stress disorder. Biol. Psychiatry 2004; 55: 940-5). In such patients, determined by salivary cortisol testing, administration of a GCR antagonist is expected to be therapeutic or beneficial for the symptoms of PTSD. Prevention of Weight Gain in Patients Using Anti-Psychotic and Anti-Depressant Medications. Anti-psychotic and some anti-depressant medications (e.g., SSRIs) are amongst the most important tools for treating psychiatric conditions of all kinds. However, management of patients on who take many of these medications for chronic, long term disease is made difficult by their significant side effect profiles. One of the most important of these is weight gain and the attendant metabolic syndrome that follows. For example, it is estimated that 40-80% of patients who are under chronic anti-psychotic administration experience substantial weight gain, often exceeding 20% or more over their ideal body weights (Umbricht et al. J. Clin. Psychiatry 1994; 55: 157-160; Khan A Y, et al. J Psychiatr Pract. 2010; 16: 289-96; Pramyothin P, Khaodhiar L. Curr Opin Endocrinol Diabetes Obes. 2010; 17: 460-6; Rummel-Kluge C et al. Schizophr Res. 2010; 123: 225-33). Such weight gain is one of the most common causes of poor compliance with anti-psychotic and anti-depressant regimens and, therefore, of long term failure of therapy. Furthermore, anti-psychotic medications specifically are commonly associated with development of insulin resistance and metabolic syndrome (with development of type 2 diabetes mellitus and hyper/dyslipidemia states) and the potentially and significantly increased risks for cardiovascular disease; these conditions are of tremendous medical consequence for patients who are thereby caught in a "can't live with them, can't live without them" treatment scenario. While weight gain is potentially seen with all anti-psychotic medications, they are particularly common and tend to more severe with the newer or "atypical" AP drugs (Allison et al. Am J Psychiatry 1999; 156:1686-1696; Rummel-Kluge C et al. Schizophr Res. 2010; 123: 225-33). Elevations in cortisol are associated with changes in body fat and insulin resistance. Several years ago, in a proof of principle clinical experiment, it was reported that one GCR antagonist (mifepristone) was a highly effective treatment for multiple medical complications in a patient with Cushing's disease whose illness had not responded to surgery and radiation, including reversal of insulin dependent diabetes: the patient was able to stop insulin within a month (Chu et al., J. Clin. Endocrinol. Metab. 2001; 86, 3568-3573.). These data suggest that a GCR antagonist could be useful for blocking and reversing the insulin resistance and weight changes seen in some patients treated with atypical antipsychotic agents. To this end, this compound was tested in rats who had olanzapine-induced weight gain and increases in abdominal fat; reversal of weight gain was seen and reduction of abdominal fat was obtained (Beebe et al. Behav. Brain Res. 2006; 171, 225-229). A clinical trial with this compound then confirmed this benefit in humans with a 2 week study of 600 mg/day of mifepristone that reduced olanzapine-induced weight gain in 57 non-overweight healthy males with Body Mass Indices less than 25 (Gross et al., Adv Ther. 2009; 26: 959-69.). Thus, GCR antagonist or active agent therapy could prove a useful mechanism to target in treating psychotic patients with atypical antipsychotic agents. The present invention relates to the use of a GCR antagonist, such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, for the prevention or treatment of PTSD.

Cushing's Syndrome

Cushing's Syndrome is a set of conditions in which high levels of circulating cortisol or other GCR agonists cause a set of seriously debilitating and sometimes life threatening signs and symptoms including, but not limited to, psychiatric disturbances (e.g. anxiety, depression, psychosis), immunosuppression, insulin resistance and metabolic syndrome, skin conditions, hypertension and osteoporosis. Endogenous cortisol may be produced by ACTH-secreting, benign or malignant tumors of the pituitary gland ("Cushing's Disease") or of the adrenal cortex. These are rare conditions and therefore Cushing's Syndrome is considered an "orphan disease." A proof of concept trial using RU486 to treat patients with tumor-related Cushing's Syndrome demonstrated efficacy in remitting symptoms such as glucose metabolic abnormalities (i.e., glucose intolerance; (group 1) and hypertension (group 2). Statistically significant improvement was achieved for both groups: with 60% responding in the glucose intolerant group and 43% in the hypertensive group (Corcept Therapeutics Press Release Dec. 22, 2010). Thus, GCR antagonist or active agent therapy can be expected to provide clinical benefits for patients with Cushing's Syndrome administered prior to tumor surgery to improve surgical outcomes and/or post-surgery to mitigate symptoms in patients for whom surgical cure is not achievable.

In addition, GCR antagonist or active agent therapy can be expected to provide clinical benefits for patients, for example, in hospitals, nursing homes, nurseries, daycares, schools, work environments, public transportation, healthcare settings, psychiatric institutions, and long-term nursing facilities.

The present invention relates to the use of a GCR antagonist, such as for example, ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof, for the prevention or treatment of Cushing's Syndrome.

The invention provides a pharmaceutical composition comprising: a therapeutically effective amount of one or more of ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof; at least one additional active agent selected from the group consisting of molecules with potential to bind viral PS, annexin-5, anti-PS monoclonal or polyclonal antibodies, bavituximab, and/or bind to viral glucocorticoid response elements (GREs), retinazone and RU486 or derivatives, cell entry inhibitors, uncoating inhibitors, reverse transcriptase inhibitors, integrase inhibitors, transcription inhibitors, antisense translation inhibitors, ribozyme translation inhibitors, prein processing and targeting inhibitors, protease inhibitors, assembly inhibitors, release phase inhibitos, immunosystem modulators and vaccines, including, but not limited to Abacavir, Ziagen, Trizivir, Kivexa/Epzicom, Aciclovir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Novir, Oseltamivir (Tamiflu), Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer, Tea tree oil, Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, Zidovudine, and combinations thereof; at least one pharmaceutically acceptable carrier; and optionally, and at least one blister package; a lidded blister; a blister card or packet; a clamshell; an intravenous (IV) package, IV packette or IV container; a tray or a shrink wrap comprising the pharmaceutical composition and instructions for use of the pharmaceutical composition.

Addiction and Withdrawal

The present invention relates to methods of and compositions for treating and relieving symptoms associated with substance abuse and withdrawal. The present invention relates to methods of and compositions for treating addiction to, for example, alcohol, drugs, caffeine, sugar, food, nicotine, opiates, and/or marijuana, etc.

Substance addiction and abuse is a multi-factorial neurological disease. Over time, repeated exposure to various substances, both endogenous and exogenous, causes modification of the neurotransmission circuits and adaptations in post-receptor signaling cascades. There are several effects of this neuronal modification. Among them, there is a reduction in the ability of natural rewards to activate the reward pathways leading to depressed motivation and mood and an increased compulsion to compensate for the physiological change.

While the common perception underlying addiction is that of a "reward circuit", pleasure may not necessarily be a strong enough impetus to drive people towards their addictions. Rather, addictive behavior arises from an intense desire to manage and/or avoid the anxiety that arises when someone is experiencing withdrawal.

Traditional treatments for substance dependency, such as benzodiazepine abuse, have been based upon cognitive-behavioral therapy or drug therapy, or a combination thereof. Conventional methods of treatment fail, however, in that they do not address the physiochemical changes that occur with addiction and dependence. Thus, conventional treatments for controlling withdrawal symptoms and cravings for addictive substances have had limited success and often have undesirable side effects.

What is therefore needed are improved methods of, and compositions for, preventing addiction to, and physiological dependence upon addictive substances. What is also needed is an improved treatment methodology for controlling cravings and withdrawal symptoms caused by substance abuse.

Accordingly, the invention provides methods of, and compositions for, preventing addiction to, and physiological dependence upon addictive substances. Also provided are methods of and compositions for an improved treatment methodology for controlling cravings and withdrawal symptoms caused by substance abuse.

The present invention relates to the use of cortisol blockers (glucocorticoid receptor [GR] antagonists) for the prevention or addiction induced anxiety and withdrawal side effects as a therapeutic and in concert with a diagnostic.

The compounds of the invention may be administered enterally or parenterally. Mixed with pharmaceutically suitable auxiliaries, e.g. as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

The compounds of the invention can be administered orally, topically, intravenously, etc. By means of pharmaceutically suitable liquids the compounds can be applied in the form of a solution, suspension, or emulsion. The compounds can also be formulated in a patch, ointment or can be enclosed in a device for local administration to the skin.

The present invention reflects the role of endogenous glucocorticoids (GCs) in withdrawal from substances of abuse and addictive substances (hereafter referred to as "drug" or "drugs", inclusive of, but not restricted to, alcohol, nicotine, caffeine, cocaine (including crack cocaine), cannabis, amphetamines (including crystal methamphetamine), opiates and opiate analogues (including heroine, oxycodone, hydrocodone, hydromorphone, methadone), dextromethorphan, benzodiazepines, ecstacy (MDMA), GHB, barbiturates, khat, kratom, PCP, LSD, ketamine, peyote, mescaline, psilocybin, rohypnol, Salvia divinorum, antidepressants, anti-anxiety 5 medications, sleep aids, allergy medications.

Increased circulating levels of GCs may relate to direct elevating effects of substances of abuse or from stress-associated GC elevations in response to neuropsychiatric and physical stresses of withdrawal.

The present invention relates to co-administration of a selective GC receptor antagonist, such as ORG34517, PT150, TPR-1, OR-1, MR-1, TCY1, PT150, PT157, PT158, PT159, PT160, PT162, PT163, PT164, PT165, PT166, PT167, combinations thereof, and pharmaceutically acceptable salts thereof administered during the active intoxication phase of drug use, prior to drug use, or after cessation of drug use to reduce neuropsychiatric and physical symptoms of withdrawal, such as anxiety, hallucinations, dysphoria, depression, delirium tremens, chills, shakes, tremors, akathisia, restlessness, restless leg syndrome, musculoskeletal aches and pains, cramping, chills, weakness.

The present invention relates to single dose of GC receptor antagonist or sustained administration of GC receptor antagonist for hours, days, weeks, or months for prevention of and/or treatment of symptoms of drug withdrawal.

The present invention may be considered for co-administration with anti-anxiety drugs and anti-depressant drugs to better control sporadic episodes, flare-ups of anxiety or depression. Regular co-administration of the present invention with anti-anxiety and/or anti-depressant drugs.

The present invention may also be used in concert with a diagnostic (for example, a diagnostic test using saliva, blood, plasma, serum, urine or tears as substrate) for the specific constituent i.e.: alcohol, cocaine, caffeine, nicotine, etc. to monitor the specific level of said constituent in the individual to prevent from occurrences of anxiety and withdrawals.

The present invention may also be used in concert with a diagnostic (for example, a diagnostic test using saliva, blood, plasma, serum, urine or tears as substrate) for cortisol to determine which individuals have elevated circulating cortisol or dysregulated cortisol and may therefore be most likely to benefit from administration of GC receptor antagonist.

The present invention may be packaged for use alone, as a single dose (by prescription or over the counter), as a limited number of timed doses in packaging designed to specifically guide self-administration, and in combination with drug or cortisol diagnostic test (using saliva, blood, plasma, serum, urine or tears as substrate) for self-administration or administration by health care professional or technician.

ORG 34517/PT150

Purification of Crude ORG34517 (PT150): (11β, 17β)-17-hydroxy-11-[3,4-(methylenedioxy)phenyl]-17-(1-propyn-1-yl)estra-4,9-dien-3-one

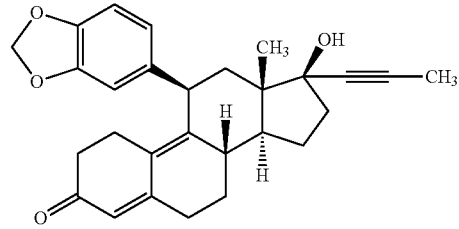

ORG34517

Materials:

ORG34517 [Palisades Therapeutics, a division of Pop Test Oncology LLC, Cliffside Park, N.J., USA; manufactured by Wilmington PharmaTech Company LLC, Newark, Del., USA; delivered by TD2 Translational Drug Development, Scottsdale, Ariz., USA, Lot: 1930-120-23], CAS Registry Number: [189035-07-2] Doubly-distilled water, purified and sterile, Ethyl acetate pro analysi[PanReac AppliChem GmbH, Lot: 0000518022; w (n/n)=99.9% (gas chromatography), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity<0.0005 meq/g]

Instruction:

ORG34517 (M=430.54 g/mol, 4.000 g, 9.2907 mmol) was suspended in distilled water (200 ml) in a 1000 ml round-bottomed flask. Then ethyl acetate pro analysi (EtOAc, 100 ml) was added as a supernatant. The flask was stoppered carefully, and the mixture was shaken vigorously for exactly 1 min. After standing at room temperature (RT, 16.4° C.) for 1 min, the biphasic mixture was shaken vigorously for exactly 1 min. The initially yellow EtOAc phase lightened in color through the shaking procedures. After standing at RT for 1 min, the mixture was transferred into a 500 ml separation funnel and the phases were separated (ca. 10 min). The EtOAc phase was isolated. The isolated aqueous phase was re-extracted with EtOAc (100 ml) by shaking for exactly 10 s. The phases were separated (ca. 10 min). The first and the second EtOAc phase were combined. The isolated residual aqueous phase was re-extracted with EtOAc (50 ml) by shaking for exactly 5 s. The phases were separated (ca. 20 min). All EtOAc phases were combined [the residual aqueous phase was cooled at +0-2° C. for 1 h, the evolved EtOAc phase was separated (ca. 20 min) and combined with the frozen EtOAc phase], and were frozen at −25° C. for 1.5 h. The ice-cold, ice-containing EtOAc phase was decanted from the frozen aqueous residues sticking at the glass surface into a 500 ml round-bottomed flask. The volume of the EtOAc solution was reduced at low temperature (30-40° C.) in vacuo to a volume of ca. 20 ml when crystalline masses appeared (the evaporation was stopped before evaporating to dryness!). The crystalline material sticking at the glass surface was rinsed with 90% (v/v) aqueous ethanol (10 ml). Then the mixture was frozen at −25° C. for 80 min. Afterwards, water (30 ml) was added and the crystallizing suspension was frozen at −25° C. for 15 min. The evolved first yield (2.076 g) of beautiful crystalline ORG34517 (nearly white crystalline chucks) was filtered and dried over CaCl2 in vacuo. The sticky residues in the flask. The volume of the EtOAc solution was reduced at low temperature (30-40° C.) in vacuo to a volume of ca. 20 ml when crystalline masses appeared (the evaporation was stopped before evaporating to dryness!). The crystalline material sticking at the glass surface was rinsed with 90% (v/v) aqueous ethanol (10 ml). Then the mixture was frozen at −25° C. for 80 min. Afterwards, water (30 ml) was added and the crystallizing suspension was frozen at −25° C. for 15 min. The evolved first yield (2.076 g) of beautiful crystalline ORG34517 (nearly white crystalline chucks) was filtered and dried over CaCl2 in vacuo. The sticky residues in the flask were rinsed with 90% (v/v) aqueous ethanol (5 ml) and combined with the first filtrate. A phase separation occurred. The separated EtOAc phase was evaporated in the complete filtrate at the lowest possible temperature in vacuo (ca. 30 min). The crystallizing suspension was frozen at −25° C. for 15 min. The evolved second yield (1.573 g) of ORG34517 was filtered and dried over CaCl2 in vacuo. Residues in the flask (and the vacuum flask) were rinsed with 90% (v/v) aqueous ethanol (4 ml), and were combined with the second filtrate. The crystallizing suspension was frozen at −25° C. for 1.5 h. The evolved third yield (210 mg) of ORG34517 was filtered and dried over CaCl2 in vacuo. From the third filtrate few substance (difference to 100%: 141 mg) could be additionally recovered, if desired, by freezing for 1 h and treatment as before.

Compound: ORG34517 (PT150)
Molecular formula: $C_{28}H_{30}O_4$
Molecular weight: 430.54 g/mol
Yield: 3.859 g (96%)
Elemental analysis: calculated: C, 78.11%; H, 7.02%; O, 14.86%.
found: C, 78.26%; H, 7.04%; O, 14.71%; C, 78.44%; H, 7.04%; O, 14.71%.
$^1$H-NMR: (DMSO-$d_6$, ppm) 0.44 (3H, s; 18-$CH_3$), 1.24-2.76 (m; steroid CH and $CH_2$), 1.82 (3H, s; R—C≡C—$CH_3$methyl), 4.37 (1H, d; $^3J(H, H)$=7.7 Hz; 11□-CH), 5.14 (1H, s; 17□-OH), 5.66 (1H, s; 4-CH), 5.97 (2H, s; O—$CH_2$—O benzodioxole), 6.60 (1H, d; $^3J$ (H, H)=7.7 Hz; 5'-CH benzodioxole), 6.78 (1H, s; 2'-CH benzodioxole), 6.79 (1H, d; $^3J(H, H)$=8.3 Hz; 6'-CH benzodioxole).

TPR-1:

Nω-[3-(Trimethylsilyl)prop-2-yn-1-yl]rifampicinium-4-olate×¾HBr×H2O=(2S,12Z,14E,16S,17S, 18R,19R,20R,21S,22R,23S,24E)-21-(acetyloxy)-1, 2-dihydro-5,6,17,19-tetrahydroxy-23-methoxy-2,4, 12,16,18,20,22-heptamethyl-8-[(E)-({4-methyl-4-[3-(trimethylsilyl)prop-2-yn-1-yl]piperazin-4-ium-1-yl}imino)methyl]-1,11-dioxo-2,7-(epoxypentadeca [1,11,13]trienimino)naphtho[2,1-b]furan-9-olate×¾HBr×1120 (TPR-1)

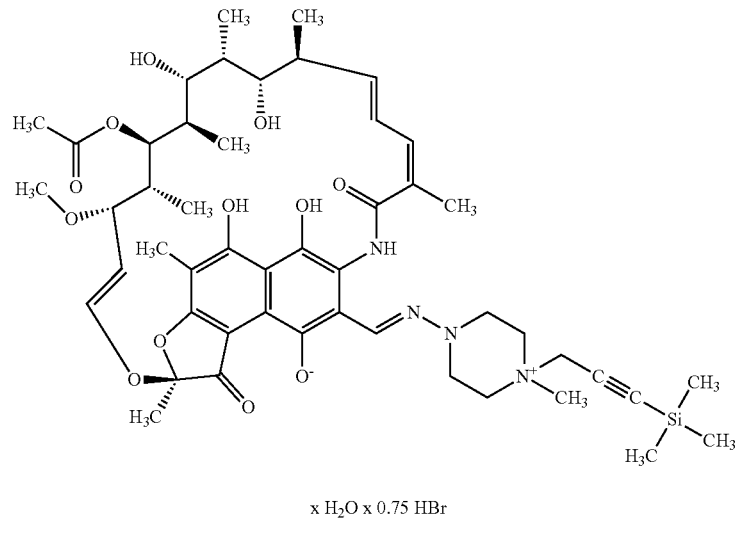 [SMILES: CO[C@H]1/C=C/O[C@@]2(C)Oc3c(C)c(O)c4c(O)c(c(/C=N/N5CC[N+](C)(CC#C[Si](C)(C)C)CC5)c([O-])c4c3C2=O)NC(=O)/C(C)=C\C=C\[C@H](C)[C@H](O)[C@@H](C)[C@@H](O)[C@@H](C)[C@H](OC(C)=O)[C@@H]1C]

x H2O x 0.75 HBr or pharmaceutically acceptable salts thereof;
Materials:
Rifampicin (rifampin) n hydrate [AppliChem GmbH, Lot: 2Q005529; w (n/n)=99% (HPLC), w (H2O)=0.3% (m/m)→0.1375 hydrate, heavy metals (as Pb)<0.002%]
3-Bromo-1-(trimethylsilyl)-1-propyne≥98% [Sigma-Aldrich Corp., St. Louis, Mo., USA, Lot: MKBK4851V; w (n/n)=98.2% (GC, area), □=1.17 g/ml, n=1.483, bp 44-45° C. (2 Torr)]
Ethyl acetate pro analysi [PanReac AppliChem GmbH, Lot: 0000518022; w (n/n)=99.9% (gas chromatography), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity<0.0005 meq/g]
Instruction:
Rifampicin (rifampin) n hydrate (M=825.43 g/mol, 2.983 g, 3.6139 mmol) was dissolved in ethyl acetate pro analysi (EtOAc, 80 ml) at room temperature (RT, □Ø=18.0° C.). A dilution of 3-bromo-1-(trimethylsilyl)-1-propyne≥98% (M=191.14 g/mol, 691 mg, 3.6152 mmol) in EtOAc (2 ml) was added under stirring at RT. The resulting deep red solution was heated to 40-50° C. for 8 min (heatgun). The deep red solution was left standing at room temperature for 1 h 35 min, then it was heated again to 40-50° C. for 8 min (heatgun). The deep red solution was additionally left standing at room temperature (☐∅=17.8° C.) for 1 h 20 min. Afterwards, the volume of the deep dark red solution was reduced in vacuo at the lowest possible temperature from 82 ml to 15-20 ml. Then the reddish-black concentrate was transferred with acetone (19 ml) into an open 150 ml crystallization dish. The latter transferred concentrate was evaporated to dryness over CaCl2 in vacuo. The yielded blackish-red material (3.892 g) was suspended in acetone (5 ml), and was again evaporated to dryness over CaCl2 in vacuo.

Compound: TPR-1

Molecular formula: C49H68N4O12Si×% HBr×H2O

Molecular weight: 1011.87 g/mol

Yield: 3.766 g (103%, the excess difference represents the solvent acetone)

Elemental analysis: calculated: C, 58.16%; H, 7.05%; N, 5.54%; O, 20.56%.

found: C, 58.17%; H, 7.07%; N, 5.16%; O, 20.60%.

C, 57.90%; H, 7.23%; N, 5.14%; O, 20.57%.

1H-NMR:

(CDCl3, ppm) −0.30 (3H, d; 3J (H,H)=7.1 Hz; 34-CH3), 0.18 (2.25H, s; R—C≡C—Si(CH3)3, zwitterion), 0.22 (6.75H, s; R—C≡C—Si(CH3)3, hydrobromide), 0.60 (3H, m; 33-CH3), 0.86 (2.25H, d; 3J (H,H)=7.1 Hz; 31-CH3, hydrobromide), 0.88 (0.75H, d; 3J (H,H)=7.1 Hz; 31-CH3, zwitterion), 1.02 (2.25H, d; 3J (H,H)=7.1 Hz; 32-CH3, hydrobromide), 1.02 (2.25H, d; 3J (H,H)=7.1 Hz; 32-CH3, zwitterion), 1.26 (0.9H, t; 3J (H,H)=7.1 Hz; EtOAc ethyl CH3), 1.36 (1H, m; 26-CH), 1.54 (1H, m; 24-CH), 1.71 (1H, m; 22-CH), 1.80 (0.75H, s; 13-CH3, zwitterion), 1.81 (2.25H, s; 13-CH3, hydrobromide), 2.05 (0.9H, s; EtOAc acetyl CH3), 2.06 (0.75H, s; acetyl 36-CH3, zwitterion), 2.07 (2.25H, s; acetyl 36-CH3, hydrobromide), 2.09 (0.75H, s; 30-CH3, zwitterion), 2.10 (2.25H, s; 30-CH3, hydrobromide), 2.17 (4.7H, s; acetone CH3), 2.23 (3H, s; 14-CH3), 2.30-2.50 (2H, m; 20-CH, all forms, +piperazine 3',5'-CH2, zwitterion), 2.63 (0.75H, br s; piperazine 3',5'-CH2, hydrobromide), 2.66 (0.75H, br s; piperazine 3',5'-CH2, hydrobromide), 3.02-3.03 (1H, m; 23-CH), 3.05 (3H, s; methoxy 37-OCH3), 3.08-3.18 (1H, br s; piperazine 2',6'-CH2, zwitterion), 3.23 (0.75H, br s; piperazine 3',5'-CH2, hydrobromide), 3.35 (0.75H, m; piperazine 3',5'-CH2, hydrobromide), 3.43 (0.5H, m; piperazine 2',6'-CH2, zwitterion), 3.46 (0.5H, m; piperazine 2',6'-CH2, zwitterion), 3.48 (0.25H, d; 3J (H,H)=7.1 Hz; 27-CH, zwitterion), 3.50 (0.75H, d; 3J (H,H)=7.1 Hz; 27-CH, hydrobromide), 3.55 (1H, m; hydroxyl 21-O—H), 3.64 (1H, m; hydroxyl 23-O—H), 3.68 (2H, s; piperazine N+—CH3, 66.67% ammonium), 3.73 (1H, m; 21-CH, hydrobromide, +piperazine 2',6'-CH2, hydrobromide), 3.77 (0.25H, d; 3J (H,H)=9.6 Hz; 21-CH, zwitterion), 3.91 (0.4H, s; R3N+—CH2-C≡C—R, 20% ammonium), 3.96-4.10 (2.75H, m; piperazine 2',6'-CH2, hydrobromide), 4.12 (0.6H, q; 3J (H,H)=7.1 Hz; EtOAc ethyl CH2), 4.94 (1H, m; 25-CH), 5.06 (0.8H, br s; R3N+—CH—C≡C—R↔R3N=CH—C≡C—R, 80% nitrogen ylide), 5.09 (0.75H, t; 3J (H,H)=6.4 Hz; 28-CH, hydrobromide), 5.11 (0.25H, m; 28-CH, zwitterion), 5.16 (0.667H, br s; 2J (14N, 1H)=15.9 Hz; piperazine R3N+—CH2-↔R3N=CH2, 33.33% nitrogen ylide), 5.94 (0.25H, m; 19-CH), 5.97 (0.75H, dd; 3J (H,H)=15.7 Hz, 3J (H,H)=5.4 Hz; 19-CH, hydrobromide), 6.17 (0.75H, d; 3J (H,H)=12.8 Hz; 29-CH, hydrobromide), 6.20 (0.25H, d; 3J (H,H)=11.5 Hz; 29-CH, zwitterion), 6.39 (0.25H, d; 3J (H,H)=11.5 Hz; 17-CH, zwitterion), 6.43 (0.75H, d; 3J (H,H)=11.5 Hz; 17-CH, hydrobromide), 6.58 (1H, m; 18-CH), 8.30 (0.25H, s; azomethine 1'—CH=NR, zwitterion), 8.45 (0.75H, s; azomethine 1'—CH=NR, hydrobromide), 12.03 (0.25H, s; hydroxyl 8-O—H, zwitterion), 12.20 (0.75H, s; hydroxyl 8-O—H, hydrobromide)*, 12.39 (0.75H, br s; 4-O—H, hydrobromide)*, 13.14 (0.75H, br s; amide 15-N—H, hydrobromide), 13.24 (1.25H, br s; hydroxyl 1-O—H, all forms, +amide 15-N—H, zwitterion).

* these assignments are tentative and interchangeable (they could not be assigned unequivocally to the individual hydrogens)

OR-1

3-Formylrifamycin SV (E)-oxime 1.2 hydrate=(2S, 12Z,14E,16S,17S,18R,19R,20R,21S,22R,23S,24E)-21-(acetyloxy)-5,6,9,17,19-pentahydroxy-8-[(E)-(hydroxyimino)methyl]-23-methoxy-2,4,12,16,18, 20,22-heptamethyl-2,7-(epoxypentadeca[1,11,13] trienimino)naphtho[2,1-b]furan-1,11(2H)-dione×1.2 H2O (OR-1)

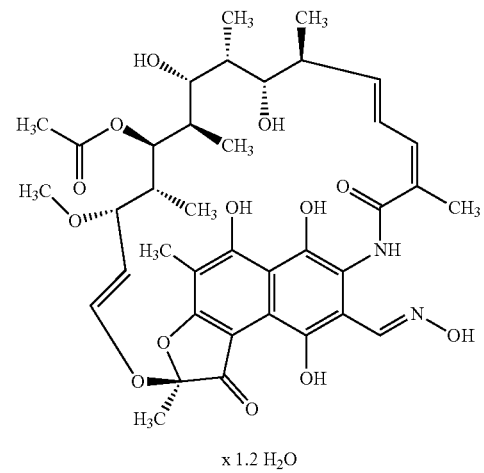 [SMILES: CO[C@H]1/C=C/O[C@@]2(C)Oc3c(C)c(O)c4c(O)c(c(/C=N/O)c(O)c4c3C2=O)NC(=O)/C(C)=C\C=C\[C@H](C)[C@H](O)[C@@H](C)[C@@H](O)[C@@H](C)[C@H](OC(C)=O)[C@@H]1C]

x 1.2 H₂O or pharmaceutically acceptable salts thereof;

Materials:

Rifampicin (rifampin) n hydrate [AppliChem GmbH, Lot: 2Q005529; w (n/n)=99% (HPLC), w (H2O)=0.3% (m/m)→0.1375 hydrate, heavy metals (as Pb)<0.002%]

47%-53% (m/m) aqueous hydroxylamine solution [Merck KGaA-EMD Millipore Corp., Lot: 56377341; w (m/m)=49.1% (manganometric titration), pH 10.6 (H2O, 20° C.), ☐=1.122 g/ml]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Instruction:

Rifampicin (rifampin) n hydrate (M=825.43 g/mol, 2.500 g, 3.0287 mmol) was dissolved in 90% (v/v) aqueous ethanol (125 ml) supplied with 10.27 M [32% (m/m)] aqueous hydrochloric acid (2500 μl, 25.6750 mmol). The red solution was mixed with 47%-53% (m/m) aqueous hydroxylamine solution (H2N—OH, M=33.02 g/mol, 1250 μl, 688.6 mg, 20.8549 mmol), and the resulting deep red solution was heated to 40-50° C. for 10 min (heatgun). The deep red solution was left standing at room temperature (□=17.8° C.) for 85 min. The evolved first yield of the orange-red crude product was filtered and dried over CaCl2 in vacuo. The filtrate was frozen at −25° C. for 90 min. Afterwards, water (100 ml) was added. The suspension was additionally frozen at −25° C. for 4 h. The evolved second yield of the orange-red crude product was filtered and dried over CaCl2 in vacuo. Both yields were combined. The filtrate was discarded.

Purification: the orange-red first crude product (2.175 g) was suspended in acetone (100 ml) supplied with water (10 ml). The resulting orange suspension was heated to 40-50° C. for 5 min (heatgun). The resulting orange solution was frozen at −25° C. for 1 h. After adding water (100 ml), the precipitating suspension was frozen at −25° C. for 3 h. The evolved yield of the orange-red product was filtered and dried over CaCl2 in vacuo. The filtrate was discarded.

Compound: OR-1

Molecular formula: C38H48N2O13×1.2 H2O

Molecular weight: 762.41 g/mol

Yield: 2.018 g (87%)

Elemental analysis: calculated: C, 59.86%; H, 6.66%; N, 3.67%; O, 29.80%.

found: C, 59.89%; H, 6.92%; N, 3.31%; O, 29.80%.

C, 59.99%; H, 6.91%; N, 3.34%; O, 29.66%.

1H-NMR:

(CDCl3, ppm) −0.30 (3H, d; 3J (H,H)=7.1 Hz; 34-CH3), 0.69 (3H, d; 3J (H,H)=7.1 Hz; 33-CH3), 0.89 (3H, d; 3J (H,H)=7.1 Hz; 31-CH3), 1.03 (3H, d; 3J (H,H)=7.1 Hz; 32-CH3), 1.39 (1H, m; 26-CH), 1.56 (1H, m; 24-CH), 1.59 (H2O in CDCl3), 1.77 (1H, m; 22-CH), 1.81 (3H, s; 13-CH3), 2.07 (3H, s; acetyl 36-CH3), 2.08 (3H, s; 30-CH3), 2.17 (s; acetone CH3), 2.25 (3H, s; 14-CH3), 2.40 (1H, m; 20-CH), 3.03-3.06 (1H, m; 23-CH), 3.05 (3H, s; methoxy 37-OCH3), 3.50 (1H, d; 3J (H,H)=7.1 Hz; 27-CH), 3.53 (1H, m; hydroxyl 21-O—H), 3.65 (1H, d; 3J (H,H)=5.1 Hz; hydroxyl 23-O—H), 3.81 (1H, d; 3J (H,H)=9.6 Hz; 21-CH), 4.93 (1H, d; 3J (H,H)=10.9 Hz; 25-CH), 5.11 (1H, dd; 3J (H,H)=12.5 Hz, 3J (H,H)=7.4 Hz; 28-CH), 5.97 (1H, dd; 3J (H,H)=15.4 Hz, 3J (H,H)=5.1 Hz; 19-CH), 6.24 (1H, dd; 3J (H,H)=12.8 Hz, 3J (H,H)=1.3 Hz; 29-CH), 6.37 (1H, d; 3J (H,H)=10.9 Hz; 17-CH), 6.53 (1H, ddd; 3J (H,H)=15.5 Hz, 3J (H,H)=11.1 Hz, 3J (H,H)=1.6 Hz; 18-CH), 7.34 (1H, s; oxime OH), 8.90 (1H, s; azomethine 1'—CH═N), 11.74 (1H, s; hydroxyl 4-O—H), 12.18 (1H, s; hydroxyl 8-O—H), 13.16 (1H, s; amide 15-N—H), 13.37 (1H, s; hydroxyl 1-O—H)

MR-1

(2S,12Z,14E,16S,17S,18R,19R,20R,21S,22R,23S, 24E)-21-(acetyloxy)-5,6,9,17,19-pentahydroxy-23-methoxy-8-[(E)-(methoxyimino)methyl]-2,4,12,16, 18,20,22-heptamethyl-2,7-(epoxypentadeca[1,11,13] trienimino)naphtho[2,1-b]furan-1,11(2H)-dione

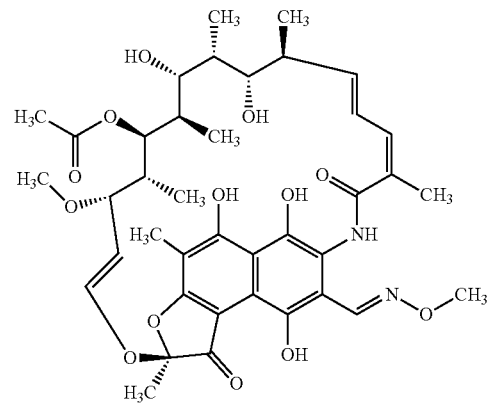 [SMILES: CO/N=C/c1c2c(O)c3c(O)c(C)c4c(c3c1O)C(=O)[C@@](C)(O/C=C/[C@H](OC)[C@@H](C)[C@@H](OC(C)=O)[C@H](C)[C@H](O)[C@H](C)[C@@H](O)[C@@H](C)/C=C/C=C(/C)C(=O)N2)O4]

or pharmaceutically acceptable salts thereof

Materials:
Rifampicin (rifampin) n hydrate [AppliChem GmbH, Lot: 2Q005529; w (n/n)=99% (HPLC), w (H2O)=0.3% (m/m)→0.1375 hydrate, heavy metals (as Pb)<0.002%]

24.0%-26.0% (m/m) aqueous O-methyl hydroxylammonium chloride solution in 17.0%-19.0% (m/m) aqueous hydrochloric acid solution [Merck KGaA-EMD Millipore Corp., Lot: 50699440; w (m/m)=24.3% (acidimetric titration) in 18.6% (m/m) (acidimetric titration) aqueous hydrochloric acid, □=1.105 g/ml]

Instruction:

Rifampicin (rifampin) n hydrate (M=825.43 g/mol, 2.500 g, 3.0287 mmol) was dissolved in 90% (v/v) aqueous ethanol (125 ml). The red solution was mixed with a 24.0%-26.0% (m/m) aqueous O-methyl hydroxylammonium chloride solution in 17.0%-19.0% (m/m) aqueous hydrochloric acid solution (H2N—OCH3×HCl, M=83.51 g/mol, 5.00 ml, 5.5250 g, 16.0768 mmol), and the resulting deep red solution was heated to 40-50° C. for 10 min (heatgun). The deep red solution was left standing at room temperature for 70 min, then it was frozen at −25° C. for 90 min. Afterwards, water (100 ml) was added. The suspension was frozen at −25° C. for 4 h. After adding water (100 ml), the precipitating suspension was frozen at −25° C. for 90 min. The evolved yield of the light yellow-orange first crude product (1.180 g) was filtered and dried over CaCl2 in vacuo. The filtrate was discarded. This first crude product contained rifampicin [TLC, silica gel 60 F254, eluent 80% (v/v) acetone].

1st Purification: the yellow-orange first crude product (1.180 g) was suspended in acetone (40 ml) supplied with water (10 ml). The resulting orange suspension was heated to 40-50° C. for 5 min (heatgun). Afterwards, acetone (100 ml) was added, and the suspension was heated to 40-50° C. for 3 min (heatgun). The resulting orange solution was frozen at −25° C. for 1 h. After adding water (100 ml), the precipitating suspension was frozen at −25° C. for 1 h. After adding additional water (100 ml), the precipitating suspension was frozen at −25° C. for 4 h. The evolved yield (877 mg) of the light orange second crude product was filtered and dried over CaCl2 in vacuo. The filtrate was discarded. This second crude product contained traces of rifampicin [TLC, silica gel 60 F254, eluent 80% (v/v) acetone].

2nd Purification: the light orange second crude product (877 mg) was suspended in acetone (20 ml) supplied with water (10 ml). The resulting suspension was frozen at −25° C. for 90 min. Then water (20 ml) was added, and the precipitating suspension was frozen at −25° C. for 50 min. The evolved yield of the light orange product was filtered and dried over CaCl2 in vacuo.

Compound: MR-1
Molecular formula: C39H50N2O13
Molecular weight: 754.82 g/mol
Yield: 844 mg (37%)
Elemental analysis: calculated: C, 62.06%; H, 6.68%; N, 3.71%; O, 27.56%.
found: C, 62.03%; H, 7.21%; N, 3.75%; O, 27.74%.
C, 62.10%; H, 7.23%; N, 3.76%; O, 27.61%.
1H-NMR:
(CDCl3, ppm) −0.29 (3H, d; 3J (H,H)=7.1 Hz; 34-CH3), 0.67 (3H, d; 3J (H,H)=6.4 Hz; 33-CH3), 0.90 (3H, d; 3J (H,H)=7.1 Hz; 31-CH3), 1.03 (3H, d; 3J (H,H)=7.1 Hz; 32-CH3), 1.39 (1H, m; 26-CH), 1.56 (1H, m; 24-CH), 1.59 (H2O in CDCl3), 1.77 (1H, m; 22-CH), 1.80 (3H, s; 13-CH3), 2.07 (3H, s; acetyl 36-CH3), 2.10 (3H, s; 30-CH3), 2.17 (s; acetone CH3), 2.24 (3H, s; 14-CH3), 2.40 (1H, m; 20-CH), 3.03-3.06 (1H, m; 23-CH), 3.05 (3H, s; methoxy 37-OCH3), 3.48 (1H, m; hydroxyl 21-O—H), 3.50 (1H, d; 3J (H,H)=7.1 Hz; 27-CH), 3.64 (1H, d; 3J (H,H)=5.1 Hz; hydroxyl 23-O—H), 3.79 (1H, d; 3J (H,H)=9.0 Hz; 21-CH), 3.87 (3H, s; methoxime=N—OCH3), 4.94 (1H, d; 3J (H,H)=10.9 Hz; 25-CH), 5.11 (1H, dd; 3J (H,H)=12.5 Hz, 3J (H,H)=6.7 Hz; 28-CH), 5.96 (1H, dd; 3J (H,H)=15.4 Hz, 3J (H,H)=5.1 Hz; 19-CH), 6.23 (1H, m; 29-CH), 6.39 (1H, d; 3J (H,H)=10.3 Hz; 17-CH), 6.48 (1H, m; 18-CH), 8.81 (1H, s; azomethine 1'—CH═N), 11.85 (1H, s; hydroxyl 4-O—H), 12.13 (1H, s; hydroxyl 8-O—H), 13.15 (1H, s; amide 15-N—H), 13.36 (1H, s; hydroxyl 1-O—H)

TCY-1:

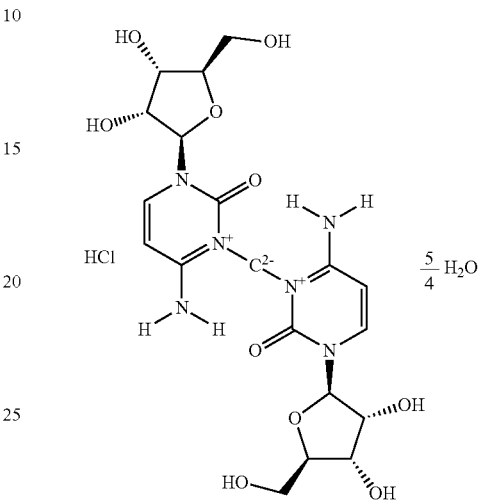

or pharmaceutically acceptable salts thereof.

KM-1

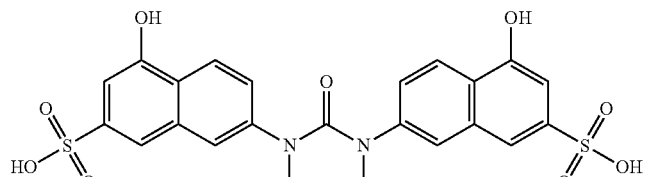

carbonyl J acid (mirror-symmetric)

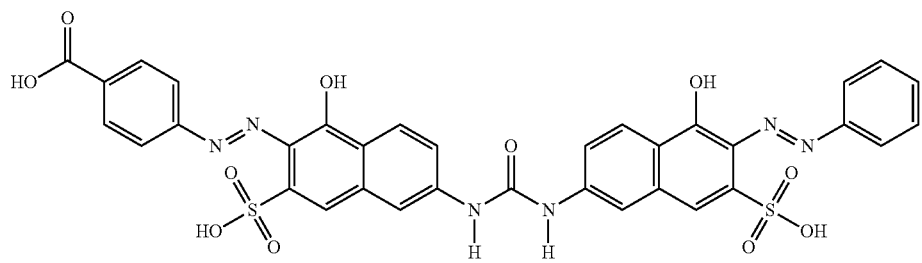

calcomine orange 2RS

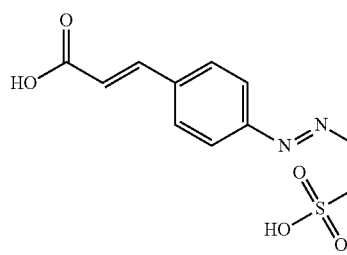
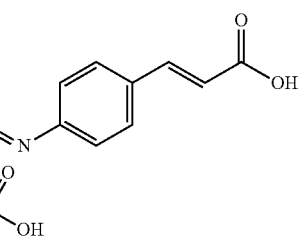

KM-1 or pharmaceutically acceptable salts thereof.
PT155-3

⅓(11β,17β)-17-Hydroxy-11-[3,4-(methylenedioxy)phenyl]-17-(1-propyn-1-yl)estra-4,9-dien-3-one (PT150)×(2EZ)-2-{(11β,17β)-17-hydroxy-11-[3,4-(methylenedioxy)phenyl]-17-(1-propyn-1-yl)estra-4,9-dien-3-ylidene}hydrazinecarbothioamide [71.8% (E), 28.2% (Z)]×⅓H$_2$O×⅞ acetone (PT155-3)

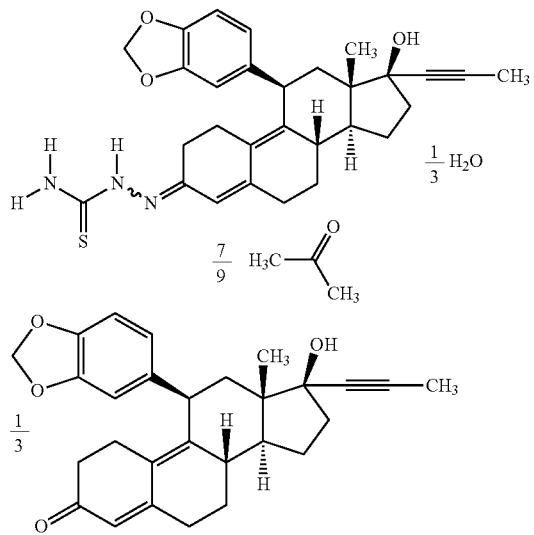

or pharmaceutically acceptable salts thereof.
Materials:
  PT150 [Pop Test Oncology LLC, Cliffside Park, N.J., USA; manufactured by Sai Life Sciences Ltd., Pune, India, Lot: SPO-PO1601-009; w (n/n)=99.92% (HPLC, UV detection at 210 nm), =+73.02° (c=1 in EtOH)]
  Thiosemicarbazide puriss. p.a. [Sigma-Aldrich Corp., St. Louis, Mo., USA, Lot: 1167177V (Fluka); w (m/m)=100.1% (iodometric titration), mp 181° C. (dec.), residue on ignition<0.05%, metal trace analysis (inductively coupled plasma mass spectrometry)≤50-5 mg/kg]
  Glacial acetic acid (acetic acid 100% p.a.) [AppliChem GmbH, Darmstadt, Germany; Lot: 8Y002937; w (m/m)=100.0% (titration), water 0.0% (Karl Fischer titration), acetic anhydride≤0.05%, formic acid≤0.01%, non-volatile matter≤0.001%]

Instruction:
PT150 (M=430.54 g/mol, 8.017 g, 18.6208 mmol) and thiosemicarbazide puriss. p.a. (M=91.14 g/mol, 1.740 g, 19.0915 mmol) were suspended in in 90% (v/v) aqueous ethanol (400 ml). Glacial acetic acid (4000 µl, 69.9417 mmol) was added. The suspension was refluxed gently for 1 h 15 min (75 min). All solids went into solution which turned light yellow during reflux. Afterwards, the yellow solution was left standing at room temperature (RT, □=20.0° C.) for 12 min. Then the still warm yellow solution was filtered through one layer of filter paper. Residues were transferred and rinsed with 90% (v/v) aqueous ethanol (30 ml), and, successively, with water (60 ml). The yellow filtrate was cooled at +0-2° C. for 30 min. After addition of water (100 ml), the precipitating suspension was frozen at -25° C. for 1 h. After addition of water (145 ml), the precipitating suspension was frozen at -25° C. for 1.5 h. The evolved first yield (7.372 g) of the cream yellow, crude PT155 was filtered and dried over CaCl2 in vacuo. The filtrate was mixed with water (120 ml), and was frozen at -25° C. for 4 h. The evolved second yield (789 mg) of the cream yellow, crude PT155 was filtered and dried over CaCl2 in vacuo. The filtrate was mixed with water (200 ml), and was frozen at -25° C. for 8 h. The evolved third yield (1.116 g) of the cream yellow, crude PT155 was filtered and dried over CaCl2 in vacuo. All yields were combined (9.277 g, 100%).

The crude product (9.277 g) was dissolved in acetone (120 ml). Afterwards, water (80 ml) was added in portions under stirring to yield a yellowish emulsion. The precipitating emulsion with sticky yellow material pieces was frozen at -25° C. for 1 h. Afterwards, water (40 ml) was added. The precipitating emulsion with an sticky/oily yellow material piece was frozen at -25° C. for 1 h. The evolved first yield (7.449 g) of the yellow PT155 was filtered and dried over CaCl2 in vacuo. The material was transferred onto a sintered-glass filter and set under vacuum, whereby the oily residue inflated to a yellow crystallisate. The filtrate was mixed with water (40 ml), and was frozen at -25° C. for 4 h. The evolved second yield (637 mg) of the yellow PT155 was filtered and dried over CaCl2 in vacuo. The filtrate was mixed with water (200 ml), and was frozen at -25° C. for 4 h. The sintered-glass filter applied was rinsed with acetone (22 ml), and the acetone extract was combined with the filtrate. The evolved third yield (1.084 g) of the yellow PT155 was filtered and dried over CaCl2 in vacuo. All yields were combined (9.170 g).

Compound: PT155
Molecular formula: ⅓C28H30O4×C29H33N3O3S× C3H6O×⅓H2O
Molecular weight: 664.23 g/mol
Yield: 9.170 g (99%)
Elemental analysis: calculated: C, 70.72%; H, 6.79%; N, 6.33%; S, 4.83%; O, 11.33%.
found: C, 70.72%; H, 7.10%; N, 5.15%; S, 0.00%; O, 13.49%.
C, 70.71%; H, 7.10%; N, 5.35%; S, 0.00%; O, 13.03%.
1H-NMR:
(DMSO-d6, ppm) 0.41 (3H, s; 18-CH3, (E)-TSC*), 0.42 (1.18H, s; 18-CH3, (Z)-TSC**), 0.44 (2.09H, s; 18-CH3, PT150), 1.23-2.77 (m; steroid CH and CH2), 1.83 (5.28H, br s; R—C≡C—CH3 methyl, all three species), 2.09 (9.64H, s; acetone CH3), 4.28 (0.393H, m; 11alpha-CH, (Z)-TSC), 4.30 (1H, d; 3J (H,H)=7.2 Hz; 11□-CH, (E)-TSC), 4.38 (0.697H, d; 3J (H,H)=7.2 Hz; 11alpha-CH, PT150), 5.11 (1H, s; 17beta-OH, (E)-TSC), 5.12 (0.393H, s; 17beta-OH, (Z)-TSC), 5.14 (0.697H, s; 17beta-OH, PT150), 5.66 (0.697H, s; 4-CH, PT150), 5.86 (1H, s; 4-CH, (E)-TSC), 5.97 (4.18H, br s; O—CH2-O benzodioxole, all three species), 5.97 (0.393H, s; 4-CH, (Z)-TSC), 6.60 (2.09H, d; 3J (H,H)=8.0 Hz; 5'-CH benzodioxole, all three species), 6.67 (0.393H, s; 2'-CH benzodioxole, (Z)-TSC), 6.77 (1.697H, s; 2'-CH benzodioxole, (E)-TSC and PT150), 6.79 (0.393H, m; 6'-CH benzodioxole, (Z)-TSC), 6.79 (1.697H, d; 3J (H,H)=8.0 Hz; 6'-CH benzodioxole, (E)-TSC and PT150), 7.51 (0.393H, br s; NH2, HA, (Z)-TSC), 7.57 (1H, br s; NH2, HA, (E)-TSC), 7.97 (0.393H, br s; NH2, HB, (Z)-TSC), 8.09 (1H, br s; NH2, HB, (E)-TSC), 10.05 (1H, br s; N—H, (E)-TSC), 10.42 (0.393H, br s; N—H, (Z)-TSC).
*,** (E or Z)-TSC=(E or Z)-thiosemicarbazone.
PT157:

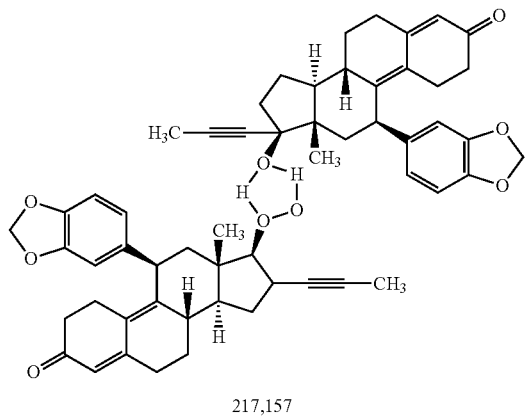

217,157 or pharmaceutically acceptable salts thereof;
PT158:

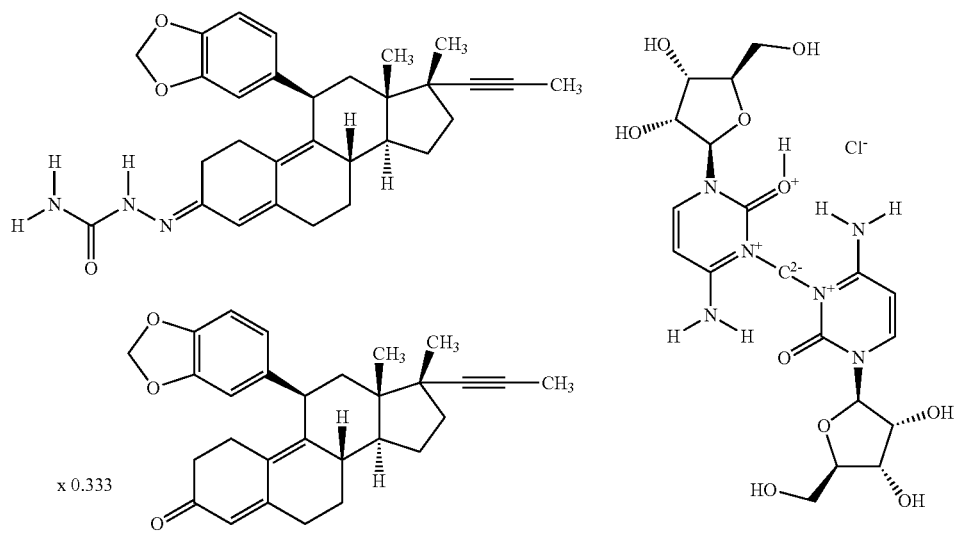

or pharmaceutically acceptable salts thereof;
PT159:

(11β,17β)-17-Hydroxy-11-[3,4-(methylenedioxy)phenyl]-17-(1-propyn-1-yl)estra-4,9-dien-3-one(2S,12Z,14E,16S,17S,18R,19R,20R,21S,22R,23S,24E)-21-(acetyloxy)-1,2-dihydro-5,6,17,19-tetrahydroxy-23-methoxy-2,4,12,16,18,20,22-heptamethyl-8-[(E)-({4-methyl-4-[3-(trimethylsilyl)prop-2-yn-1-yl]piperazin-4-ium-1-yl}imino)methyl]-1,11-dioxo-2,7-(epoxypentadeca[1,11,13]trienimino)naphtho[2,1-b]furan-9-olate×¾HBr×H$_2$O (PT159)

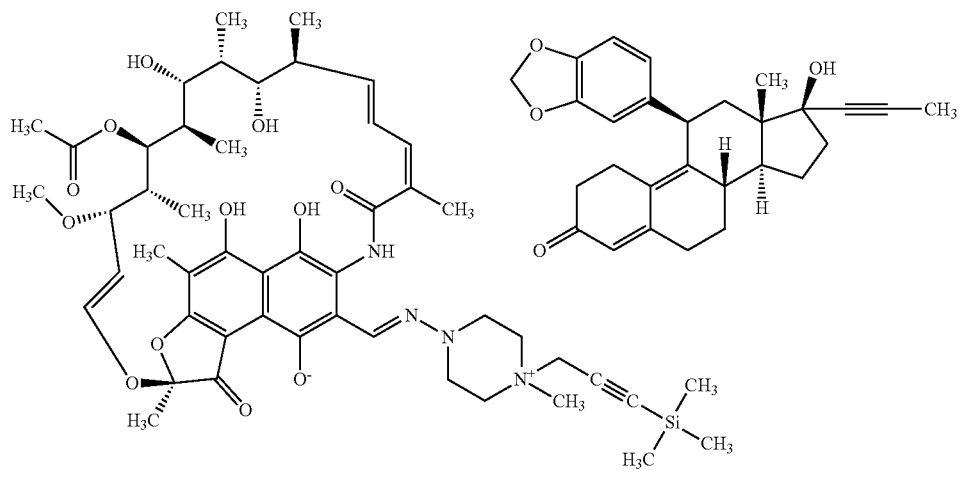

x H$_2$O x 0.75 HBr or pharmaceutically acceptable salts thereof;

Materials:
PT150 [Pop Test Oncology LLC, Cliffside Park, N.J., USA; manufactured by Sai Life Sciences Ltd., Pune, India, Lot: SPO-P01601-009; w (n/n)=99.92% (HPLC, UV detection at 210 nm), $[\alpha]_D^{20}$=+73.02° (c=1 in EtOH)]

TPR-1=N-[3-(trimethylsilyl)prop-2-yn-1-yl]rifampicinium-4-olate×¾HBr×H$_2$O ($C_{49}H_{68}N_4O_{12}Si$×¾HBr×H$_2$O) (M=1011.87 g/mol) [synthesized by Andreas J. Kesel at Saturday, May 30, 2015; w (n/n)≥98% ($^1$H NMR and elemental analysis)]

Instruction:
PT150 (M=430.54 g/mol, 215 mg, 499.3729 μmol) and TPR-1 (M=1011.87 g/mol, 505 mg, 499.0760 μmol) (this complete mixture had M=1442.67 g/mol before drying) were carefully weighed and thoroughly mixed as solid powders with a spatula. The mixture was then carefully dried over CaCl$_2$) in vacuo to yield PT159 as a brownish-maroon amorphous powder.

Compound: PT159

Molecular formula: ($C_{28}H_{30}O_4$)×($C_{49}H_{68}N_4O_{12}Si$)×¾HBr×H$_2$O

Molecular weight: 1442.67 g/mol

Yield: 721 mg (100%)

PT160:

⅓ (11β,17β)-17-Hydroxy-11-[3,4-(methylenedioxy)phenyl]-17-(1-propyn-1-yl)estra-4,9-dien-3-one-(2EZ)-2-{(11β,17β)-17-hydroxy-11-[3,4-(methylenedioxy)phenyl]-17-(1-propyn-1-yl)estra-4,9-dien-3-ylidene}hydrazinecarbothioamide [71.8% (E), 28.2% (Z)]-(2S,12Z,14E,16S,17S,18R,19R,20R,21S,22R,23S,24E)-21-(acetyloxy)-1,2-dihydro-5,6,17,19-tetrahydroxy-23-methoxy-2,4,12,16,18,20,22-heptamethyl-8-[(E)-({4-methyl-4-[3-(trimethylsilyl)prop-2-yn-1-yl]piperazin-4-ium-1-yl}imino)methyl]-1,11-dioxo-2,7-(epoxypentadeca[1,11,13]trienimino)naphtho[2,1-b]furan-9-olate×¾HBr×C₃H₆O×1⅓H₂O (PT160)

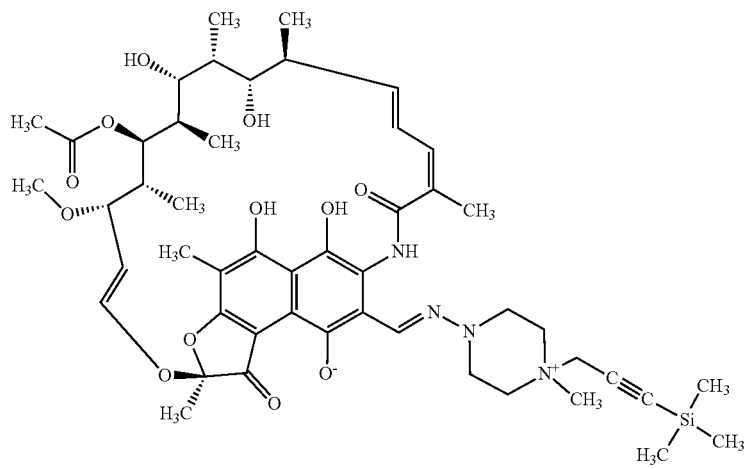

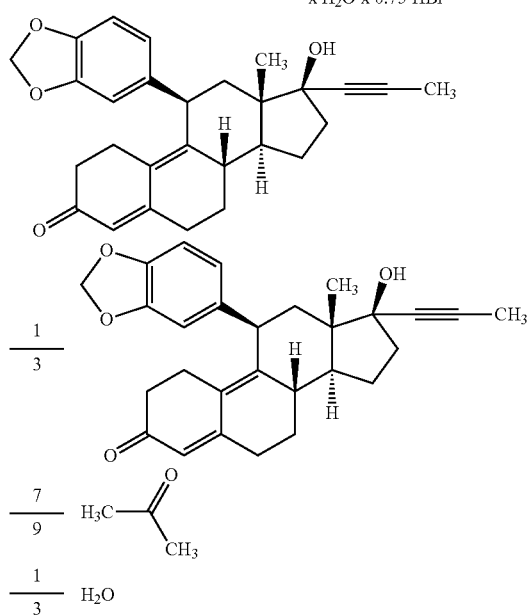

or pharmaceutically acceptable salts thereof.
Materials:
PT155 (third batch: PT155-3) (⅓C28H30O4×C29H33N3O3S×C3H6O×⅓H2O) (M=664.23 g/mol) [Pop Test Oncology LLC, Cliffside Park, N.J., USA; third batch synthesized by Andreas J. Kesel at Saturday, Sep. 10, 2016; w (n/n)≥98% (1H NMR)]

TPR-1=N☐-[3-(trimethylsilyl)prop-2-yn-1-yl]rifampicinium-4-olate×¾HBr×H2O (C49H68N4O12Si×¾HBr×H2O) (M=1011.87 g/mol) [synthesized by Andreas J. Kesel at Saturday, May 30, 2015; w (n/n)≥98% (1H NMR and elemental analysis)]

Instruction:
PT155-3 (M=664.23 g/mol, 329 mg, 495.3104 μmol) and TPR-1 (M=1011.87 g/mol, 501 mg, 495.1229 μmol) (this complete mixture had M=1676.35 g/mol before drying) were carefully weighed and thoroughly mixed as solid powders with a spatula. The mixture was then carefully dried over CaCl2) in vacuo to yield PT160 as yellowish-maroon amorphous powder.

Compound: PT160
Molecular formula: (⅓C28H30O4×C29H33N3O3S)×(C49H68N4O12Si)×¾HBr×C3H6O×1⅓H2O
Molecular weight: 1676.35 g/mol
Yield: 829 mg (100%)

PT161-1:

(11β,17β)-17-Hydroxy-11-[3,4-(methylenedioxy)phenyl]-17-(1-propyn-1-yl)estra-4,9-dien-3-one (PT150)×⅓(17β)-17-hydroxy-11-[3,4-(methylenedioxy)phenyl]-17-(1-propyn-1-yl)estra-5(10),9(11)-dien-3-one (iso-PT50)×¼ 2-thioxothiazolidin-4-one (PT161-1)

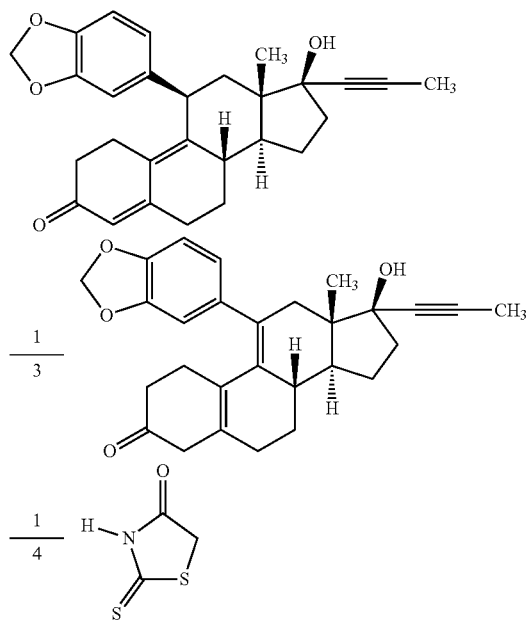

or pharmaceutically acceptable salts thereof.
Materials:
- ORG34517 [Pop Test Oncology LLC, Cliffside Park, N.J., USA; manufactured by Sai Life Sciences Ltd., Pune, India, Lot: SPO-P01601-009; w (n/n)=99.92% (HPLC, UV detection at 210 nm), =+73.02° (c=1 in EtOH)]
- Rhodanine (2-thioxothiazolidin-4-one) for synthesis [Merck-Schuchardt OHG, Merck KGaA-EMD Millipore Corp., Lot: 575261; w (m/m)≥98% (from sulfur content), mp 166-168° C.]
- 10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Instruction:
ORG34517 (M=430.54 g/mol, 505 mg, 1.1729 mmol) and rhodanine for synthesis (M=133.19 g/mol, 201 mg, 1.5091 mmol) were suspended in in 90% (v/v) aqueous ethanol (20 ml). Then 10.27 M [32% (m/m)] aqueous hydrochloric acid (500 μl, 5.1350 mmol) was added. The suspension was refluxed gently for 2 h. All solids went into solution which turned light yellow during reflux.

Afterwards, the yellow solution was left standing at room temperature (RT, □=17.1° C.) for 5 min. Then water (15 ml) was added, and the precipitating suspension was cooled at +0-2° C. After addition of water (10 ml), the precipitating suspension was frozen at −25° C. for 1.5 h. The evolved yield (451 mg) of the light yellow, crude PT161-1 was filtered. The material was vacuum sucked dry for 30 min on the sintered-glass filter. The complete filtrate was mixed with water (6 ml), and was filtered on the main product in the same sintered-glass filter. The combined material was vacuum sucked dry for 30 min on the sintered-glass filter, and then was washed thoroughly with water (50 ml). The material was then dried over CaCl2 in vacuo.

Compound: PT161-1 (crude product)
Molecular formula: C28H30O4×⅓C28H30O4×¼C3H3NOS2
Molecular weight: 607.35 g/mol (calculated solvent-free)
Yield: 451 mg (84%)
1H-NMR:
(DMSO-d6, ppm) 0.44 (3H, s; 18-CH3, PT150), 0.85 (1H, s; 18-CH3, iso-PT150), 1.23-2.80 (m; steroid CH and CH2), 1.76 (1H, br s; R—C≡C—CH3 methyl, iso-PT150), 1.83 (3H, br s; R—C≡C—CH3 methyl, PT150), 4.23 (0.5H, s; 5-CH2, rhodanine), 4.37 (1H, d; 3J (H,H)=7.2 Hz; 11□-CH, PT150), 5.14 (1H, s; 17□-OH, PT150), 5.22 (0.333H, s; 17□-OH, iso-PT150), 5.66 (1H, s; 4-CH, PT150), 5.97 (2H, br s; O—CH2-O benzodioxole, PT150), 6.01 (0.666H, br s; O—CH2-O benzodioxole, iso-PT150), 6.60 (1.333H, d; 3J (H,H)=8.0 Hz; 5'-CH benzodioxole, PT150 and iso-PT150), 6.78 (1.333H, s; 2'-CH benzodioxole, PT150 and iso-PT150), 6.79 (1.333H, d; 3J (H,H)=8.0 Hz; 6'-CH benzodioxole, PT150 and iso-PT150), 13.14 (0.25H, br s; 3-N—H, rhodanine)

PT161:

(11β,17β)-17-Hydroxy-11-[3,4-(methylenedioxy)phenyl]-17-(1-propyn-1-yl)estra-4,9-dien-3-one (PT150)×0.3 (17β)-17-hydroxy-11-[3,4-(methylenedioxy)phenyl]-17-(1-propyn-1-yl)estra-5(10),9(11)-dien-3-one (iso-PT50)×0.1 2-thioxothiazolidin-4-one (PT161-2=PT161)

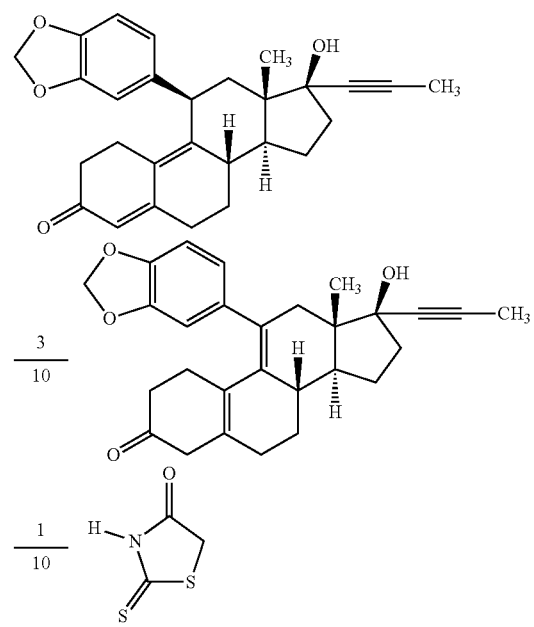

or pharmaceutically acceptable salts thereof;
Materials:
- PT161-1 [C28H30O4×⅓C28H30O4×¼C3H3NOS2, M=607.35 g/mol (calculated solvent-free)] as synthesized in the preceding step Rhodanine (2-thioxothiazolidin-4-one) for synthesis [Merck-Schuchardt OHG, Merck KGaA-EMD Millipore Corp., Lot: 575261; w (m/m)≥98% (from sulfur content), mp 166-168° C.]

Sodium carbonate (Na2CO3) pro analysi [AppliChem GmbH, Darmstadt, Germany; Lot: 6E004295; w (m/m)=99.62% (titration), H2O=0.1% (m/m), potassium (K)≤0.01%, calcium (Ca)≤0.001%, magnesium (Mg)≤0.001%, solubility in water (20° C.) 210 g/l, mp 891° C.]

Glacial acetic acid (acetic acid 100% p.a.) [AppliChem GmbH, Darmstadt, Germany; Lot: 8Y002937; w (m/m)=100.0% (titration), water 0.0% (Karl Fischer titration), acetic anhydride≤0.05%, formic acid≤0.01%, non-volatile matter≤0.001%]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Instruction:

PT161-1 [M=607.35 g/mol (calculated solvent-free), 423 mg, 0.6965 mmol], rhodanine for synthesis (M=133.19 g/mol, 145 mg, 1.0887 mmol) and anhydrous sodium carbonate Na2CO3 pro analysi (M=105.99 g/mol, 100 mg, 0.9435 mmol) were suspended in in 90% (v/v) aqueous ethanol (20 ml). Then glacial acetic acid HOAc (M=60.05 g/mol, 24 mg, 0.3997 mmol) was added by transferring with 90% (v/v) aqueous ethanol (5 ml). The suspension was refluxed for 50 min. After 20 min reflux, a dilution of 10.27 M [32% (m/m)] aqueous hydrochloric acid (800 µl, 8.2160 mmol) in water (3 ml) was added through the reflux condensor. After 10 min further reflux, water (20 ml) was added through the reflux condensor. After 10 min further reflux, water (20 ml) was added through the reflux condensor. After 10 min further reflux, the opaque yellow solution was cooled at room temperature (RT, =17.1° C.) for 5 min. The still hot solution was filtered through one layer of filter paper. Residues were transferred and rinsed with 90% (v/v) aqueous ethanol (7 ml). The filtrate was cooled at RT for 1 h, then cooled at +0-2° C. for 1 h, then frozen at −25° C. for 1.5 h. The evolved yield (345 mg) of the light yellow PT161-2 was filtered. The residual sticky material in the round-bottomed flask was dissolved in 90% (v/v) aqueous ethanol (4 ml), and re-precipitated by addition of water (16 ml), and twice transferred by addition of water (2×6 ml). Finally, the combined material on the sintered-glass filter was washed with water (10 ml). The material was vacuum sucked dry for 30 min on the sintered-glass filter, and was then dried over CaCl2 in vacuo.

Compound: PT161-2 (=PT161)

Molecular formula: C28H30O4×0.3C28H30O4×0.1C3H3NOS2

Molecular weight: 573.02 g/mol

Yield: 345 mg (86%)

Elemental analysis: calculated: C, 76.93%; H, 6.91%; N, 0.240%; S, 1.120%; O, 14.80%.

found: C, 77.27%; H, 7.09%; N, 0.169%; S, 0.709%; O, 14.70%.

C, 76.98%; H, 7.06%; N, 0.183%; S, 0.735%; O, 14.73%.

1H-NMR:

(DMSO-d6, ppm) 0.44 (3H, s; 18-CH3, PT150), 0.85 (0.9H, s; 18-CH3, iso-PT150), 1.23-2.80 (m; steroid CH and CH2), 1.76 (0.9H, br s; R—C≡C—CH3 methyl, iso-PT150), 1.83 (3H, br s; R—C≡C—CH3 methyl, PT150), 4.21 (0.2H, s; 5-CH2, rhodanine), 4.38 (1H, d; 3J (H,H)=7.7 Hz; 11☐-CH, PT150), 5.14 (1H, s; 17☐-OH, PT150), 5.22 (0.3H, s; 17☐-OH, iso-PT150), 5.66 (1H, s; 4-CH, PT150), 5.97 (2H, br s; 0-CH2-0 benzodioxole, PT150), 6.01 (0.6H, br s; 0-CH2-0 benzodioxole, iso-PT150), 6.60 (1.3H, d; 3J (H,H)=8.3 Hz; 5'-CH benzodioxole, PT150 and iso-PT150), 6.78 (1.3H, s; 2'-CH benzodioxole, PT150 and iso-PT150), 6.79 (1.3H, d; 3J (H,H)=8.3 Hz; 6'-CH benzodioxole, PT150 and iso-PT150), 13.14 (0.1H, br s; 3-N—H, rhodanine)

PT162:

Tetrakis{3-[(tricyclo[3.3.1.1$^{3,7}$]decan-1-ammonio)methyl]benzyl}ammonium pentachloride (PT162)

217,157

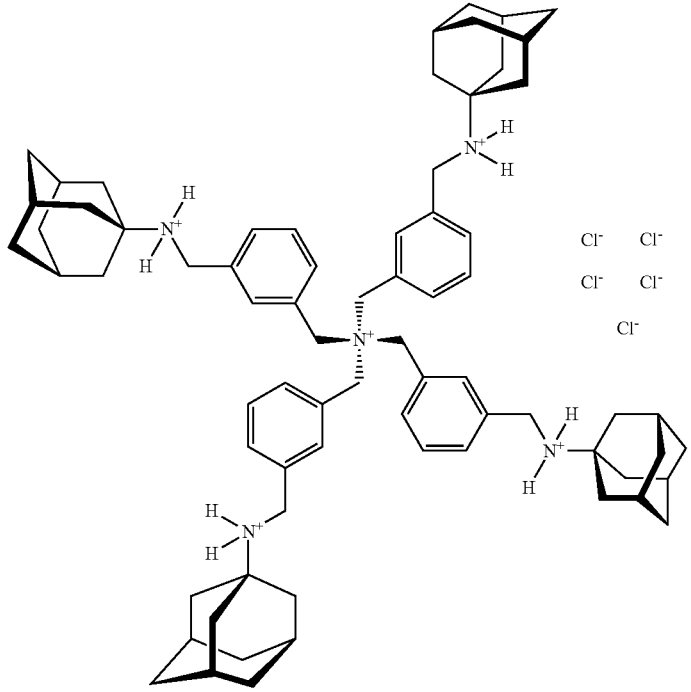

or pharmaceutically acceptable salts thereof.

Materials:
- 1-Adamantanammonium chloride (INN: amantadine hydrochloride) (1-aminoadamantane hydrochloride) [Merck KGaA-EMD Millipore Corp., Lot: 54247215; w (m/m)=100.0% (argentometric titration), mp>360° C. (dec.)]
- Sodium hydroxide (NaOH) pearls pure Ph. Eur., BP, Food Grade [AppliChem, Darmstadt, Germany, Lot: 2J002792; w (m/m)=99.31% (titration), sodium carbonate<0.5%, SiO2<0.001%, NaCl<0.008%, Na2SO4<0.0025%, As<0.00001%, heavy metals (Cu, Fe, Mn, Ni, Pb, Hg)<0.001%]
- 1,3-Bis(chloromethyl)benzene (alpha,alpha'-dichloro-m-xylene) purum≥98% (GC) [Fluka Chemie AG, Buchs, Switzerland, Lot: 385191/1; w (m/m)=100.6% (argentometric titration after oxygen combustion), w (n/n)=99.9% (gas chromatography, area %), mp 33.2-34.0° C.]
- Absolute ethanol pro analysi EMPLURA® [Merck KGaA-EMD Millipore Corp., Lot: K48011060; w (n/n)=99.9% (gas chromatography, area %), □=0.789-0.790 g/ml, w (H2O) (m/m)=0.06%, non-volatile matter<0.0001%]
- Acetone (USP, BP, Ph. Eur.) Pharma Quality [PanReac AppliChem GmbH, Darmstadt, Germany, Lot: 0000869897; w (n/n)=99.9% (gas chromatography, area %), ρ=0.791 g/ml, ρ<0.789 g/ml, w (H2O) (m/m)=0.3%, non-volatile matter 0.0002%, methanol<0.05%, propan-2-ol<0.05%, benzene<0.0002%, ethanol<500 ppm, heavy metals (Fe, Zn)<1300 ppm, heavy metals (Cu, Mn)<250 ppm]
- 10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]
- Ethyl acetate pro analysi [PanReac AppliChem GmbH, Darmstadt, Germany, Lot: 0000518022; w (n/n)=99.9% (gas chromatography, area %), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity <0.0005 meq/g]

1-Aminoadamantane hydrochloride (M=187.71 g/mol, 10.075 g, 53.6732 mmol) was dissolved in water (100 ml). A solution of sodium hydroxide NaOH (2.160 g, 54.0000 mmol) in water (20 ml) was added. Residues were transferred with water (20 ml). A heavy precipitate of the free base 1-aminoadamantane formed instantly. The suspension was frozen at −25° C. for 1 h. The evolved white precipitate of the yield of 1-aminoadamantane (free base) was filtered and vacuum-sucked dry (ca. 1 h).

The still wet 1-aminoadamantane (free base) and 1,3-bis(chloromethyl)benzene (□,□'-dichloro-m-xylene) (M=175.06 g/mol, 7.498 g, 42.8310 mmol) were suspended in absolute ethanol (200 ml). The suspension was refluxed for 3 h. After 40 min reflux a clear colorless solution formed. After 5 min pre-cooling at +0-2° C., the colorless solution with few suspended impurities was hot filtrated through one layer of filter paper. Residues were transferred and rinsed with absolute ethanol (10 ml) and acetone (30 ml). The filtrate was mixed with acetone (300 ml), 10.27 M [32% (m/v)] hydrochloric acid (3200 µl, 32.8640 mmol), and ethyl acetate (EtOAc) (200 ml), and was frozen at −25° C. for 2.5 h. Afterwards, water (200 ml) and EtOAc (1000 ml) were added, the mixture was shaken vigorously for 1 min, and was frozen at −25° C. for 2.5 h. Then 10.27 M [32% (m/v)] hydrochloric acid (3000 µl, 30.8100 mmol) was added, the mixture was shaken vigorously for 1 min, and was frozen at −25° C. for 30 min. The upper phase was then decanted and the lower aqueous phase was isolated. The isolated upper EtOAc phase was re-extracted with water (90 ml), the aqueous phase was isolated after phase separation, and was combined with the first aqueous phase. Finally, the isolated upper EtOAc phase was re-extracted with acidified (3000 µl 10.27 M [32% (m/v)] hydrochloric acid, 30.8100 mmol) water (100 ml), the aqueous phase was isolated after phase separation, and was combined with the two prior aqueous phases. The combined aqueous phases (V=500 ml) were then evaporated in vacuo at the lowest possible temperature to a volume of 200 ml until heavy crystallization started. The crystallizing suspension was then cooled at +0-2° C. for 6 h, and frozen at −25° C. for 20 min, to complete crystallization. The evolved first yield (1.543 g) of white crystals were filtered and dried over CaCl2 in vacuo. The filtrate was cooled at +0-2° C. for 50 h. The evolved second yield (62 mg) of white crystals was filtered and dried over CaCl2 in vacuo. Both yields were combined.

Compound: PT162

Molecular formula: $C_{72}H_{100}Cl_5N_5$

Molecular weight: 1212.86 g/mol

Yield: 1.605 g (12.4%)

Elemental analysis: calculated: C, 71.30%; H, 8.31%; N, 5.77%; O, 0.000%.

found: C, 65.67%; H, 7.76%; N, 4.29%; O, 0.669%.

C, 65.66%; H, 7.74%; N, 4.27%; O, 0.691%.

FT-IR (cm-1): 2925, 2850, 2760, 2710, 2436, 1610, 1585, 1494, 1459, 1269, 1108, 1074, 1011, 973, 794, 777, 762, 731, 693

1H-NMR:

(DMSO-d6, ppm) 1.61 (3H, d; 2Jgem=−11.7 Hz; delta-CHaxial), 1.68 (3H, d; 2Jgem=−11.7 Hz; delta-CHequatorial), 2.00 (6H, s; beta-CH2), 2.14 (3H, s; gamma-CH), 4.09 (2H, t; 3Jvicinal=6.4 Hz; 8-CH2), 4.77 (2H, s; 7-CH2), 7.43-7.48 (2H, m; H-4, H-6), 7.64 (1H, d; 3Jortho=7.1 Hz; H-5), 7.68 (1H, s; H-2), 9.24 (2H, br s; 8-NH2+ammonium)

13C-NMR:

(DMSO-d6, ppm) 28.50 (gamma-CH), 35.25 (delta-CH2), 37.35 (beta-CH2), 42.31 (8-CH2), 45.84 (7-CH2), 57.06 (alpha-C), 128.87 (C-4)*, 129.14 (C-6)*, 130.36 (C-2)*, 130.62 (C-5)*, 133.22 (C-3), 137.84 (C-1)

* these assignments are tentative and interchangeable (they could not be assigned unequivocally to the individual carbons)

PT163:

(11β,17β)-17-Hydroxy-11-[3,4-(methylenedioxy)phenyl]-17-(1-propyn-1-yl)estra-4,9-dien-3-one tetrakis{3-[(tricyclo[3.3.1.1$^{3,7}$]decan-1-ammonio)methyl]benzyl}ammonium pentachloride (1:1) (PT163)

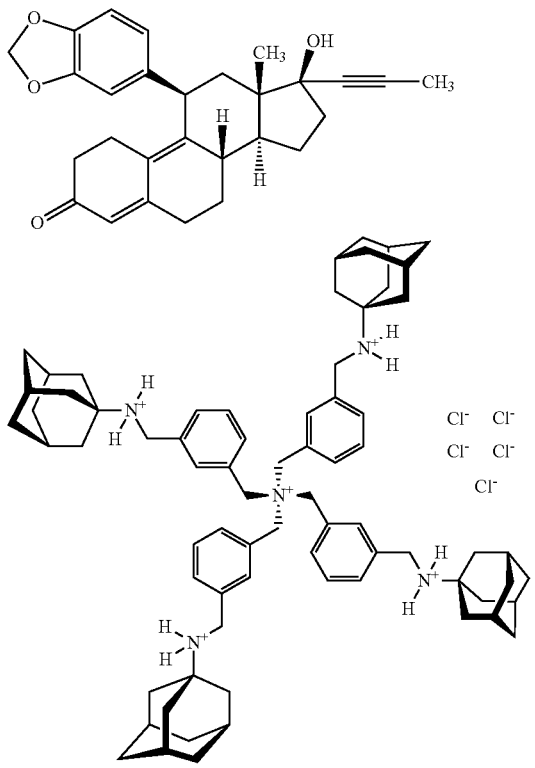

or pharmaceutically acceptable salts thereof.

Materials:

PT150 [Pop Test Oncology LLC, Cliffside Park, N.J., USA; manufactured by Sai Life Sciences Ltd., Pune, India, Lot: SPO-P01601-009; w (n/n)=99.92% (HPLC, UV detection at 210 nm), =+73.02° (c=1 in EtOH)]

PT162=tetrakis{3-[(tricyclo[3.3.1.13,7]decan-1-ammonio)methyl]benzyl}ammonium pentachloride (C72H100Cl5N5) (M=1212.86 g/mol) [synthesized by Andreas J. Kesel at Friday, Dec. 30, 2016; w (n/n)≥99% (1H NMR and elemental analysis)]

Instruction:

PT150 (M=430.54 g/mol, 200 mg, 464.5329 µmol) and PT162 (M=1212.86 g/mol, 564 mg, 465.0166 µmol) were carefully weighed and thoroughly mixed as solid powders with a spatula. The mixture was then carefully dried over CaCl2 in vacuo to yield PT163 as an off-white amorphous powder.

Compound: PT163

Molecular formula: C28H30O4×C72H100Cl5N5

Molecular weight: 1643.40 g/mol

Yield: 764 mg (100%)

PT164:

(11β,17β)-17-Hydroperoxy-11-[3,4-(methylenedioxy)phenyl]-17-(1-propyn-1-yl)estra-4,9-dien-3-one-(11β,17β)-17-hydroxy-11-[3,4-(methylenedioxy)phenyl]-17-(1-propyn-1-yl)estra-4,9-dien-3-one-tetrakis{3-[(tricyclo[3.3.1.1$^{3,7}$]decan-1-ammonio)methyl]benzyl}ammonium pentachloride (1:1:1) (PT164)

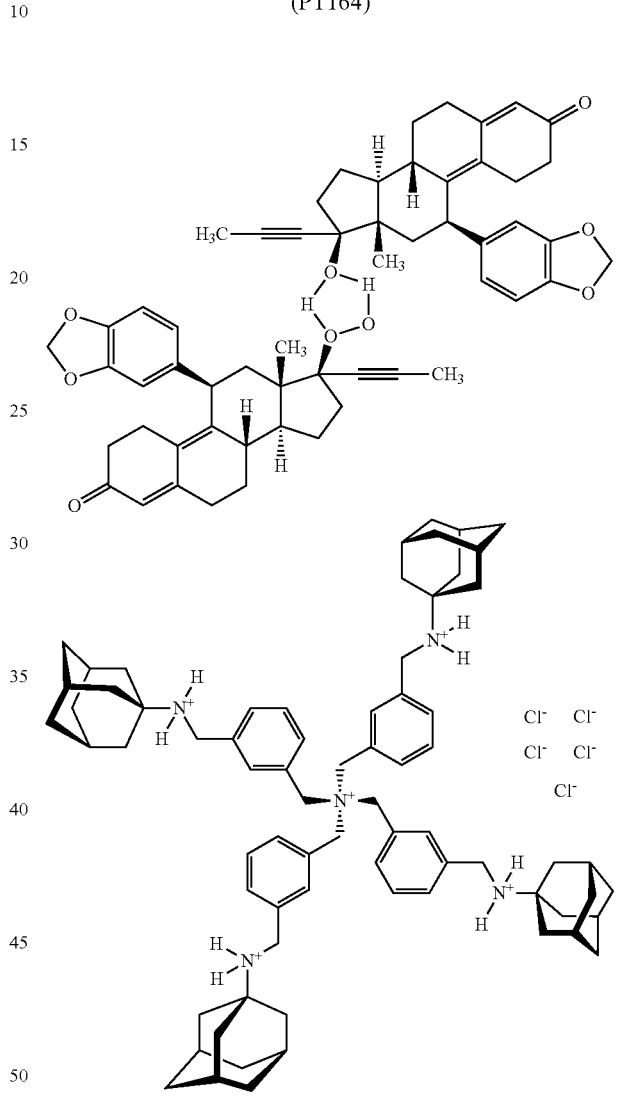

or pharmaceutically acceptable salts thereof.

Materials:

PT157=(11□,17□)-17-Hydroperoxy-11-[3,4-(methylenedioxy)phenyl]-17-(1-propyn-1-yl)estra-4,9-dien-3-one-(11□,17□)-17-hydroxy-11-[3,4-(methylenedioxy)phenyl]-17-(1-propyn-1-yl)estra-4,9-dien-3-one (1:1) (C56H60O9) (M=877.07 g/mol) [synthesized by Andreas J. Kesel at Saturday, May 21, 2016; w (n/n)≥98% (1H NMR and elemental analysis)]

PT162=tetrakis{3-[(tricyclo[3.3.1.13,7]decan-1-ammonio)methyl]benzyl}ammonium pentachloride (C72H100Cl5N5) (M=1212.86 g/mol) [synthesized by Andreas J. Kesel at Friday, Dec. 30, 2016; w (n/n)≥99% (1H NMR and elemental analysis)]

Instruction:

PT157 (M=877.07 g/mol, 400 mg, 456.0639 µmol) and PT162 (M=1212.86 g/mol, 554 mg, 456.7716 µmol) were carefully weighed and thoroughly mixed as solid powders with a spatula. The mixture was then carefully dried over CaCl2 in vacuo to yield PT164 as an ochre-yellow amorphous powder.

Compound: PT164
Molecular formula: C56H60O9×C72H100Cl5N5
Molecular weight: 2089.93 g/mol
Yield: 954 mg (100%)

PT165:

Undeca{(11β,17β)-17-hydroxy-11-[3,4-(methylenedioxy)phenyl]-17-(1-propyn-1-yl)estra-4,9-dien-3-one}-di[(tricyclo[3.3.1.1$^{3,7}$]decan-1-yl)ammonio]methyl}benzyl)ammonium pentachloride] dihydrate (PT165)

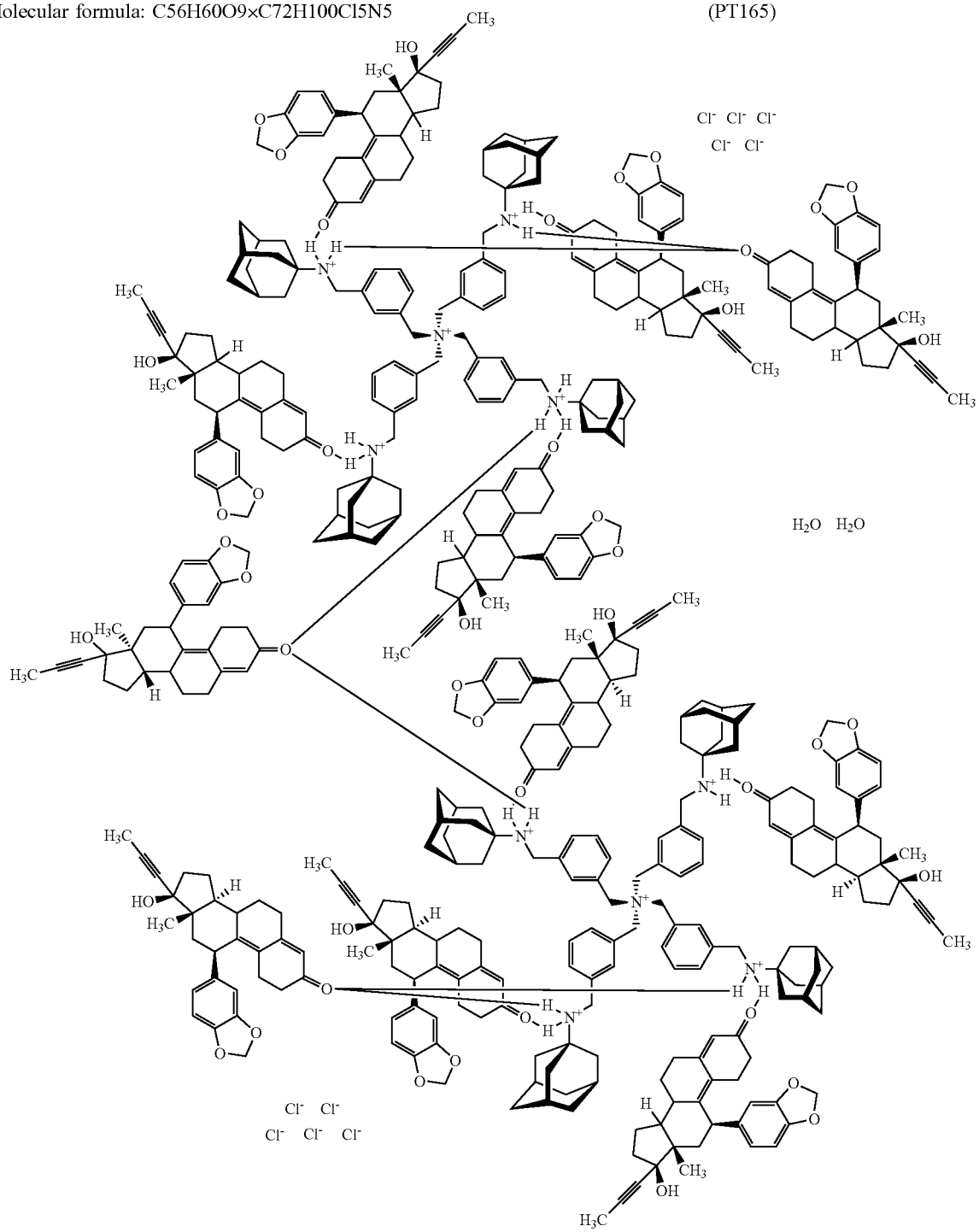

or pharmaceutically acceptable salts thereof.

Materials:

PT150 [Pop Test Oncology LLC, Cliffside Park, N.J., USA; manufactured by Sai Life Sciences Ltd., Pune, India, Lot: SPO-P01601-009; w (n/n)=99.92% (HPLC, UV detection at 210 nm), =+73.02° (c=1 in EtOH)]

PT162=tetrakis{3-[(tricyclo[3.3.1.13,7]decan-1-ammonio)methyl]benzyl}ammonium pentachloride (C72H100Cl5N5) (M=1212.86 g/mol) [synthesized by Andreas J. Kesel at Friday, Dec. 30, 2016; w (n/n)≥99% (1H NMR and elemental analysis)]

Absolute ethanol pro analysi EMPLURA® [Merck KGaA-EMD Millipore Corp., Lot: K48011060; w (n/n)=99.9% (gas chromatography, area %), p=0.789-0.790 g/ml, w (H2O) (m/m)=0.06%, non-volatile matter<0.0001%]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

PT162 (M=1212.86 g/mol, 300 mg, 247.3492 µmol) and PT150 (M=430.54 g/mol, 421 mg, 977.8418 µmol) were suspended in water (15 ml). Then 10.27 M [32% (m/v)] hydrochloric acid (10.0 ml, 102.7000 mmol) was added under stirring at room temperature (RT, □=15.5° C.). The suspension was kept standing at RT for 5 min. Then absolute ethanol (25 ml) was added, and the suspension was heated to 40-50° C. for 10 min (heatgun). After adding absolute ethanol (5 ml) and water (1 ml), the suspension was heated to 40-50° C. for 7 min (heatgun). After adding water (10 ml), the suspension was heated to 40-50° C. for 5 min (heatgun). Then the still warm very light yellow suspension was filtered through one layer of filter paper. Residues were transferred with absolute ethanol (15 ml), and, successively, water (20 ml). The filtrate already crystallized then. The residues in the filter were treated with absolute ethanol (2×9 ml), and filtered into the already crystallizing filtrate. The crystallizing filtrate was then mixed with water (20 ml). After 1 h pre-cooling at +0-2° C., the crystallizing suspension was frozen at −25° C. for 1 h. After adding water (20 ml), the crystallizing suspension was frozen at −25° C. for 4 h. The evolved first yield (453 mg) of the slightly yellowish white crystals was filtered, carefully dried by vacuum suction for 1 h on the sintered glass filter, and dried over CaCl2 in vacuo. The filtrate was transferred with water (2×20 ml), and was frozen at −25° C. for 3 h. The evolved second yield (91 mg) of the slightly yellowish white crystals was filtered, carefully dried by vacuum suction for 1 h on the sintered glass filter, and dried over CaCl2 in vacuo. Both yields were combined.

Compound: PT165
Molecular formula: C452H530Cl10N10O44×2H2O
Molecular weight: 7197.65 g/mol
Yield: 544 mg (85%)
Elemental analysis: calculated: C, 75.43%; H, 7.48%; N, 1.95%; O, 10.23%.
found: C, 74.15%; H, 7.37%; N, 1.30%; O, 10.10%.
C, 74.18%; H, 7.45%; N, 1.51%; O, 10.12%

1H-NMR:
(DMSO-d6, ppm) 0.44 (33H, s; 18-CH3), 1.29-2.76 (m; steroid CH and CH2), 1.62 (24H, d; 2Jgem=−11.5 Hz; delta-CHaxial), 1.69 (24H, d; 2Jgem=−12.2 Hz; delta-CHequatorial), 1.83 (33H, s; R—C≡C—CH3 methyl), 1.99 (48H, s; beta-CH2), 2.15 (24H, s; gamma-CH), 4.11 (16H, m; 8-CH2), 4.38 (11H, d; 3J (H,H)=7.1 Hz; 11alpha-CH), 4.78 (16H, s; 7-CH2), 5.14 (11H, s; 17beta-OH), 5.66 (11H, s; 4-CH), 5.97 (22H, s; O—CH2-O benzodioxole), 6.60 (11H, d; 3J (H,H)=7.7 Hz; 5'-CH benzodioxole), 6.78 (11H, s; 2'-CH benzodioxole), 6.79 (11H, d; 3J (H,H)=8.3 Hz; 6'-CH benzodioxole), 7.44-7.49 (16H, m; H-4, H-6), 7.61 (8H, d; 3Jortho=7.7 Hz; H-5), 7.66 (8H, s; H-2), 9.08 (16H, br s; 8-NH2+ammonium)

PT166:

(P)-10-(2-Carbamothioylhydrazinyl)-10-demethoxy-colchicine monohydrate×⅔(ethyl acetate)=N-[(aR, 7S)-10-(2-carbamothioylhydrazinyl)-1,2,3-trimethoxy-9-oxo-5,6,7,9-tetrahydrobenzo[a]heptalen-7-yl]acetamide monohydrate×⅔(ethyl acetate) (PT166)

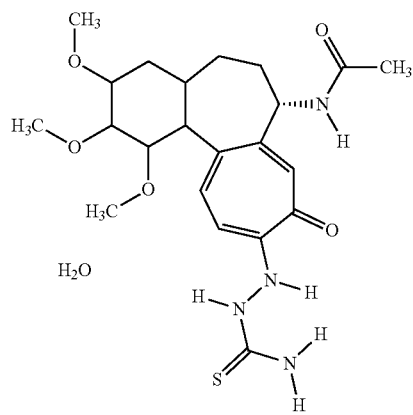

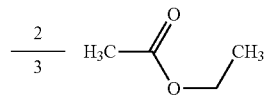

or pharmaceutically acceptable salts thereof.

Materials:

(−)-Colchicine sesquihydrate (×1½H2O)=colchicine Bio-Chemica [AppliChem, Darmstadt, Germany; w (m/m) ≥98% (HPLC), =−240° to −250° (c=1 in EtOH), w (H2O) (m/m)≤3% (Karl Fischer titration)]

Thiosemicarbazide puriss. p.a. [Sigma-Aldrich Corp., St. Louis, Mo., USA, Lot: 1167177V (Fluka); w (m/m)=100.1% (iodometric titration), mp 181° C. (dec.), residue on ignition<0.05%, metal trace analysis (inductively coupled plasma mass spectrometry)≤50-5 mg/kg]

Absolute ethanol pro analysi EMPLURA® [Merck KGaA-EMD Millipore Corp., Lot: K48011060; w (n/n)=99.9% (gas chromatography, area %), □=0.789-0.790 g/ml, w (H2O) (m/m)=0.06%, non-volatile matter<0.0001%]

Sodium hydroxide pearls pure Ph. Eur., BP, Food Grade [AppliChem, Darmstadt, Germany, Lot: 2J002792; w (m/m)=99.31% (acidimetric titration), H2O-insoluble matter≤0.025%, NaCl≤0.008%, total nitrogen (as N)≤0.002%, phosphate (as PO4)≤0.002%, sulfate (as Na2SO4)≤0.0025%, carbonate (as Na2CO3)≤0.5%, Si (as SiO2)≤0.001%, heavy metals (as Pb)≤0.002%, iron (as Fe)≤0.001%]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Ethyl acetate pro analysi [PanReac AppliChem GmbH, Lot: 0000518022; w (n/n)=99.9% (gas chromatography), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity<0.0005 meq/g]

Sodium hydrogen carbonate (sodium bicarbonate) pro analysi NaHCO3 [AppliChem GmbH, Lot: 4W000829; w (m/m)=100.42% (titration), pH (5% in H2O) 8.04 (20° C.), chloride≤0.001%, sulfate≤0.005%, phosphate≤0.005%, cations (K, Mg, Ca)≤0.005%, As≤0.0001%, heavy metals (Cu, Fe, Pb)≤0.0005%]

Acetone (USP, BP, Ph. Eur.) Pharma Quality [PanReac AppliChem GmbH, Darmstadt, Germany, Lot: 0000869897; w (n/n)=99.9% (gas chromatography, area %), □□=0.791 g/ml, □□<0.789 g/ml, w (H2O) (m/m)=0.3%, non-volatile matter 0.0002%, methanol<0.05%, propan-2-ol<0.05%, benzene<0.0002%, ethanol<500 ppm, heavy metals (Fe, Zn)<1300 ppm, heavy metals (Cu, Mn)<250 ppm]

5.00 g (−)-Colchicine sesquihydrate (×1½H2O) (M=426.46 g/mol, 11.72 mmol) and 1.08 g thiosemicarbazide (11.85 mmol) were dissolved in 25 ml of 90% (v/v) aqueous ethanol by refluxing for 5 min. After adding a solution of 0.48 g sodium hydroxide (12.00 mmol) in 2 ml of water, the deep orange-red solution was refluxed for 5 min.

The cold deep orange-red solution, after pre-cooling at −25° C. for 20 min, was titrated by dropwise addition of 1.1 ml of 10.27 M [32% (m/v)] hydrochloric acid (11.30 mmol) which was diluted with 2 ml of water. Afterwards, the volume of the solution was reduced in vacuo approximately by one half.

The reddish-brown solution was then mixed with 100 ml of water, and was titrated with 1.1 ml of 10.27 M [32% (m/v)] hydrochloric acid (11.30 mmol) which was diluted with 2 ml of water. The oily emulsion was extracted with 50 ml of ethyl acetate (EtOAc). The separated aqueous layer (pH 2) was additionally extracted with 40 ml of EtOAc. After neutralization of this aqueous phase with sodium hydrogen carbonate NaHCO3, the aqueous phase (pH 7-8) was extracted twice with 40 ml of EtOAc each. The EtOAc phases were combined and washed twice with 100 ml of water each.

The washed EtOAc phase, which already precipitated, was mixed with 50 ml of acetone and was frozen at −25° C. for 10 h. If precipitation did not start spontaneously, the volume of the solution was reduced in vacuo until coagulation started. The evolved yellow precipitate of PT166 was filtered (1.01 g) and dried over CaCl2 in vacuo. From the combined aqueous phases by cooling two days at +0-2° C. a second crop of PT166 could be obtained (1.75 g). It was treated as before and combined with the main yield.

Compound: PT166

Molecular formula: $C_{22}H_{26}N_4O_5S \times H_2O \times \frac{2}{3}(C_4H_8O_2)$ Molecular weight: 535.28 g/mol Yield: 2.76 g (44%)

Elemental analysis: calculated: C, 55.35%; H, 6.28%; N, 10.47%; S, 5.99%.

found: C, 55.34%; H, 6.29%; N, 10.35%; S, 6.00%.

C, 55.38%; H, 6.14%; N, 10.34%; S, 6.00%.

FT-IR ($cm^{-1}$): 3421, 3249, 2934, 1727, 1703, 1660, 1601, 1543, 1488, 1449, 1432, 1402, 1375, 1350, 1322, 1282, 1241, 1193, 1142, 1091, 1042, 917, 899, 863, 781

1H-NMR:

(DMSO-d6, ppm) 1.18 (1.5H, t; $^3J$=7.1 Hz; O—CH2-CH3 ethyl acetate), 1.85 (1H, m; HA-6), 1.86 (3H, s; 17-CH3), 1.99 (1.5H, s; ROOC—CH3 ethyl acetate), 2.05 (1H, m; HB-6), 2.19 (1H, m; HA-5), 2.57 (1H, m; HB-5), 3.51 (3H, s; 13-OCH3)*, 3.79 (3H, s; 15-OCH3)*, 3.83 (3H, s; 14-OCH3)*, 4.03 (1H, q; $^3J$=7.1 Hz; O—CH2-CH3 ethyl acetate), 4.37 (1H, m; H-7), 6.60 (1H, d; $^3J$=11.1 Hz; H-11), 6.76 (1H, s; H-4), 7.14 (1H, s; H-8), 7.20 (1H, d; $^3J$=10.9 Hz; H-12), 7.56 (1H, br s; H2N—C═S amino, 4'-HA), 7.96 (1H, br s; H2N—C═S amino, 4'-HB), 8.56 (1H, d; $^3J$=7.6 Hz; N—H acetamide), 9.06 (1H, s; 1'-N—H), 9.59 (1H, s; 2'-N—H)

13C-NMR:

(DMSO-d6, ppm) 14.05 (O—CH2-CH3 ethyl acetate), 20.72 (ROOC—CH3 ethyl acetate), 22.49 (C-17, CH3 acetamide), 29.33 (C-5), 36.34 (C-6), 51.38 (C-7), 55.84 (14-OCH3), 59.72 (O—CH2-CH3 ethyl acetate), 60.62 (13-OCH3, 15-OCH3), 107.61 (C-4), 108.27 (C-11), 126.23 (C-8), 131.57 (C-1a), 134.26 (C-4a), 137.21 (C-12), 140.71 (C-3)*, 150.34 (C-1)*, 150.40 (C-10), 150.46 (C-12a), 152.61 (C-2)***, 152.73 (C-7a), 168.39 (C-16, HN—C═O amide), 170.30 (C═O ester carbonyl, ethyl acetate), 174.81 (C-9, C═O carbonyl), 181.86 (C-3', C═S thiocarbonyl)

*,  * these assignments are tentative and interchangeable (they could not be assigned unequivocally to the individual protons or carbons, respectively)

PT167:

[(Bis{3-[(tricyclo[3.3.1.1$^{3,7}$]decan-1-ylamino)methyl] benzyl}ammonio) bis (methanediylbenzene-3,1-diylmethanediyl)]di-2-[(7S)-7-(acetylamino)-1,2,3-trimethoxy-9-oxo-5,6,7,9-tetrahydrobenzo[a]heptalen-10-yl]-N-(tricyclo[3.3.1.1$^{3,7}$]decan-1-yl)hydrazinecarbothioamide chloride pentahydrate (PT167)

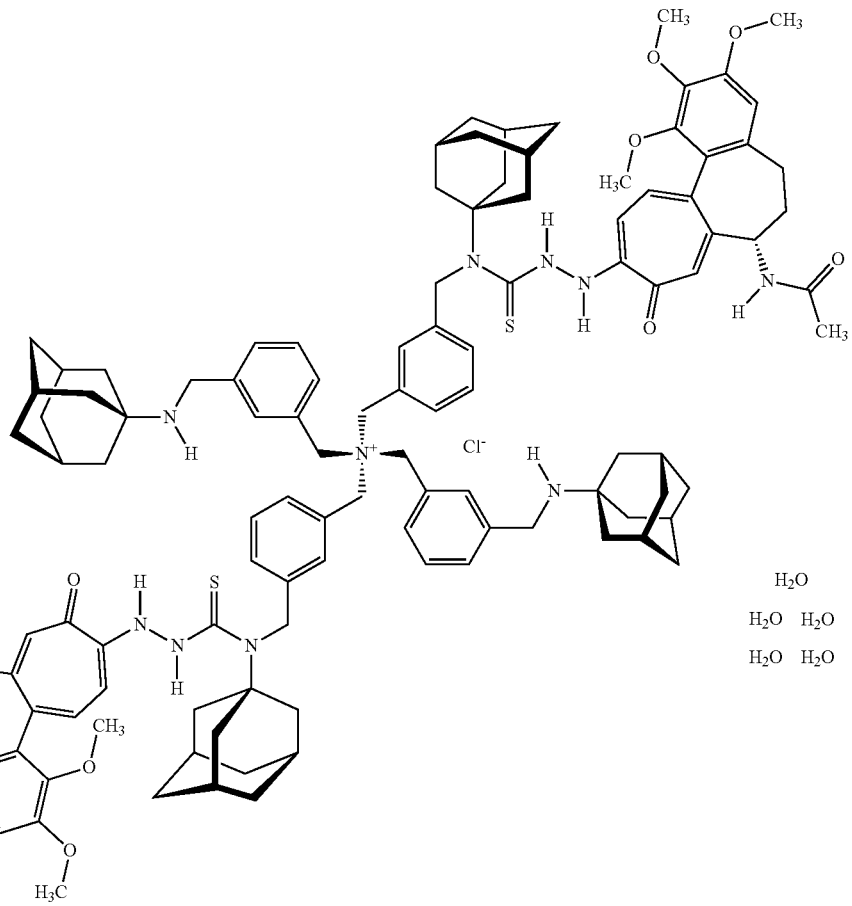

or pharmaceutically acceptable salts thereof.

Materials:

PT162 (NSC 796018=PT162 was in NCI 60-cancer cell testing)=tetrakis{3-[(tricyclo[3.3.1.13,7]decan-1-ammonio)methyl]benzyl}ammonium pentachloride (C72H100Cl5N5) (M=1212.86 g/mol) [synthesized by Andreas J. Kesel at Friday, Dec. 30, 2016; w (n/n)≥99% (1H NMR and elemental analysis)]

PT166 (NSC 750423=PT166 was in NCI 60-cancer cell testing)=N-[(7S)-10-(2-carbamothioylhydrazinyl)-1,2,3-trimethoxy-9-oxo-5,6,7,9-tetrahydrobenzo[a]heptalen-7-yl] acetamide monohydrate×⅔(ethyl acetate) [C22H26N4O5S×H2O×⅔(C4H8O2)] (M=535.28 g/mol) [synthesized by Andreas J. Kesel at Thursday, Jan. 29, 2009; w (n/n)≥98% (1H NMR and elemental analysis)]

Absolute ethanol pro analysi EMPLURA® [Merck KGaA-EMD Millipore Corp., Lot: K48011060; w (n/n)=99.9% (gas chromatography, area %), ☐=0.789-0.790 g/ml, w (H2O) (m/m)=0.06%, non-volatile matter<0.0001%]

Sodium hydroxide pearls pure Ph. Eur., BP, Food Grade [AppliChem, Darmstadt, Germany, Lot: 2J002792; w (m/m)=99.31% (acidimetric titration), H2O-insoluble matter≤0.025%, NaCl≤0.008%, total nitrogen (as N)≤0.002%, phosphate (as PO4)≤0.002%, sulfate (as Na2SO4)≤0.0025%, carbonate (as Na2CO3)≤0.5%, Si (as SiO2)≤0.001%, heavy metals (as Pb)≤0.002%, iron (as Fe)≤0.001%]

PT162 (M=1212.86 g/mol, 300 mg, 247.3492 μmol) and PT166 (M=535.28 g/mol, 300 mg, 560.4543 μmol) were suspended in absolute ethanol (20 ml), and the yellow suspension was heated to 40-50° C. for 4 min (heatgun). Then water (1000 μl) was added under stirring and all material dissolved to give a bright yellow solution. Afterwards, a solution of sodium hydroxide (37 mg, 925.0000 μmol) in water (2000 μl) was added under stirring. The color of the solution changed to orange-yellow. After 12 min cooling at +0-2° C., the mixture was frozen at −25° C. for 10 min. After adding water (10 ml), the precipitating emulsion was frozen at −25° C. for 2 h. The evolved first yield (212 mg) of the bright yellow, amorphous substance PT167 was filtered, carefully dried by vacuum suction for 30 min on the sintered glass filter, and dried over CaCl2 in vacuo. The filtrate was transferred with water (20 ml), and was frozen at −25° C. for 30 min. After cooling at +0-2° C. for 1 h, the evolved second yield (17 mg) of the bright yellow, amorphous substance PT167 was filtered [the initial turbid filtrate was transferred with water (10 ml), and was re-filtered on the same sintered glass filter used before], carefully dried by vacuum suction for 30 min on the sintered glass filter, and dried over CaCl2 in vacuo. Both yields were combined.

Compound: PT167
Molecular formula: C116H142ClN11O10S2×5 H2O
Molecular weight: 2040.10 g/mol
Yield: 229 mg (45%)
Elemental analysis: calculated: C, 68.29%; H, 7.51%; N, 7.55%; S, 3.14%; O, 11.76%.
found: C, 60.31%; H, 6.68%; N, 8.01%; S, 3.34%; O, 11.84%.
C, 60.24%; H, 6.45%; N, 7.98%; S, 3.38%; O, 11.64%.
1H-NMR:
(DMSO-d6, ppm) 1.48-1.68 (24H, br m; delta-CH2, adamantane), 1.83 (2H, m; HA-6, colch), 1.86 (6H, s; 17-CH3, colch), 2.01 (2H, m; HB-6, colch), 2.17 (2H, m; HA-5, colch), 2.52 (2H, m; HB-5, colch), 3.47, 3.48 (6H, s; 13-OCH3, colch)*, 3.65 (2H, br s; secondary amine N—H), 3.77 (6H, s; 15-OCH3, colch)*, 3.82 (6H, s; 14-OCH3, colch)*, 4.26 (br m; 8-CH2, m-xylylene), 4.32-4.39 (2H, br m; H-7, colch), 4.76 (s; 7-CH2, m-xylylene), 6.73 (2H, s; H-4, colch), 7.03 (2H, br m; H-11, colch), 7.06 (2H, s; H-8, colch), 7.12-7.72 (br m; H-4, H-6, H-5, H-2, m-xylylene), 7.17 (2H, br m; H-12, colch), 8.54 (2H, d; 3J=7.7 Hz; N—H acetamide, colch), 9.59 (4H, s; 1'-N—H, 2'-N—H, hydrazinecarbothioamide) colch=the colchicoid part of PT167; * these assignments are tentative and interchangeable (they could not be assigned unequivocally to the individual methoxy groups); the adamantane resonances 2.00 (24H; beta-CH2), 2.14 (12H; gamma-CH) could not being detected PENT Tetrakis{3-[(tricyclo[3.3.1.1$^{3,7}$]decan-1-ammonio)methyl]benzyl}ammonium pentachloride (PENT)

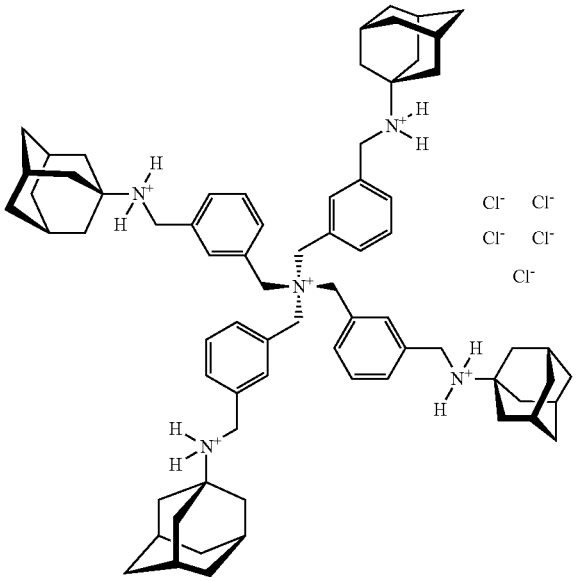

Materials:
1-Adamantanammonium chloride (INN: amantadine hydrochloride) (1-aminoadamantane hydrochloride) [Merck KGaA-EMD Millipore Corp., Lot: S4247215; w (m/m)=100.0% (argentometric titration), mp>360° C. (dec.)]

Sodium hydroxide (NaOH) pearls pure Ph. Eur., BP, Food Grade [AppliChem, Darmstadt, Germany, Lot: 2J002792; w (m/m)=99.31% (titration), sodium carbonate<0.5%, SiO2<0.001%, NaCl<0.008%, Na2SO4<0.0025%, As<0.00001%, heavy metals (Cu, Fe, Mn, Ni, Pb, Hg)<0.001%]

1,3-Bis(chloromethyl)benzene (alpha,alpha'-dichloro-m-xylene) purum≥98% (GC) [Fluka Chemie AG, Buchs, Switzerland, Lot: 385191/1; w (m/m)=100.6% (argentometric titration after oxygen combustion), w (n/n)=99.9% (gas chromatography, area %), mp 33.2-34.0° C.]

Absolute ethanol pro analysi EMPLURA® [Merck KGaA-EMD Millipore Corp., Lot: K48011060; w (n/n)=99.9% (gas chromatography, area %), $\rho_4^{20}$=0.789-0.790 g/ml, w (H2O) (m/m)=0.06%, non-volatile matter<0.0001%]

Acetone (USP, BP, Ph. Eur.) Pharma Quality [PanReac AppliChem GmbH, Darmstadt, Germany, Lot: 0000869897; w (n/n)=99.9% (gas chromatography, area %), $\rho_{20}^{20}$=0.791 g/ml, $\rho_{25}^{25}$<0.789 g/ml, w (H2O) (m/m)=0.3%, non-volatile matter 0.0002%, methanol<0.05%, propan-2-ol<0.05%, benzene<0.0002%, ethanol<500 ppm, heavy metals (Fe, Zn)<1300 ppm, heavy metals (Cu, Mn)<250 ppm]

10.27 M [32% (m/m)] aqueous hydrochloric acid pro analysi [AppliChem, Darmstadt, Germany, Lot: 3A001639; w (m/m)=33.09% (titration), bromide<0.005%, phosphate<0.00005%, sulfate<0.0001%, As<0.000001%, Fe<0.00002%, heavy metals (Ni, Pb, Zn)<0.000005%]

Ethyl acetate pro analysi [PanReac AppliChem GmbH, Darmstadt, Germany, Lot: 0000518022; w (n/n)=99.9% (gas chromatography, area %), w (H2O) (m/m)=0.01% (Karl Fischer titration), ethanol<0.1%, methanol<0.02%, methyl acetate<0.02%, trace elements (Cr, Fe, Ni, Pb, Zn, P, S, K, Mg)<0.00001%, Si<0.00002%, Na<0.0002%, non-volatile matter<0.001%, acidity/alkalinity <0.0005 meq/g]

1-Aminoadamantane hydrochloride (M=187.71 g/mol, 10.075 g, 53.6732 mmol) was dissolved in water (100 ml). A solution of sodium hydroxide NaOH (2.160 g, 54.0000 mmol) in water (20 ml) was added. Residues were transferred with water (20 ml). A heavy precipitate of the free base 1-aminoadamantane formed instantly. The suspension was frozen at −25° C. for 1 h. The evolved white precipitate of the yield of 1-aminoadamantane (free base) was filtered and vacuum-sucked dry (ca. 1 h).

The still wet 1-aminoadamantane (free base) and 1,3-bis(chloromethyl)benzene (☐,☐'-dichloro-m-xylene) (M=175.06 g/mol, 7.498 g, 42.8310 mmol) were suspended in absolute ethanol (200 ml). The suspension was refluxed for 3 h. After 40 min reflux a clear colorless solution formed. After 5 min pre-cooling at +0-2° C., the colorless solution with few suspended impurities was hot filtrated through one layer of filter paper. Residues were transferred and rinsed with absolute ethanol (10 ml) and acetone (30 ml). The filtrate was mixed with acetone (300 ml), 10.27 M [32% (m/v)] hydrochloric acid (3200 µl, 32.8640 mmol), and ethyl acetate (EtOAc) (200 ml), and was frozen at −25° C. for 2.5 h. Afterwards, water (200 ml) and EtOAc (1000 ml) were added, the mixture was shaken vigorously for 1 min, and was frozen at −25° C. for 2.5 h. Then 10.27 M [32% (m/v)] hydrochloric acid (3000 µl, 30.8100 mmol) was added, the mixture was shaken vigorously for 1 min, and was frozen at −25° C. for 30 min. The upper phase was then decanted and the lower aqueous phase was isolated. The isolated upper EtOAc phase was re-extracted with water (90 ml), the aqueous phase was isolated after phase separation, and was combined with the first aqueous phase. Finally, the isolated upper EtOAc phase was re-extracted with acidified (3000 µl 10.27 M [32% (m/v)] hydrochloric acid, 30.8100 mmol) water (100 ml). The aqueous phase was isolated after phase separation, and was combined with the two prior aqueous phases. The combined aqueous phases (V=500 ml) were then evaporated in vacuo at the lowest possible temperature to a volume of 200 ml until heavy crystallization started. The crystallizing suspension was then cooled at +0-2° C. for 6 h, and frozen at −25° C. for 20 min, to complete crystallization. The evolved first yield (1.543 g) of white crystals were filtered and dried over $CaCl_2$) in vacuo. The filtrate was cooled at +0-2° C. for 50 h. The evolved second yield (62 mg) of white crystals was filtered and dried over $CaCl_2$) in vacuo. Both yields were combined.

Compound: PENT
Molecular formula: $C_{72}H_{100}Cl_5N_5$
Molecular weight: 1212.86 g/mol
Yield: 1.605 g (12.4%)
Elemental analysis: calculated: C, 71.30%; H, 8.31%; N, 5.77%; O, 0.00%.
found: C, 00.00%; H, 0.00%; N, 0.00%; O, 0.00%.
C, 00.00%; H, 0.00%; N, 0.00%; O, 0.00%.
FT-IR ($cm^{-1}$): 2925, 2850, 2760, 2710, 2436, 1610, 1585, 1494, 1459, 1269, 1108, 1074, 1011, 973, 794, 777, 762, 731, 693
$^1$H-NMR: 1.61 (3H, d; $^2J_{gem}$=11.7 Hz; delta-$CH_{axial}$), 1.68 (3H, d; $^2J_{gen}$=11.7
(DMSO-d6, ppm) Hz; delta-$CH_{equatorial}$) 2.00 (6H, s; beta$CH_2$), 2.14 (3H, s; gamma-CH), 4.09 (2H, t; $^3J_{vicinal}$=6.4 Hz; 8-$CH_2$), 4.77 (2H, s; 7-$CH_2$), 7.43-7.48 (2H, m; H-4, H-6), 7.64 (1H, d; $^3J_{ortho}$=7.1 Hz; H-5), 7.68 (1H, s; H-2), 9.24 (2H, br s; 8-$NH_2^+$ ammonium)
$^{13}$C-NMR: 28.50 (gamma-CH), 35.25 (delta-$CH_2$), 37.35 (beta-$CH_2$), 42.31 (8-$CH_2$),
(DMSO-$d_6$, ppm) 45.84 (7-$CH_2$), 57.06 (alpha-C), 128.87 (C-4)*, 129.14 (C-6)*, 130.36 (C-2)*, 130.62 (C-5)*, 133.22 (C-3), 137.84 (C-1)
* these assignments are tentative and interchangeable (they could not be assigned unequivocally to the individual carbons)
RU 486
Mifepristone, also known as RU-486 is an example of a non-selective GCR antagonist.

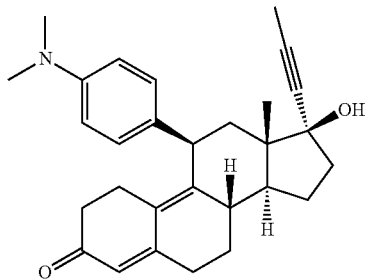

Antibiotics

Two known[1-3] 3-formylrifamycin SV derivatives were re-synthesized in high purity and were thoroughly analyzed. The first represents 3-formylrifamycin SV (E)-oxime (synthesis code: OR-1=ARIF-2), the second 3-formylrifamycin SV (E)-O-methyloxime [=3-formylrifamycin SV (E)-methoxime] (synthesis code: MR-1). In the following report known properties of these antibiotics are summarized. They are both very active versus gram-positive bacteria and *Mycobacterium tuberculosis*, and are both orally bioavailable (MR-1 is more orally bioavailable than OR-1). Their acute toxicities are low, and in vivo activity is good.

TABLE 1

Data regarding biological parameters of OR-1 and MR-1

| | In vivo effective dose 50% ($ED_{50}$) (mg/kg) in curing *Staphylococcus aureus* infection in mice | | In vivo lethal dose 50% ($LD_{50}$) (mg/kg) intravenous |
|---|---|---|---|
| Antibiotic | per os | subcutaneous | in mice |
| OR-1 | 5.66 | 2.46 | 690 |
| MR-1 | 0.53 | 0.87 | 152 |

The third derivative was synthesized from rifampicin by reaction with 3-bromo-1-(trimethylsilyl)-1-propyne. The rationale behind this synthesis was the synthesis of tigecycline from minocycline[5-7]. Tigecycline (TYGACIL™; Wyeth) circumvents antibiotic tetracycline resistance [induced active efflux (tetA-tetD, tetK) and ribosomal protection (tetM) proteins][7] by introduction of a bulky N-(tert.-butyl)-glycyl-amido group at position 9 of minocycline:

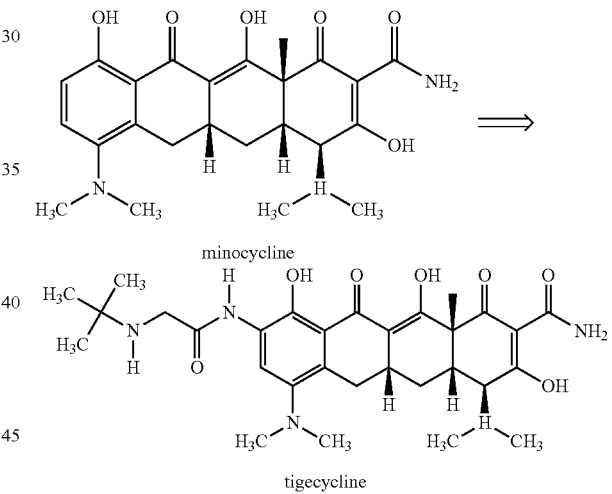

The bulky, lipophilc trimethylsilylpropyne substituent 3-bromo-1-(trimethylsilyl)-1-propyne was introduced into rifampicin. The trimethylsilyl group is isosteric to the tert.-butyl group in tigecycline. The reaction was successful and the product TPR-1 did not contain rifampicin anymore which was proved by proton NMR and elemental analysis. The reaction was performed in excellent 100% yield. The TPR-1 product apparently exists in two ionic forms, the zwitterion and the hydrobromide of the zwitterion. This is analogous to the situation with rifampicin itself which was proved to exist in two discernable forms, the zwitterion and the undissociated molecule itself[8]. Both forms of rifampicin are able to coexist in pharmaceutical bulk rifampicin powder, and can be isolated separately in substance[8]. In TPR-1 the hydrobromide of the zwitterion tends to loose hydrobromic acid (HBr), and, analogously to rifampicin, both forms coexist in solid and dissolved TPR-1 as proved by thin-layer chromatography (TLC) on silica gel 60 (Merck)

plates [eluent: 80% (v/v) aqueous acetone]. The rifampicin derivative TPR-1 is entirely new.

The proton nuclear magnetic resonance ('H NMR) spectra of OR-1, MR-1, and TPR-1, each dissolved in deuterated chloroform (CDCl3), respectively, are presented. Our own antitubercular results on OR-1, MR-1, and TPR-1 are summarized.

TABLE 2

Antitubercular properties of 3-formylrifamycin SV (E)-oxime (OR-1), 3-formylrifamycin SV (E)-O-methyloxime [=3-formylrifamycin SV (E)-methoxime] (MR-1), and N$^\omega$-[3-(trimethylsilyl)prop-2-yn-1-yl]rifampicinium-4-olate × ¾ HBr × H$_2$O (TPR-1) as compared to rifampicin (rifampin) In vitro antibacterial activities of rifamycin antibiotics versus *Mycobacterium tuberculosis* virulent standard strain H$_{37}$Rv (sensitive to rifampicin) in standard resazurin-resorufin assay

| Rifamycin antibiotic | Bacterial strain | Minimal inhibitory concentration 99% (MIC$_{99}$) in μg/ml | Minimal inhibitory concentration 99% (MIC$_{99}$) in nmol/Liter (nM) |
|---|---|---|---|
| OR-1 | H$_{37}$Rv | 0.6 | 787.0 |
| MR-1 | H$_{37}$Rv | 0.08 | 106.0 |
| TPR-1 | H$_{37}$Rv | 0.02-0.04 | 19.8-39.5 |
| Rifampicin | H$_{37}$Rv | 0.06 | 72.7 |

TABLE 3

Antimicrobial properties of 3-formylrifamycin SV (E)-oxime (synthesis code: OR-1) and 3-formylrifamycin SV (E)-O-methyloxime [=3-formylrifamycin SV (E)-methoxime] (synthesis code: MR-1) as compared to rifampicin (rifampin) [MIC = (visual) minimal inhibitory concentration 99%]

| Bacterium | Bacterial strain | OR-1 MIC (μg/ml) reference 1 (1966) | OR-1 MIC (μg/ml) reference 2 (1974) | MR-1 MIC (μg/ml) reference 1 (1966) | MR-1 MIC (μg/ml) reference 2 (1974) | Rifampicin (Rif) MIC (μg/ml) reference 1 (1966) |
|---|---|---|---|---|---|---|
| *Gram-positive* | | | | | | |
| *Staphylococcus aureus* | ATCC 6538 | 0.02 | — | 0.0005 | — | 0.002 |
| *Staphylococcus aureus* | Tour$^l$ | — | 0.02 | — | 0.002 | — |
| *Staphylococcus aureus* | Tour Rif-resistant | — | >100 | — | >100 | — |
| *Streptococcus haemolyticus* = *S. pyogenes* | C 203 | 0.01 | 0.01 | 0.01 | 0.01 | 0.02 |
| *Diplococcus pneumoniae* = *Streptococcus pneumoniae* | U.C. 41 | — | 0.01 | — | 0.01 | — |
| *Gram-negative* | | | | | | |
| *Proteus vulgaris* | ATCC 881 | 10 | 10 | 2 | 2 | 5 |
| *Escherichia coli* | ATCC 10536 | 5 | 5 | 5 | 5 | 1 |
| *Klebsiella pneumoniae* | ATCC 10031 | 20 | 20 | 10 | 10 | 5 |
| *Pseudomonas aeruginosa* | ATCC 10145 | 10 | 10 | 10 | 10 | 10 |
| *Mycobacteria* | | | | | | |
| *Mycobacterium tuberculosis* | ATCC 9360 H$_{37}$Rv | 5 | 5 | 0.1 | 0.05 | 0.5 |

Treatment of Alcoholic and Non-Alcoholic Fatty Liver Disease

Fatty liver, also known as fatty liver disease (FLD) or hepatic steatosis, is a reversible condition wherein large vacuoles of triglyceride fat accumulate in liver cells via the process of steatosis (abnormal intracellular retention of lipids). Despite having multiple causes, fatty liver can be considered a single disease that occurs worldwide in those with excessive alcohol intake and the obese (with or without effects of insulin resistance). The condition is also associated with other diseases that influence lipid metabolism. When this process of fat metabolism is disrupted, the fat can accumulate in the liver in excessive amounts, thus resulting in a fatty liver. It is difficult to distinguish alcoholic FLD from non-alcoholic FLD, and both show microvesicular and macrovesicular fatty changes at different stages.

Accumulation of fat may also be accompanied by a progressive inflammation of the liver (hepatitis), called steatohepatitis. By considering the contribution by alcohol, fatty liver may be termed alcoholic steatosis or non-alcoholic fatty liver disease (NAFLD), and the more severe forms as alcoholic steatohepatitis (part of alcoholic liver disease) and non-alcoholic steatohepatitis (NASH).
Causes:

Fatty liver (FL) is commonly associated with alcohol abuse and/or metabolic syndrome (diabetes & hypertension & obesity & dyslipidemia=horrible tetrad), but can also be caused by:

Metabolic

Abetalipoproteinemia, glycogen storage diseases, Weber-Christian disease, acute fatty liver of pregnancy, lipodystrophy due to AIDS highly active antiretroviral therapy (HAART).

Nutritional

Malnutrition (starvation), total parenteral nutrition, severe weight loss (cancer cachexia), refeeding syndrome, jejunoileal bypass, gastric bypass, jejunal diverticulosis with bacterial overgrowth.

Drugs and Toxins

Amiodarone (cardial antiarrhythmic), diltiazem (calcium antagonist), expired tetracycline (overstored antibiotic degradation products), highly active antiretroviral therapy (HAART), glucocorticoids (artificial Cushing syndrome), tamoxifen (selective estrogen receptor modulator), environmental hepatotoxins [white phosphorus, *Amanita phalloides* (death cap): alpha-amanitin, phalloidin, *Senecio* sp.: pyrrolizidine alkaloids (senecionine), cyanobacteria: microcystins].

Alcoholic

Alcoholism is one of the major causes of fatty liver due to production of toxic metabolites like acetaldehyde during metabolism of alcohol in the liver. This phenomenon most commonly occurs with chronic alcoholism.

Other

Inflammatory bowel disease (colitis ulcerosa/ulcerative colitis, Morbus Crohn/Crohn's disease), AIDS, hepatitis C (especially genotype 3), □1-antitrypsin deficiency.

Pathology

Fatty change represents the intracytoplasmatic accumulation of triglycerides (neutral fats). At the beginning, the hepatocytes present small fat vacuoles (liposomes) around the nucleus (microvesicular fatty change). In this stage, liver cells are filled with multiple fat droplets that do not displace the centrally located nucleus. In the late stages, the size of the vacuoles increases, pushing the nucleus to the periphery of the cell, giving characteristic signet ring appearance (macrovesicular fatty change). These vesicles are well-delineated and optically "empty" because fats dissolve during tissue processing. Large vacuoles may coalesce and produce fatty cysts, which are irreversible lesions. Macrovesicular steatosis is the most common form and is typically associated with alcohol abuse, diabetes, obesity, and corticosteroids. Acute fatty liver of pregnancy and Reye's syndrome are examples of severe liver disease caused by microvesicular fatty change. The diagnosis of steatosis is made when fat in the liver exceeds 5-10% by weight.

Defects in fatty acid metabolism are responsible for pathogenesis of FLD, which may be due to imbalance in energy consumption and its combustion, resulting in lipid storage, or can be a consequence of peripheral resistance to insulin, whereby the transport of fatty acids from adipose tissue to the liver is increased. Impairment or inhibition of nuclear receptor molecules [peroxisome proliferator-activated receptors (PPAR-alpha, PPAR-gamma, delta-PPAR) and transcription factors [sterol regulatory element-binding protein 1 (SREBP-1)] that control the enzymes responsible for the oxidation and synthesis of fatty acids appears to contribute to fat accumulation. In addition, alcoholism is known to damage mitochondria and other cellular structures, further impairing cellular energy mechanism. On the other hand, non-alcoholic FLD may begin as excess of unmetabolised energy in liver cells. Hepatic steatosis is considered reversible and to some extent non-progressive if the underlying cause is reduced or removed.

Role of Glucocorticosteroids in Fatty Liver Disease:

Ulrike Lemke, Anja Krones-Herzig, Mauricio Berriel Diaz, Prachiti Narvekar, Anja Ziegler, Alexandros Vegiopoulos, Andrew C. B. Cato, Sebastian Bohl, Ursula Klingmüller, Robert A. Screaton, Karin Müller-Decker, Sander Kersten, Stephan Herzig. The glucocorticoid receptor controls hepatic dyslipidemia through Hes1. *Cell Metab* 2008, 8, 212-223.

ABSTRACT: Aberrant accumulation of lipids in the liver ("fatty liver" or hepatic steatosis) represents a hallmark of the metabolic syndrome and is tightly associated with obesity, type II diabetes, starvation, or glucocorticoid (GC) therapy. While fatty liver has been connected with numerous abnormalities of liver function, the molecular mechanisms of fatty liver development remain largely enigmatic. Here we show that liver specific disruption of glucocorticoid receptor (GR) action improves the steatotic phenotype in fatty liver mouse models and leads to the induction of transcriptional repressor hairy enhancer of split 1 (Hes1) gene expression. The GR directly interferes with Hes1 promoter activity, triggering the recruitment of hi stone deacetylase (HDAC) activities to the Hes1 gene. Genetic restoration of hepatic Hes1 levels in steatotic animals normalizes hepatic triglyceride (TG) levels. As glucocorticoid action is increased during starvation, myotonic dystrophy, and Cushing's syndrome, the inhibition of Hes1 through the GR might explain the fatty liver phenotype in these subjects.

What is Hes1?

Transcription factor Hes1 (hairy and enhancer of split-1) is a protein that is encoded by the Hes1 gene, and is the mammalian homolog of the hairy gene in *Drosophila*. Hes1 is one of the seven members of the Hes gene family (Hes1-7). Hes genes code nuclear proteins that repress transcription. This protein belongs to the class B basic helix-loop-helix (bHLH) family of transcription factors. It is a transcriptional repressor of genes that require a bHLH protein for their transcription. The protein has a particular type of basic domain that contains a helix interrupting protein that binds to the N-box promoter region rather than the canonical enhancer box (E-box). As a member of the bHLH family, it is a transcriptional repressor that influences cell proliferation and differentiation in embryogenesis. Hes1 regulates its own expression via negative feedback loop, and oscillates with approximately 2-hour bio-periodicity.

There are three conserved domains in Hes proteins that impart transcriptional functions: the bHLH domain, the Orange domain, and the WRPW motif. Hes genes differ from other bHLH factors in that they have a proline reside in the middle of the basic DNA binding region. This proline has been proposed to give Hes proteins unique DNA binding capacity. While most bHLH factors bind to the E-box consensus sequence (CANNTG) that is present in the promoter region of target genes, Hes factors bind preferentially to the Class C site or N box Hes1 and Stem Cells Hes1 influences the maintenance of certain stem cells and progenitor cells. Specifically, Hes1 influences the timing of differentiation by repressing bHLH activators, and determines binary cell fate. Hes1 has been shown to play a large role in both the nervous and the digestive system development. Hes1 has been shown to influence their differentiation patterns partially through the Notch signaling pathway.

Hes1 and Neural Development

Hes1 is expressed in both neuroepithelial cells and radial glial cells, both neural stem cells. Hes1 expression, along with that of Hes5, covers the majority of the developing embryo at embryonic day 10.5 (E10.5). Hes1 also plays an important role in the Notch signaling pathway. Notch signaling activates Hes1 expression. Notch signaling also occurs in the intestinal crypt cells. Hyperactivated Notch causes a reduction in the number of secretory cell types (goblet cells, enteroendocrine cells, and Paneth cells).

Hes1 and Hepatobiliary Tract

Hes1 has been shown to influence the differentiation decision of cells in the gastrointestinal tract. In pancreatic progenitor cells, Hes1 expression inhibits the expression of PTF1A (pancreas transcription factor 1 subunit □), which controls exocrine cell differentiation, and NGN3 (neurogenin-3), which drives differentiation of endocrine cell types that will form the islets of Langerhans. The absence of Hes1 in the developing intestine of mice promotes the increase of Math1 (a protein required for the production of intestinal secretory cell types; Math1 is also a bHLH transcription factor expressed in neural progenitor cells in multiple regions of the nervous system), which leads to an increase of goblet, enteroendocrine, and Paneth cells. When Hes1 is deleted in mouse and zebrafish, surplus goblet cells and enteroendocrine cells are made, while few enterocytes are made. Liver progenitor cells differentiate into two different cell types: hepatocytes and biliary epithelial cells. When Hes1 expression is low, hepatocytes form normally, but bile ducts are completely absent. This phenotype resembles autosomal dominant Alagille syndrome (hepatic ductular hypoplasia; arteriohepatic dysplasia), a hallmark of which are mutations in Jagged1 (JAG1) and/or Notch2. Therefore, Hes1-Notch protein interactions also play an important role in hepatobiliary organ development. ESSENCES:

Glucocorticosteroids activate glucocorticoid receptor isoform in the mammalian liver Activated glucocorticoid receptor represses the hepatic murine Hes1 gene expression by binding to a minimal glucocorticoid response element (GRE) half-site TGTTCC in the promoter of *Mus musculus* Hes1 gene on mouse chromosome 16:

Hes1 protein normally does activate expression of lipid degradation enzymes, including lipases which digest triglycerides to fatty acids prone to degradation in □-oxidation Hes1 protein seems to predominantly control the "lipase arm" of glucocorticoid receptor-dependent triglyceride metabolism, as the most significant transcriptional effects of Hes1 protein synthesis were found to be related to PNL (pancreatic lipase) and PNLRP2 (pancreatic lipase-related protein 2) gene expression (ref. 1). In the liver, pancreatic lipase and pancreatic lipase-related protein 2 contribute to triglyceride hydrolysis and the subsequent stimulation of fatty acid □-oxidation (degradation) and ketogenesis (ref. 3). It is tempting to speculate that the inhibition of Hes1 expression by glucocorticosteroids in fatty liver mouse models represents a key mechanism in the prevention of lipase activities, thereby promoting triglyceride accumulation under these conditions (ref. 1)

Cholesterol metabolism seems to be unaffected by Hes1 expression (ref. 1)

When Hes1 protein is absent in liver by repression through glucocorticosteroid-activated glucocorticoid receptor, triglyceride ("fat") is deposited in hepatocyte fat vacuoles PT150 and PT155 should be therefore suitable as treatment of alcoholic and non-alcoholic fatty liver disease of multiple etiology, since it antagonizes glucocorticoid receptor action First reports (four at PubMed) claim efficacy of mifepristone in animal models of fatty liver disease or related partial ailments (refs Hashimoto T, Igarashi J, Hasan AU, Ohmori K, Kohno M, Nagai Y, Yamashita T, Kosaka H. 2013. Mifepristone promotes adiponectin production and improves insulin sensitivity in a mouse model of diet-induced-obesity. PLoS ONE 8:e79724. doi:10.1371/journal.pone.0079724.

Macfarlane D P, Raubenheimer P J, Preston T, Gray C D, Bastin M E, Marshall I, Iredale J P, Andrew R, Walker B R. 2014. Effects of acute glucocorticoid blockade on metabolic dysfunction in patients with type 2 diabetes with and without fatty liver. Am. J. Physiol. Gastrointest. Liver Physiol. 307:G760-G768.

Regardless of the detailed etiological pathophysiological mechanism(s), glucocorticosteroids do induce the group of fatty liver syndromes. The glucocorticoid antagonists PT150 and PT155 should relieve the repression of the Hes1 gene of the repressor protein Hes1 by glucocorticoid receptor. The repressor protein Hes1 stimulates (under disputed detailed mechanisms) enzyme expression (pancreatic lipase, pancreatic lipase-related protein 2) leading to digestion and □-oxidation of triglycerides ("fat") in the mouse and human liver. PT150 and PT155 could restore normal triglyceride degradation by counteracting cortisol action which represses the repressor Hes1. The details of these actions remain to be elucidated, since literature reports are differing in experimental data and scientific conclusion(s).

Advantages of TPR-1, PT159, and PT160, in comparison to rifampicin:

The major disadvantage of rifampicin (rifampin) for agricultural applications is its chemical instability. Rifampicin is easily oxidized by atmospheric oxygen to its naphthoquinone form[1]. Furthermore, rifampicin is easily hydrolysed, in reversal of its synthesis reaction, to 3-formylrifamycin SV and 1-amino-4-methylpiperazine[1]. These both chemical instabilities prevent use of rifampicin for free field agricultural applications, since rifampicin is not stable enough against atmospheric oxygen, humidity, and other environmental influences like UV irradiation by sun light.

TPR-1 is not oxidized by atmospheric oxygen, since it is zwitterionic like rifampicin[2], but its zwitterionic state is locked by the quaternary ammonium moiety at the piperazine. TPR-1 also shows enhanced stability towards hydrolysis and UV light. This enables agricultural free field applications of TPR-1, PT159, and PT160.

TPR-1 might be able to circumvent multidrug-resistant tuberculosis (MDR-TB) and extensively drug-resistant tuberculosis (XDR-TB) resistance mechanisms of circulating *M. tuberculosis* strains[3], by scavenging the *M. tuberculosis* virulence factor sulfolipid-1 (SL-1), a tetraacyl-sulfotrehalose glycolipid[4,5], and its congeners like diacyl sulfoglycolipid ($Ac_2SGL$)[6,7]. SL-1 is contained in pathogenic mycobacteria ($H_{37}Rv$, Vallée), but not in apathogenic ($H_{37}Ra$); its amounts have been positively correlated with strain virulence[4].

| The Following Listed Bacteria are Highly Susceptible towards TPR-1, PT159, and PT160 | | | |
|---|---|---|---|
| Bacterium | Host | Characteristics (Concise) | Diseases (Concise) |
| *Bacilli, Lactobacillales, Streptococcaceae, Streptococcus* (Gram-Positive) | | | |
| *Streptococcus agalactiae* | Human Neonatal, Cattle | Lancefield Group B streptococci (GBS), hemolytic, catalase-negative, facultative anaerobic | Human: GBS is the most common pathogen causing neonatal infection. It is often fatal<br>Cattle: GBS udder mastitis |
| *Streptococcus anginosus* group | Human | *Viridans streptococci* group, *S. anginosus, S. intermedins* and *S. constellatus*, hemolytic, hemolytic or non-hemolytic | Human: abscesses (liver, peritoneum), Douglas abscess, subcutaneous and organ abscesses, meningitis, respiratory infections |
| *Streptococcus bovis* group | Human, Animal (Cattle, Sheep, Horse) | *S. gallolyticus, S. equinus* and *S. infantarius*, Lancefield Group D non-enterococcal streptococci, hemolytic, hemolytic or non-hemolytic, catalase-negative, facultative anaerobic | Human: biliary and urinary tract infections, endocarditis, septicemia, neonatal meningitis |
| *Streptococcus canis* | Human, Cats, Dogs, Cattle | Lancefield Group G streptococci (GBS), hemolytic, catalase-positive, facultative anaerobic | Human (rare): meningitis, sepsis.<br>Animal: neonatal septicemia, abortion, cellulitis, lymphadenitis, arthritis, mastitis |
| *Streptococcus downei* | Human | Recently discovered (?) | Human: human oral cavity, dental caries (cariogenic) |
| *Streptococcus dysgalactiae* | Human (SDSE), Animal (SDSD) | *S. dysgalactiae* subsp. *equisimilis* (SDSE), hemolytic, catalase-negative, facultative anaerobic<br>*S. dysgalactiae* subsp. *dysgalactiae* (SDSD), □-hemolytic, catalase-negative, facultative anaerobic | Human: SDSE: superficial skin-infections, tonsillitis, severe necrotizing fasciitis, bacteremia, bone & joint infections, pneumonia, endocarditis, intraabdominal infections<br>Animal: SDSD: bovine mastitis, polyarthritis, neonatal mortality, caudal necrotic ulcers (fish) |
| *Streptococcus equi* | Animal, Human | *S. equi* subsp. *equi*, Lancefield Group C streptococci, hemolytic, catalase-positive, facultative anaerobic<br>*S. equi* subsp. *ruminatorum*, recently discovered (?) | Animal: *S. equi* subsp. *equi*: strangles (also equine distemper), contagious upper respiratory tract infection of horses and other equines; *S. equi* subsp. *ruminatorum*: sheep milk, goats affected with mastitis |
| Streptococcus ferus | Animal | *Viridans streptococci* group, □-hemolytic, catalase-negative, anaerobic | Animal: in wild rats and pigs, no human infection known |
| *Streptococcus iniae* | Animal (Fish), Human | Including susp. *S. shiloi*, emolytic, catalase-positive, facultative anaerobic | Animal: major pathogen in dolphin and fish (highly pathogenic in freshwater, marine, and euryhaline fish), highly lethal, meningoencephalitis, skin lesions, septicemia, CNS damage<br>Human (rare): sepsis, toxic shock syndrome, bacteremic cellulitis, endocarditis, meningitis, osteomyelitis, septic arthritis |
| *Streptococcus milleri* | — | Old name for *S. anginosus* group | — |
| *Streptococcus mitis* group | Human | Including susp. *S. oralis*, old name for *S. mitis*: *S. mitior*, □-hemolytic, catalase-negative, facultative anaerobic | Human: found in throat, nasopharynx, mouth; can cause native valve infective endocarditis (*S. oralis*) |
| *Streptococcus mutans* | Human | "Caries bacilli", non-hemolytic, catalase-positive, facultative anaerobic | Human: human oral cavity, dental caries (cariogenic), heart infections |
| *Streptococcus orisratti* | Animal (Rat) | Recently discovered (?), facultative anaerobic | Animal: oral cavity (tooth) of rats (Sprague-Dawley laboratory rats) |
| *Streptococcus parasanguinis* | Human | *Viridans streptococci* group, hemolytic, catalase-positive, facultative anaerobic | Human: human oral cavity, presence of *S. parasanguinis* in the oral cavity is associated with a healthy microflora |
| *Streptococcus peroris* | Human | Hemolytic, catalase-negative, facultative anaerobic | Human: human oral cavity, tooth surface |
| *Streptococcus pneumoniae* group | Human | Non-Lancefield streptococci hemolytic (under aerobic | Human: major human pathogen; main cause |

The Following Listed Bacteria are Highly Susceptible towards TPR-1, PT159, and PT160

| Bacterium | Host | Characteristics (Concise) | Diseases (Concise) |
|---|---|---|---|
| *Bacilli, Lactobacillales, Streptococcaceae, Streptococcus* (Gram-Positive) | | | |
| (*Pneumococcus*) | | conditions), or hemolytic (under anaerobic conditions), optochin-sensitive, catalase-negative, facultative anaerobic | of community acquired pneumonia and meningitis in children and the elderly, and of septicemia in HIV-infected persons; many other infections include: bronchitis, rhinitis, acute sinusitis, otitis media, conjunctivitis, meningitis, bacteremia, sepsis, osteomyelitis, septic arthritis, endocarditis, peritonitis, pericarditis, cellulitis, brain abscess |
| *Streptococcus pseudopneumoniae* | Human | □-Hemolytic, optochin-sensitive when incubated in ambient air, catalase-negative, facultative anaerobic | Human: pneumonia, most cases of *S. pseudopneumoniae* pneumonia are misdiagnosed as *S. pneumoniae* |
| *Streptococcus pyogenes* | Human | Lancefield Group A streptococci, hemolytic, catalase-negative, facultative anaerobic | Human: major human pathogen; *S. pyogenes* is the cause of many important human diseases, ranging from mild superficial skin infections to life-threatening systemic diseases; pharyngitis, impetigo, erysipelas, cellulitis, necrotizing fasciitis, scarlet fever, streptococcal toxic shock syndrome (STSS), sepsis, bacteremia |
| *Streptococcus ratti* | Animal, Human | Facultative anaerobic | Animal: oral cavity (tooth) of rats (caries lesion in rat) |
| *Streptococcus salivarius* | Human | *Viridans streptococci* group, *S. salivarius* subsp. *salivarius*□ hemolytic, catalase-negative, facultative anaerobic *Viridans streptococci* group, *S. salivarius* subsp. *thermophilus*, non-hemolytic, catalase-negative, facultative anaerobic | Human: usually colonizes the mouth and upper respiratory tract of humans just a few hours after birth; very rarely causes sepsis in immunocompromised hosts |
| Streptococcus *tigurinus* | Human | Recently discovered (?), hemolytic, catalase-negative, facultative anaerobic | Human: infective endocarditis; serious invasive infections: spondylodiscitis, bacteremia, meningitis, empyema |
| *Streptococcus sanguinis* | Human | *Viridans streptococci* group, old name for *S. sanguinis*: *S. sanguis*, □-hemolytic, catalase-negative, facultative anaerobic | Human: normal inhabitant of the healthy human mouth where it is particularly found in dental plaque; can cause infective endocarditis |
| *Streptococcus sobrinus* | Human | Non-hemolytic, catalase-negative, facultative anaerobic | Human: human oral cavity, dental caries (cariogenic) |
| *Streptococcus suis* | Animal, Human | Hemolytic, catalase-negative, anaerobic | Animal: endemic in pigs; pyrexia, sudden death, pneumonia, meningitis Human: streptococcal toxic shock syndrome (STSS), sepsis |
| *Streptococcus uberis* | Animal (Cattle) | Recently discovered (?), non-hemolytic, catalase-negative, facultative anaerobic | Animal: bovine mastitis |
| *Streptococcus vestibularis* | Human | *Viridans streptococci* group, □-hemolytic, catalase-negative, facultative anaerobic | Human: vestibular mucosa of human oral cavity; can cause native valve infective endocarditis |
| *Streptococcus zooepidemicus* | Animal, Human | *S. equi* subsp. *zooepidemici*, Lancefield Group C *streptococci*, hemolytic, catalase-negative, facultative anaerobic | Animal: commensal and opportunistic pathogen Human (very rare): systemic infections |

| The Following Listed Bacteria are Highly Susceptible towards TPR-1, PT159, and PT160 | | | |
|---|---|---|---|
| Bacterium | Host | Characteristics (Concise) | Diseases (Concise) |
| *Bacilli, Bacillales, Staphylococcaceae, Staphylococcus* (Gram-Positive) | | | |
| *Staphylococcus aureus* group | Human, Animal | *S. aureus* subsp. *aureus*, non-hemolytic, catalase-positive, facultative anaerobic *S. aureus* subsp. *anaerobius*, hemolytic, catalase-positive, facultative anaerobic *S. simiae*, recently discovered (?), hemolytic, catalase-positive, facultative anaerobic | Human: major human pathogen; *S. aureus* is one of the most common causes of bacteremia, infective endocarditis, osteomyelitis, septic arthritis; it can cause various skin and soft tissue infections (folliculitis, impetigo, cellulitis, invasive soft-tissue infections, prosthetic joint infection, Ritter's disease) Animals: bovine mastitis, ulcerative pododermatitis |
| *Staphylococcus auricularis* group | Human | *S. auricularis*, non-hemolytic, catalase-positive | Human (rare): commensal and opportunistic pathogen; was isolated from human external ear; can cause sepsis in neonates and immunocompromised hosts |
| *Staphylococcus carnosus* group | Human, Animal | *S. carnosus* subsp. *carnosus*, *S. carnosus* subsp. *utilis*, *S. condimenti*, *S. massiliensis*, *S. piscifermentans*, non-hemolytic, catalase-positive, facultative anaerobic | Human (rare): pathogenic: *S. massiliensis* (brain abscess) |
| *Staphylococcus epidermidis* group | Human, Animal | *S. capitis* subsp. *capitis*, hemolytic, catalase-positive, facultative anaerobic *S. capitis* subsp. *urealyticus*, hemolytic, catalase-positive *S. caprae*, *S. epidermidis*, non-hemolytic, catalase-positive *S. saccharolyticus*, anaerobic | Human: pathogenic: *S. epidermidis* (human skin bacterium), *S. saccharolyticus*, *S. capitis* (human skin bacterium), *S. caprae* (goat milk) |
| *Staphylococcus haemolyticus* group | Human, Animal | *S. devriesei*, *S. haemolyticus*, hemolytic, catalase-positive, *S. hominis* subsp. *hominis*, catalase-positive, *S. hominis* subsp. *novobiosepticus*, non-hemolytic, catalase-positive | Human: pathogenic: *S. haemolyticus* (human skin bacterium), *S. hominis* |
| *Staphylococcus hyicus-intermedius* group | Animal, Human | *S. agnetis, S. chromogenes, S. felis, S. delphini, S. hyicus, S. intermedius, S. lutrae, S. microti, S. muscae, S. pseudintermedius, S. rostri, S. schleiferi* subsp. *coagulans, S. schleiferi* subsp. *schleiferi* | Human (rare): pathogenic: *S. schleiferi* Animal: many pathologies |
| *Staphylococcus lugdunensis* group | Human | *S. lugdunensis*, non-hemolytic, catalase-positive | Human: pathogenic: *S. lugdunensis* |
| *Staphylococcus saprophyticus* group | Human, Animal | *S. arlettae*, *S. cohnii* subsp. *cohnii*, *S. cohnii* subsp. *urealyticus*, *S. equorum* subsp. *equorum*, *S. equorum* subsp. *linens*, *S. gallinarum*, *S. kloosii, S. leei*, *S. nepalensis*, *S. saprophyticus* subsp. *bovis*, *S. saprophyticus* subsp. *saprophyticus*, *S. succinus* subsp. *casei*, *S. succinus* subsp. *succinus*, *S. xylosus* | Human: pathogenic: *S. cohnii, S. saprophyticus, S. xylosus* (rare) Animal: many pathologies |
| *Staphylococcus sciuri* group | Animal | *S. fleurettii, S. lentus*, *S. sciuri* subsp. *carnaticus* *S. sciuri* subsp. *rodentium* | Animal: found on animal food products |

| | | | |
|---|---|---|---|
| | | S. sciuri subsp. sciuri, S. stepanovicii, S. vitulinus (S. pulvereri) | |
| Staphylococcus simulans group | Human | S. simulans, hemolytic, catalase-positive | Human: pathogenic: S. simulans (human skin bacterium) |
| Staphylococcus warneri group | Animal, Human | S. pasteuri, S. warneri, catalase-positive | Human: pathogenic: S. warneri (human skin bacterium) |
| S. lyticans, S. pettenkoferi, S. petrasii, S. pseudolugdunensis | Animal, Human | The taxonomic position of these staphylococci has yet to be clarified | |

The Following Listed Mycobacteria are Highly Susceptible towards TPR-1, PT159, and PT160

| Bacterium | Host | Characteristics (Concise) | Diseases (Concise) |
|---|---|---|---|
| Actinobacteria, Actinomycetales, Corynebacterineae, Mycobacteriaceae, Mycobacterium | | | |
| Mycobacterium tuberculosis complex | Human, Animal | M. africanum, M. bovis, M. bovis BCG (Bacillus Calmette-Guérin), M. canetti, M. caprae, M. microti, M. mungi, M. orygis, M. pinnipedii, M. suricattae, M. tuberculosis | Human: major human pathogen; M. tuberculosis is the causative agent of tuberculosis (TB); M. africanum, M. bovis, M. canetti, M. caprae, M. orygis, also can cause TB in humans Animal: M. bovis, M. microti, M. mungi, M. pinnipedii, M. suricattae, cause TB-like illness in animals |
| Mycobacterium avium complex | Human, Animal | M. avium subsp. avium, M. avium subsp. hominissuis, M. avium subsp. paratuberculosis, M. avium subsp. silvaticum, M. avium intracellulare, M. colombiense, M. indicus pranii | Human: major human pathogen; M. avium and M. avium intracellulare cause TB-like illness in humans (atypical mycobacteria of Mycobacterium avium-intracellulare complex), M. colombiense (emerging pathogen) Animal: M. avium subsp. paratuberculosis (paratuberculosis or Johne's disease), M. avium subsp. avium (birds), M. avium subsp. hominissuis (pigs), M. avium subsp. silvaticum |
| Mycobacterium leprae | Human | M. leprae | Human: major human pathogen; causes leprosy (Hansen's disease), a chronic debilitating, mutilating, humiliating disease |
| Mycobacterium lepromatosis | Human | M. lepromatosis | Human: minor human pathogen; causes diffuse lepromatous leprosy |
| Mycobacterium chelonae clade | Human | M. abscessus subsp. abscessus, M. abscessus subsp. bolletii, M. chelonae subsp. chelonae | Human: M. abscessus (chronic lung disease, post-traumatic wound infections, skin infections, otitis media in immunodeficient patients), M. chelonae (abscesses) |
| Mycobacterium fortuitum clade | Animal, Human | M. fortuitum subsp. fortuitum, M. fortuitum subsp. acetamidolyticum, M. boenickei, M. brisbanense, M. cosmeticum, M. mageritense, M. mucogenicum, M. neworleansense, M. peregrinum, M. porcinum, M. senegalense, M. septicum | Human: these mycobacteria are widely distributed in soil, water and environment, and can cause human disease (skin and soft-tissue abscesses with associated osteomyelitis, bacteremia, endocarditis, keratitis, lymphadenitis, peritonitis, post-surgical infections, pulmonary infections and disseminated disease) |
| Mycobacterium kansasii clade | Human | M. gastri M. kansasii | Human: generally non-pathogenic mycobacteria; M. kansasii (rarely chronic human pulmonary disease resembling tuberculosis), |

| | | | |
|---|---|---|---|
| | | | *M. gastri* (casual resident of human stomach) |
| *Mycobacterium simiae* clade | Animal, Human | *M. florentinum, M. genavense, M. heidelbergense, M. interjectum, M. lentiflavum, M. palustre, M. simiae, M. triplex* | Human (rare): these mycobacteria can cause disease in immunodeficient hosts (neonates, pre-term neonates) |
| Mycolactone-producing mycobacteria | Human, Animal | *M. pseudoshottsii M. shottsii, M. ulcerans* | Human: *M. ulcerans* causes Buruli ulcer (Bairnsdale ulcer, Searle's ulcer, Daintree ulcer) in humans |
| *Mycobacterium bohemicum* | Human | *M. bohemicum* | Human (rare): can cause disease (non-tuberculous) in humans |
| *Mycobacterium intermedium* | Human | *M. intermedium* | Human (rare): can cause pulmonary disease in humans |
| *Mycobacterium marinum* | Animal, Human | *M. marinum* | Human (rare): *M. marinum* from fish can cause the disease known as aquarium granuloma |
| *Mycobacterium neoaurum* | Human | *Mycobacterium parafortuitum* clade, *M. neoaurum* | Human (rare): soil bacterium; emerging pathogen, associated with meningoencephalitis, rapidly progressive dementia |
| *Mycobacterium phlei* | Animal, Human | *M. phlei* | Human (rare): generally non-pathogenic mycobacteria; occasionally causes human disease (non-tuberculous) |
| *Mycobacterium smegmatis* | Human | *M. goodii, M. smegmatis, M. wolinskyi* | Human (rare): generally non-pathogenic mycobacteria; occasionally causes human disease (non-tuberculous) |

The Following Listed Gram-Negative Bacteria are Probably Highly Susceptible towards TPR-1, PT159, and PT160

*Proteobacteria, Rhizobiales, Rhizobiaceae, Candidatus* Liberibacter (Gram-Negative)

| | | | |
|---|---|---|---|
| Candidatus Liberibacter group | Plant | *Ca. L. africanus, Ca. L. americanus, Ca. L. asiaticus, Ca. L. crescens, Ca. L. europaeus, Ca. L. psyllaurous, Ca. L. solanacearum* | Plant: major emerging plant pathogen(s); not yet fully characterized phloem-restricted gram-negative bacteria (prokaryotes) causing citrus 'huanglongbing' (citrus greening disease), potato zebra chip disease (and diseases of other solanaceous crops), carrot psyllid damage disease |

The Following Listed Bacteria are Moderately to Weakly Susceptible towards TPR-1, PT159, and PT160

| Bacterium | Host | Characteristics (Concise) | Diseases (Concise) |
|---|---|---|---|
| *Bacilli, Lactobacillales, Enterococcaceae, Enterococcus* (Gram-Positive) | | | |
| *Enterococcus faecalis* | Human, Animal | *E. faecalis*, acetoin-positive, catalase-negative, facultative anaerobic | Human: major human nosocomial pathogen; resistant to most antibiotics (vancomycin-resistant enterococci, VRE); endocarditis, septicemia, urinary tract infections, meningitis, and other infections |
| *Enterococcus faecium* | Human, Animal | *E. faecium*, hemolytic, facultative anaerobic | Human: human nosocomial pathogen; resistant to most antibiotics (vancomycin-resistant enterococci, VRE); endocarditis, (neonatal) meningitis, cholecystitis, peritonitis, urinary tract infections, urosepsis, and other infections |

-continued

| | | | |
|---|---|---|---|
| *Proteobacteria, Enterobacteriales, Enterobacteriaceae, Escherichia* (Gram-Negative) ||||
| *Escherichia coli* | Human, Animal | *E. coli*, component of normal human and animal intestinal flora, facultative anaerobic | Human: facultative human pathogen; gastrointestinal infections, gastroenteritis, diarrhea, urinary tract infections, peritonitis, mastitis, septicemia, neonatal meningitis; subtypes: neonatal meningitis *E. coli* (NMEC), enterotoxigenic *E. coli* (ETEC), enteropath ogenic *E. coli* (EPEC), enteroinvasive *E. coli* (EIEC), enterohemorrhagic *E. coli* (EHEC, hemolytic- uremic syndrome), enteroaggregative *E. coli* (EAEC), adherent-invasive *E. coli* (AIEC) |
| *Proteobacteria, Enterobacteriales, Enterobacteriaceae, Proteus* (Gram-Negative) ||||
| *Proteus mirabilis* | Human, Animal | *P. mirabilis*, component of normal human and animal intestinal flora, catalase-positive, (normally) indole-test negative, $H_2S\uparrow$-positive, urease-positive ($NH_3\uparrow$), facultative anaerobic | Human: facultative human pathogen; nosocomial infections, *P. mirabilis* causes 90% of all *Proteus* infections in humans; pneumonia, septicemia, urinary tract infections, wound infections |
| *Proteus vulgaris* | Human, Animal | *P. vulgaris*, component of normal human and animal intestinal flora, indole-test positive, $H_2S\uparrow$-positive, urease-positive ($NH_3\uparrow$), facultative anaerobic | Human: facultative human pathogen; nosocomial infections, urinary tract infections, (catheter) sepsis, wound infections |
| The Following Listed Gram-Negative Bacteria are Non-Susceptible towards TPR-1, PT159, and PT160 ||||
| *Proteobacteria, Enterobacteriales, Enterobacteriaceae, Klebsiella* (Gram-Negative) ||||
| *Klebsiella* group | Human, Animal | *K granulomatis*, *K. oxytoca*, *K. michiganensis*, *K. pneumioniae* subsp. *ozaenae*, *K. pneumioniae* subsp. *pneumoniae*, *K. pneumoniae* subsp. *rhinoscleromatis*, *K. quasipneumoniae* subsp. *quasipneumoniae*, *K. quasipneumoniae* subsp. *similipneumoniae*, *K. variicola*, all species facultative anaerobic | Human: major human nosocomial pathogen; pneumonia, thrombophlebitis, urinary tract infections, cholecystitis, diarrhea, upper respiratory tract infections, wound infections, osteomyelitis, meningitis, bacteremia, septicemia; includes carbapenem-resistant *Klebsiella pneumoniae* (CRKP), extended-spectrum beta-lactamase (ESBL) producer(s) |
| *Proteobacteria, Pseudotnonadales, Pseudomonadaceae, Pseudomonas* (Gram-Negative) ||||
| *Pseudomonas aeruginosa* | Human, Animal | *P. aeruginosa*, catalase-positive, pyocyanin(e)-positive (characteristic blue-green pigment), aerobic (or faculatative anaerobic) | Human: major human nosocomial and/or opportunistic pathogen; wide range of infections include: pneumonia, septic shock, urinary tract infections, gastrointestinal infections, skin and soft tissue infections, wound infections (skin burn infection) |

Human Pathogenic Fungi Susceptible towards the Antibiotics
The Following Listed Fungi are Potentially
Susceptible towards TPR-1, PT159, and PT160

| Fungus | Pathogenic Species (Concise) | Diseases (Concise) |
|---|---|---|
| *Ascomycota, Saccharomycetales, Saccharomycetaceae, Candida* | | |
| *Candida* yeast group | *C. albicans, C. dublinensis, C. glabrata, C. parapsilosis, C. rugosa, C. tropicalis* | Candidiasis |
| *Ascomycota, Eurotiales, Trichocomaceae, Aspergillus* | | |
| *Aspergillus* group | *A. clavatus, A. flavus, A. fumigatus* | Aspergillosis [chronic pulmonary aspergillosis (CPA), aspergilloma, allergic bronchopulmonary aspergillosis (ABPA)] |
| *Ascomycota, Onygenales, Ajellomycetaceae, Blastomyces* | | |
| *Blastomyces dermatitidis* | *B. dermatitidis* | Blastomycosis (North American blastomycosis, blastomycetic dermatitis, Gilchrist's disease) |
| *Ascomycota, Onygenales, Ajellomycetaceae, Histoplasma* | | |
| *Histoplasma capsulatum* | *H. capsulatum* subsp. *duboisii, H. capsulatum* subsp. *farciminosum* | Histoplasmosis (*H. capsulatum* subsp. *duboisii* causes African histoplasmosis; *H. capsulatum* subsp. *farciminosum* causes epizootic lymphangitis in horses) |
| *Ascomycota, Onygenales, Ajellomycetaceae, Paracoccidioides* | | |
| *Paracoccidioides brasiliensis* | *P. brasiliensis* | Paracoccidioidomycosis (Brazilian blastomycosis, South American blastomycosis, Lutz-Splendor e-de Almeida disease, paracoccidioidal granuloma) |
| *Ascomycota, Onygenales, Onygenaceae, Coccidioides* | | |
| *Coccidioides* group | *C. immitis, C. posadasii* | Coccidioidomycosis |
| *Ascomycota, Ophiostomatales, Ophiostomataceae, Sporothrix* | | |
| *Sporothrix schenckii* | *S. schenckii* | Sporotrichosis (also known as "rose gardener's disease") |
| *Ascomycota, Hypocreales, Stachybotryaceae, Stachybotrys* | | |
| *Stachybotrys* group | *S. chartarum* | Black mold disease |
| *Ascomycota, Pneumocystidales, Pneumocystidaceae, Pneumocystis* | | |
| *Pneumocystis jirovecii* | *P. jirovecii* (formerly: *Pneumocystis carinii*) | Pneumocystosis, pneumocystis pneumonia |
| *Basidiomycota, Tremellales, Tremellaceae, Cryptococcus* | | |
| *Cryptococcus* group | *C. gattii, C. neoformans* | Cryptococcosis |

Superficial and Cutaneous Fungal Infections (Dermatomycosis)

1. Ascomycota (dermatophytes); *Epidermophyton floccosum; Microsporum canis; Microsporum audouinii; Piedraia hortae; Trichophyton interdigitale/mentagrophytes; Trichophyton tonsurans; Trichophyton schoenleini; Trichophyton rubrum; Trichophyton verrucosum;*

2. Ascomycota; *Hortaea werneckii* yeast 3. Basidiomycota; *Malassezia furfur; Trichosporon* yeasts Subcutaneous, Systemic, and Opportunistic Fungal Infections 1. Ascomycota (dimorphic: yeast & mold, Onygenales); *Coccidioides immitis/Coccidioides posadasii;* Coccidioidomycosis; Disseminated coccidioidomycosis; Primary cutaneous coccidioidomycosis; Primary pulmonary coccidioidomycosis; *Histoplasma capsulatum;* Histoplasmosis; Primary cutaneous histoplasmosis; Primary pulmonary histoplasmosis; Progressive disseminated histoplasmosis; *His-* toplasma duboisii; African histoplasmosis; *Lacazia loboi*; Lobomycosis; *Paracoccidioides brasiliensis*; Paracoccidioidomycosis 2. Ascomycota (dimorphic: yeast & mold, other); *Blastomyces dermatitides*; Blastomycosis; North American blastomycosis; South American blastomycosis; *Sporothrix schenckii*; Sporotrichosis; *Penicillium marneffei*; Penicilliosis 3. Ascomycota (yeast-like); *Candida albicans*; Candidiasis; Oral; Esophageal; Vulvovaginal; Chronic mucocutaneous; Antibiotic candidiasis; Candidal intertrigo; Candidal onychomycosis; Candidal paronychia; Candidid; Diaper candidiasis; Congenital cutaneous candidiasis; Perianal candidiasis; Systemic candidiasis; Erosio interdigitalis blastomycetica; *Candida glabrata; Candida tropicalis; Candida lusitaniae; Pneumocystis jirovecii* Pneumocystosis; *Pneumocystis* pneumonia; Ascomycota (mold-like); *Aspergillus* ssp.; Aspergillosis; Aspergilloma; Allergic bronchopulmonary aspergillosis; Primary cutaneous aspergillosis; *Exophiala jeanselmei*; Eumycetoma; *Fonsecaea pedrosoi/Fonsecaea compacta/Phialophora verrucosa*; Chromoblastomycosis; *Geotrichum candidum*; Geotrichosis; *Pseudallescheria boydii*; Allescheriasis; 5. Basidiomycota; *Cryptococcus neoformans*; Cryptococcosis; *Trichosporon* spp.; Trichosporonosis; 6. Zygomycota (Zygomycosis); Mucorales (Mucormycosis); *Rhizopus oryzae; Mucor indicus; Lichtheimia corymbifera; Syncephalastrum racemosum; Apophysomyces variabilis*; Entomophthorales (Entomophthoramycosis); *Basidiobolus ranarum*; Basidiobolomycosis; *Conidiobolus coronatus/Conidiobolus incongruous*; Conidiobolomycosis; 7. Microsporidia (Microsporidiosis); *Enterocytozoon bieneusi/Encephalitozoon intestinalis* Ungrouped fungal human infections; *Rhinosporidium seeberi* (Mesomycetozoea); Rhinosporidiosis, *Alternaria* ssp.; Alternariosis; *Fusarium* ssp.; Fusariosis; Hyalohyphomycosis Antibiotics PT159, PT160 and TPR-1 against *Neisseria gonorrhoeae* (gonorrhoea) and *Bacillus anthracis* (anthrax)

- PT159, PT160 and TPR-1 are with nearly 100% security active against *Neisseria gonorrhoea*, since rifampicin is highly active versus *Neisseria gonorrhoea*[1]
- PT159, PT160 and TPR-1 should be highly active against rosoxacin/spectinomycin- and azithromycin/ceftriaxone/doxycycline-resistant *Neisseria gonorrhoea*, since rifampicin is partially active versus these clones', and the inhibiting type is irreversible and bactericidal
- PT159, PT160 and TPR-1 are orally bioavailable, since the zwitterionic state of rifampicin is retained in them. The zwitterionic state is the prerequisite for oral absorption of rifamycins. Complete lipophilic rifamycins like rifamycin SV, rifamide and rifaximin are not orally absorbed, since their lack of zwitterionicity
- PT159, PT160 and TPR-1 are with nearly 100% security active against *Bacillus anthracis*, since all three antibiotics are highly active versus *Bacillus subtilis* and *Bacillus megaterium*, bacilli which are closely related to *Bacillus anthracis*:

|       | 1 µg | 10 µg |
|-------|------|-------|
| TPR-1 | 18.3 | 21.1  |
| PT159 | 15.7 | 18.0  |
| PT160 | 17.7 | 17.0  |

Mueller-Hinton Agar Disk Diffusion Assay with *B. subtilis*

Nutrient Agar (NA) plates were inoculated with 500 µl of *B. subtilis* and spread over the plate to achieve confluence after growth occurred. Paper discs were treated with 1 and 10 µg of each compound and placed on the plate surfaces in triplicate. Plates were inverted and allowed to grow overnight at 30° C. The diameters of the clearing zones were measured the following day and checked for resistant mutants 72 hours later. No resistant mutants were observed. Clearance zones (in mm) are detailed in the Table (inset).

Some of the Theory Behind PT159, PT160 and TPR-1 is Presented at the Following Pages The derivative was synthesized from rifampicin by reaction with 3-bromo-1-(trimethylsilyl)-1-propyne. The rationale behind this synthesis was the synthesis of tigecycline from minocycline[2-4] Tigecycline (TYGACIL™; Wyeth) circumvents antibiotic tetracycline resistance [induced active efflux (tetA-tetD, tetK) and ribosomal protection (tetM) proteins][4] by introduction of a bulky N-(tert.-butyl)-glycylamido group at position 9 of minocycline:

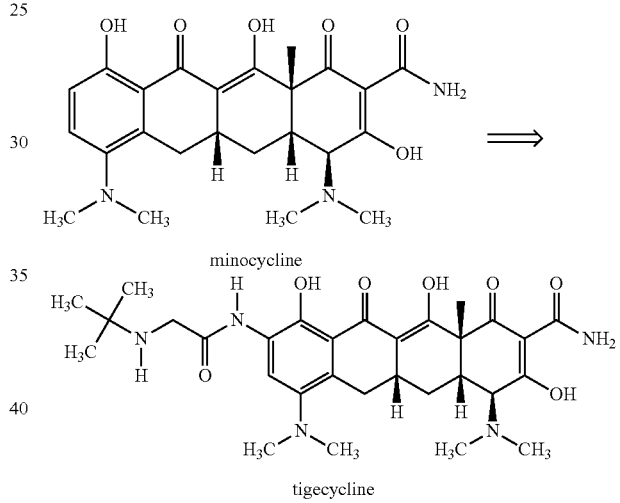

Since we had 3-bromo-1-(trimethylsilyl)-1-propyne at hand, we decided to try to introduce the bulky, lipophile trimethylsilylpropyne substituent into rifampicin. The trimethylsilyl group is isosteric to the tert.-butyl group in tigecycline. The reaction was successful and the product TPR-1 did not contain rifampicin anymore which was proved by proton NMR and elemental analysis. The reaction was performed in excellent 100% yield. The TPR-1 product apparently exists in two ionic forms, the zwitterion and the hydrobromide of the zwitterion. This is analogous to the situation with rifampicin itself which was proved to exist in two discernable forms, the zwitterion and the undissociated molecule itself[5]. Both forms of rifampicin are able to coexist in pharmaceutical bulk rifampicin powder, and can be isolated separately in substance[5]. In TPR-1 the hydrobromide of the zwitterion tends to loose hydrobromic acid (HBr), and, analogously to rifampicin, both forms coexist in solid and dissolved TPR-1 as proved by thin-layer chromatography (TLC) on silica gel 60 (Merck) plates [eluent: 80% (v/v) aqueous acetone]. The rifampicin derivative TPR-1 is entirely new [never synthesized before according to Chemical Abstracts Service (CAS) SciFinder® search]:

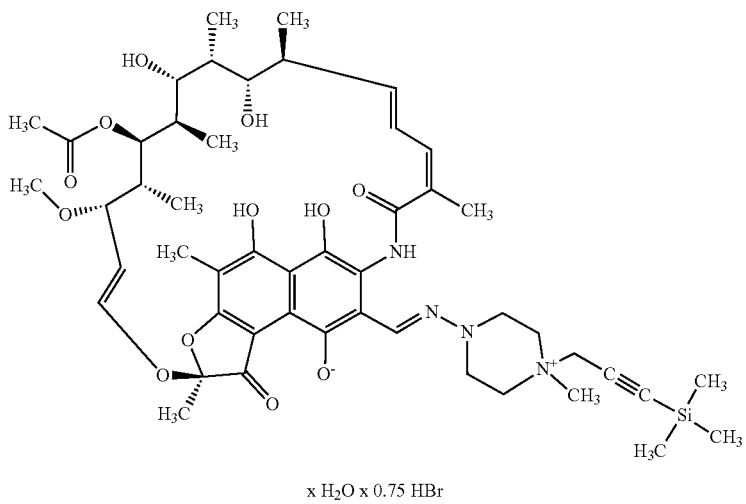 [SMILES: CO[C@H]1/C=C/O[C@@]2(C)Oc3c(C)c(O)c4c(O)c(c(/C=N/N5CC[N+](C)(CC#C[Si](C)(C)C)CC5)c([O-])c4c3C2=O)NC(=O)/C(C)=C\C=C\[C@H](C)[C@H](O)[C@@H](C)[C@@H](O)[C@@H](C)[C@H](OC(C)=O)[C@@H]1C]

x $H_2O$ x 0.75 HBr

TPR-1 is expected to represent the most promising rifamycin derivative of the two known and one new ansamycins synthesized, since TPR-1 is able to circumvent multidrug-resistant tuberculosis (MDR-TB), and, possibly, also extensively drug-resistant tuberculosis (XDR-TB) resistance mechanisms of circulating *M. tuberculosis* strains[6].

PT159, PT160 and TPR-1 are active against multidrug-resistant tuberculosis (MDR-TB), since the loss of free energy liberation (binding enthalpy) on binding to mutated □ subunit of bacterial DNA-dependent RNA polymerase is overcompensated by excessive liberation of free energy due to the perfect fit of the additional substituent in TPR-1 (in comparison to rifampicin) into the hollow pocket of the mutated □ subunit of bacterial DNA-dependent RNA polymerase, which is commonly not mutated, and constitutes a loosely threonine- and serine-lined hollow space in the structure of both wild-type and mutated (resistant against rifampicin) □ subunit of bacterial DNA-dependent RNA polymerase.

The Antiviral Efficacy of PT150, PT155, PT156, and PT158 Versus Human Hepatitis B Virus:

The anti-$HBV_{ayw}$-viral efficacy is increasing in the order →PT150→PT155→PT156→PT158:

In Vitro Antiviral Activity of PT Compounds versus Human Hepatitis B Virus Subtype ayw Replication

| PT Compound | Host cell | Assay type | $EC_{50}$ (μM) | $EC_{90}$ (μM) | $CC_{50}$ (μM) |
|---|---|---|---|---|---|
| PT150 | HepG2 2.2.15 | RT-qPCR | 69.3 | >100 | 31.8 |
| PT155 | HepG2 2.2.15 | RT-qPCR | 10.8 | >100 | >100 |
| PT156 | HepG2 2.2.15 | RT-qPCR | 9.9 | >100 | 34.0 |
| PT158 | HepG2 2.2.15 | RT-qPCR | 3.4 | >100 | >100 |
| PT158 | HepG2 2.2.15 | DNA (Southern) hybridization | 2.7 | 8.5 | >100 |
| Lamivudine (3TC) | HepG2 2.2.15 | DNA (Southern) hybridization | 0.026 | 0.116 | 2188 |

Legend: EC50, effective inhibitory (antiviral) concentration 50%; EC90, effective inhibitory (antiviral) concentration 90%; CC50, host cytotoxic concentration 50%.

Important observation: PT158 did not show the in vitro gain in activity in comparison to PT155 in the case of HIV-1 strain LAI ($HIV-1_{LAI}$) infection, as it did in the case of HBV ayw Therefore, to explain the extraordinary activity of PT158 versus HBV ayw we searched for the difference in the replication mechanisms of $HIV-1_{LAI}$ and HBV ayw We could exclude that PT158 exerts its synergistic activity gain by action on HBV surface antigen HBsAg (SHBsAg, MHBsAg, LHBsAg), HBV core antigen (HBcAg, HBeAg), and HBV X antigen (HBxAg). This was substantiated by experiences by one of us with HBV surface antigen protein chemistry (gel filtration), truncated middle surface antigen ($MHBs^t$) protein chemistry, and X antigen protein chemistry (chemical determination of disulfide bonds)

Therefore, PT158 should act on the replication cycle involving HBV P protein polymerase/reverse transcriptase (pol/RT). HBV P is a typical RT protein like $HIV-1_{LAI}$ RT The difference between $HIV-1_{LAI}$ and HBV ayw replication is the usage of a N-terminal part of the P pol/RT as 'terminal protein' which serves as primer for the (−)-strand synthesis from the pregenomic RNA [(+)-pgRNA][1-3]. The P polymerase protein donates a tyrosine residue (Y63) as priming site for (−)-ssDNA synthesis[1-3]. Thereby the P protein is kept covalently bound to the HBV genome through a rare protein-nucleic acid linkage (via a phosphotyrosine) seen also in the family of Picornaviridae (VPg)[1] and Adenoviridae (TP)[4]. $HIV-1_{LAI}$ does not use such a priming strategy, as it exploits human lysine transfer RNA 3 ($tRNA_{LYS3}$) as a primer Fortunately, the crucial hint for the origin of the in vitro gain in anti-HBV ayw activity of PT158 in comparison to PT155, not seen in the case of HIV-1 strain LAI ($HIV-1_{LA1}$) infection, came from a recent publication[5] investigating carbonyl J acid (mirror-symmetric) derivatives The carbonyl J acid derivatives (carbonyl J acid, calcomine orange 2RS, KM-1) did inhibit initiation of HBV (−)-ssDNA synthesis by binding to HBV pol/RT in the region normally occupied by the (+)-pgRNA hairpin □ stem-loop secondary structure[5]. The symmetric carbonyl J acid derivatives (see FIG. 1A) displace the □ RNA from the P protein. Therefore, HBV DNA synthesis can be efficiently blocked by symmetric molecules bearing hydrophilic groups, since □ is indispensable for (+)-pgRNA encapsidation and initiation of RT[5]

The PT158 component called TCY-1 (PT158=PT155+ TCY-1) also has a mirror-symmetric structure (see FIG. 1B). Therefore, we believe that the PT158 component TCY-1 acts in the same way that the carbonyl J acid derivatives by mimicking the HBV (+)-pgRNA □ hairpin Unfortunately, the carbonyl J acid derivatives cannot being pursued as potential anti-HBV drugs, since they virtually do not cross any cell membrane[5]. They show almost no activity in cell culture, and their anti-HBV mechanism was determined in cell-free in vitro systems[5]. This is a general problem for polyanionic dye derivatives, also faced in the case of HIV-1 (Ref. 6)

Fortunately, PT158 shows excellent anti-HBV activity in vitro in cellular systems. This proves that cell penetration is good and that PT158 is suitable as an anti-HBV experimental agent.

We identified[7] a good putative glucocorticoid nuclear receptor (GR) response DNA cis-element (glucocorticoid response element, GRE) inverted repeat 3 (IR3), the PT158 component PT155, as well as PT155 as a single agent, binds to the human GR (hGR), is transported through the nuclear pore complex to the intranuclear HBV genome by the PT155-liganded hGR, the PT155-hGR complex binds to GREs, and, finally, the co-transported, metabolically activated PT155 (carbodiimide) switches to the HBV DNA and covalently modifies amine group-containing nucleobases (cytosine, guanine, adenine) by carbodiimide addition Thereby integrated HBV proviruses could be inactivated covalently and the HBV replication would stop permanently Development of comprehensive antibiotic solutions for treatment and prevention of anthrax caused by *Bacillus anthracis*: TPR-1, PT159, PT160. Additionally, posttraumatic stress disorder (PTSD), alcohol and drug addiction, head trauma, stroke, bone healing/ossification are targeted by PT150 and PT155. There are already clinical studies that validate PT150 for treatment of alcohol addiction. PT155 may be even better suited than PT150 for treatment of alcoholism. Opiate and cocaine addiction are also investigated for relief by supportive PT150 and PT155. PT150 and PT155 could decrease craving and drug seeking behaviour, and suppress drug withdrawal syndromes by antagonizing action of cortisol.

Development of a warfighter first-aid package including an antibiotic, lipophilic wound ointment for immediate use in the battlefield to prevent wound infections by staphylococci and streptococci (wound infections like necrotizing fasciitis), and for prophylaxis of war-related gas gangrene (*Clostridium perfringens*):

0.5% Antibiotic, Long-Term Storage-Stable, Lipophilic Warfare Ointment (in Lanae alcoholum unguentum)

Cetostearyl alcohol (cetylstearyl alcohol)
Lanolin alcohols (Eucerin®)
Petrolatum white (white vaseline)
Paraffinum subliquidum (liquid petrolatum)
TPR-1 or PT159 or PT160
0,4975
5,9700
83,0325
10,0000
0,5000 100,0000

This ointment contains no water, is not washable from the skin with water, is long-time adhesive, requires no antimycotic preservatives, and provides long-term storage stability. Fungal contamination is self-limiting, since in this lipophilic micro-environment fungi do not grow. Fungi need water to grow, and the lanolin alcohols act intrinsically antimycotic. The stability of the antibiotic itself is high because of the anhydrous environment preventing hydrolysis. Stable under warfare conditions (abrasion, humidity, sweat, heat). Topical pleasure is secured by partial substitution of vaseline by liquid petrolatum. The ointment can absorb water (sweat, humidity) and take up water to yield Lanae alcoholum unguentum aquosum.

Included herein is a list of bacteria proven or potentially susceptible towards TPR-1, PT159, and PT160.

Agents Known Susceptible to PT Compounds Potentially Affecting Warfare and Security

| Compound | Application | Agent | Diseases (Concise) |
|---|---|---|---|
| PT150 | infusion | JC virus (John Cunningham virus) | Progressive multi focal leukoencephalopathy (PML); rare disease affecting the brain in immunocompromised hosts |
| PT150 | orally or intramuscular | Human norovirus (Norwalk virus) | Acute gastroenteritis with diarrhea and vomiting; suitable for prevention and prophylaxis of mass infections of personnel serving in U.S. Army Military Bases |
| PT155 | orally | Zika virus | Flavivirus affecting reproductive organs; suspected to cause malformations in embryos; suspected to damage male reproductive organs (testis) |
| PT155 | orally or intramuscular | Ebola virus | Causative agent of Ebola hemorrhagic fever; serious List 1 pathogen of national security interest; can be weaponized |

-continued

| Agents Known Susceptible to PT Compounds Potentially Affecting Warfare and Security | | | |
|---|---|---|---|
| Compound | Application | Agent | Diseases (Concise) |
| PT155 | orally | Human immunodeficiency virus type 1 (HIV-1) | Causative agent of acquired immunodeficiency syndrome (AIDS); well-known pandemic pathogen affecting high-risk groups |
| PT155 | orally | Human hepatitis B virus (HBV) | Can cause chronic liver disease leading to hepatocellular carcinoma (HCC); widely distributed, ca. 400 million people infected; highly contagious in military settings |
| PT158 | orally | Zika virus | Flavivirus affecting reproductive organs; suspected to cause malformations in embryos; suspected to damage male reproductive organs (testis) |
| PT158 | orally or intramuscular | Ebola virus | Causative agent of Ebola hemorrhagic fever; serious List 1 pathogen of national security interest; can be weaponized |
| PT158 | orally | Human hepatitis B virus (HBV) | Can cause chronic liver disease leading to hepatocellular carcinoma (HCC); widely distributed, ca. 400 million people infected; highly contagious in military settings |
| PT158 | orally | Hepatitis C virus (HCV) | Can cause chronic liver disease leading to hepatocellular carcinoma (HCC); widely distributed, ca. 170 million people infected; highly contagious in military settings |
| TPR-1 PT159 PT160 | orally or intramuscular | *Bacillus anthracis* (anthrax) | Causative agent of anthrax; gram-positive, sporulating bacilli; serious List 1 pathogen of national security interest; is/was weaponized |
| TPR-1 PT159 PT160 | orally, intramuscular or topical | *Staphylococci* and *streptococci* | Widely distributed pathogens in wound infections; can cause serious systemic disease (sepsis) following warfare injury; can cause necrotizing fasciitis (extreme condition) following warfare injury |
| TPR-1 PT159 PT160 | orally, intramuscular or topical | *Clostridium perfringens* (gas gangrene) | Causative agent of gas gangrene; gram-positive, sporulating bacterium; can cause extreme disease following warfare injury |

Improvements in the immediate medical and surgical care of battle casualties and in body armor mean that soldiers are surviving injuries which would have killed them if sustained in previous conflicts. This has resulted in an increase in the complexity of the wounds that require reconstruction and new challenges for the responding medical teams. Management of wound exudate, pain and nutrition are vitally important, as is control of the wound microbiology. These issues are complicated by the high levels of circulating cortisol, the human stress hormone, that are likely to inhibit wound healing and suppress the immune system leading to greater risk of infection. At the same time, cortisol is playing important homeostatic roles for helping someone survive the stress and trauma of combat. Thus, systemic suppression of the effects of elevated cortisol, through blockade by a glucorticoid receptor (GR) antagonist, might be helpful for wound healing, but might simultaneously deprive the soldier of other physiologic responses that are helpful for responding to global stress.

To split the difference between these two competing needs of the wounded soldier, localized inhibition of the effects of cortisol, at the site of the wound, may be beneficial. Thus, we local applications of the potent and specific GR blocking compounds PT-150 and PT-155. Such applications could be topical, in the face of cutaneous wounds, applied as ointments or as impregnated bandaging materials, or administed by direct injection or local vascular infusion for deeper musculo-skeletal injuries. Thus, the benefits of cortisol blockade at the local level would not mitigate beneficial effects of stress-response cortisol elevations systemically. Moreover, such simple treatments might be easily initiated on site, improving early intervention and, thereby, long term outcomes.

We can also envision such a system extending beyond GR antagonists. For example, other molecules which are specific for wound repair (e.g. BMP-2, BMP-4, OP-1, FGF-1, FGF-2, TGF-beta1, TGF-beta2, TGF-beta3; VEGF; collagen;

laminin: fibronectin; vitronectin) could also be part of the application system. Thus, combination local of topical therapies with other wound healing modulating compounds may also have value. They may even result in unexpected synergies, given the complexity of cortisol's participation in physiologic pathways.

Proof of principle studies behind these concepts involve suppression of infections by PT-150 in elderly individuals after hip fracture, a combination of physical trauma and the dysregulation leading to marked elevation of serum cortisol in a rough mimic of the battle field wounds. In mouse models and in early clinical trials, bacterial infections were reduced.

PT-150 is already known to be safe in humans, having passed phase 2b clinical trials for psychotic depression, its original intended use. It has a flexible IND associated and clinical trials for other purposes are already being planned. PT-155 has similar effective antagonist binding to GR, yet requires pre-clinical enabling studies.

PT150 and PT155 as wound healing promoters—Included in the antibiotics TPR-1, PT159, and PT160. PT150 and PT155 are cortisol antagonists. PT155 additionally bears a thiosemicarbazone group. Both compounds are not soluble in water initially, but if solubilized first in DMSO they can be dispersed in aqueous media and then stay in solution. Both compounds are very soluble in ethanol, acetone, DMSO, DMF, ethyl acetate, and chloroform. They build the basis for the antibiotics PT159 (PT150+TPR-1) and PT160 (PT155+TPR-1). TPR-1 is a completely new developed highly active rifamycin related to INN: rifampicin (USAN: rifampin). TPR-1 is highly active versus mycobacteria, including multidrug-resistant tuberculosis (MDR-TB), and versus staphylococci (including MRSA), streptococci (including *Streptococcus pneumoniae*), and bacilli like anthrax (*Bacillus anthracis*). Probably TPR-1 is active versus *Clostridium perfringens*, the agent of gas gangrene. Therefore, PT159 and PT160 are highly suitable for an antibiotic wound healing ointment, since the implemented cortisol antagonism promotes wound healing, granulocyte acquisition and immune function. Cortisol, the principal human glucocorticosteroid of the adrenal cortex, represents a stress hormone suppressing immune surveillance by inhibiting the function of T lymphocytes. Therefore, a cortisol antagonism in turn promotes T lymphocyte signaling at injuries, including sequestering of granulocytes to the point of injury by chemoattraction (mainly by secernation of various interleukins). Moreover, a cortisol antagonism generally promotes antimicrobial defense activity by attracting monocytes/macrophages and other phagocytic cells to the point of injury. Also natural killer cell (NK cells) function is promoted for antimicrobial defense. In addition, cortisol antagonism promotes the activity of the following factors critically involved in the signaling, regulation and organization of the wound healing process.

TABLE 4

| Growth Factor | Abbreviation | Main Effector Cell(s) | General Effects on Wound Healing Regulation |
|---|---|---|---|
| Epidermal growth factor | EGF | Activated macrophages Salivary glands Keratinocytes | Keratinocyte and fibroblast mitogen Keratinocyte migration Granulation tissue formation |
| Transforming growth factor-α | TGF-α | Activated macrophages T lymphocytes Keratinocytes | Hepatocyte and epithelial cell proliferation Expression of antimicrobial peptides Expression of chemotactic cytokines |
| Hepatocyte growth factor | HGF | Mesenchymal cells | Epithelial and endothelial cell proliferation Hepatocyte motility |
| Vascular endothelial growth factor | VEGF | Mesenchymal cells | Vascular permeability Endothelial cell proliferation |
| Platelet derived growth factor | PDGF | Platelets Macrophages Endothelial cells Smooth muscle cells Keratinocytes | Granulocyte, macrophage, fibroblast and smooth muscle cell chemotaxis Granulocyte, macrophage and fibroblast activation Fibroblast, endothelial cell and smooth muscle cell proliferation Matrix metalloproteinase, fibronectin and hyaluronan producton Angiogenesis Wound remodeling Integrin expression regulation |
| Fibroblast growth factor 1 and 2 | FGF-1, FGF-2 | Macrophages Mast cells T lymphocytes Endothelial cells Fibroblasts | Fibroblast chemotaxis Fibroblast and keratinocyte proliferation Keratinocyte migration Angiogenesis Wound contraction Matrix (collagen fibers) deposition |
| Transforming growth factor-β | TGF-β | Platelets T lymphocytes Macrophages Endothelial cells Keratinocytes Smooth muscle cells Fibroblasts | Granulocyte, macrophage, lymphocyte, fibroblast and smooth muscle cell chemotaxis TIMP synthesis Angiogenesis Fibroplasia Matrix metalloproteinase production inhibition Keratinocyte proliferation |
| Keratinocyte growth factor | KGF | Keratinocytes | Keratinocyte migration, proliferation and differentiation |

Antineoplastics
PT162 is water-soluble and can be infused. It represents a quaternary ammonium salt with highly lipophilic substituents, adamantane and m-xylylidene.
PT162 was found to act extremely cytotoxic to cancer cells.
PT162 was synthesized in highest purity. Technical synthesis and purity problems were successfully fixed by utilizing the self-prepared free base of 1-aminoadamantane, instead of its commercial hydrochloride.

The Putative Mechanism-of-Action of PT162:
PT162 is supposed to act as a protein p53-reactivating cell cycle checkpoint inhibitor', inducing cell cycle arrest and/or apoptosis in cancer cells by restoring DNA-binding activity of mutant p53 protein.
Tumor protein p53 (TP53) has been described as "the guardian of the genome" because of its role in conserving stability by preventing genome mutation. Hence its gene TP53 is classified as a tumor suppressor gene.
TP53 protein is mutated in ca. 50% of human cancers, in fact TP53 is the most commonly mutated gene in human cancer[3]. TP53 is the 'guardian of the genome' with DNA-binding activity. Upon DNA damage p53 is activated by tetramerization to bind like a transcription factor to p53 response elements in human genomic DNA[2-4]. The transcriptional activity leads to induction of apoptosis in cancer cells. However, in cancer cells p53 can be mutated in such a way that p53 tetramerization and DNA binding[2-4] is prevented. Therefore, these cancer cells survive instead of DNA damage induced by antineoplastic chemotherapy (alkylating agents, platinum complexes, and other currently applied cytostatics/cytotoxics).
TP53 reactivators are already known[3,5], acting by several mechanisms. Many of them inhibit MDM2 (also called HDM2 in humans), an ubiquitin ligase rendering p53 protein being destroyed in the human proteasome. Other investigational drugs reactivate mutant p53 tetramerization and DNA binding capacity, and restore transcriptional activity of p53 protein in malignant cells.
PT162 should fall into the last category. PT162 could bind to the p53 tetramerization domain (p53 TD), since p53 TD contains a large proportion of acidic (glutamate, E; aspartate, D) and hydrophobic amino acid residues, and PT162 itself is pentacationic and hydrophobic. This would enable binding by both electrostatic interaction and hydrophobic interaction. The combination of PT162 with PT150 or PT157, to yield PT163 and PT164, respectively:
The combinations of PT162 with PT150 or PT157 to yield PT163 and PT164, respectively, are expected to show intrinsically increased antineoplastic activity through the synergistic effects by the steroid admixture. PT150 and PT157 are validated antineoplastic drugs.

The invention will be illustrated in more detail with reference to the following Examples, but it should be understood that the present invention is not deemed to be limited thereto.

EXAMPLES

Example 1

OR-1, MR-1 and TPR-1 Compounds Test Protocol versus *Mycobacterium tuberculosis* $H_{37}Rv$ (Resazurin Assay)

Drug Stock $$iC \times iV = fC \times fV$$

$$\frac{20\ \mu g/ml \times 0.2\ ml}{0.01\ ml} = 400\ \mu g/ml$$

1) Add 10 ml of DMSO to reconstitute powder of 40 mg which provides the concentration of 4 mg/ml and is stored 1 ml in aliqouts.
2) This further needs to be diluted 1:10 before use. 500 μl in 4.5 ml of DMSO.
3) This gives working solution of 20 μg/ml aliquoted in a 200 μl (25 vials)

Assay Plate Design:
1. Aliquot 200 μl $H_2O$ in peripheral wells of the 96-well plate (rows 1 and 8, columns 1 and 12). This is to prevent evaporation of the test wells.
2. Aliquot 90 μl of the media in column 2 (wells B2-G2) and 190 μl in column 3 (wells B3-G3). Aliquot 100 μl of 7H9GC-OADC in all the empty wells in columns 4-11.
3. Add 10 μl of the drug in columns 2 and 3.
4. Resuspend the liquid in column 3 and take 100 μl and transfer to column 4 using a multipipette. Serially dilute further across the plate from columns 4-10 and finally take 100 μl out of column 10. This should give 2 fold serial dilutions across the plate. Column 11 is the growth control.
5. Add 100 μl of *M. tuberculosis* $H_{37}Rv$ into all wells containing media. The final volume in each well will be 200 μl. Place the lid and seal the lid onto the plate with parafilm.
6. Incubate at 37° C. for 6 days. On day 6, add 50 μl resazurin dye (0.01% mix to well B11—the colour of the dye should be blue. Wrap in foil and incubate at 37° C. for 24 hrs.
7. If the well remained blue after 24 hrs, incubate for further 24 hrs until the dye changes colour to pink.
8. Once the dye in the control well B11 turns pink, add 20 μl resazurin dye mix to all the remaining wells. Wrap in foil and incubate at 37° C. for 24 hrs.
9. Determine the MIC by observation—MIC is defined as the concentration at which there is no observed colour change. If colour change is difficult to observe, read the plate on a plate reader at 595 nm.
10. If contamination is suspected, check the control well with acid-fast stain.

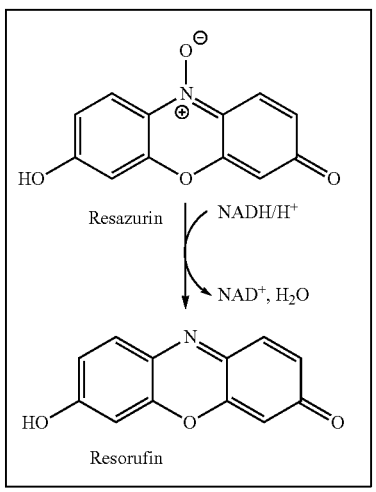 [SMILES: O=c1ccc2[n+]([O-])c3ccc(O)cc3oc-2c1 ; O=c1ccc2nc3ccc(O)cc3oc-2c1]

Example 2

Purity Determination of TPR-1, PT159, and PT160 Compounds

| Test Compounds | | | | | | |
|---|---|---|---|---|---|---|
| IDRI Compound ID | Submitter Compound ID | Assay Date | % Purity | MS Analysis Mode | Observed Molecular Weight or Ion | Expected Molecular Weight or Ion |
| NCI-0003488 | TPR-1 | 2017 Jan. 23 | 59 | Positive | 933.2 | 1012.9 |
| NCI-0003487 | PT159 | 2017 Jan. 23 | 42 | Positive | 933.2 | 1443.7 |
| NCI-0003488 | PT160 | 2017 Jan. 23 | 42 | Positive | 614.1 | 1677.4 |

| Control Compounds | | | | | | |
|---|---|---|---|---|---|---|
| IDRI Compound ID | Control Compound ID | Assay Date | % Purity | MS Analysis Mode | Observed Molecular Weight or Ion | Expected Molecular Weight or Ion |
| NCI-0000015 | Tamoxifen | 2017 Jan. 23 | 100 | Positive | 372.2 | 372.9 |

Introduction

Compound purity is determined by liquid chromatography (LC) coupled to mass spectrometry (MS) with detection by ultraviolet (UV) absorbance and total ion count from MS. MS data is used to corroborate or challenge putative compound identity.

Protocol

Compound stock solutions were diluted to 2 mM in DMSO and injected into an Agilent 1100 HPLC system using the following conditions for separation: Phenomenex Gemini C18 column, 3×50 mm; flow rate 0.45 ml/min; gradient 5-95% acetonitrile in water over 8 min with all solvents containing 0.05% formic acid. Detection used the following: UV detector—Agilent diode array, monitored at 214 and 254 nm; mass spectrometry detector (MSD)-Agilent MSD, electrospray ionization, positive mode.

Purity was determined by comparing the area under the curve of the test compound peak to the combined areas of all peaks in the chromatogram, excluding DMSO and peaks appearing in blank runs. Priority reporting was given to the UV traces (since mass spectrometer response can vary widely depending on a given compound's ease of ionization). Purity of compounds lacking UV activity was reported using evaporative light scattering detection (ELSD). The identity of compounds was corroborated or challenged based on whether the molecular mass found in the mass spectrum was that of the expected compound.

Note

Note that purity is reported for the most abundant sample component based on the integrated area under the 214 nm UV peak (AUC). Detailed information is available in the raw data files. Additionally, FW is reported based on the most abundant peak whether or not it matches the expected (submitter's) FW. Details can be mined from the raw data, where the molecular ion trace of interest may not be the strongest signal, but is present in the data and should be evident to the submitter.

Figures 15A, 15B, 15C:
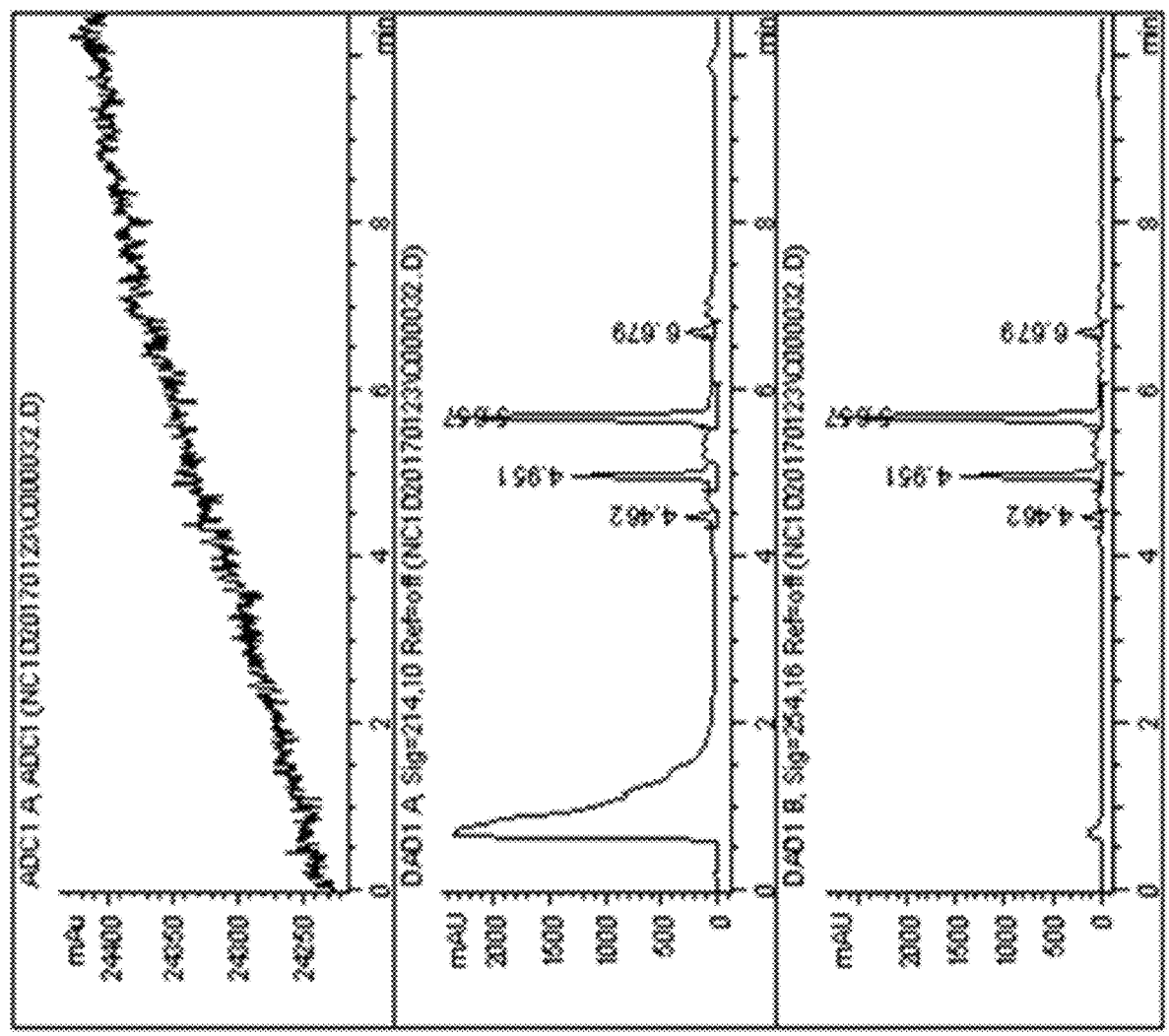
FIG. 15A shows the HPLC chromatogram of TPR-1.
FIG. 15B shows the mass spectrometric ion detected after HPLC of TPR-1 (m/z 933.2) is the cationic form.
FIG. 15C shows the 3-formylrifamycin SV was not detected in any trace in the proton nuclear magnetic resonance (1H-NMR) spectrum of TPR-1 dissolved in deuterated chloroform (CDCl3).

The chromatographic separation of TPR-1 is given in FIGS. 15A to C.

- There are four peaks (4.462 min, 4.951 min, 5.657 min, 6.679 min) at 214 nm and 254 nm diode array UV detection
- No other significant peaks are seen
- The two main peaks (4.951 min, 5.657 min) stem from the two discernible, coexisting ionic forms of the rifamycin. In 2014 this peculiar property was proved for rifampicin (Ref. 1)
- The two discernible forms in the case of TPR-1 are shown as:

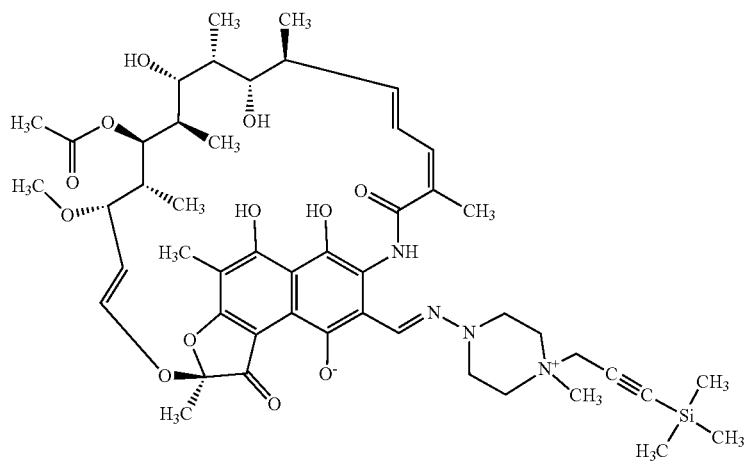

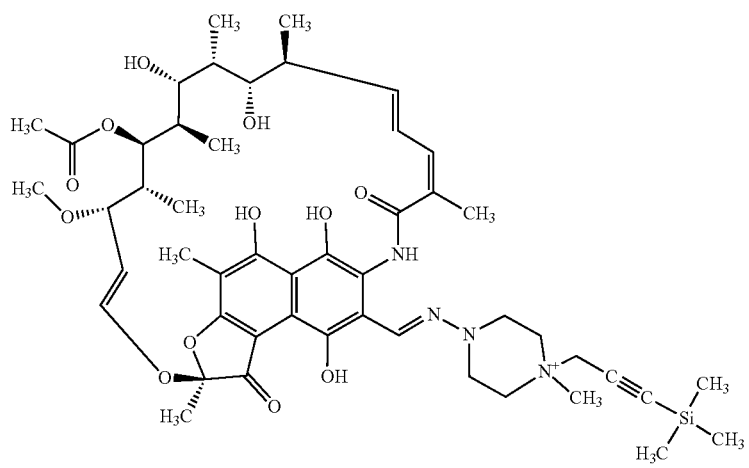

In the above picture the left formula is zwitterionic, whereas the right formula is cationic. The zwitterionic form elutes at 4.951 min, since it is more polar, and the cationic form elutes at 5.657 min, since it is more lipophilic. The cationic form was integrated by IDRI as 59%. So the cationic form dominates in the formic acid-acidified (0.05%) HPLC eluent, as to be expected The two small side peaks stem from hydrolysis of TPR-1by the formic acid-acidified (0.05%) HPLC eluent. This is a phenomenon well-known for rifampcin (Ref. 2). The hydrazone imine group, a kind of Schiff base, is hydrolysed in acidic media (Ref 2)

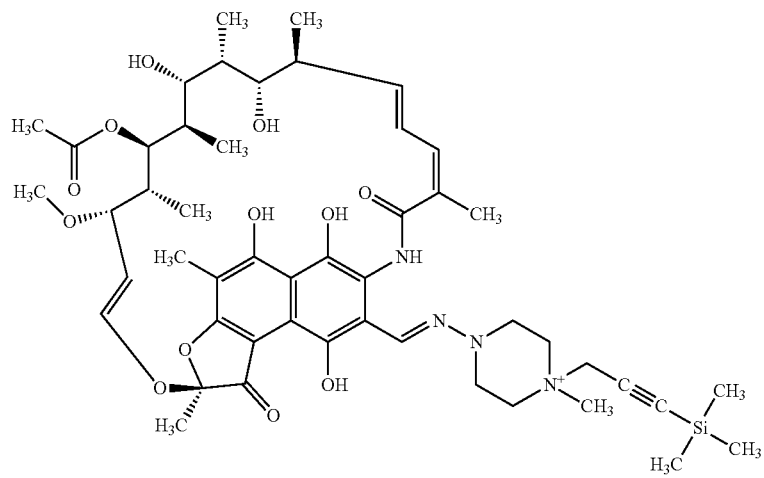

TPR-1

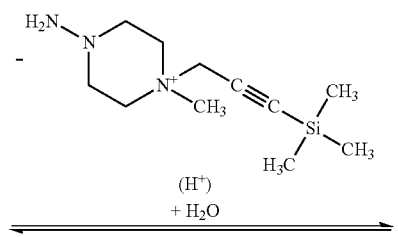

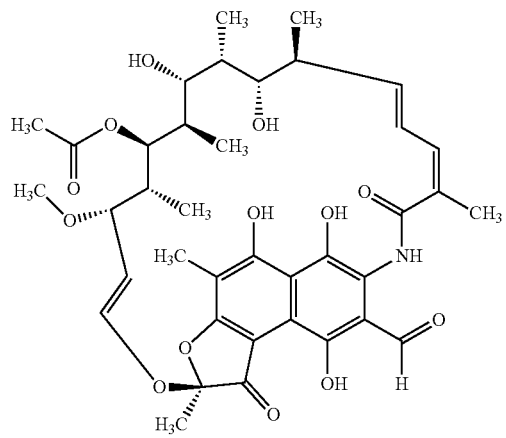

3-formylrifamycin SV

The split product 3-formylrifamycin SV is very lipophilic and elutes at 6.679 min. This is also the product of rifampicin hydrolysis. However, TPR-1 is more susceptible to this hydrolysis than rifampicin. In turn, TPR-1 is resistant to oxidation, whereas rifampicin is readily oxidized to the naphthoquinone form (Ref 2) The second split product 4-amino-1-[3-(trimethylsilyl) prop-2-yn-1-yl]-1-methylpiperazin-1-ium is UV active and elutes at 4.462 min, since it is polar:

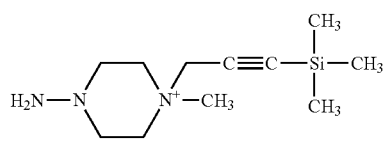

This piperazine derivative absorbs more at 214 nm than at 254 nm, as can be seen in the HPLC chromatogram So the purity of TPR-1 is proved to be >98%, as the characteristic aldehyde proton (☐10.65 ppm) (Ref. 1) of 3-formylrifamycin SV was not detected in any trace in the proton nuclear magnetic resonance ($^1$H-Wit) spectrum of TPR-1 dissolved in deuterated chloroform ($CDCl_3$). This spectrum is shown in FIG. 15.

The mass spectrometric ion detected after HPLC of TPR-1 (m/z 933.2) is the cationic form, the main peak which was integrated as 59%, of TPR-1 eluting at 5.657 min:

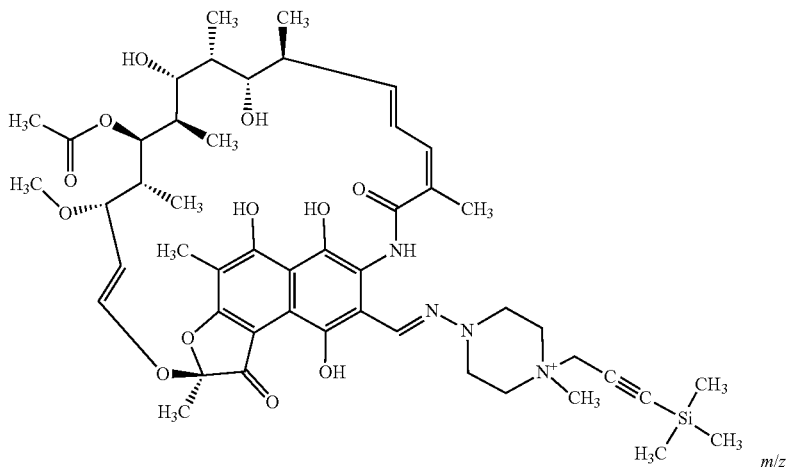 [SMILES: CO[C@H]1/C=C/O[C@@]2(C)Oc3c(C)c(O)c4c(O)c(c(/C=N/N5CC[N+](C)(CC#C[Si](C)(C)C)CC5)c(O)c4c3C2=O)NC(=O)/C(C)=C\C=C\[C@H](C)[C@H](O)[C@@H](C)[C@@H](O)[C@@H](C)[C@H](OC(C)=O)[C@@H]1C]

933.467576 Da

So also the chemical identity of TPR-1 is secured unequivocally

The compounds PT159 and PT160 were prepared as solid powder mixtures. Therefore, the purity is guaranteed by the production process. In the $^1$H-NMR spectra shown at the next pages no in situ intercomponent reaction of the components was detected. Therefore, the statements of purity for TPR-1 are valid also for the compounds PT159 and PT160

While the invention has been described in detail and with reference to specific examples thereof, it will be apparent to one skilled in the art that various changes and modifications can be made therein without departing from the spirit and scope thereof.

What is claimed is:

1. A method of preventing and/or treating a pathogenic infection in a patient, the method comprising the steps of: selecting a patient in need of preventing and/or treating a pathogenic infection; administering to the patient at least one agent selected from the group consisting of TPR-1, TCY-1, PT150, PT157, PT158, PT159, PT160, PT162, PT163, PT164, PT165, PT166, PT167, combinations thereof, and pharmaceutically acceptable salts thereof; wherein the pathogenic infection is prevented and/or treated in the patient.

2. The method of claim 1, wherein the pathogenic infection is selected from the group consisting of viral infection, bacterial infection, fungal infection, parasitic infection, and combinations thereof.

3. The method of claim 1, wherein the pathogenic infection is a viral infection.

4. The method of claim 1, wherein the viral infection is selected from the group consisting of Hepatitis C virus, Bovine Viral Diarrhea virus, Ebola-like viruses, Hepatitis B virus, Mouse mammary tumor virus, Human Immunodeficiency Virus-1 (HIV-1), Varicella-Zoster virus (chicken pox; VZV), Cytomegalovirus (CMV), Human Herpes Virus-6 (HHV-6), Human Herpes Virus-7 (HHV-7), Kaposi's Sarcoma-Associated Herpes virus (HHV-8), Variola (Small Pox) virus, Vaccinia virus, Cowpox virus, Monkeypox virus, Influenza A virus, Influenza B virus, and Coronavirus.

5. The method of claim 4, wherein the Coronavirus is at least one of Severe Acute Respiratory Syndrome Coronavirus (SARS-CoV) and Middle East Respiratory Syndrome Coronavirus (MERS-CoV).

6. The method of claim 5, wherein the Coronavirus is Severe Acute Respiratory Syndrome Coronavirus 2 (SARS-CoV-2).

* * * * *